(12) United States Patent
Chaki et al.

(10) Patent No.: US 6,384,065 B1
(45) Date of Patent: May 7, 2002

(54) SPIRO COMPOUNDS OR SALTS THEREOF AND PREVENTIVES/REMEDIES FOR AUTOIMMUNE DISEASES AND AP-1 INHIBITORS CONTAINING THE SAME

(75) Inventors: Hisaaki Chaki; Yukihiko Aikawa; Mikako Miyajima; Morihiro Nishio, all of Toyama; Hiroshi Kuroda, Kanazawa; Keiichi Tanaka, Toyama; Shuichi Hirono, Tokyo; Shunichi Shiozawa, Kobe, all of (JP)

(73) Assignee: Toyama Chemical Co., Ltd., Tokyo (JP)

(*) Notice: Subject to any disclaimer, the term of this patent is extended or adjusted under 35 U.S.C. 154(b) by 0 days.

(21) Appl. No.: 09/674,483
(22) PCT Filed: Apr. 28, 1999
(86) PCT No.: PCT/JP99/02262
  § 371 Date: Nov. 8, 2000
  § 102(e) Date: Nov. 8, 2000
(87) PCT Pub. No.: WO99/58515
  PCT Pub. Date: Nov. 18, 1999

(30) Foreign Application Priority Data

May 8, 1998 (JP) ............................................ 10-142200
Jun. 11, 1998 (JP) ............................................ 10-179649

(51) Int. Cl.$^7$ ..................... A61K 31/426; C07D 277/60
(52) U.S. Cl. ....................... 514/365; 548/247; 546/168; 546/269.7; 544/336; 514/255; 514/314; 514/342
(58) Field of Search .................................. 514/369, 365, 514/342, 314, 255; 548/147; 546/269.7, 168; 544/336

(56) References Cited

U.S. PATENT DOCUMENTS 3,932,423 A   1/1976  Arimura et al.
4,587,250 A   5/1986  Klauser et al.

FOREIGN PATENT DOCUMENTS

JP  49-124075  11/1974
JP  50-5392     1/1975
JP  50-26547    9/1975
JP  52-77079    6/1977
JP  58-148871   9/1983

*Primary Examiner*—Charanjit S. Aulakh
(74) *Attorney, Agent, or Firm*—Oblon, Spivak, McClelland, Maier & Neustadt, P.C.

(57) ABSTRACT

The spiro compounds of the present invention represented by the general formula:

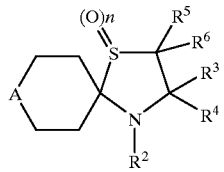

wherein A, $R^2$, $R^3$, $R^4$, $R^5$, $R^6$ and n are as defined in the specification, exhibit an AP-1 activity inhibitory action and, based on the AP-1 inhibitory action, suppresses the expression of a wide variety of genes and are useful as an agent for treating and preventing autoimmune diseases with lessoned side reactions.

11 Claims, No Drawings

SPIRO COMPOUNDS OR SALTS THEREOF AND PREVENTIVES/REMEDIES FOR AUTOIMMUNE DISEASES AND AP-1 INHIBITORS CONTAINING THE SAME

TECHNICAL FIELD

The present invention relates to novel spiro compounds or salts thereof that inhibit the activity of a transcription factor AP-1 and are useful as agents for treating autoimmune diseases, agents for preventing and/or treating autoimmune diseases and an AP-1 inhibitor containing the same.

BACKGROUND ART

Up to today, therapeutic drugs for many diseases have been developed to control the functions of proteins such as enzymes and receptors. For example, for treating inflammatory diseases such as rheumatoid arthritis, etc., cycloxygenase synthesizing prostaglandins from arachidonic acid or 5-lipoxygenase synthesizing leucotrienes have been taken as a target, and a number of non-steroidal antiinflammatory drugs such as indomethacin have been developed and put to therapeutic uses (J. Pharm. Sci., Vol. 73, Pages 579–589, 1984). Inflammatory cytokines such as interleukins (IL)-1 and IL-6 and tumor necrotic factor (TNF) have attracted intention as amplifying or aggravating factors in inflammatory reaction. As agents for regulating the functions of these proteins, monoclonal antibodies for respective proteins (Arthritis Rheum., Vol. 36, Pages 1681–1690, 1993), low molecular weight cytokine production inhibitors (Ann. Rep. Med. Chem., Vol. 27, Pages 209–218, 1992), etc. are being developed. Further, the use of antibodies for those cytokine receptors is also being attempted clinically (Rheumatism, Vol. 37, No. 2, Page 174, 1997).

In the diseases caused by a quantitative abnormality of functional proteins existing in cells or on cell membranes or of functional molecules secreted from cells, however, it is considered that a therapy in the true sense is to regulate the quantity of transcription of functional molecule gene and thereby normalize the quantity of expression rather than to inhibit the activity of the functional molecules. It is known that not only the quantitative abnormalities of the above-mentioned inflammatory cytokines and lipid mediators synthesized from arachidonic acid but also the quantitative abnormalities of many functional proteins such as adhesion molecules and matrix metallo proteinases take part in the cause of autoimmune diseases such as rheumatoid arthritis and chronic inflammatory diseases (N. Engl. J. Med., Vol. 322, Pages 1277–1289, 1990). Although gene expression and production of these functional proteins are regulated by a plurality of transcription factors, it is known that the promoter region of a majority of such genes commonly involves a consensus sequences of transcription factor AP-1 (TRE sequence). Further, it has been reported that expression of some of these functional proteins is regulated by binding of AP-1 to the promoter region (Nature, Vol. 337, Pages 661–663, 1989).

A living body exhibits various defensive reactions against outer stimulation and attack, and shows immune responses and inflammatory reactions.

Cellular and molecular analyses of such reactions have made a surprising progress in the recent years, due to which it has become apparent that gene expression and production of proteins to make sure the physiological functions was induced the stimulation in all the cells constituting a living body.

The immune responses and inflammatory reactions are amplified and regulated by the interaction of these genes including inflammatory cytokines such as IL-1 and TNFα, cell surface molecules such as cell-adhesion molecules and various cytokine receptors and enzymes such as matrix metallo-proteinases. On the other hand, autoimmune diseases typified by rheumatoid arthritis and other intractable chronic inflammatory diseases are considered caused by an excessive immunity and inflammatory reactions. That is, it is prospected that, in these inflammatory diseases, such a wide variety of genes directly relating to the etiology of disease are expressed in an excessive quantity, so that a mere inhibition or control of only one genetic product (protein) is incapable of realizing a sufficient therapy (radical therapy).

At the present time, non-steroidal anti-inflammatory agents and steroidal agents are used for the pharmaceutical treatment of chronic inflammatory diseases such as rheumatoid arthritis. Non-steroidal anti-inflammatory agents such as indomethacin and the like inhibit cycloxygenase and thereby suppress the production of lipid mediators such as prostaglandin $E_2$ and the like. However, such a treatment is not sufficient as a radical therapy because the use of these drugs is to suppress only one inflammatory mediator, cycloxygenase, and the effect thereof is nothing but an expectation of a conservative treatment. On the other hand, steroidal agents are known to exhibit regulating effect at the stage of expression of gene through intermediation of a glucocorticoid receptor, and it has actually been reported that these agents inhibit the activity of transcription factor AP-1 and thereby suppress the production of cytokines and other proteins (Cell, Vol. 62, Pages 1189–1204, 1990). Although effectiveness of such steroidal agents are sufficiently recognized, the use of such steroidal agents is restricted by the hormonal and side effects thereof, and they cannot be administered over a long period of time. Especially, the inflammatory diseases such as autoimmune diseases are generally chronic and require a long-term therapy, so that drugs having intense side effects cannot be used at least at the present time.

Thus, it has been desired to develop an agent for treating and/or preventing autoimmune diseases which inhibits AP-1 activity and can suppress the expression of a wide variety of genes through inhibiting AP-1 activity thereof, with lessened side reactions.

DISCLOSURE OF THE INVENTION

The present inventors have conducted extensive studies with the aim of developing an agent for treating and/or preventing autoimmune diseases which inhibits AP-1 activity and can suppress the expression of a wide variety of genes through inhibiting AP-1 activity thereof, with lessened side reactions. As a result, it has been found-that spiro compounds having a spiro ring skeleton represented by the following general formula [1]:

[1]

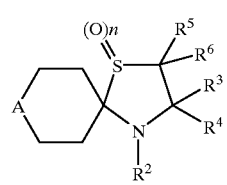

wherein A is a group of the following general formula:

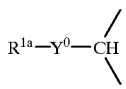

wherein $R^{1a}$ represents hydrogen atom, halogen atom, cyano group, nitro group, an unprotected or protected carboxyl group, an unprotected or protected hydroxyl group, or an unsubstituted or substituted alkyl, alkenyl, cycloalkyl, aryl, aralkyl, alkoxy, aryloxy, acyl, alkoxycarbonyl, aryloxycarbonyl, carbamoyl, amino or heterocyclic group; and $Y^0$ represents oxygen atom, sulfur atom, an unsubstituted or substituted imino group, carbonyl group, methylene group, vinylene group, sulfinyl group, sulfonyl group or group —CH(OH)—; or a group of the following general formula:

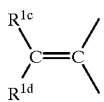

wherein $R^{1c}$ and $R^{1d}$, same or different, each represents hydrogen atom, halogen atom, cyano group, nitro group, an unprotected or protected carboxyl group, an unprotected or protected hydroxyl group, mercapto group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group;

or a group of the following general formula:

wherein $R^{1e}$ and $R^{1f}$, same or different, each represents halogen atom, cyano group, nitro group, an unprotected or protected carboxyl group, an unprotected or protected hydroxyl group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group; or a group of the following general formula:

wherein $R^{1g}$ represents an unsubstituted or substituted heterocyclic group;

$R^2$ represents hydrogen atom or an unsubstituted or substituted alkyl, alkenyl, cycloalkyl, acyl, aryl, aralkyl, alkylsulfonyl, arylsulfonyl or heterocyclic group; $R^3$ and $R^4$, same or different, each represents hydrogen atom, halogen atom, cyano group, an unprotected or protected carboxyl group, an unprotected or protected hydroxyl group, or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group or $R^3$ and $R^4$, taken conjointly, represent an oxo group; $R^5$ and $R^6$, same or different, each represents hydrogen atom, halogen atom, cyano group, an unprotected or protected carboxyl group, an unprotected or protected hydroxyl group, or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group or $R^5$ and $R^6$, taken conjointly with the terminal carbon atom to which $R^5$ and $R^6$ are combined, represent an alkenyl group; and n represents 0, 1 or 2;

spiro compounds represented by the general formula [1] wherein A is a group represented by the following general formula:

wherein $R^{1h}$ represents a group of the following general formula:

wherein $R^{11}$ represents hydrogen atom, halogen atom, cyano group, an unprotected or protected carboxyl, hydroxyl or mercapto group or an unsubstituted or substituted alkyl, alkenyl, cycloalkyl, aryl, alkoxy, alkylthio, alkylsulfonyl, arylsulfonyl, sulfamoyl, acyl, acyloxy, alkoxycarbonyl, aryloxycarbonyl, amino, carbamoyl, carbamoyloxy or heterocyclic group; and $Y^2$ represents methylene group, an unsubstituted or substituted imino group, carbonyl group or sulfonyl group; or a group of the following general formula:

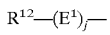

wherein $E^1$ represents amino acid residue; $R^{12}$ represents hydrogen atom or a protecting group for amino group; and j represents 2 or 3;

$R^2$ represents hydrogen atom, an unsubstituted or substituted alkyl, alkenyl, cycloalkyl, acyl, aryl, arylsulfonyl, alkylsulfonyl, aralkyl or heterocyclic group;

$R^3$ and $R^4$, taken conjointly, represent an oxo group; $R^5$ represents hydrogen atom; $R^6$ represents a group of the following general formula:

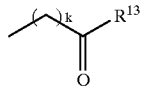

wherein $R^{13}$ represents hydrogen atom, halogen atom, an unprotected or protected hydroxyl, hydroxyamino, amino, alkylamino, arylamino, acylamino, alkoxycarbonylamino, arylsulfonylamino or alkylsulfonylamino group, an unsubstituted or substituted alkyl, aryloxy, aralkyloxy, alkylthio, alkoxy, aryl or heterocyclic group, or a group of the following general formula:

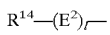

wherein $E^2$ represents amino acid residue; $R^{14}$ represents hydroxyl group or amino group; and l represents 1, 2 or 3; k represents 1, 2 or 3; and n represents 0, 1 or 2;

spiro compounds represented by general formula [1] wherein A represents a group of the following general formula:

wherein $R^{1h}$ represents a group of the following general formula:

wherein $R^{15}$ represents hydrogen atom, halogen atom, cyano group, an unprotected or protected carboxyl, hydroxyl or mercapto group, or an unsubstituted or substituted alkyl, alkenyl, cycloalkyl, aryl, alkoxy, alkylthio, alkylsulfonyl, arylsulfonyl, sulfamoyl, acyl, acyloxy, alkoxycarbonyl, aryloxycarbonyl, amino, carbamoyl, carbamoyloxy or heterocyclic group; and $Y^3$ represents methylene group, an unsubstituted or substituted imino group, carbonyl group or sulfonyl group; or a group of the following general formula:

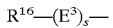

wherein $E^3$ represents amino acid residue; $R^{16}$ represents hydrogen atom or a protecting group for amino group; and s represents 2 or 3;

$R^2$ represents hydrogen atom, an unsubstituted or substituted alkyl, alkenyl, cycloalkyl, acyl, aryl, arylsulfonyl, alkylsulfonyl, aralkyl or heterocyclic group; $R^3$ and $R^4$, same or different, each represents hydrogen atom, halogen atom, cyano group, an unprotected or protected hydroxyl group or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group; or a group of the following general formula:

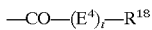

wherein $E^4$ represents amino acid residue; $R^{18}$ represents hydroxyl group or amino group; and t represents 1, 2 or 3; $R^5$ and $R^6$, same or different, each represents hydrogen atom, halogen atom, cyano group, an unprotected or protected carboxyl group, an unprotected or protected hydroxyl group, an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group; and n represents 0, 1 or 2; and salts of the above-mentioned spiro compounds inhibit the activity of transcription factor AP-1 and are useful as an agent for preventing and/or treating autoimmune diseases. Based on this finding, the present invention has been accomplished.

The compounds of the present invention inhibit the activity of transcription factor AP-1. That is to say, the compound of the present invention inhibits the transcription of DNAs having a TRE alignment in the promoter region thereof. Thereby, it is possible to inhibit the production of proteins corresponding to the gene in genes having TRE sequence. Accordingly, the compounds of the present invention can suppress the expression of genes of cytokines group such as IL-1β, IL-2, IL-3, IL-8, TNFα, granulocyte-macrophage colony stimulating factor (GM-CSF), monocyte chemoattractant protein 1 (MCP-1), etc., MMPs such as collagenase (MMP-1), stromelycin (MMP-3), collagenase IV (MMP-9), etc., cell surface molecules such as immunoglobulins, major histocompatibility complex (MHC) class II, vascular cell adhesion molecule 1 (VCAM-1), fibroblast growth factor (FGF) receptor, etc., growth factors such as monocyte growth factor, insulin-related growth factor (IGF), nerve growth factor (NGF), etc., and metallothionein, collagen, osteocarcin, osteopontin, amyloid precursor protein, apolipoprotein-1, etc. Accordingly, the compounds of the present invention can prevent and/or treat the diseases is related to these genes.

As the diseases is related these genes, for example, collagen diseases (rheumatoid arthritis, systemiclupus erythematosus, general scleroderma, rheumatic fever, multiple myositis, periarteritis nodosa, Sjögren's syndrome and Behçet's syndrome), idiopathic ulcerative colitis, glomerulonephritis, various autoimmune diseases such as autoimmune hemolytic anemia and the like, active chronic hepatitis, osteoarthritis, gout, atherosclerosis, psoriasis, atopic dermatitis, lungal diseases accompanied by granuloma such as interstitial pneumonia, various meningitises, Alzheimer's disease, and other intractable chronic inflammatory diseases can be referred to.

Hereunder, the compounds of the present invention will be detailed.

Unless otherwise referred to, the term "halogen atom" used in this specification means fluorine atom, chlorine atom, bromine atom and iodine atom; the term "alkyl group" means a straight or branched chain $C_{1-12}$ alkyl group such as methyl, ethyl, n-propyl, isopropyl, n-butyl, sec-butyl, isobutyl, tert-butyl, pentyl, hexyl, heptyl, octyl and the like; the term "alkenyl group" means a straight or branched chain $C_{2-12}$ alkenyl group such as vinyl, allyl, propenyl, isopropenyl, butenyl, isobutenyl, pentenyl, hexenyl, heptenyl, octenyl and the like; the term "cycloalkyl group" means a $C_{3-6}$ cycloalkyl group such as cyclopropyl, cyclobutyl, cyclopentyl, cyclohexyl and the like; the term "aryl group" means a group such as phenyl, tolyl, naphthyl and the like; the term "alkoxy group" means a straight or branched chain $C_{1-12}$ alkoxy group such as methoxy, ethoxy, n-propoxy, isopropoxy, n-butoxy, isobutoxy, sec-butoxy, tert-butoxy, pentyloxy, hexyloxy, heptyloxy, octyloxy and the like; the term "alkoxyimino group" means a straight or branched chain $C_{1-12}$ alkoxyimino group such as methoxyimino, ethoxyimino and the like; the term "alkoxycarbonylamino group" means a straight or branched chain $C_{1-12}$ alkoxycarbonylamino group such as methoxycarbonylamino, ethoxycarbonylamino, n-propoxycarbonylamino, isopropoxycarbonylamino, n-butoxycarbonylamino, isobutoxycarbonylamino, sec-butoxycarbonylamino, tert-butoxycarbonylamino, pentyloxycarbonylamino, hexyloxycarbonylamino, heptyloxycarbonylamino, octyloxycarbonylamino and the like; the term "arylsulfonylamino group" means an aryl-$SO_2NH$— group such as phenylsulfonylamino, naphthylsulfonylamino and the like; the term "alkylsulfonylamino group" means a straight or branched chain $C_{1-12}$ alkylsulfonylamino group such as methylsulfonylamino, ethylsulfonylamino, n-propylsulfonylamino, isopropylsulfonylamino, n-butylsulfonylamino, isobutylsulfonylamino, sec-butylsulfonylamino, tert-butylsulfonylamino, pentylsulfonylamino, hexylsulfonylamino, heptyl-sulfonylamino, octylsulfonylamino and the like; the term "aryloxy group" means a group represented by aryl-O— such as phenoxy, tolyloxy, naphthoxy and the like; the term "aryloxycarbonyl group" means a group represented by aryl-O—CO— such as phenoxycarbonyl, naphthoxycarbonyl and the like; the term "arylamino group" means a group such as phenylamino, naphthylamino and the like; the term "alkylamino group" means a mono- or di-$C_{1-12}$ alkylamino group such as methylamino, ethylamino, propylamino, butylamino, pentylamino, hexylamino, heptylamino, octylamino, dimethylamino, diethylamino, methylethylamino, dipropylamino, dibutylamino, dipentylamino, dihexylamino, diheptylamino, dioctylamino and the like; the term "aralkyl group" means an ar-$C_{1-12}$-alkyl group such as benzyl, phenethyl, 4-methylbenzyl, naphthylmethyl and the like; the term "alkylidene group" means a $C_{1-12}$ alkylidene group such as methylene, ethylidene, propylidene, isopropylidene, butylidene, hexylidene, octylidene and the like; the term "aralkyloxy group" means an ar-$C_{1-12}$-alkyloxy group such as benzyloxy, phenethyloxy, 4-methylbenzyloxy, naphthylmethyloxy and the like; the term "aralkyloxycarbonyl group" means an ar-$C_{1-12}$-alkyloxycarbonyl group such as benzyloxycarbonyl, phenethyloxycarbonyl, 4-methylbenzyloxycarbonyl, naphthylmethyloxycarbonyl and the like; the term "aralkylcarbonyloxy group" means an ar-$C_{1-12}$-alkylcarbonyloxy group such as benzylcarbonyloxy, phenethylcarbonyloxy, 4-methylbenzylcarbonyloxy, naphthylmethylcarbonyloxy and the like; the term "aralkylcarbonyl group" means a group represented by aralkyl-CO— wherein aralkyl is as defined above; the term "acyl group" means acyl groups including $C_{2-12}$ alkanoyl groups such as formyl, acetyl, propionyl and the like, aralkylcarbonyl groups such as benzylcarbonyl and the like, aroyl groups such as benzoyl, naphthoyl and the like and heterocycle-carbonyl groups such as nicotinoyl, thenoyl, pyrrolidinocarbonyl, furoyl and the like; the term "acyloxy group" means a group represented by acyl-O— wherein acyl is as defined above; the term "acylamino group" means a $C_{1-6}$ acylamino group such as formylamino, acetylamino, propionylamino, butyrylamino and the like; the term "aralkyloxycarbonyl group" means an ar-$C_{1-12}$-alkyloxy-CO— group such as benzyloxycarbonyl, phenethyloxycarbonyl, 4-methylbenzyloxycarbonyl, naphthylmethyloxycarbonyl and the like; the term "cyclic amino group" means a cyclic amino group which may be any of saturated and unsaturated cyclic amino groups and may contain at least one heteroatom such as nitrogen atom, oxygen atom, sulfur atom or the like and a carbonyl carbon in the ring thereof and may be any of monocyclic, bicyclic and tricyclic amino groups, of which more specific examples include saturated or unsaturated, monocyclic, 3- to 7-membered cyclic amino groups containing one nitrogen atom such as aziridin-1-yl, azetidin-1-yl, pyrrolidin-1-yl, pyrrolin-1-yl, pyrrol-1-yl, dihydropyridin-1-yl, piperidino, dihydroazepin-1-yl, perhydroazepin-1-yl and the like; saturated or unsaturated, monocyclic, 3- to 7-membered cyclic amino groups containing two nitrogen atoms such as imidazol-1-yl, imidazolidin-1-yl, imidazolin-1-yl, pyrazolidin-1-yl, piperazin-1-yl, 1,4-dihydropyrazin-1-yl, 1,2-dihydropyrimidin-1-yl, perhydropyrazin-1-yl, homopiperazin-1-yl and the like; saturated or unsaturated, monocyclic, 3- to 7-membered cyclic amino groups containing three or more nitrogen atoms such as 1,2,4-triazol-1-yl, 1,2,3-triazol-1-yl, 1,2-dihydro-1,2,4-triazin-1-yl, perhydro-S-triazin-1-yl and the like; saturated or unsaturated, monocyclic, 3- to 7-membered cyclic amino groups containing 1 to 4 heteroatoms selected from the group consisting of oxygen atom and sulfur atom in addition to nitrogen atom such as oxazolidin-3-yl, isoxazolidin-2-yl, morpholino, 1,3-oxazolidin-3-yl, thiazolidin-1-yl, isothiazolidin-1-yl, thiomorpholino, homothiomorpholin-1-yl, 1,2,4-thiadiazolin-2-yl and the like; saturated or unsaturated, bicyclic or tricyclic cyclic amino groups such as isoindolin-2-yl, indolin-1-yl, 1H-indazol-1-yl, purin-7-yl, tetrahydroquinolin-1-yl and the like; and spiro or crosslinked, saturated or unsaturated, 5- to 12-membered cyclic amino groups such as 5-azaspiro[2,4]heptan-5-yl, 2,8-diazabicyclo[4.3.0]-nonan-8-yl, 3-azabicyclo[3.1.0]hexan-3-yl, 2-oxa-5,8-diazabicyclo[4.3.0]nonan-8-yl, 2,8-diazaspiro[4,4]-nonan-2-yl, 7-azabicyclo[2.2.1]heptan-7-yl and the like; the term "heterocyclic group" means a 4- to 7-membered or fused heterocyclic group containing at least one heteroatom selected from the group consisting of oxygen atom, nitrogen atom and sulfur atom such as azetidinyl, thienyl, furyl, pyrrolyl, imidazolyl, pyrazolyl, thiazolyl, isothiazolyl, oxazolyl, isoxazolyl, furazanyl, pyrrolidinyl, pyrrolinyl, imidazolidinyl, imidazolinyl, pyrazolidinyl, pyrazolinyl, 1,3,4-oxadiazolyl, 1,2,3-thiadiazolyl, 1,2,4-thiazidiazolyl, 1,3,4-thiadiazolyl, 1,2,3-triazolyl, 1,2,4-triazolyl, tetrazolyl, thiatriazolyl, pyridyl, pyrazinyl, pyrimidinyl, pyridazinyl, piperidinyl, piperazinyl, pyranyl, morpholinyl, 1,2,4-triazinyl, benzothienyl, naphthothienyl, benzofuryl, isobenzofuryl, chromenyl, indolidinyl, isoindolyl, indolyl, indazolyl, purinyl, quinolyl, isoquinolyl, phthalazinyl, naphthylidinyl, quinoxalinyl, quinazolinyl, cinnolinyl, pteridinyl, isochromanyl, chromanyl, indolinyl, isoindolinyl, benzoxazolyl, triazolopyridyl, tetrazolopyridazinyl, tetrazolopyrimidinyl, thiazolopyridazinyl, thiadiazolopyridazinyl, triazolopyridazinyl, benzimidazolyl, benzothiazolyl, 1,2,3, 4-tetrahydroquinolyl, imidazo[1,2-b][1,2,4]triazinyl, quinuclidinyl and the like; the term "alkanoyl group" means a $C_{2-12}$ alkanoyl group such as acetyl, propionyl and the like; the term "aroyl group" means an aroyl group such as benzoyl, naphthoyl and the like; the term "heterocycle-carbonyl group" means a group represented by heterocycle-CO— wherein heterocycle is as defined above); the term "alkylthio group" means a straight or branched chain $C_{1-12}$ alkylthio group such as methylthio, ethylthio, n-propylthio, isopropylthio, n-butylthio, isobutylthio, sec-butylthio, tert-butylthio, pentylthio, hexylthio, heptylthio, octylthio and the like; the term "alkylsulfinyl group" means a straight or branched chain $C_{1-12}$ alkylsulfinyl group such as methylsulfinyl, ethylsulfinyl, n-propylsulfinyl, isopropylsulfinyl, n-butylsulfinyl, isobutylsulfinyl, sec-butylsulfinyl, tert-butylsulfinyl, pentylsulfinyl, hexylsulfinyl, heptylsulfinyl, octylsulfinyl and the like; the term "alkylsulfonyl group" means a straight or branched chain $C_{1-12}$ alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, hexylsulfonyl, heptylsulfonyl, octylsulfonyl and the like; the term "arylsulfonyl group" means, for example, phenylsulfonyl group or naphthylsulfonyl group; the term "alkylsulfonyloxy group" means a straight or branched chain $C_{1-12}$ alkylsulfonyloxy group such as methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, pentylsulfonyloxy, hexylsulfonyloxy, heptylsulfonyloxy, octylsulfonyloxy and the like; the term "arylsulfonyloxy group" means a group such as phenylsulfonyloxy, naphthylsulfonyloxy and the like; the term "alkoxycarbonyl group" means a straight or branched chain $C_{1-12}$ alkyloxycarbonyl group such as methoxycarbonyl, ethoxycarbonyl, propoxycarbonyl and the like; and the term "alkoxycarbonyloxy group" means a straight or branched chain $C_{1-12}$ alkyloxycarbonyloxy group such as methoxycarbonyloxy, ethoxycarbonyloxy, propoxycarbonyloxy and the like.

As $R^{1a}$, $R^{1b}$, $R^{1c}$, $R^{1d}$, $R^{1e}$, $R^{1f}$, $R^{1g}$, $R^{1aa}$, $R^{1ba}$, $R^{1ca}$, $R^{1da}$, $R^{1ea}$, $R^{1fa}$, $R^{1la}$, $R^{aa}$, $R^{bb}$, $R^{cc}$, $R^{dd}$, $R^{ee}$, $R^{ff}$, $R^{aaa}$, $R^{bbb}$, $R^{ccc}$, $R^{ddd}$, $R^{eee}$, $R^{fff}$, $R^2$, $R^{2a}$, $R^3$, $R^4$, $R^5$, $R^6$, $R^{11}$, $R^{13}$, $R^{13a}$, $R^{13aa}$, $R^{15}$, $R^{15a}$, $Y$, $Y^0$, $Y^2$, $Y^3$ and the substituents used in the formulas of production processes, for example, halogen atom, cyano group, nitro group, sulfo group, mercapto group, an unprotected or protected carboxyl group, an unprotected or protected hydroxyl and hydroxyimino groups, an unprotected or protected amino group, an unprotected or protected imino group, an unsubstituted or substituted alkyl, alkoxy, alkoxycarbonyl, alkoxyimino, acyl, acyloxy, carbamoyl, carbamoyloxy, aralkylcarbonyloxy, aryl, aryloxycarbonyl, aralkyloxycarbonyl, cycloalkyl, alkenyl, aralkyl, alkylthio, alkylsulfonyl, alkylsulfonyloxy, alkylidene and heterocyclic groups, an unprotected or protected cyclic amino, aminosulfonyl, aminosulfinyl, alkoxycarbonylamino and alkylamino groups can be referred to. If desired, these groups may be substituted with at least one of these substituents. As the substituted alkyl group in $R^{1b}$, $R^{1ba}$, $R^{bb}$ and $R^{bbb}$, the same groups as above can be referred to, and they are substituted with at least one of these substituents.

The protecting groups for carboxyl group which can be used include all the groups conventionally usable as a protecting group for carboxyl group. As examples thereof, there can be referred to alkyl groups such as methyl, ethyl, n-propyl, iso-propyl, 1,1-dimethylpropyl, n-butyl, tert-butyl and the like; aryl groups such as phenyl, naphthyl and the like; aralkyl groups such as benzyl, diphenylmethyl, trityl, p-nitrobenzyl, p-methoxybenzyl, bis(p-methoxyphenyl) methyl and the like; acyl-alkyl groups such as acetylmethyl, benzoylmethyl, p-nitrobenzoylmethyl, p-bromobenzoylmethyl, p-methanesulfonylbenzoylmethyl and the like; oxygen-containing heterocyclic groups such as 2-tetrahydropyranyl, 2-tetrahydrofuranyl and the like; halogeno-alkyl groups such as 2,2,2-trichloroethyl and the like; alkylsilylalkyl groups such as 2-(trimethylsilyl)ethyl and the like; acyloxyalkyl groups such as acetoxymethyl, propionyloxymethyl, pivaloyloxymethyl and the like; nitrogen-containing heterocycle-alkyl groups such as phthalimidomethyl, succinimidomethyl and the like; cycloalkyl groups such as cyclohexyl and the like; alkoxyalkyl groups such as methoxymethyl, methoxyethoxymethyl, 2-(trimethylsilyl)ethoxymethyl and the like; ar-alkoxy-alkyl groups such as benzyloxymethyl and the like; alkylthio-alkyl groups such as methylthiomethyl, 2-methylthioethyl and the like; arylthio-alkyl groups such as phenylthiomethyl and the like; alkenyl groups such as 1,1-dimethyl-2-propenyl, 3-methyl-3-butenyl, allyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The protecting groups for amino group which can be used include all the groups conventionally usable as a protecting group for amino group. As examples thereof, there can be referred to acyl groups such as trichloroethoxycarbonyl, tribromoethoxycarbonyl, benzyloxycarbonyl, p-nitrobenzylcarbonyl, o-bromobenzyloxycarbonyl, (mono-, di-, tri-)chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxybenzyloxycarbonyl, 4-(phenylazo) benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl and the like; aralkyl groups such as benzyl, diphenylmethyl, trityl and the like; arylthio groups such as 2-nitrophenylthio, 2,4-dinitrophenylthio and the like; alkyl- and aryl-sulfonyl groups such as methanesulfonyl, paratoluenesulfonyl and the like; dialkylamino-alkylidene groups such as N,N-dimethylaminomethylene and the like; aralkylidene groups such as benzylidene, 2-hydroxybenzylidene, 2-hydroxy-5-chlorobenzylidene, 2-hydroxy-1-naphthylmethylene and the like; nitrogen-containing heterocyclic alkylidene groups such as 3-hydroxy-4-pyridylmethylene and the like; cycloalkylidene groups such as cyclohexylidene, 2-ethoxycarbonylcyclohexylidene, 2-ethoxycarbonylcyclopentylidene, 2-acetylcyclohexylidene, 3,3-dimethyl-5-oxycyclohexylidene and the like; diaryl- and diaralkylphosphoryl groups such as diphenylphosphoryl, dibenzylphosphoryl and the like; oxygen-containing heterocyclic alkyl groups such as 5-methyl-2-oxo-2H-1,3-dioxol-4-yl-methyl and the like; and substituted silyl groups such as trimethylsilyl and the like.

The protecting groups for hydroxyl group which can be used include all the groups conventionally usable as a protecting group for hydroxyl group. As examples thereof, there can be referred to acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)-ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenyloxyacetyl, pivaloyl, benzoyl and the like; alkyl groups such as methyl, tert-butyl, 2,2,2-trichloroethyl, 2-trimethylsilylethyl and the like; alkenyl groups such as allyl and the like; aralkyl groups such as benzyl, p-methoxybenzyl, 3,4-dimethoxybenzyl, diphenylmethyl, trityl and the like; oxygen-containing and sulfur-containing heterocyclic groups such as tetrahydrofuryl, tetrahydropyranyl, tetrahydrothiopyranyl and the like; alkoxy-alkyl groups such as methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl and the like; alkyl- and aryl-sulfonyl groups such as methanesulfonyl, paratoluenesulfonyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The term "amino acid residue" means an —NH(CHR)$_Z$ CO— part (R is an amino acid side chain, and Z is an integer of 1 to 6) which appears when an amino acid is introduced into a protein molecule or a peptide molecule while forming a peptide bonding with loss of a water molecule. Herein, the term "amino acid" means a compound having a carboxyl group and an amino group in one molecule such as glycine, alanine, valine, leucine, isoleucine, serine, threonine, asparagine, aspartic acid, glutamine, glutamic acid, lysine, alginine, histidine, methionine, thyrosine, phenylalanine, tryptophane, proline, cysteine, homocysteine, β-alanine, γ-aminobutyric acid, ornithine, 3,4-dihydroxyphenylalanine and the like.

As the salt of the compound of general formula [1], usually known salts formed at the site of basic group such as amino group and the like and at the site of acidic group such as hydroxyl or carboxyl group and the like can be referred to. As the salt formed at the site of a basic group, for example, salts of a mineral acid such as hydrochloric acid, hydrobromic acid, sulfuric acid and the like; salts of an organic acid such as tartaric acid, formic acid, citric acid, trichloroacetic acid, trifluoroacetic acid and the like; and salts of a sulfonic acid such as methanesulfonic acid, benzenesulfonic acid, paratoluenesulfonic acid, mesitylenesulfonic acid, naphthalenesulfonic acid and the like can be referred to. As the salts formed at the site of an acid group, for example, salts of alkali metals such as sodium, potassium and the like; salts of alkaline earth metals such as calcium, magnesium and the like; ammonium salts; and salts of nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine and the like can be referred to. Of the salts mentioned above, preferred salts of the compound of general formula [1] are pharmacologically acceptable ones.

Among the compounds of the present invention, preferred are the compounds in which A represents a group of the following general formula:

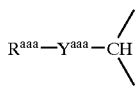

wherein $R^{aaa}$ represents hydrogen atom, an unprotected or protected carboxyl group, an unprotected or protected hydroxyl group or an unsubstituted or substituted alkyl, alkenyl, cycloalkyl, aryl, aralkyl, alkoxy, acyl, alkoxycarbonyl, amino or heterocyclic group; and $Y^{aaa}$ represents oxygen atom, sulfur atom, carbonyl group, vinylene group, sulfinyl group or sulfonyl group; a group of the following general formula:

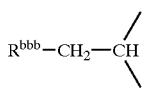

wherein $R^{bbb}$ represents an unprotected or protected carboxyl group, an unprotected or protected hydroxyl group, substituted alkyl group or an unsubstituted or substituted alkenyl, cycloalkyl, aryl, aralkyl, alkoxy, acyl, alkoxycarbonyl, amino or heterocyclic group; a group of the following general formula:

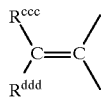

wherein $R^{ccc}$ and $R^{ddd}$, same or different, each represents hydrogen atom, an unprotected or protected carboxyl group or an unsubstituted or substituted alkyl, alkenyl, cycloalkyl, aryl, alkoxy, acyl, alkoxycarbonyl, amino or heterocyclic group; or a group of the following general formula:

wherein $R^{eee}$ and $R^{fff}$, same or different, each represents an unprotected or protected carboxyl group, an unprotected or protected hydroxyl group or an unsubstituted or substituted alkyl, alkenyl, cycloalkyl, aryl, alkoxy, acyl, alkoxycarbonyl, amino or heterocyclic group; $R^2$ represents hydrogen atom or an unsubstituted or substituted alkyl, alkenyl, acyl, aryl, aralkyl, alkylsulfonyl, arylsulfonyl or heterocyclic group; $R^3$ and $R^4$, same or different, each represents hydrogen atom, an unprotected or protected carboxyl group or an unsubstituted or substituted alkyl, acyl, alkoxycarbonyl, carbamoyl group or a group of the following general formula:

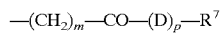

wherein D represents amino acid residue; $R^7$ represents hydroxyl group or amino group; p represents 1, 2 or 3; and m represents 0, 1, 2 or 3, or $R^3$ and $R^4$, taken conjointly, represent an oxo group; $R^5$ and $R^6$, same or different, each represents hydrogen atom, halogen atom, cyano group, an unprotected or protected carboxyl group, an unprotected or protected hydroxyl group, or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group, or $R^5$ and $R^6$, taken conjointly with the terminal carbon atom to which $R^5$ and $R^6$ are combined, represent an alkenyl group; and n represents 0, 1 or 2.

Also, preferred are the compounds in which A represents a group of the following general formula:

wherein $R^{1ha}$ represents a group of the following general formula:

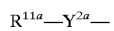

wherein $R^{11a}$ represents an unsubstituted or substituted alkyl, alkenyl, aryl, alkoxy or heterocyclic group; and $Y^{2a}$ represents methylene group, carbonyl group or sulfonyl group; or a group represented by the following general formula:

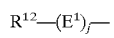

wherein $E^1$ represents amino acid residue; $R^{12}$ represents hydrogen atom or a protecting group for amino group; and j represents 2 or 3; $R^2$ represents hydrogen atom or an unsubstituted or substituted alkyl, alkenyl, aryl, aralkyl or heterocyclic group; $R^6$ represents a group of the following general formula:

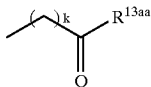

wherein $R^{13aa}$ represents an unprotected or protected hydroxyl, amino, alkylamino, acylamino, alkoxycarbonylamino, arylsulfonylamino or alkylsulfonylamino group or an unsubstituted or substituted alkyl or alkoxy group; and k represents 1, 2 or 3; or a group of the following general formula:

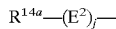

wherein $E^2$ represents amino acid residue; $R^{14a}$ represents hydroxyl group or amino group; and j represents 1, 2 or 3.

Also, preferred are the compounds in which A represents a group of the following general formula:

wherein $R^{1hb}$ represents a group of the following general formula:

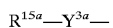

wherein $R^{15a}$ represents an unsubstituted or substituted alkyl, alkenyl, aryl or heterocyclic group; and $Y^{3a}$ represents carbonyl group or a group of the following general formula:

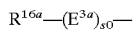

wherein $E^{3a}$ represents amino acid residue; $R^{16a}$ represents hydrogen atom or a protecting group for amino group; and s0 represents 2 or 3; $R^2$ represents hydrogen atom or an unsubstituted or substituted acyl group; $R^3$ represents hydrogen atom; $R^4$ represents carbamoyl group or a group of the following general formula:

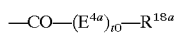

wherein $E^{4a}$ represents amino acid residue; $R^{18a}$ represents hydroxyl group or amino group; and t0 represents 1, 2 or 3; $R^5$ and $R^6$, same or different, each represents hydrogen atom, an unsubstituted or substituted alkyl group; and n represents 0.

Among the compounds of the present invention, further preferred are the compounds in which A represents a group of the following general formula:

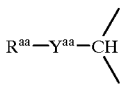

wherein $R^{aa}$ represents an unsubstituted or substituted alkyl, alkenyl, aryl or heterocyclic group; and $Y^{aa}$ represents oxygen atom or vinylene group; a group of the following general formula:

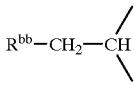

wherein $R^{bb}$ represents an unsubstituted or substituted alkyl group or an unsubstituted or substituted alkenyl, aryl or heterocyclic group; a group of the following general formula:

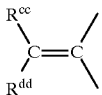

wherein $R^{cc}$ and $R^{dd}$, same or different, each represents hydrogen atom or an unsubstituted or substituted alkyl, alkenyl, aryl or heterocyclic group; or a group of the following general formula:

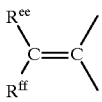

wherein $R^{ee}$ and $R^{ff}$, same or different, each represents an unprotected or protected hydroxyl group or an unsubstituted or substituted aryl group; $R^2$ represents hydrogen atom, formyl group, alkanoyl group, aralkylcarbonyl group or an unsubstituted or substituted alkyl, alkenyl, aroyl, heterocycle-carbonyl, aryl, aralkyl or heterocyclic group; $R^3$ and $R^4$, same or different, each represents hydrogen atom, an unsubstituted or substituted alkoxycarbonyl, carbamoyl group or a group of the following general formula:

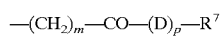

wherein D represents amino acid residue; $R^7$ represents hydroxyl group or amino group; p represents 1, 2 or 3; and m represents 0, 1, 2 or 3, or $R^3$ and $R^4$, taken conjointly, represent an oxo group; $R^5$ and $R^6$, same or different, each represents hydrogen atom or an unsubstituted or substituted alkyl group; and n represents 0 or 2.

Also, further preferred are the compounds in which A represents a group of the following general formula:

wherein $R^{1ha}$ represents a group of the following general formula:

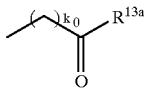

wherein $R^{11a}$ represents an unsubstituted or substituted alkyl, alkenyl, aryl or heterocyclic group; and $Y^{2a}$ represents methylene group, carbonyl group or sulfonyl group; $R^2$ represents hydrogen atom or an unsubstituted or substituted alkyl or aralkyl group; $R^6$ represents a group of the following general formula:

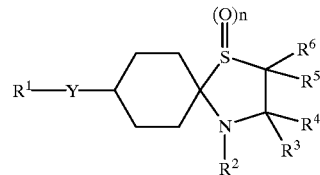

wherein $R^{13a}$ represents an unprotected or protected hydroxyl, amino, alkylamino, acylamino, alkoxycarbonylamino, arylsulfonylamino or alkylsulfonylamino group or an unsubstituted or substituted alkoxy group; and $k_0$ represents 1; and n represents 0.

As representative examples of the compound of the present invention, the compounds of the following Tables 1 to 51 can be referred to.

TABLE 1

| No. | n | $R^1$—Y— | $R^2$ | $R^3$ | $R^4$ | $R^5$ | $R^6$ |
|---|---|---|---|---|---|---|---|
| 1 | 0 | 4-$CH_3CH(CH_3)C_6H_4O$— | H | COOH | H | H | H |
| 2 | 0 | 4-$CH_3CH(CH_3)C_6H_4O$— | $CH_3$ | COOH | H | H | H |
| 3 | 0 | 4-$CH_3CH(CH_3)C_6H_4O$— | $CH_2CH_3$ | COOH | H | H | H |
| 4 | 0 | 4-$CH_3CH(CH_3)C_6H_4O$— | $CH_2CH_2CH_3$ | COOH | H | H | H |
| 5 | 0 | 4-$CH_3CH(CH_3)C_6H_4O$— | $CH_2CH_2CH_2CH_3$ | COOH | H | H | H |
| 6 | 0 | 4-$CH_3CH(CH_3)C_6H_4O$— | $CH_2CH_2CH_2CH_2CH_3$ | COOH | H | H | H |
| 7 | 0 | 4-$CH_3CH(CH_3)C_6H_4O$— | $CH(CH_3)CH_3$ | COOH | H | H | H |
| 8 | 0 | 4-$CH_3CH(CH_3)C_6H_4O$— | $CH_2CH(CH_3)CH_3$ | COOH | H | H | H |
| 9 | 0 | 4-$CH_3CH(CH_3)C_6H_4O$— | $CH_2CH_2CH(CH_3)CH_3$ | COOH | H | H | H |
| 10 | 0 | 4-$CH_3CH(CH_3)C_6H_4O$— | $CH_2CH_2CH_2CH(CH_3)CH_3$ | COOH | H | H | H |
| 11 | 0 | 4-$CH_3CH(CH_3)C_6H_4O$— | $CH_2CH(CH_3)C_2H_5$ | COOH | H | H | H |
| 12 | 0 | 4-$CH_3CH(CH_3)C_6H_4O$— | $CH_2CH_2CH(CH_3)C_2H_5$ | COOH | H | H | H |
| 13 | 0 | 4-$CH_3CH(CH_3)C_6H_4O$— | $CH_2CH_2CH(C_2H_5)C_2H_5$ | COOH | H | H | H |
| 14 | 0 | 4-$CH_3CH(CH_3)C_6H_4O$— | $CH_2F$ | COOH | H | H | H |
| 15 | 0 | 4-$CH_3CH(CH_3)C_6H_4O$— | $CH_2OH$ | COOH | H | H | H |

TABLE 2

| No. | n | $R^1$—Y— | $R^2$ | $R^3$ | $R^4$ | $R^5$ | $R^6$ |
|---|---|---|---|---|---|---|---|
| 16 | 0 | 4-$CH_3CH(CH_3)C_6H_4O$— | $CH_2CH_2OH$ | COOH | H | H | H |
| 17 | 0 | 4-$CH_3CH(CH_3)C_6H_4O$— | $CH_2CH_2CH_2OH$ | COOH | H | H | H |
| 18 | 0 | 4-$CH_3CH(CH_3)C_6H_4O$— | $CH_2CH_2CH_2CH_2OH$ | COOH | H | H | H |
| 19 | 0 | 4-$CH_3CH(CH_3)C_6H_4O$— | $CH_2CH_2CH_2CH_2CH_2OH$ | COOH | H | H | H |
| 20 | 0 | 4-$CH_3CH(CH_3)C_6H_4O$— | $CH(OH)CH_2OH$ | COOH | H | H | H |
| 21 | 0 | 4-$CH_3CH(CH_3)C_6H_4O$— | $CH_2CH(OH)CH_2OH$ | COOH | H | H | H |
| 22 | 0 | 4-$CH_3CH(CH_3)C_6H_4O$— | $CH_2CH(OH)CH_2CH_2OH$ | COOH | H | H | H |
| 23 | 0 | 4-$CH_3CH(CH_3)C_6H_4O$— | $CH_2CH_2CH(OH)CH_2CH_2OH$ | COOH | H | H | H |
| 24 | 0 | 4-$CH_3CH(CH_3)C_6H_4O$— | $CH_2OC(O)NH_2$ | COOH | H | H | H |
| 25 | 0 | 4-$CH_3CH(CH_3)C_6H_4O$— | $CH_2OC(O)CH_3$ | COOH | H | H | H |
| 26 | 0 | 4-$CH_3CH(CH_3)C_6H_4O$— | $CH_2COOH$ | COOH | H | H | H |
| 27 | 0 | 4-$CH_3CH(CH_3)C_6H_4O$— | $CH_2CH_2COOH$ | COOH | H | H | H |
| 28 | 0 | 4-$CH_3CH(CH_3)C_6H_4O$— | $CH_2CH_2CH_2COOH$ | COOH | H | H | H |
| 29 | 0 | 4-$CH_3CH(CH_3)C_6H_4O$— | $CH_2CH_2CH_2CH_2COOH$ | COOH | H | H | H |
| 30 | 0 | 4-$CH_3CH(CH_3)C_6H_4O$— | $CH_2CH_2CH_2CH_2CH_2COOH$ | COOH | H | H | H |
| 31 | 0 | 4-$CH_3CH(CH_3)C_6H_4O$— | $CH_2COOCH_3$ | COOH | H | H | H |
| 32 | 0 | 4-$CH_3CH(CH_3)C_6H_4O$— | $CH_2COOC_2H_5$ | COOH | H | H | H |
| 33 | 0 | 4-$CH_3CH(CH_3)C_6H_4O$— | $CH_2COO$-n-$C_3H_7$ | COOH | H | H | H |
| 34 | 0 | 4-$CH_3CH(CH_3)C_6H_4O$— | $CH_2COO$-i-$C_3H_7$ | COOH | H | H | H |
| 35 | 0 | 4-$CH_3CH(CH_3)C_6H_4O$— | $CH_2COOC_6H_5$ | COOH | H | H | H |

TABLE 3

| No. | n | R¹—Y— | R² | R³ | R⁴ | R⁵ | R⁶ |
|---|---|---|---|---|---|---|---|
| 36 | 0 | 4-CH$_3$CH(CH$_3$)C$_6$H$_4$O— | CH$_2$COOCH$_2$C$_6$H$_5$ | COOH | H | H | H |
| 37 | 0 | 4-CH$_3$CH(CH$_3$)C$_6$H$_4$O— | CH$_2$CONH$_2$ | COOH | H | R | H |
| 38 | 0 | 4-CH$_3$CH(CH$_3$)C$_6$H$_4$O— | CH$_2$CONHOH | COOH | H | H | H |
| 39 | 0 | 4-CH$_3$CH(CH$_3$)C$_6$H$_4$O— | CH$_2$CONHCH$_3$ | COOH | H | H | H |
| 40 | 0 | 4-CH$_3$CH(CH$_3$)C$_6$H$_4$O— | CH$_2$CONHC$_2$H$_5$ | COOH | H | H | H |
| 41 | 0 | 4-CH$_3$CH(CH$_3$)C$_6$H$_4$O— | CH$_2$CONH-n-C$_3$H$_7$ | COOH | H | H | H |
| 42 | 0 | 4-CH$_3$CH(CH$_3$)C$_6$H$_4$O— | CH$_2$CONH-i-C$_3$H$_7$ | COOH | H | H | H |
| 43 | 0 | 4-CH$_3$CH(CH$_3$)C$_6$H$_4$O— | CH$_2$CON(CH$_3$)$_2$ | COOH | H | H | H |
| 44 | 0 | 4-CH$_3$CH(CH$_3$)C$_6$H$_4$O— | CH$_2$CON(n-C$_3$H$_7$)$_2$ | COOH | H | H | H |
| 45 | 0 | 4-CH$_3$CH(CH$_3$)C$_6$H$_4$O— | CH$_2$CON(C$_2$H$_5$)$_3$ | COOH | H | H | H |
| 46 | 0 | 4-CH$_3$CH(CH$_3$)C$_6$H$_4$O— | CH$_2$CONHC$_6$H$_5$ | COOH | H | H | H |
| 47 | 0 | 4-CH$_3$CH(CH$_3$)C$_6$H$_4$O— | CH$_2$CH$_2$COOCH$_3$ | COOH | H | H | H |
| 48 | 0 | 4-CH$_3$CH(CH$_3$)C$_6$H$_4$O— | CH$_2$CH$_2$COOCH$_2$C$_6$H$_5$ | COOH | H | H | H |
| 49 | 0 | 4-CH$_3$CH(CH$_3$)C$_6$H$_4$O— | CH(CH$_3$)COOH | COOH | H | H | H |
| 50 | 0 | 4-CH$_3$CH(CH$_3$)C$_6$H$_4$O— | CH(CH$_2$OH)COOH | COOH | H | H | H |
| 51 | 0 | 4-CH$_3$CH(CH$_3$)C$_6$H$_4$O— | CH(CH$_2$COOH)COOH | COOH | H | H | H |
| 52 | 0 | 4-CH$_3$CH(CH$_3$)C$_6$H$_4$O— | CH(CH$_2$CONH$_2$)COOH | COOH | H | H | H |
| 53 | 0 | 4-CH$_3$CH(CH$_3$)C$_6$H$_4$O— | CH(CH$_2$CH$_2$COOH)COOH | COOH | H | H | H |
| 54 | 0 | 4-CH$_3$CH(CH$_3$)C$_6$H$_4$O— | CH(CH$_2$CH$_2$CONH$_2$)COOH | COOH | H | H | H |
| 55 | 0 | 4-CH$_3$CH(CH$_3$)C$_6$H$_4$O— | CH(4-Imidazolylmethyl)COOH | COOH | H | H | H |

TABLE 4

| No. | n | R¹—Y— | R² | R³ | R⁴ | R⁵ | R⁶ |
|---|---|---|---|---|---|---|---|
| 56 | 0 | 4-CH$_3$CH(CH$_3$)C$_6$H$_4$O— | CH(CH(C$_2$H$_5$)CH$_3$)COOH | COOH | H | H | H |
| 57 | 0 | 4-CH$_3$CH(CH$_3$)C$_6$H$_4$O— | CH(CH$_2$CH(CH$_3$)CH$_3$)COOH | COOH | H | H | H |
| 58 | 0 | 4-CH$_3$CH(CH$_3$)C$_6$H$_4$O— | CH(CH$_2$CH$_2$SCH$_3$)COOH | COOH | H | H | H |
| 59 | 0 | 4-CH$_3$CH(CH$_3$)C$_6$H$_4$O— | CH(CH(OH)CH$_3$)COOH | COOH | H | H | H |
| 60 | 0 | 4-CH$_3$CH(CH$_3$)C$_6$H$_4$O— | CH(CH$_2$-(4-HO)C$_6$H$_5$)COOH | COOH | H | H | H |
| 61 | 0 | 4-CH$_3$CH(CH$_3$)C$_6$H$_4$O— | CH(CH$_2$C$_6$H$_5$)COOH | COOH | H | H | H |
| 62 | 0 | 4-CH$_3$CH(CH$_3$)C$_6$H$_4$O— | CH(3-Indolylmethyl)COOH | COOH | H | H | H |
| 63 | 0 | 4-CH$_3$CH(CH$_3$)C$_6$H$_4$O— | CH(i-C$_3$H$_7$) COOH | COOH | H | H | H |
| 64 | 0 | 4-CH$_3$CH(CH$_3$)C$_6$H$_4$O— | CH$_2$CN | COOH | H | H | H |
| 65 | 0 | 4-CH$_3$CH(CH$_3$)C$_6$H$_4$O— | CH$_2$NO$_2$ | COOH | H | H | H |
| 66 | 0 | 4-CH$_3$CH(CH$_3$)C$_6$H$_4$O— | CH$_2$COCH$_3$ | COOH | H | H | H |
| 67 | 0 | 4-CH$_3$CH(CH$_3$)C$_6$H$_4$O— | CH$_2$C(NOH)CH$_3$ | COOH | H | H | H |
| 68 | 0 | 4-CH$_3$CH(CH$_3$)C$_6$H$_4$O— | CH$_2$SO$_3$H | COOH | H | H | H |
| 69 | 0 | 4-CH$_3$CH(CH$_3$)C$_6$H$_4$O— | CH$_2$S(O)$_2$CH$_3$ | COOH | H | H | H |
| 70 | 0 | 4-CH$_3$CH(CH$_3$)C$_6$H$_4$O— | CH$_2$S(O)CH$_3$ | COOH | H | H | H |
| 71 | 0 | 4-CH$_3$CH(CH$_3$)C$_6$H$_4$O— | CH$_2$SO$_2$NH$_2$ | COOH | H | H | H |
| 72 | 0 | 4-CH$_3$CH(CH$_3$)C$_6$H$_4$O— | CH$_2$SO$_3$CH$_3$ | COOH | H | H | H |
| 73 | 0 | 4-CH$_3$CH(CH$_3$)C$_6$H$_4$O— | CH$_2$OCH$_3$ | COOH | H | H | H |
| 74 | 0 | 4-CH$_3$CH(CH$_3$)C$_6$H$_4$O— | CH$_2$CH$_2$OCH$_3$ | COOH | H | H | H |
| 75 | 0 | 4-CH$_3$CH(CH$_3$)C$_6$H$_4$O— | CH$_2$CH$_2$CH$_2$OCH$_3$ | COOH | H | H | H |

TABLE 5

| No. | n | R¹—Y— | R² | R³ | R⁴ | R⁵ | R⁶ |
|---|---|---|---|---|---|---|---|
| 76 | 0 | 4-CH$_3$CH(CH$_3$)C$_6$H$_4$O— | CH$_2$SCH$_3$ | COOH | H | H | H |
| 77 | 0 | 4-CH$_3$CH(CH$_3$)C$_6$H$_4$O— | CHCH$_2$ | COOH | H | H | H |
| 78 | 0 | 4-CH$_3$CH(CH$_3$)C$_6$H$_4$O— | CH$_2$CHCH$_2$ | COOH | H | H | H |
| 79 | 0 | 4-CH$_3$CH(CH$_3$)C$_6$H$_4$O— | CHCHCH$_3$ | COOH | H | H | H |
| 80 | 0 | 4-CH$_3$CH(CH$_3$)C$_6$H$_4$O— | Cyclopropyl | COOH | H | H | H |
| 81 | 0 | 4-CH$_3$CH(CH$_3$)C$_6$H$_4$O— | Cyclobutyl | COOH | H | H | H |
| 82 | 0 | 4-CH$_3$CH(CH$_3$)C$_6$H$_4$O— | Cyclopentyl | COOH | H | H | H |
| 83 | 0 | 4-CH$_3$CH(CH$_3$)C$_6$H$_4$O— | Cyclohexyl | COOH | H | H | H |
| 84 | 0 | 4-CH$_3$CH(CH$_3$)C$_6$H$_4$O— | CH$_2$C$_6$H$_5$ | COOH | H | H | H |
| 85 | 0 | 4-CH$_3$CH(CH$_3$)C$_6$H$_4$O— | CH$_2$CH$_2$C$_6$H$_5$ | COOH | H | H | H |
| 86 | 0 | 4-CH$_3$CH(CH$_3$)C$_6$H$_4$O— | CH$_2$C$_6$H$_{11}$ | COOH | H | H | H |
| 87 | 0 | 4-CH$_3$CH(CH$_3$)C$_6$H$_4$O— | CH(CH$_3$)C$_6$H$_5$ | COOH | H | H | H |
| 88 | 0 | 4-CH$_3$CH(CH$_3$)C$_6$H$_4$O— | 2-Thienylmethyl | COOH | H | H | H |
| 89 | 0 | 4-CH$_3$CH(CH$_3$)C$_6$H$_4$O— | 2-Furfuryl | COOH | H | H | H |
| 90 | 0 | 4-CH$_3$CH(CH$_3$)C$_6$H$_4$O— | 2-Pyranylmethyl | COOH | H | H | H |
| 91 | 0 | 4-CH$_3$CH(CH$_3$)C$_6$H$_4$O— | 1-Isobenzofurylmethyl | COOH | H | H | H |
| 92 | 0 | 4-CH$_3$CH(CH$_3$)C$_6$H$_4$O— | 2-Pyrrolylmethyl | COOH | H | H | H |
| 93 | 0 | 4-CH$_3$CH(CH$_3$)C$_6$H$_4$O— | 1-Imidazolylmethyl | COOH | H | H | H |
| 94 | 0 | 4-CH$_3$CH(CH$_3$)C$_6$H$_4$O— | 1-Pyrazolylmethyl | COOH | H | H | H |
| 95 | 0 | 4-CH$_3$CH(CH$_3$)C$_6$H$_4$O— | 3-Isothiazolylmethyl | COOH | H | H | H |

TABLE 6

| No. | n | R$^1$—Y— | R$^2$ | R$^3$ | R$^4$ | R$^5$ | R$^6$ |
|---|---|---|---|---|---|---|---|
| 96 | 0 | 4-CH$_3$CH(CH$_3$)C$_6$H$_4$O— | 3-Isoxazolylmethyl | COOH | H | H | H |
| 97 | 0 | 4-CH$_3$CH(CH$_3$)C$_6$H$_4$O— | 2-Pyridylmethyl | COOH | H | H | H |
| 98 | 0 | 4-CH$_3$CH(CH$_3$)C$_6$H$_4$O— | 2-Pyrazinylmethyl | COOH | H | H | H |
| 99 | 0 | 4-CH$_3$CH(CH$_3$)C$_6$H$_4$O— | 2-Pyrimidinylmethyl | COOH | H | H | H |
| 100 | 0 | 4-CH$_3$CH(CH$_3$)C$_6$H$_4$O— | 3-Pyridazinylmethyl | COOH | H | H | H |
| 101 | 0 | 4-CH$_3$CH(CH$_3$)C$_6$H$_4$O— | 1-Isoindolylmethyl | COOH | H | H | H |
| 102 | 0 | 4-CH$_3$CH(CH$_3$)C$_6$H$_4$O— | 2-Indolylmethyl | COOH | H | H | H |
| 103 | 0 | 4-CH$_3$CH(CH$_3$)C$_6$H$_4$O— | 3-(1H—Indazolyl)methyl | COOH | H | H | H |
| 104 | 0 | 4-CH$_3$CH(CH$_3$)C$_6$H$_4$O— | 2-Purinylmethyl | COOH | H | H | H |
| 105 | 0 | 4-CH$_3$CH(CH$_3$)C$_6$H$_4$O— | 1-Isoquinolylmethyl | COOH | H | H | H |
| 106 | 0 | 4-CH$_3$CH(CH$_3$)C$_6$H$_4$O— | 2-Quinolylmethyl | COOH | H | H | H |
| 107 | 0 | 4-CH$_3$CH(CH$_3$)C$_6$H$_4$O— | 1-Phthalazinylmethyl | COOH | H | H | H |
| 108 | 0 | 4-CH$_3$CH(CH$_3$)C$_6$H$_4$O— | 2-Naphthylidinylmethyl | COOH | H | H | H |
| 109 | 0 | 4-CH$_3$CH(CH$_3$)C$_6$H$_4$O— | 2-Quinoxalinylmethyl | COOH | H | H | H |
| 110 | 0 | 4-CH$_3$CH(CH$_3$)C$_6$H$_4$O— | 2-Quinazolinylmethyl | COOH | H | H | H |
| 111 | 0 | 4-CH$_3$CH(CH$_3$)C$_6$H$_4$O— | 3-Cinnolinylmethyl | COOH | H | H | H |
| 112 | 0 | 4-CH$_3$CH(CH$_3$)C$_6$H$_4$O— | 2-Oxazolylmethyl | COOH | H | H | H |
| 113 | 0 | 4-CH$_3$CH(CH$_3$)C$_6$H$_4$O— | 2-Thiazolylmethyl | COOH | H | H | H |
| 114 | 0 | 4-CH$_3$CH(CH$_3$)C$_6$H$_4$O— | 2-Benzo[b]furylmethyl | COOH | H | H | H |
| 115 | 0 | 4-CH$_3$CH(CH$_3$)C$_6$H$_4$O— | 2-Benzo[b]thienylmethyl | COOH | H | H | H |

TABLE 7

| No. | n | R$^1$—Y— | R$^2$ | R$^3$ | R$^4$ | R$^5$ | R$^6$ |
|---|---|---|---|---|---|---|---|
| 116 | 0 | 4-CH$_3$CH(CH$_3$)C$_6$H$_4$O— | 3-(l,2,4-Triazinyl)methyl | COOH | H | H | H |
| 117 | 0 | 4-CH$_3$CH(CH$_3$)C$_6$H$_4$O— | 2-Benz[d]imidazolylmethyl | COOH | H | H | H |
| 118 | 0 | 4-CH$_3$CH(CH$_3$)C$_6$H$_4$O— | 2-Benz[d]oxazolylmethyl | COOH | H | H | H |
| 119 | 0 | 4-CH$_3$CH(CH$_3$)C$_6$H$_4$O— | Phenyl | COOH | H | H | H |
| 120 | 0 | 4-CH$_3$CH(CH$_3$)C$_6$H$_4$O— | 2-Thiazolyl | COOH | H | H | H |
| 121 | 0 | 4-CH$_3$CH(CH$_3$)C$_6$H$_4$O— | 4-Imidazolyl | COOH | H | H | H |
| 122 | 0 | 4-CH$_3$CH(CH$_3$)C$_6$H$_4$O— | 3-Pyrazolyl | COOH | H | H | H |
| 123 | 0 | 4-CH$_3$CH(CH$_3$)C$_6$H$_4$O— | 3-Isoxazolyl | COOH | H | H | H |
| 124 | 0 | 4-CH$_3$CH(CH$_3$)C$_6$H$_4$O— | 5-Isothiazolyl | COOH | H | H | H |
| 125 | 0 | 4-CH$_3$CH(CH$_3$)C$_6$H$_4$O— | 2-Pyrimidinyl | COOH | H | H | H |
| 126 | 0 | 4-CH$_3$CH(CH$_3$)C$_6$H$_4$O— | 3-(1,2,4-Triazolyl) | COOH | H | H | H |
| 127 | 0 | 4-CH$_3$CH(CH$_3$)C$_6$H$_4$O— | 2-Pyridyl | COOH | H | H | H |
| 128 | 0 | 4-CH$_3$CH(CH$_3$)C$_6$H$_4$O— | 2-Benzoxazolyl | COOH | H | H | H |
| 129 | 0 | 4-CH$_3$CH(CH$_3$)C$_6$H$_4$O— | 3-Benzothienyl | COOH | H | H | H |
| 130 | 0 | 4-CH$_3$CH(CH$_3$)C$_6$H$_4$O— | 2-Benzofuryl | COOH | H | H | H |
| 131 | 0 | 4-CH$_3$CH(CH$_3$)C$_6$H$_4$O— | 5-Indolyl | COOH | H | H | H |
| 132 | 0 | 4-CH$_3$CH(CH$_3$)C$_6$H$_4$O— | 2-Pyrazinyl | COOH | H | H | H |
| 133 | 0 | 4-CH$_3$CH(CH$_3$)C$_6$H$_4$O— | 3-Quinolinyl | COOH | H | H | H |
| 134 | 0 | 4-CH$_3$CH(CH$_3$)C$_6$H$_4$O— | 5-Tetrazolyl | COOH | H | H | H |
| 135 | 0 | 4-CH$_3$CH(CH$_3$)C$_6$H$_4$O— | Methylsulfonyl | COOH | H | H | H |

TABLE 8

| No. | n | R$^1$—Y— | R$^2$ | R$^3$ | R$^4$ | R$^5$ | R$^6$ |
|---|---|---|---|---|---|---|---|
| 136 | 0 | 4-CH$_3$CH(CH$_3$)C$_6$H$_4$O— | Benzenesulfonyl | COOH | H | H | H |
| 137 | 0 | 4-CH$_3$CH(CH$_3$)C$_6$H$_4$O— | COCH$_3$ | COOH | H | H | H |
| 138 | 0 | 4-CH$_3$CH(CH$_3$)C$_6$H$_4$O— | COCH$_2$CH$_3$ | COOH | H | H | H |
| 139 | 0 | 4-CH$_3$CH(CH$_3$)C$_6$H$_4$O— | COCH$_2$CH$_2$CH$_3$ | COOH | H | H | H |
| 140 | 0 | 4-CH$_3$CH(CH$_3$)C$_6$H$_4$O— | COCH$_2$CH$_2$CH$_2$CH$_3$ | COOH | H | H | H |
| 141 | 0 | 4-CH$_3$CH(CH$_3$)C$_6$H$_4$O— | COCH$_2$CH$_2$CH$_2$CH$_2$CH$_3$ | COOH | H | H | H |
| 142 | 0 | 4-CH$_3$CH(CH$_3$)C$_6$H$_4$O— | COCH(CH$_3$)CH$_3$ | COOH | H | H | H |
| 143 | 0 | 4-CH$_3$CH(CH$_3$)C$_6$H$_4$O— | COCH$_2$CH(CH$_3$)CH$_3$ | COOH | H | H | H |
| 144 | 0 | 4-CH$_3$CH(CH$_3$)C$_6$H$_4$O— | COCH$_2$C$_6$H$_5$ | COOH | H | H | H |
| 145 | 0 | 4-CH$_3$CH(CH$_3$)C$_6$H$_4$O— | 2-Thienylmethylcarbonyl | COOH | H | H | H |
| 146 | 0 | 4-CH$_3$CH(CH$_3$)C$_6$H$_4$O— | 2-Furylcarbonyl | COOH | H | H | H |
| 147 | 0 | 4-CH$_3$CH(CH$_3$)C$_6$H$_4$O— | 2-Pyridylmethylcarbonyl | COOH | H | H | H |
| 148 | 0 | 4-CH$_3$CH(CH$_3$)C$_6$H$_4$O— | 2-Quinolymethylcarbonyl | COOH | H | H | H |
| 149 | 0 | 4-CH$_3$CH(CH$_3$)C$_6$H$_4$O— | 2-Benzothienylmethylcarbonyl | COOH | H | H | H |
| 150 | 0 | 4-CH$_3$CH(CH$_3$)C$_6$H$_4$O— | 2-Naphthylidinylmethylcarboxyl | COOH | H | H | H |
| 151 | 0 | 4-CH$_3$CH(CH$_3$)C$_6$H$_4$O— | 2-thiazolylmethylcarbonyl | COOH | H | H | H |
| 152 | 0 | 4-CH$_3$CH(CH$_3$)C$_6$H$_4$O— | 2-Pyrimidinylmethylcarbonyl | COOH | H | H | H |
| 153 | 0 | 4-CH$_3$CH(CH$_3$)C$_6$H$_4$O— | 2-Benzoxazolylmethylcarbonyl | COOH | H | H | H |
| 154 | 0 | 4-CH$_3$CH(CH$_3$)C$_6$H$_4$O— | 2-Indolylmethylcarbonyl | COOH | H | H | H |
| 155 | 0 | 4-CH$_3$CH(CH$_3$)C$_6$H$_4$O— | 2-Thiazolylcarbonyl | COOH | H | H | H |

TABLE 9

| No. | n | R¹—Y— | R² | R³ | R⁴ | R⁵ | R⁶ |
|---|---|---|---|---|---|---|---|
| 156 | 0 | 4-CH₃CH(CH₃)C₆H₄O— | 2-Pyrimidinylcarbonyl | COOH | H | H | H |
| 157 | 0 | 4-CH₃CH(CH₃)C₆H₄O— | 2-Indolylcarbonyl | COOH | H | H | H |
| 158 | 0 | 4-CH₃CH(CH₃)C₆H₄O— | 2-Benzothienylcarbonyl | COOH | H | H | H |
| 159 | 0 | 4-CH₃CH(CH₃)C₆H₄O— | 5-Quinolylcarbonyl | COOH | H | H | H |
| 160 | 0 | 4-CH₃CH(CH₃)C₆H₄O— | CH₂CONHCH₂C₆H₅ | COOH | H | H | H |
| 161 | 0 | 4-FC₆H₄O— | COC₆H₅ | COOH | H | H | H |
| 162 | 0 | 2-CH₃C₆H₄O— | COC₆H₅ | COOH | H | H | H |
| 163 | 0 | 3-CH₃C₆H₄O— | COC₆H₅ | COOH | H | H | H |
| 164 | 0 | 4-CH₃C₆H₄O— | COC₆H₅ | COOH | H | H | H |
| 165 | 0 | 2,4-(CH₃)₂C₆H₃O— | COC₆H₅ | COOH | H | H | H |
| 166 | 0 | 3,4-(CH₃)₂C₆H₃O— | COC₆H₅ | COOH | H | H | H |
| 167 | 0 | 2,3-(CH₃)₂C₆H₃O— | COC₆H₅ | COOH | H | H | H |
| 168 | 0 | 3,5-(CH₃)₂C₆H₃O— | COC₆H₅ | COOH | H | H | H |
| 169 | 0 | 3,6-(CH₃)₂C₆H₃O— | COC₆H₅ | COOH | H | H | H |
| 170 | 0 | 2,6-(CH₃)₂C₆H₃O— | COC₆H₅ | COOH | H | H | H |
| 171 | 0 | 2,5-(CH₃)₂C₆H₃O— | COC₆H₅ | COOH | H | H | H |
| 172 | 0 | 2,4,6-(CH₃)₃C₆H₂O— | COC₆H₅ | COOH | H | H | H |
| 173 | 0 | 2,3,5-(CH₃)₃C₆H₂O— | COC₆H₅ | COOH | H | H | H |
| 174 | 0 | 2,4,5-(CH₃)₃C₆H₂O— | COC₆H₅ | COOH | H | H | H |
| 175 | 0 | 2,5,6-(CH₃)₃C₆H₂O— | COC₆H₅ | COOH | H | H | H |

TABLE 10

| No. | n | R¹—Y— | R² | R³ | R⁴ | R⁵ | R⁶ |
|---|---|---|---|---|---|---|---|
| 176 | 0 | 4-HOC₆H₄O— | COC₆H₅ | COOH | H | H | H |
| 177 | 0 | 4-CH₃OC₆H₄O— | COC₆H₅ | COOH | H | H | H |
| 178 | 0 | 4-C₂H₅OC₆H₄O— | COC₆H₅ | COOH | H | H | H |
| 179 | 0 | 4-CH₃CH(CH₃)OC₆H₄O— | COC₆H₅ | COOH | H | H | H |
| 180 | 0 | 4-C₆H₅OC₆H₄O— | COC₆H₅ | COOH | H | H | H |
| 181 | 0 | 4-C₆H₅CH₂OC₆H₄O— | COC₆H₅ | COOH | H | H | H |
| 182 | 0 | 4-HO₂CC₆H₄O— | COC₆H₅ | COOH | H | H | H |
| 183 | 0 | 4-CH₃COC₆H₄O— | COC₆H₅ | COOH | H | H | H |
| 184 | 0 | 4-CH₃OC(O)C₆H₄O— | COC₆H₅ | COOH | H | H | H |
| 185 | 0 | 4-H₂NC(O)C₆H₄O— | COC₆H₅ | COOH | H | H | H |
| 186 | 0 | 4-HONHC(O)C₆H₄O— | COC₆H₅ | COOH | H | H | H |
| 187 | 0 | 4-H₃CNHC(O)C₆H₄O— | COC₆H₅ | COOH | H | H | H |
| 188 | 0 | 4-(H₃C)₂NC(O)C₆H₄O— | COC₆H₅ | COOH | H | H | H |
| 189 | 0 | 4-O₂NC₆H₄O— | COC₆H₅ | COOH | H | H | H |
| 190 | 0 | 4-H₂NC₆H₄O— | COC₆H₅ | COOH | H | H | H |
| 191 | 0 | 4-H₃CNHC₆H₄O— | COC₆H₅ | COOH | H | H | H |
| 192 | 0 | 4-(H₃C)₂NC₆H₄O— | COC₆H₅ | COOH | H | H | H |
| 193 | 0 | 4-OHCC₆H₄O— | COC₆H₅ | COOH | H | H | H |
| 194 | 0 | 4-CH(NOH)C₆H₄O— | COC₆H₅ | COOH | H | H | H |
| 195 | 0 | 4-OHCNHC₆H₄O— | COC₆H₅ | COOH | H | H | H |

TABLE 11

| No. | n | R¹—Y— | R² | R³ | R⁴ | R⁵ | R⁶ |
|---|---|---|---|---|---|---|---|
| 196 | 0 | 4-CH₃C(O)NHC₆H₄O— | COC₆H₅ | COOH | H | H | H |
| 197 | 0 | 4-CH₃OC(O)NHC₆H₄O— | COC₆H₅ | COOH | H | H | H |
| 198 | 0 | 4-H₂NC(O)OC₆H₄O— | COC₆H₅ | COOH | H | H | H |
| 199 | 0 | 4-HSC₆H₄O— | COC₆H₅ | COOH | H | H | H |
| 200 | 0 | 4-H₃CSC₆H₄O— | COC₆H₅ | COOH | H | H | H |
| 201 | 0 | 4-H₃CS(O)C₆H₄O— | COC₆H₅ | COOH | H | H | H |
| 202 | 0 | 4-H₃CS(O)₂C₆H₄O— | COC₆H₅ | COOH | H | H | H |
| 203 | 0 | 3,4-(OCH₂O)C₆H₃O— | COC₆H₅ | COOH | H | H | H |
| 204 | 0 | 3,4-(CH₂CH₂CH₂)C₆H₃O— | COC₆H₅ | COOH | H | H | H |
| 205 | 0 | 4-HO₃SC₆H₄O— | COC₆H₅ | COOH | H | H | H |
| 206 | 0 | 4-NCC₆H₄O— | COC₆H₅ | COOH | H | H | H |
| 207 | 0 | 4-H₂NC(NH)C₆H₄O— | COC₆H₅ | COOH | H | H | H |
| 208 | 0 | 3-Isoxazoloxy | COC₆H₅ | COOH | H | H | H |
| 209 | 0 | 2-Imidazoloxy | COC₆H₅ | COOH | H | H | H |
| 210 | 0 | 2-Benzimidazoloxy | COC₆H₅ | COOH | H | H | H |
| 211 | 0 | 2-Thiazoloxy | COC₆H₅ | COOH | H | H | H |
| 212 | 0 | 5-Benzo[b]thienyloxy | COC₆H₅ | COOH | H | H | H |
| 213 | 0 | 2-Thiazolylamino | COC₆H₅ | COOH | H | H | H |
| 214 | 0 | 4-Imidazolylamino | COC₆H₅ | COOH | H | H | H |
| 215 | 0 | 3-Pyrazolylamino | COC₆H₅ | COOH | H | H | H |

TABLE 12

| No. | n | R¹—Y— | R² | R³ | R⁴ | R⁵ | R⁶ |
|---|---|---|---|---|---|---|---|
| 216 | 0 | 3-Isoxazolylamino | COC₆H₅ | COOH | H | H | H |
| 217 | 0 | 5-Isothiazolylamino | COC₆H₅ | COOH | H | H | H |
| 218 | 0 | 2-Pyrimidinylamino | COC₆H₅ | COOH | H | H | H |
| 219 | 0 | 3-(1,2,4-Triazolyl)amino | COC₆H₅ | COOH | H | H | H |
| 220 | 0 | 2-Pyridylamino | COC₆H₅ | COOH | H | H | H |
| 221 | 0 | 2-Benzoxazolylamino | COC₆H₅ | COOH | H | H | H |
| 222 | 0 | 3-Benzothienylamino | COC₆H₅ | COOH | H | H | H |
| 223 | 0 | 2-Benzofurylamino | COC₆H₅ | COOH | H | H | H |
| 224 | 0 | 5-Indolylamino | COC₆H₅ | COOH | H | H | H |
| 225 | 0 | 2-Pyrazinylamino | COC₆H₅ | COOH | H | H | H |
| 226 | 0 | 3-Quinolylamino | COC₆H₅ | COOH | H | H | H |
| 227 | 0 | 5-Tetrazolylamino | COC₆H₅ | COOH | H | H | H |
| 228 | 0 | 2-Imidazolylthioxy | COC₆H₅ | COOH | H | H | H |

TABLE 12-continued

| No. | n | R¹—Y— | R² | R³ | R⁴ | R⁵ | R⁶ |
|---|---|---|---|---|---|---|---|
| 229 | 0 | 2-Pyridylthioxy | $COC_6H_5$ | COOH | H | H | H |
| 230 | 0 | 2-Benzothiazolylthioxy | $COC_6H_5$ | COOH | H | H | H |
| 231 | 0 | 2-Benzothienylethenyl | $COC_6H_5$ | COOH | H | H | H |
| 232 | 0 | 2-Benzothienylmethyl | $COC_6H_5$ | COOH | H | H | H |
| 233 | 0 | $4-CH_3CH(CH_3)C_6H_4S(O)_2$— | $COC_6H_5$ | COOH | H | H | H |
| 234 | 0 | $4-CH_3CH(CH_3)C_6H_4S$— | $COC_6H_5$ | COOH | H | H | H |
| 235 | 0 | $4-CH_3CH(CH_3)C_6H_4NH$— | $COC_6H_5$ | COOH | H | H | H |

TABLE 13

| No. | n | R¹—Y— | R² | R³ | R⁴ | R⁵ | R⁶ |
|---|---|---|---|---|---|---|---|
| 236 | 0 | $4-CH_3CH(CH_3)C_6H_4CO$— | $COC_6H_5$ | COOH | H | H | H |
| 237 | 0 | $4-CH_3CH(CH_3)C_6H_4CH(OH)$— | $COC_6H_5$ | COOH | H | H | H |
| 238 | 0 | $4-CH_3CH(CH_3)C_6H_4CH_2OC(O)$— | $COC_6H_5$ | COOH | H | H | H |
| 239 | 0 | $4-CH_3CH(CH_3)C_6H_4NHC(O)$— | $COC_6H_5$ | COOH | H | H | H |
| 240 | 0 | $4-CH_3CH(CH_3)C_6H_4OC(O)NH$— | $COC_6H_5$ | COOH | H | H | H |
| 241 | 0 | $4-CH_3CH(CH_3)C_6H_4CH_2OC(O)NH$— | $COC_6H_5$ | COOH | H | H | H |
| 242 | 0 | $4-CH_3CH(CH_3)C_6H_4C(O)NH$— | $COC_6H_5$ | COOH | H | H | H |
| 243 | 0 | $4-CH_3CH(CH_3)C_6H_4CH_2C(O)NH$— | $COC_6H_5$ | COOH | H | H | H |
| 244 | 0 | $4-CH_3CH(CH_3)C_6H_4CH_2CO$— | $COC_6H_5$ | COOH | H | H | H |
| 245 | 0 | $4-CH_3CH(CH_3)C_6H_4CH_2OCH_2$— | $COC_6H_5$ | COOH | H | H | H |
| 246 | 0 | $4-CH_3CH(CH_3)C_6H_4C(NOH)$— | $COC_6H_5$ | COOH | H | H | H |
| 247 | 0 | $4-CH_3CH(CH_3)C_6H_4CHCH$— | $COC_6H_5$ | COOH | H | H | H |
| 248 | 0 | $4-CH_3CH(CH_3)C_6H_4CH_2$— | $COC_6H_5$ | COOH | H | H | H |
| 249 | 0 | $4-CH_3CH(CH_3)C_6H_4O$— | $COC_6H_5$ | $CH_2OH$ | H | H | H |
| 250 | 0 | $4-CH_3CH(CH_3)C_6H_4O$— | $COC_6H_5$ | CHFCOOH | H | H | H |
| 251 | 0 | $4-CH_3CH(CH_3)C_6H_4O$— | $COC_6H_5$ | COCOOH | H | H | H |
| 252 | 0 | $4-CH_3CH(CH_3)C_6H_4O$— | $COC_6H_5$ | C(NOH)COOH | H | H | H |
| 253 | 0 | $4-CH_3CH(CH_3)C_6H_4O$— | $COC_6H_5$ | $CH(CH_2OH)COOH$ | H | H | H |
| 254 | 0 | $4-CH_3CH(CH_3)C_6H_4O$— | $COC_6H_5$ | $CH(NH_2)COOH$ | H | H | H |
| 255 | 0 | $4-CH_3CH(CH_3)C_6H_4O$— | $COC_6H_5$ | CH(NHCHO)COOH | H | H | H |

TABLE 14

| No. | n | R¹—Y— | R² | R³ | R⁴ | R⁵ | R⁶ |
|---|---|---|---|---|---|---|---|
| 256 | 0 | $4-CH_3CH(CH_3)C_6H_4O$— | $COC_6H_5$ | $CF_2COOH$ | H | H | H |
| 257 | 0 | $4-CH_3CH(CH_3)C_6H_4O$— | $COC_6H_5$ | CH(OH)COOH | H | H | H |
| 258 | 0 | $4-CH_3CH(CH_3)C_6H_4O$— | $COC_6H_5$ | $CH(OCH_3)COOH$ | H | H | H |
| 259 | 0 | $4-CH_3CH(CH_3)C_6H_4O$— | $COC_6H_5$ | $CH(CH_3)COOH$ | H | H | H |
| 260 | 0 | $4-CH_3CH(CH_3)C_6H_4O$— | $COC_6H_5$ | $CH(C_6H_5)COOH$ | H | H | H |
| 261 | 0 | $4-CH_3CH(CH_3)C_6H_4O$— | $COC_6H_5$ | $C(CH_3)_2COOH$ | H | H | H |
| 262 | 0 | $4-CH_3CH(CH_3)C_6H_4O$— | $COC_6H_5$ | $C(C_2H_4)COOH$ | H | H | H |
| 263 | 0 | $4-CH_3CH(CH_3)C_6H_4O$— | $COC_6H_5$ | $C(C_3H_6)COOH$ | H | H | H |
| 264 | 0 | $4-CH_3CH(CH_3)C_6H_4O$— | $COC_6H_5$ | $C(C_4H_6)COOH$ | H | H | H |
| 265 | 0 | $4-CH_3CH(CH_3)C_6H_4O$— | $COC_6H_5$ | $C(C_5H_{10})COOH$ | H | H | H |
| 266 | 0 | $4-CH_3CH(CH_3)C_6H_4O$— | $COC_6H_5$ | CONHOH | H | H | H |
| 267 | 0 | $4-CH_3CH(CH_3)C_6H_4O$— | $COC_6H_5$ | $CON(CH_3)_2$ | H | H | H |
| 268 | 0 | $4-CH_3CH(CH_3)C_6H_4O$— | $COC_6H_5$ | $CONHC_6H_5$ | H | H | H |
| 269 | 0 | $4-CH_3CH(CH_3)C_6H_4O$— | $COC_6H_5$ | $COC_6H_5$ | H | H | H |
| 270 | 0 | $4-CH_3CH(CH_3)C_6H_4O$— | $COC_6H_5$ | $COCH_3$ | H | H | H |
| 271 | 0 | $4-CH_3CH(CH_3)C_6H_4O$— | $COC_6H_5$ | $CH_2COOH$ | H | H | H |
| 272 | 0 | $4-CH_3CH(CH_3)C_6H_4O$— | $COC_6H_5$ | $CH_2COOCH_3$ | H | H | H |
| 273 | 0 | $4-CH_3CH(CH_3)C_6H_4O$— | $COC_6H_5$ | $CH_2CH_2COOH$ | H | H | H |
| 274 | 0 | $4-CH_3CH(CH_3)C_6H_4O$— | $COC_6H_5$ | $CH_2CH(OH)COOH$ | H | H | H |
| 275 | 0 | $4-CH_3CH(CH_3)C_6H_4O$— | $COC_6H_5$ | $CH(OH)CH_2COOH$ | H | H | H |

TABLE 15

| No. | n | R¹—Y— | R² | R³ | R⁴ | R⁵ | R⁶ |
|---|---|---|---|---|---|---|---|
| 276 | 0 | $4-CH_3CH(CH_3)C_6H_4O$— | $COC_6H_5$ | $CH_2CF_2COOH$ | H | H | H |
| 277 | 0 | $4-CH_3CH(CH_3)C_6H_4O$— | $COC_6H_5$ | $CH_2CHFCOOH$ | H | H | H |
| 278 | 0 | $4-CH_3CH(CH_3)C_6H_4O$— | $COC_6H_5$ | $CH_2CH_2OH$ | H | H | H |
| 279 | 0 | $4-CH_3CH(CH_3)C_6H_4O$— | $COC_6H_5$ | $CH_2CH_2OCH_3$ | H | H | H |
| 280 | 0 | $4-CH_3CH(CH_3)C_6H_4O$— | $COC_6H_5$ | $CH_2CH_2OC_6H_5$ | H | H | H |
| 281 | 0 | $4-CH_3CH(CH_3)C_6H_4O$— | $COC_6H_5$ | $CH_2CH_2OCH_2C_6H_5$ | H | H | H |
| 282 | 0 | $4-CH_3CH(CH_3)C_6H_4O$— | $COC_6H_5$ | $CH_2CH_2F$ | H | H | H |
| 283 | 0 | $4-CH_3CH(CH_3)C_6H_4O$— | $COC_6H_5$ | $CH_2F$ | H | H | H |

TABLE 15-continued

| No. | n | R¹—Y— | R² | R³ | R⁴ | R⁵ | R⁶ |
|---|---|---|---|---|---|---|---|
| 284 | 0 | 4-CH₃CH(CH₃)C₆H₄O— | COC₆H₅ | CH₂NH₂ | H | H | H |
| 285 | 0 | 4-CH₃CH(CH₃)C₆H₄O— | COC₆H₅ | CH₂CH₂NH₂ | H | H | H |
| 286 | 0 | 4-CH₃CH(CH₃)C₆H₄O— | COC₆H₅ | CH₂CH₂NHCHO | H | H | H |
| 287 | 0 | 4-CH₃CH(CH₃)C₆H₄O— | COC₆H₅ | CH₂CH₂NHCOOCH₃ | H | H | H |
| 288 | 0 | 4-CH₃CH(CH₃)C₆H₄O— | COC₆H₅ | CH₂CH₂N(CH₃)₂ | H | H | H |
| 289 | 0 | 4-CH₃CH(CH₃)C₆H₄O— | COC₆H₅ | CH₂CH₂NHCH₃ | H | H | H |
| 290 | 0 | 4-CH₃CH(CH₃)C₆H₄O— | COC₆H₅ | CH₂SH | H | H | H |
| 291 | 0 | 4-CH₃CH(CH₃)C₆H₄O— | COC₆H₅ | CH₂CH₂SH | H | H | H |
| 292 | 0 | 4-CH₃CH(CH₃)C₆H₄O— | COC₆H₅ | CH₂SCH₃ | H | H | H |
| 293 | 0 | 4-CH₃CH(CH₃)C₆H₄O— | COC₆H₅ | CH₂S(O)₂CH₃ | H | H | H |
| 294 | 0 | 4-CH₃CH(CH₃)C₆H₄O— | COC₆H₅ | CH₂S(O)CH₃ | H | H | H |
| 295 | 0 | 4-CH₃CH(CH₃)C₆H₄O— | COC₆H₅ | CONHCH(CH₂COOH)COOH | H | H | H |

TABLE 16

| No. | n | R¹-Y- | R² | R³ | R⁴ | R⁵ | R⁶ |
|---|---|---|---|---|---|---|---|
| 296 | 0 | 4-CH₃CH(CH₃)C₆H₄O— | COC₆H₅ | CONHCH(CH₃)COOH | H | H | H |
| 297 | 0 | 4-CH₃CH(CH₃)C₆H₄O— | COC₆H₅ | CONHCH(CHCH₂(CH₃)COOH | H | H | H |
| 298 | 0 | 4-CH₃CH(CH₃)C₆H₄O— | COC₆H₅ | CONHCH(CH₂OH)COOH | H | H | H |
| 299 | 0 | 4-CH₃CH(CH₃)C₆H₄O— | COC₆H₅ | CONHCH(CH₂CH₂SCH₃)COOH | H | H | H |
| 300 | 0 | 4-CH₃CH(CH₃)C₆H₄O— | COC₆H₅ | CONHCH((CH₂)₄NH₂)COOH | H | H | H |
| 301 | 0 | 4-CH₃CH(CH₃)C₆H₄O— | COC₆H₅ | CONHCH(C₆H₅)COOH | H | H | H |
| 302 | 0 | 4-CH₃CH(CH₃)C₆H₄O— | COC₆H₅ | CONHCH(CH₂CONH₂)COOH | H | H | H |
| 303 | 0 | 4-CH₃CH(CH₃)C₆H₄O— | COC₆H₅ | CONH₂ | H | H | H |
| 304 | 0 | 4-CH₃CH(CH₃)C₆H₄O— | COC₆H₅ | CH₂CONH₂ | H | H | H |
| 305 | 0 | 4-CH₃CH(CH₃)C₆H₄O— | COC₆H₅ | CONHCH₂ | H | H | H |
| 306 | 0 | CH₃C(O)S— | COC₆H₅ | COOH | H | H | H |
| 307 | 0 | OHC— | COC₆H₅ | COOH | H | H | H |
| 308 | 0 | O₂NCHCH— | COC₆H₅ | COOH | H | H | H |
| 309 | 0 | CH₂CHCHCH— | COC₆H₅ | COOH | H | H | H |
| 310 | 0 | CH₃OCHCH— | COC₆H₅ | COOH | H | H | H |
| 311 | 0 | CH₃COCHCH— | COC₆H₅ | COOH | H | H | H |
| 312 | 0 | CH₂CH— | COC₆H₅ | COOH | H | H | H |
| 313 | 0 | ClCH₂CH₂— | COC₆H₅ | COOH | H | H | H |
| 314 | 0 | NCCH₂— | COC₆H₅ | COOH | H | H | H |
| 315 | 0 | O₂NCH₂— | COC₆H₅ | COOH | H | H | H |

TABLE 17

| No. | n | R¹—Y— | R² | R³ | R⁴ | R⁵ | R⁶ |
|---|---|---|---|---|---|---|---|
| 316 | 0 | CH₃OC(O)CH₂— | COC₆H₅ | COOH | H | H | H |
| 317 | 0 | HOC(O)CH₂— | COC₆H₅ | COOH | H | H | H |
| 318 | 0 | 4-CH₃CH(CH₃)C₆H₄O— | COCH₃ | COOH | H | CH₃ | CH₃ |
| 319 | 0 | 4-CH₃CH(CH₃)C₆H₄O— | COCH₂CH₃ | COOH | H | CH₃ | CH₃ |
| 320 | 0 | 4-CH₃CH(CH₃)C₆H₄O— | COCH₂CH₂CH₃ | COOH | H | CH₃ | CH₃ |
| 321 | 0 | 4-CH₃CH(CH₃)C₆H₄O— | COCH₂CH₂CH₂CH₃ | COOH | H | CH₃ | CH₃ |
| 322 | 0 | 4-CH₃CH(CH₃)C₆H₄O— | COCH₂CH₂CH₂CH₂CH₃ | COOH | H | CH₃ | CH₃ |
| 323 | 0 | 4-CH₃CH(CH₃)C₆H₄O— | COCH(CH₃)CH₃ | COOH | H | CH₃ | CH₃ |
| 324 | 0 | 4-CH₃CH(CH₃)C₆H₄O— | COCH₂CH(CH₃)CH₃ | COOH | H | CH₃ | CH₃ |
| 325 | 0 | 4-CH₃CH(CH₃)C₆H₄O— | COCH₂C₆H₅ | COOH | H | CH₃ | CH₃ |
| 326 | 0 | 4-CH₃CH(CH₃)C₆H₄O— | 2-Thienylmethylcarbonyl | COOH | H | CH₃ | CH₃ |
| 327 | 0 | 4-CH₃CH(CH₃)C₆H₄O— | 2-Furfurylcarbonyl | COOH | H | CH₃ | CH₃ |
| 328 | 0 | 4-CH₃CH(CH₃)C₆H₄O— | 2-Pyridylmethylcarbonyl | COOH | H | CH₃ | CH₃ |
| 329 | 0 | 4-CH₃CH(CH₃)C₆H₄O— | 2-Quinolylmethylcarbonyl | COOH | H | CH₃ | CH₃ |
| 330 | 0 | 4-CH₃CH(CH₃)C₆H₄O— | 2-Benzothienylmethylcarbonyl | COOH | H | CH₃ | CH₃ |
| 331 | 0 | 4-CH₃CH(CH₃)C₆H₄O— | 2-Naphthylidinylmethylcarbonyl | COOH | H | CH₃ | CH₃ |
| 332 | 0 | 4-CH₃CH(CH₃)C₆H₄O— | 2-Thiazolylmethylcarbonyl | COOH | H | CH₃ | CH₃ |
| 333 | 0 | 4-CH₃CH(CH₃)C₆H₄O— | 2-Pyrimidinylmethylcarbonyl | COOH | H | CH₃ | CH₃ |
| 334 | 0 | 4-CH₃CH(CH₃)C₆H₄O— | 2-Benzoxazolylmethylcarbonyl | COOH | H | CH₃ | CH₃ |
| 335 | 0 | 4-CH₃CH(CH₃)C₆H₄O— | 2-Indolylmethylcarbonyl | COOH | H | CH₃ | CH₃ |

TABLE 18

| No. | n | R¹—Y— | R² | R³ | R⁴ | R⁵ | R⁶ |
|---|---|---|---|---|---|---|---|
| 336 | 0 | 4-CH₃CH(CH₃)C₆H₄O— | 2-Thiazolylcarbonyl | COOH | H | CH₃ | CH₃ |
| 337 | 0 | 4-CH₃CH(CH₃)C₆H₄O— | 2-Pyrimidinylcarbonyl | COOH | H | CH₃ | CH₃ |
| 338 | 0 | 4-CH₃CH(CH₃)C₆H₄O— | 2-Indolylcarbonyl | COOH | H | CH₃ | CH₃ |
| 339 | 0 | 4-CH₃CH(CH₃)C₆H₄O— | 2-Benzothienylcarbonyl | COOH | H | CH₃ | CH₃ |
| 340 | 0 | 4-CH₃CH(CH₃)C₆H₄O— | 5-Quinolylcarbonyl | COOH | H | CH₃ | CH₃ |
| 341 | 0 | HO— | COC₆H₅ | COOH | H | H | H |
| 342 | 0 | O₂NO— | COC₆H₅ | COOH | H | H | H |
| 343 | 0 | H₂NC(O)O— | COC₆H₅ | COOH | H | H | H |
| 344 | 0 | HS— | COC₆H₅ | COOH | H | H | H |
| 345 | 0 | HOS— | COC₆H₅ | COOH | H | H | H |
| 346 | 0 | (HO₂)CH— | COC₆H₅ | COOH | H | H | H |
| 347 | 0 | CH₃O— | COC₆H₅ | COOH | H | H | H |
| 348 | 0 | CH₃S— | COC₆H₅ | COOH | H | H | H |
| 349 | 0 | CH₃NH— | COC₆H₅ | COOH | H | H | H |
| 350 | 0 | CH₃CO— | COC₆H₅ | COOH | H | H | H |
| 351 | 0 | 4-CH₃CH(CH₃)C₆H₄O— | COC₆H₅ | C(NOH)CH₃ | H | H | H |
| 352 | 0 | 4-CH₃CH(CH₃)C₆H₄O— | COC₆H₅ | CHO | H | H | H |
| 353 | 0 | 4-CH₃CH(CH₃)C₆H₄O— | COC₆H₅ | CH₂OC(O)NH₂ | H | H | H |
| 354 | 0 | 4-CH₃CH(CH₃)C₆H₄O— | COC₆H₅ | CH₂OC(O)CH₃ | H | H | H |
| 355 | 0 | 4-CH₃CH(CH₃)C₆H₄O— | COC₆H₅ | CH₂OC(O)C₆H₅ | H | H | H |

TABLE 19

| No. | n | R¹—Y— | R² | R³ | R⁴ | R⁵ | R⁶ |
|---|---|---|---|---|---|---|---|
| 356 | 1 | 4-CH₃CH(CH₃)C₆H₄O— | COC₆H₅ | CH₂COOH | H | H | H |
| 357 | 2 | 4-CH₃CH(CH₃)C₆H₄O— | COC₆H₅ | CH₂COOH | H | H | H |
| 358 | 0 | CH₃COCH₂— | COC₆H₅ | COOH | H | H | H |
| 359 | 0 | H₂NCH₂ | COC₆H₅ | COOH | H | H | H |
| 360 | 0 | HOCH₂— | COC₆H₅ | COOH | H | H | H |
| 361 | 0 | HONH— | COC₆H₅ | COOH | H | H | H |
| 362 | 0 | CH₃C(O)NCl— | COC₆H₅ | COOH | H | H | H |
| 363 | 0 | O₂NNH— | COC₆H₅ | COOH | H | H | H |
| 364 | 0 | CH₃ONH— | COC₆H₅ | COOH | H | H | H |
| 365 | 0 | H₂NNH— | COC₆H₅ | COOH | H | H | H |
| 366 | 0 | H₂N— | COC₆H₅ | COOH | H | H | H |
| 367 | 0 | ClCO— | COC₆H₅ | COOH | H | H | H |
| 368 | 0 | ClCHCH | COC₆H₅ | COOH | H | H | H |
| 369 | 0 | ClS(O)₂— | COC₆H₅ | COOH | H | H | H |
| 370 | 0 | HOS(O)₂— | COC₆H₅ | COOH | H | H | H |
| 371 | 0 | NCS(O)₂— | COC₆H₅ | COOH | H | H | H |
| 372 | 0 | CH₃OS(O)₂— | COC₆H₅ | COOH | H | H | H |
| 373 | 0 | H₂NS(O)₂— | COC₆H₅ | COOH | H | H | H |
| 374 | 0 | NCCO— | COC₆H₅ | COOH | H | H | H |
| 375 | 0 | NCCHCH— | COC₆H₅ | COOH | H | H | H |

TABLE 20

| No. | n | R¹—Y— | R² | R³ | R⁴ | R⁵ | R⁶ |
|---|---|---|---|---|---|---|---|
| 376 | 0 | NCS— | COC₆H₅ | COOH | H | H | H |
| 377 | 0 | OCN— | COC₆H₅ | COOH | H | H | H |
| 378 | 0 | HOC(O)CO— | COC₆H₅ | COOH | H | H | H |
| 379 | 0 | CH₃OC(O)NH— | COC₆H₅ | COOH | H | H | H |
| 380 | 0 | HOC(O)CHCH— | COC₆H₅ | COOH | H | H | H |
| 381 | 0 | HOC(O)CH(OH)— | COC₆H₅ | COOH | H | H | H |
| 382 | 0 | HOO— | COC₆H₅ | COOH | H | H | H |
| 383 | 0 | HOC(O)— | COC₆H₅ | COOH | H | H | R |
| 384 | 0 | CH₃C(O)OCHCH | COC₆H₅ | COOH | H | H | H |
| 385 | 0 | CH₃C(O)SCHCH | COC₆H₅ | COOH | H | H | H |
| 386 | 0 | CH₃OC(O)— | COC₆H₅ | COOH | H | H | H |
| 387 | 0 | CH₃OC(O)CHCH— | COC₆H₅ | COOH | H | H | H |
| 388 | 0 | CH₃C(O)NHCHCH— | COC₆H₅ | COOH | H | H | H |
| 389 | 0 | 4-CH₃CH(CH₃)C₆H₄O— | COC₆H₅ | COOH | H | C₆H₅ | C₆H₅ |
| 390 | 0 | 4-CH₃CH(CH₃)C₆H₄O— | COC₆H₅ | COOH | H | C₆H₅ | CH₃ |
| 391 | 0 | CH₃CHCH— | COC₆H₅ | COOH | H | H | H |

TABLE 20-continued

| No. | n | R¹—Y— | R² | R³ | R⁴ | R⁵ | R⁶ |
|---|---|---|---|---|---|---|---|
| 392 | 0 | C₆H₅S(O)— | COC₆H₅ | COOH | H | H | H |
| 393 | 0 | CH₃S(O)— | COC₆H₅ | COOH | H | H | H |
| 394 | 0 | CH₃S(O)₂— | COC₆H₅ | COOH | H | H | H |
| 395 | 0 | NCCH(OH)— | COC₆H₅ | COOH | H | H | H |

TABLE 21

| No. | n | R¹—Y— | R² | R³ | R⁴ | R⁵ | R⁶ |
|---|---|---|---|---|---|---|---|
| 396 | 0 | CH₃OC(O)CH(OH)— | COC₆H₅ | COOH | H | H | H |
| 397 | 0 | CH₃COCH(OH)— | COC₆H₅ | COOH | H | H | H |
| 398 | 0 | CH₃CH(OH)— | COC₆H₅ | COOH | H | H | H |
| 399 | 0 | CH₂CHO— | COC₆H₅ | COOH | H | H | H |
| 400 | 0 | CH₂CHS— | COC₆H₅ | COOH | H | H | H |
| 401 | 0 | CH₂CHNH— | COC₆H₅ | COOH | H | H | H |
| 402 | 0 | CH₂CHCO— | COC₆H₅ | COOH | H | H | H |
| 403 | 0 | CH₂CHCH₂— | COC₆H₅ | COOH | H | H | H |
| 404 | 0 | CH₂CHS(O)— | COC₆H₅ | COOH | H | H | H |
| 405 | 0 | CH₂CHS(O)₂— | COC₆H₅ | COOH | H | H | H |
| 406 | 0 | 2-Thiazolylsulfonyl | COC₆H₅ | COOH | H | H | H |
| 407 | 0 | CH₂CHCH(OH)— | COC₆H₅ | COOH | H | H | H |
| 408 | 0 | C₆H₁₁O— | COC₆H₅ | COOH | H | H | H |
| 409 | 0 | C₆H₁₁S— | COC₆H₅ | COOH | H | H | H |
| 410 | 0 | C₆H₁₁NH— | COC₆H₅ | COOH | H | H | H |
| 411 | 0 | C₆H₁₁CHCH— | COC₆H₅ | COOH | H | H | H |
| 412 | 0 | C₆H₁₁S(O)— | COC₆H₅ | COOH | H | H | H |
| 413 | 0 | C₆H₁₁S(O)₂— | COC₆H₅ | COOH | H | H | H |
| 414 | 0 | C₆H₁₁CH(OH)— | COC₆H₅ | COOH | H | H | H |
| 415 | 0 | CH₃C(O)O— | COC₆H₅ | COOH | H | H | H |

TABLE 22

| No. | n | R¹—Y— | R² | R³ | R⁴ | R⁵ | R⁶ |
|---|---|---|---|---|---|---|---|
| 416 | 0 | C₆H₅CH₂C(O)O— | COC₆H₅ | COOH | H | H | H |
| 417 | 0 | CH₃C(O)NH— | COC₆H₅ | COOH | H | H | H |
| 418 | 0 | H₂NC(O)— | COC₆H₅ | COOH | H | H | H |
| 419 | 0 | C₆H₅CH₂CH₂— | COC₆H₅ | COOH | H | H | H |
| 420 | 0 | 2-Pyridylethenyl | COC₆H₅ | COOH | H | H | H |
| 421 | 0 | C₆H₅CHCH— | COC₆H₅ | COOH | H | H | H |
| 422 | 0 | CH₃COCO— | COC₆H₅ | COOH | H | H | H |
| 423 | 0 | 4-CH₃CH(CH₃)C₆H₄O— | COC₆H₅ | COOH | H | H | Cl |
| 424 | 0 | Cyclohexanecarbonyl | COC₆H₅ | COOH | H | H | H |
| 425 | 0 | 2-Thienylcarbonyl | COC₆H₅ | COOH | H | H | H |
| 426 | 0 | 4-CH₃CH(CH₃)C₆H₄O— | COC₆H₅ | COOH | CH₃ | CH₃ | CH₃ |
| 427 | 0 | 4-CH₃CH(CH₃)C₆H₄O— | COC₆H₅ | COOH | CH₂COOH | CH₃ | CH₃ |
| 428 | 0 | 4-CH₃CH(CH₃)C₆H₄O— | COC₆H₅ | COOH | CN | CH₃ | CH₃ |
| 429 | 0 | 4-CH₃CH(CH₃)C₆H₄O— | COC₆H₅ | COOH | CONH₂ | CH₃ | CH₃ |
| 430 | 0 | 4-CH₃CH(CH₃)C₆H₄O— | COC₆H₅ | COOH | F | CH₃ | CH₃ |
| 431 | 0 | 4-CH₃CH(CH₃)C₆H₄O— | COC₆H₅ | COOH | H | H | C₆H₅ |
| 432 | 0 | 4-CH₃CH(CH₃)C₆H₄O— | COC₆H₅ | COOH | Cl | H | H |
| 433 | 0 | 4-CH₃CH(CH₃)C₆H₄O— | COC₆H₅ | COOH | CN | H | H |
| 434 | 0 | 4-CH₃CH(CH₃)C₆H₄O— | COC₆H₅ | COOH | COOH | H | H |
| 435 | 0 | 4-CH₃CH(CH₃)C₆H₄O— | COC₆H₅ | COOH | COOCH₃ | H | H |

TABLE 23

| No. | n | R¹—Y— | R² | R³ | R⁴ | R⁵ | R⁶ |
|---|---|---|---|---|---|---|---|
| 436 | 0 | 4-CH₃CH(CH₃)C₆H₄O— | COC₆H₅ | COOH | CONH₂ | H | H |
| 437 | 0 | 4-CH₃CH(CH₃)C₆H₄O— | COC₆H₅ | COOH | CH₃ | H | H |
| 438 | 0 | 4-CH₃CH(CH₃)C₆H₄O— | COC₆H₅ | COOH | CHCH₂ | H | H |
| 439 | 0 | 4-CH₃CH(CH₃)C₆H₄O— | COC₆H₅ | COOH | C₆H₁₁ | H | H |
| 440 | 0 | 4-CH₃CH(CH₃)C₆H₄O— | COC₆H₅ | COOH | COCH₃ | H | H |
| 441 | 0 | 4-CH₃CH(CH₃)C₆H₄O— | COC₆H₅ | COOH | COC₆H₅ | H | H |
| 442 | 0 | 4-CH₃CH(CH₃)C₆H₄O— | COC₆H₅ | COOH | C₆H₅ | H | H |
| 443 | 0 | 4-CH₃CH(CH₃)C₆H₄O— | COC₆H₅ | COOH | 2-Pyridyl | H | H |

TABLE 24

| No. | n | $R^{1c}$ | $R^{1d}$ | $R^2$ | $R^3$ | $R^4$ | $R^5$ | $R^6$ |
|---|---|---|---|---|---|---|---|---|
| 444 | 0 | $CH_3S(O)_2$ | H | $COC_6H_5$ | COOH | H | H | H |
| 445 | 0 | $CH_3$ | H | $COC_6H_5$ | COOH | H | $CH_3$ | $CH_3$ |
| 446 | 0 | $C_2H_5$ | H | $COC_6H_5$ | COOH | H | $CH_3$ | $CH_3$ |
| 447 | 0 | $CH_2CH$ | H | $COC_6H_5$ | COOH | H | $CH_3$ | $CH_3$ |
| 448 | 0 | $CH_3CHCH$ | H | $COC_6H_5$ | COOH | H | $CH_3$ | $CH_3$ |
| 449 | 0 | $C_6H_5$ | H | $COC_6H_5$ | COOH | H | $CH_3$ | $CH_3$ |
| 450 | 0 | 2-Pyridyl | H | $COC_6H_5$ | COOH | H | $CH_3$ | $CH_3$ |
| 451 | 0 | $C_6H_5$ | H | $COC_6H_5$ | COOH | H | $CH_3$ | $CH_3$ |
| 452 | 0 | $C_6H_5CO$ | H | $COC_6H_5$ | COOH | H | $CH_3$ | $CH_3$ |
| 453 | 0 | H | H | $COC_6H_5$ | COOH | H | H | H |
| 454 | 0 | H | Cl | $COC_6H_5$ | COOH | H | H | H |
| 455 | 0 | H | NC | $COC_6H_5$ | COOH | H | H | H |
| 456 | 0 | H | HOC(O) | $COC_6H_5$ | COOH | H | H | H |
| 457 | 0 | H | $CH_3OC(O)$ | $COC_6H_5$ | COOH | H | H | H |
| 458 | 0 | H | $CH_3$ | $COC_6H_5$ | COOH | H | H | H |
| 459 | 0 | H | $CH_3O$ | $COC_6H_5$ | COOH | H | H | H |
| 460 | 0 | H | $C_6H_5CH_2$ | $COC_6H_5$ | COOH | H | H | H |

TABLE 25

| No. | n | $R^{1c}$ | $R^{1d}$ | $R^2$ | $R^3$ | $R^4$ | $R^5$ | $R^6$ |
|---|---|---|---|---|---|---|---|---|
| 461 | 0 | H | $CH_2CH$ | $COC_6H_5$ | COOH | H | H | H |
| 462 | 0 | H | $CH_3CHCH$ | $COC_6H_5$ | COOH | H | H | H |
| 463 | 0 | H | $C_6H_5$ | $COC_6H_5$ | COOH | H | H | H |
| 464 | 0 | H | 2-Pyridyl | $COC_6H_5$ | COOH | H | H | H |
| 465 | 0 | $CH_3$ | $CH_3$ | $COC_6H_5$ | COOH | H | H | H |
| 466 | 0 | $C_2H_5$ | $CH_3$ | $COC_6H_5$ | COOH | H | H | H |
| 467 | 0 | $CH_2CH$ | $CH_3$ | $COC_6H_5$ | COOH | H | H | H |
| 468 | 0 | $CH_3CHCH$ | $CH_3$ | $COC_6H_5$ | COOH | H | H | H |
| 469 | 0 | $C_6H_5$ | $CH_3$ | $COC_6H_5$ | COOH | H | H | H |
| 470 | 0 | 2-Pyridyl | $CH_3$ | $COC_6H_5$ | COOH | H | H | H |
| 471 | 0 | $CH_3$ | $CH_3$ | $CH_2C_6H_5$ | COOH | $CH_3$ | H | H |
| 472 | 0 | $CH_3$ | $CH_3$ | $CH_2C_6H_5$ | COOH | H | $CH_3$ | $CH_3$ |
| 473 | 0 | $CH_3$ | $CH_3$ | $CH_2C_6H_5$ | COOH | $CH_3$ | $CH_3$ | $CH_3$ |
| 474 | 0 | $CH_3$ | $CH_3$ | $C_6H_5$ | COOH | $CH_3$ | $CH_3$ | $CH_3$ |
| 475 | 0 | $CH_3$ | $CH_3$ | $S(O)_2C_6H_5$ | COOH | $CH_3$ | $CH_3$ | $CH_3$ |
| 476 | 0 | $CH_3$ | $CH_3$ | 2-Thiazolyl | COOH | $CH_3$ | $CH_3$ | $CH_3$ |
| 477 | 0 | $C_6H_5$ | $C_6H_5$ | $COC_6H_5$ | COOH | H | H | H |
| 478 | 0 | $C_6H_5CO$ | H | $COC_6H_5$ | COOH | H | H | H |
| 479 | 0 | $CH_3CO$ | H | $COC_6H_5$ | COOH | H | H | H |
| 480 | 0 | $CH_3NHC(O)$ | H | $COC_6H_5$ | COOH | H | H | H |
| 481 | 0 | $CH_3S$ | H | $COC_6H_5$ | COOH | H | H | H |
| 482 | 1 | $CH_2CH$ | H | $COC_6H_5$ | COOH | H | $CH_3$ | $CH_3$ |
| 483 | 1 | $CH_3CHCH$ | H | $COC_6H_5$ | COOH | H | $CH_3$ | $CH_3$ |
| 484 | 1 | $C_6H_5$ | H | $COC_6H_5$ | COOH | H | $CH_3$ | $CH_3$ |

TABLE 26

| No. | n | $R^{1c}$ | $R^{1d}$ | $R^2$ | $R^3$ | $R^4$ | $R^5$ | $R^6$ |
|---|---|---|---|---|---|---|---|---|
| 485 | 1 | 2-Pyridyl | H | $COC_6H_5$ | COOH | H | $CH_3$ | $CH_3$ |
| 486 | 1 | $C_6H_5$ | H | $COC_6H_5$ | COOH | H | $CH_3$ | $CH_3$ |
| 487 | 1 | $C_6H_5CO$ | H | $COC_6H_5$ | COOH | H | $CH_3$ | $CH_3$ |
| 488 | 1 | $CH_3CO$ | H | $COC_6H_5$ | COOH | H | $CH_3$ | $CH_3$ |
| 489 | 1 | $CH_3NHC(O)$ | H | $COC_6H_5$ | COOH | H | $CH_3$ | $CH_3$ |
| 490 | 1 | $CH_3S$ | H | $COC_6H_5$ | COOH | H | $CH_3$ | $CH_3$ |

TABLE 26-continued

| No. | n | $R^{1c}$ | $R^{1d}$ | $R^2$ | $R^3$ | $R^4$ | $R^5$ | $R^6$ |
|---|---|---|---|---|---|---|---|---|
| 491 | 0 | $CH_3CO$ | H | $COC_6H_5$ | COOH | H | $CH_3$ | $CH_3$ |
| 492 | 0 | $CH_3NHC(O)$ | H | $COC_6H_5$ | COOH | H | $CH_3$ | $CH_3$ |
| 493 | 0 | $CH_3S$ | H | $COC_6H_5$ | COOH | H | $CH_3$ | $CH_3$ |
| 494 | 0 | $CH_3S(O)_2$ | H | $COC_6H_5$ | COOH | H | $CH_3$ | $CH_3$ |
| 495 | 1 | H | H | $COC_6H_5$ | COOH | H | H | H |
| 496 | 1 | H | $CH_3$ | $COC_6H_5$ | COOH | H | H | H |
| 497 | 1 | H | $C_2H_5$ | $COC_6H_5$ | COOH | H | H | H |
| 498 | 1 | H | $CH_2CH$ | $COC_6H_5$ | COOH | H | H | H |
| 499 | 1 | H | $CH_3CHCH$ | $COC_6H_5$ | COOH | H | H | H |
| 500 | 1 | H | $C_6H_5$ | $COC_6H_5$ | COOH | H | H | H |
| 501 | 1 | H | 2-Pyridyl | $COC_6H_5$ | COOH | H | H | H |
| 502 | 1 | $CH_3$ | $CH_3$ | $COC_6H_5$ | COOH | H | H | H |
| 503 | 1 | $C_2H_5$ | $CH_3$ | $COC_6H_5$ | COOH | H | H | H |
| 504 | 1 | $CH_2CH$ | $CH_3$ | $COC_6H_5$ | COOH | H | H | H |
| 505 | 1 | $CH_3CHCH$ | $CH_3$ | $COC_6H_5$ | COOH | H | H | H |
| 506 | 1 | $C_6H_5$ | $CH_3$ | $COC_6H_5$ | COOH | H | H | H |
| 507 | 1 | 2-Pyridyl | $CH_3$ | $COC_6H_5$ | COOH | H | H | H |
| 508 | 1 | $CH_3$ | $CH_3$ | $CH_2C_6H_5$ | COOH | H | $CH_3$ | $CH_3$ |

TABLE 27

| No. | n | $R^{1c}$ | $R^{1d}$ | $R^2$ | $R^3$ | $R^4$ | $R^5$ | $R^6$ |
|---|---|---|---|---|---|---|---|---|
| 509 | 1 | $CH_3$ | $CH_3$ | $CH_2C_6H_5$ | COOH | $CH_3$ | H | H |
| 510 | 1 | $CH_3$ | $CH_3$ | $CH_2C_6H_5$ | COOH | $CH_3$ | $CH_3$ | $CH_3$ |
| 511 | 1 | $CH_3$ | $CH_3$ | $C_6H_5$ | COOH | $CH_3$ | $CH_3$ | $CH_3$ |
| 512 | 1 | $CH_3$ | $CH_3$ | $S(O)_2C_6H_5$ | COOH | $CH_3$ | $CH_3$ | $CH_3$ |
| 513 | 1 | $CH_3$ | $CH_3$ | 2-Thiazolyl | COOH | $CH_3$ | $CH_3$ | $CH_3$ |
| 514 | 1 | $C_6H_5$ | $C_6H_5$ | $COC_6H_5$ | COOH | H | H | H |
| 515 | 1 | $C_6H_5CO$ | H | $COC_6H_5$ | COOH | H | H | H |
| 516 | 1 | $CH_3CO$ | H | $COC_6H_5$ | COOH | H | H | H |
| 517 | 1 | $CH_3NHC(O)$ | H | $COC_6H_5$ | COOH | H | H | H |
| 518 | 1 | $CH_3S$ | H | $COC_6H_5$ | COOH | H | H | H |
| 519 | 1 | $CH_3S(O)_2$ | H | $COC_6H_5$ | COOH | H | H | H |
| 520 | 1 | $CH_3$ | H | $COC_6H_5$ | COOH | H | $CH_3$ | $CH_3$ |
| 521 | 1 | $C_2H_5$ | H | $COC_6H_5$ | COOH | H | $CH_3$ | $CH_3$ |
| 522 | 2 | $C_6H_5$ | H | $COC_6H_5$ | COOH | H | $CH_3$ | $CH_3$ |
| 523 | 2 | 2-Pyridyl | H | $COC_6H_5$ | COOH | H | $CH_3$ | $CH_3$ |
| 524 | 2 | $C_6H_5$ | H | $COC_6H_5$ | COOH | H | $CH_3$ | $CH_3$ |
| 525 | 2 | $C_6H_5CO$ | H | $COC_6H_5$ | COOH | H | $CH_3$ | $CH_3$ |
| 526 | 2 | $CH_3CO$ | H | $COC_6H_5$ | COOH | H | $CH_3$ | $CH_3$ |
| 527 | 2 | $CH_3NHC(O)$ | H | $COC_6H_5$ | COOH | H | $CH_3$ | $CH_3$ |
| 528 | 2 | $CH_3S$ | H | $COC_6H_5$ | COOH | H | $CH_3$ | $CH_3$ |
| 529 | 2 | $CH_3S(O)_2$ | H | $COC_6H_5$ | COOH | H | $CH_3$ | $CH_3$ |
| 530 | 1 | $CH_3$ | $CH_3$ | $COC_6H_5$ | $CH_2CH_2F$ | H | $CH_3$ | $CH_3$ |
| 531 | 1 | $CH_3S(O)_2$ | H | $COC_6H_5$ | COOH | H | $CH_3$ | $CH_3$ |

TABLE 28

| No. | n | $R^{1c}$ | $R^{1d}$ | $R^2$ | $R^3$ | $R^4$ | $R^5$ | $R^6$ |
|---|---|---|---|---|---|---|---|---|
| 532 | 2 | H | H | $COC_6H_5$ | COOH | H | H | H |
| 533 | 2 | H | $CH_3O$ | $COC_6H_5$ | COOH | H | H | H |
| 534 | 2 | H | $CH_3$ | $COC_6H_5$ | COOH | H | H | H |
| 535 | 2 | H | $C_2H_5$ | $COC_6H_5$ | COOH | H | H | H |
| 536 | 2 | H | $CH_2CH$ | $COC_6H_5$ | COOH | H | H | H |
| 537 | 2 | H | $CH_3CHCH$ | $COC_6H_5$ | COOH | H | H | H |
| 538 | 2 | H | $C_6H_5$ | $COC_6H_5$ | COOH | H | H | H |
| 539 | 2 | H | 2-Pyridyl | $COC_6H_5$ | COOH | H | H | H |
| 540 | 2 | $CH_3$ | $CH_3$ | $COC_6H_5$ | COOH | H | H | H |

TABLE 28-continued

| No. | n | R$^{1c}$ | R$^{1d}$ | R$^2$ | R$^3$ | R$^4$ | R$^5$ | R$^6$ |
|---|---|---|---|---|---|---|---|---|
| 541 | 2 | C$_2$H$_5$ | CH$_3$ | COC$_6$H$_5$ | COOH | H | H | H |
| 542 | 2 | CH$_2$CH | CH$_3$ | COC$_6$H$_5$ | COOH | H | H | H |
| 543 | 2 | CH$_3$CHCH | CH$_3$ | COC$_6$H$_5$ | COOH | H | H | H |
| 544 | 2 | C$_6$H$_5$ | CH$_3$ | COC$_6$H$_5$ | COOH | H | H | H |
| 545 | 2 | 2-Pyridyl | CH$_3$ | COC$_6$H$_5$ | COOH | H | H | H |
| 546 | 2 | CH$_3$ | CH$_3$ | CH$_2$C$_6$H$_5$ | COOH | H | CH$_3$ | CH$_3$ |
| 547 | 2 | CH$_3$ | CH$_3$ | CH$_2$C$_6$H$_5$ | COOH | CH$_3$ | H | H |
| 548 | 2 | CH$_3$ | CH$_3$ | CH$_2$C$_6$H$_5$ | COOH | CH$_3$ | CH$_3$ | CH$_3$ |
| 549 | 2 | CH$_3$ | CH$_3$ | C$_6$H$_5$ | COOH | CH$_3$ | CH$_3$ | CH$_3$ |
| 550 | 2 | CH$_3$ | CH$_3$ | S(O)$_2$C$_6$H$_5$ | COOH | CH$_3$ | CH$_3$ | CH$_3$ |
| 551 | 2 | CH$_3$ | CH$_3$ | 2-Thiazolyl | COOH | CH$_3$ | CH$_3$ | CH$_3$ |
| 552 | 2 | C$_6$H$_5$ | C$_6$H$_5$ | COC$_6$H$_5$ | COOH | H | H | H |
| 553 | 2 | C$_6$H$_5$CO | H | COC$_6$H$_5$ | COOH | H | H | H |
| 554 | 2 | CH$_3$CO | H | COC$_6$H$_5$ | COOH | H | H | H |
| 555 | 2 | CH$_3$NHC(O) | H | COC$_6$H$_5$ | COOH | H | H | H |

TABLE 29

| No. | n | R$^{1c}$ | R$^{1d}$ | R$^2$ | R$^3$ | R$^4$ | R$^5$ | R$^6$ |
|---|---|---|---|---|---|---|---|---|
| 556 | 2 | CH$_3$S | H | COC$_6$H$_5$ | COOH | H | H | H |
| 557 | 2 | CH$_3$S(O)$_2$ | H | COC$_6$H$_5$ | COOH | H | H | H |
| 558 | 2 | CH$_3$ | H | COC$_6$H$_5$ | COOH | H | CH$_3$ | CH$_3$ |
| 559 | 2 | C$_2$H$_5$ | H | COC$_6$H$_5$ | COOH | H | CH$_3$ | CH$_3$ |
| 560 | 2 | CH$_2$CH | H | COC$_6$H$_5$ | COOH | H | CH$_3$ | CH$_3$ |
| 561 | 2 | CH$_3$CHCH | H | COC$_6$H$_5$ | COOH | H | CH$_3$ | CH$_3$ |
| 562 | 1 | CH$_3$ | CH$_3$ | COC$_6$H$_5$ | COC$_6$H$_5$ | H | CH$_3$ | CH$_3$ |
| 563 | 1 | CH$_3$ | CH$_3$ | COC$_6$H$_5$ | COCH$_3$ | H | CH$_3$ | CH$_3$ |
| 564 | 1 | CH$_3$ | CH$_3$ | COC$_6$H$_5$ | C(NOH)CH$_3$ | H | CH$_3$ | CH$_3$ |
| 565 | 1 | CH$_3$ | CH$_3$ | COC$_6$H$_5$ | CHO | H | CH$_3$ | CH$_3$ |
| 566 | 1 | CH$_3$ | CH$_3$ | COC$_6$H$_5$ | CH$_2$OC(O)NH$_2$ | H | CH$_3$ | CH$_3$ |
| 567 | 1 | CH$_3$ | CH$_3$ | COC$_6$H$_5$ | CH$_2$OC(O)CH$_3$ | H | CH$_3$ | CH$_3$ |
| 568 | 1 | CH$_3$ | CH$_3$ | COC$_6$H$_5$ | CH$_2$OC(O)C$_6$H$_5$ | H | CH$_3$ | CH$_3$ |
| 569 | 1 | CH$_3$ | CH$_3$ | COC$_6$H$_5$ | CH$_2$COOH | H | CH$_3$ | CH$_3$ |
| 570 | 1 | CH$_3$ | CH$_3$ | COC$_6$H$_5$ | CH$_2$COOH | H | CH$_3$ | CH$_3$ |
| 571 | 1 | CH$_3$ | CH$_3$ | COC$_6$H$_5$ | CH$_2$CH$_2$OCH$_2$C$_6$H$_5$ | H | CH$_3$ | CH$_3$ |
| 572 | 1 | CH$_3$ | CH$_3$ | COC$_6$H$_5$ | CH$_2$F | H | CH$_3$ | CH$_3$ |
| 573 | 1 | CH$_3$ | CH$_3$ | COC$_6$H$_5$ | CH$_2$NH$_2$ | H | CH$_3$ | CH$_3$ |
| 574 | 1 | CH$_3$ | CH$_3$ | COC$_6$H$_5$ | CH$_2$CH$_2$NH$_2$ | H | CH$_3$ | CH$_3$ |
| 575 | 1 | CH$_3$ | CH$_3$ | COC$_6$H$_5$ | CH$_2$CH$_2$NHCHO | H | CH$_3$ | CH$_3$ |
| 576 | 1 | CH$_3$ | CH$_3$ | COC$_6$H$_5$ | CH$_2$CH$_2$NHCOOCH$_3$ | H | CH$_3$ | CH$_3$ |
| 577 | 1 | CH$_3$ | CH$_3$ | COC$_6$H$_5$ | CH$_2$CH$_2$N(CH$_3$)$_2$ | H | CH$_3$ | CH$_3$ |
| 578 | 1 | CH$_3$ | CH$_3$ | COC$_6$H$_5$ | CH$_2$CH$_2$NHCH$_3$ | H | CH$_3$ | CH$_3$ |
| 579 | 1 | CH$_3$ | CH$_3$ | COC$_6$H$_5$ | CH$_2$CH$_{2NHCH2}$C$_6$H$_5$ | H | CH$_3$ | CH$_3$ |

TABLE 30

| No. | n | R$^{1c}$ | R$^{1d}$ | R$^2$ | R$^3$ | R$^4$ | R$^5$ | R$^6$ |
|---|---|---|---|---|---|---|---|---|
| 580 | 1 | CH$_3$ | CH$_3$ | COC$_6$H$_5$ | CH$_2$SH | H | CH$_3$ | CH$_3$ |
| 581 | 1 | CH$_3$ | CH$_3$ | COC$_6$H$_5$ | CH$_2$CH$_2$SH | H | CH$_3$ | CH$_3$ |
| 582 | 1 | CH$_3$ | CH$_3$ | COC$_6$H$_5$ | CH$_2$SCH$_3$ | H | CH$_3$ | CH$_3$ |
| 583 | 1 | CH$_3$ | CH$_3$ | COC$_6$H$_5$ | CH$_2$S(O)$_2$CH$_3$ | H | CH$_3$ | CH$_3$ |
| 584 | 1 | CH$_3$ | CH$_3$ | COC$_6$R$_5$ | CH$_2$S(O)CH$_3$ | H | CH$_3$ | CH$_3$ |
| 585 | 1 | CH$_3$ | CH$_3$ | COC$_6$H$_5$ | CONHCH(CH$_2$COOH)COOH | H | CH$_3$ | CH$_3$ |
| 586 | 1 | CH$_3$ | CH$_3$ | COC$_6$H$_5$ | CONHCH(CH$_3$)COOH | H | CH$_3$ | CH$_3$ |
| 587 | 1 | CH$_3$ | CH$_3$ | COC$_6$H$_5$ | CONHCH(CHCH$_2$(CH$_3$)$_2$)COOH | H | CH$_3$ | CH$_3$ |
| 588 | 1 | CH$_3$ | CH$_3$ | COC$_6$R$_5$ | CONHCH(CH$_2$OH)COOH | H | CH$_3$ | CH$_3$ |
| 589 | 1 | CH$_3$ | CH$_3$ | COC$_6$H$_5$ | CONHCH(CH$_2$CH$_2$SCH$_3$)COOH | H | CH$_3$ | CH$_3$ |
| 590 | 1 | CH$_3$ | CH$_3$ | COC$_6$H$_5$ | CONHCH((CH$_2$)$_4$NH$_2$)COOH | H | CH$_3$ | CH$_3$ |
| 591 | 1 | CH$_3$ | CH$_3$ | COC$_6$H$_5$ | CONHCH(C$_6$H$_5$)COOH | H | CH$_3$ | CH$_3$ |
| 592 | 1 | CH$_3$ | CH$_3$ | COC$_6$H$_5$ | CONHCH(CH$_2$CONH$_2$)COOH | H | CH$_3$ | CH$_3$ |
| 593 | 1 | CH$_3$ | CH$_3$ | COC$_6$H$_5$ | CONH$_2$ | H | CH$_3$ | CH$_3$ |
| 594 | 1 | CH$_3$ | CH$_3$ | COC$_6$H$_5$ | CH$_2$CONH$_2$ | H | CH$_3$ | CH$_3$ |
| 595 | 1 | CH$_3$ | CH$_3$ | COC$_6$H$_5$ | CONHCH$_3$ | H | CH$_3$ | CH$_3$ |
| 596 | 1 | CH$_3$ | CH$_3$ | COC$_6$H$_5$ | CONHOH | H | CH$_3$ | CH$_3$ |

TABLE 30-continued

| No. | n | R$^{1c}$ | R$^{1d}$ | R$^2$ | R$^3$ | R$^4$ | R$^5$ | R$^6$ |
|---|---|---|---|---|---|---|---|---|
| 597 | 1 | CH$_3$ | CH$_3$ | COC$_6$H$_5$ | CON(CH$_3$)$_2$ | H | CH$_3$ | CH$_3$ |
| 598 | 1 | CH$_3$ | CH$_3$ | COC$_6$H$_5$ | CONHC$_6$H$_5$ | H | CH$_3$ | CH$_3$ |

TABLE 31

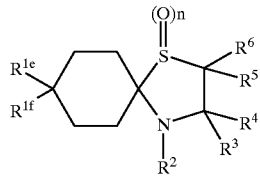

| No. | n | R$^{1e}$ | R$^{1f}$ | R$^2$ | R$^3$ | R$^4$ | R$^5$ | R$^6$ |
|---|---|---|---|---|---|---|---|---|
| 599 | 0 | CH$_3$O | C$_6$H$_5$ | COC$_6$H$_5$ | COOH | H | H | H |
| 600 | 0 | H$_2$N | C$_6$H$_5$ | COC$_6$H$_5$ | COOH | H | H | H |
| 601 | 0 | CH$_3$C(O)NH | C$_6$H$_5$ | COC$_6$H$_5$ | COOH | H | H | H |
| 602 | 0 | 2-Thienyl | C$_6$H$_5$ | COC$_6$H$_5$ | COOH | H | H | H |
| 603 | 0 | C$_6$H$_5$ | OH | CH$_2$C$_6$H$_5$ | COOH | H | H | H |
| 604 | 0 | C$_6$H$_5$ | OH | COCH$_2$C$_6$H$_5$ | COOH | H | H | H |
| 605 | 0 | C$_6$H$_5$ | OH | CH$_2$CH$_2$C$_6$H$_5$ | COOH | H | H | H |
| 606 | 0 | C$_6$H$_5$ | OH | C$_6$H$_5$ | COOH | H | H | H |
| 607 | 0 | C$_6$H$_5$ | OH | S(O)$_2$C$_6$H$_5$ | COOH | H | H | H |
| 608 | 0 | F | C$_6$H$_5$ | COC$_6$H$_5$ | COOH | H | H | H |
| 609 | 0 | Cl | C$_6$H$_5$ | COC$_6$H$_5$ | COOH | H | H | H |
| 610 | 0 | NC | C$_6$H$_5$ | COC$_6$H$_5$ | COOH | H | H | H |
| 611 | 0 | HOC(O) | C$_6$H$_5$ | COC$_6$H$_5$ | COOH | H | H | H |
| 612 | 0 | CH$_3$OC(O) | C$_6$H$_5$ | COC$_6$H$_5$ | COOH | H | H | H |
| 613 | 0 | (CH$_3$)$_2$NC(O) | C$_6$H$_5$ | COC$_6$H$_5$ | COOH | H | H | H |
| 614 | 0 | HO | C$_6$H$_5$ | COC$_6$H$_5$ | COOH | H | H | H |
| 615 | 0 | CH$_3$ | C$_6$H$_5$ | COC$_6$H$_5$ | COOH | H | H | H |

TABLE 32

| No. | n | R$^{1e}$ | R$^{1f}$ | R$^2$ | R$^3$ | R$^4$ | R$^5$ | R$^6$ |
|---|---|---|---|---|---|---|---|---|
| 616 | 0 | C$_2$H$_5$ | C$_6$H$_5$ | COC$_6$H$_5$ | COOH | H | H | H |
| 617 | 0 | CH$_2$CH | C$_6$H$_5$ | COC$_6$H$_5$ | COOH | H | H | H |
| 618 | 0 | C$_6$H$_{11}$ | C$_6$H$_5$ | COC$_6$H$_5$ | COOH | H | H | H |
| 619 | 0 | C$_5$H$_9$ | C$_6$H$_5$ | COC$_6$H$_5$ | COOH | H | H | H |
| 620 | 0 | C$_4$H$_7$ | C$_6$H$_5$ | COC$_6$H$_5$ | COOH | H | H | H |
| 621 | 0 | C$_6$H$_5$ | C$_6$H$_5$ | COC$_6$H$_5$ | COOH | H | H | H |
| 622 | 0 | C$_6$H$_5$ | OH | COC$_6$H$_5$ | CONHCH(C$_6$H$_5$)COOH | CH$_3$ | CH$_3$ | CH$_3$ |
| 623 | 0 | C$_6$H$_5$ | OH | COC$_6$H$_5$ | CONHCH(CH$_2$CONH$_2$)COOH | CH$_3$ | CH$_3$ | CH$_3$ |
| 624 | 1 | OH | C$_6$H$_5$ | COC$_6$H$_5$ | COOH | H | H | H |
| 625 | 1 | C$_6$H$_5$ | OH | COC$_6$H$_5$ | CONH$_2$ | CH$_3$ | H | H |
| 626 | 1 | C$_6$H$_5$ | OH | COC$_6$H$_5$ | COOH | H | CH$_3$ | CH$_3$ |
| 627 | 1 | C$_6$H$_5$ | OH | COC$_6$H$_5$ | CONH$_2$ | CH$_3$ | CH$_3$ | CH$_3$ |
| 628 | 2 | OH | C$_6$H$_5$ | COC$_6$H$_5$ | COOH | H | H | H |
| 629 | 2 | C$_6$H$_5$ | OH | COC$_6$H$_5$ | CONH$_2$ | CH$_3$ | H | H |
| 630 | 2 | C$_6$H$_5$ | OH | COC$_6$H$_5$ | COOH | H | CH$_3$ | CH$_3$ |
| 631 | 0 | C$_6$H$_5$ | OH | 2-Thiazolyl | COOH | H | H | H |
| 632 | 0 | C$_6$H$_5$ | OH | COC$_6$H$_5$ | COOH | CH$_3$ | H | H |
| 633 | 0 | C$_6$H$_5$ | OH | COC$_6$H$_5$ | COOH | H | CH$_3$ | CH$_3$ |
| 634 | 0 | C$_6$H$_5$ | OH | COC$_6$H$_5$ | COOH | CH$_3$ | CH$_3$ | CH$_3$ |
| 635 | 0 | C$_6$H$_5$ | OH | COC$_6$H$_5$ | COOH | CH$_3$ | CH$_3$ | CH$_3$ |
| 636 | 0 | C$_6$H$_5$ | OH | COC$_6$H$_5$ | CO(O)CH$_2$C$_6$H$_5$ | CH$_3$ | CH$_3$ | CH$_3$ |
| 637 | 0 | C$_6$H$_5$ | OH | COC$_6$H$_5$ | CO(O)C$_2$H$_5$ | CH$_3$ | CH$_3$ | CH$_3$ |

TABLE 33

| No. | n | R¹ᵉ | R¹ᶠ | R² | R³ | R⁴ | R⁵ | R⁶ |
|---|---|---|---|---|---|---|---|---|
| 638 | 0 | C₆H₅ | OH | COC₆H₅ | CONH₂ | CH₃ | CH₃ | CH₃ |
| 639 | 0 | C₆H₅ | OH | COC₆H₅ | CH₂CONH₂ | CH₃ | CH₃ | CH₃ |
| 640 | 0 | C₆H₅ | OH | COC₆H₅ | CONHCH₃ | CH₃ | CH₃ | CH₃ |
| 641 | 0 | C₆H₅ | OH | COC₆H₅ | CONHOH | CH₃ | CH₃ | CH₃ |
| 642 | 0 | C₆H₅ | OH | COC₆H₅ | CON(CH₃)₂ | CH₃ | CH₃ | CH₃ |
| 643 | 0 | C₆H₅ | OH | COC₆H₅ | CONHC₆H₅ | CH₃ | CH₃ | CH₃ |
| 644 | 0 | C₆H₅ | OH | COC₆H₅ | COC₆H₅ | CH₃ | CH₃ | CH₃ |
| 645 | 0 | C₆H₅ | OH | COC₆H₅ | COCH₃ | CH₃ | CH₃ | CH₃ |
| 646 | 0 | C₆H₅ | OH | COC₆H₅ | C(NOH)CH₃ | CH₃ | CH₃ | CH₃ |
| 647 | 0 | C₆H₅ | OH | COC₆H₅ | CHO | CH₃ | CH₃ | CR₃ |
| 648 | 0 | C₆H₅ | OH | COC₆H₅ | CH₂OC(O)NH₂ | CH₃ | CH₃ | CH₃ |
| 649 | 0 | C₆H₅ | OH | COC₆H₅ | CH₂OC(O)CH₃ | CH₃ | CH₃ | CH₃ |
| 650 | 0 | C₆H₅ | OH | COC₆H₅ | CH₂OC(O)C₆H₅ | CH₃ | CH₃ | CH₃ |
| 651 | 0 | C₆H₅ | OH | COC₆H₅ | CH₂COOH | CH₃ | CH₃ | CH₃ |
| 652 | 0 | C₆H₅ | OH | COC₆H₅ | CONHCH(CH₂COOH)COOH | CH₃ | CH₃ | CH₃ |
| 653 | 0 | C₆H₅ | OH | COC₆H₅ | CONHCH(CH₃)COOH | CH₃ | CH₃ | CH₃ |
| 654 | 0 | C₆H₅ | OH | COC₆H₅ | CONHCH(CHCH₂(CH₃)₂)COOH | CH₃ | CH₃ | CH₃ |
| 655 | 0 | C₆H₅ | OH | COC₆H₅ | CONHCH(CH₂OH)COOH | CH₃ | CH₃ | CH₃ |
| 656 | 0 | C₆H₅ | OH | COC₆H₅ | CONHCH(CH₂CH₂SCH₃)COOH | CH₃ | CH₃ | CH₃ |
| 657 | 0 | C₆H₅ | OH | COC₆H₅ | CONHCH((CH₂)₄NH₂)COOH | CH₃ | CH₃ | CH₃ |
| 658 | 2 | C₆H₅ | OH | COC₆H₅ | CONH₂ | CH₃ | CH₃ | CH₃ |

TABLE 34

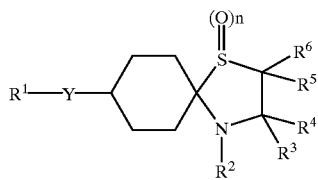

| No. | n | R¹—Y— | R² | R³, R⁴ | R⁵ | R⁶ |
|---|---|---|---|---|---|---|
| 659 | 0 | H₂NNH— | CH₂C₆H₅ | O | H | CH₂COOH |
| 660 | 0 | H₂N— | CH₂C₆H₅ | O | H | CH₂COOH |
| 661 | 0 | ClCO— | CH₂C₆H₅ | O | H | CH₂COOH |
| 662 | 0 | ClCHCH— | CH₂C₆H₅ | O | H | CH₂COOH |
| 663 | 0 | ClSO₂— | CH₂C₆H₅ | O | H | CH₂COOH |
| 664 | 0 | HOS(O)₂— | CH₂C₆H₅ | O | H | CH₂COOH |
| 665 | 0 | NCS(O)₂— | CH₂C₆H₅ | O | H | CH₂COOH |
| 666 | 0 | CH₃OS(O)₂— | CH₂C₆H₅ | O | H | CH₂COOH |
| 667 | 0 | H₂NS(O)₂— | CH₂C₆H₅ | O | H | CH₂COOH |
| 668 | 0 | HO— | CH₂C₆H₅ | O | H | CH₂COOH |
| 669 | 0 | O₂NO— | CH₂C₆H₅ | O | H | CH₂COOH |
| 670 | 0 | H₂NC(O)O— | CH₂C₆H₅ | O | H | CH₂COOH |
| 671 | 0 | HS— | CH₂C₆H₅ | O | H | CH₂COOH |
| 672 | 0 | HOS— | CH₂C₆H₅ | O | H | CH₂COOH |
| 673 | 0 | CH₃(O)S— | CH₂C₆H₅ | O | H | CH₂COOH |

TABLE 35

| No. | n | R¹—Y— | R² | R³, R⁴ | R⁵ | R⁶ |
|---|---|---|---|---|---|---|
| 674 | 0 | OHC— | CH₂C₆H₅ | O | H | CH₂COOH |
| 675 | 0 | O₂NCHCH— | CH₂C₆H₅ | O | H | CH₂COOH |
| 676 | 0 | CH₂CHCHCH— | CH₂C₆H₅ | O | H | CH₂COOH |
| 677 | 0 | CH₃OCHCH— | CH₂C₆H₅ | O | H | CH₂COOH |
| 678 | 0 | CH₃C(O)CHCH— | CH₂C₆H₅ | O | H | CH₂COOH |
| 679 | 0 | CH₂CH— | CH₂C₆H₅ | O | H | CH₂COOH |
| 680 | 0 | ClCH₂CH₂— | CH₂C₆H₅ | O | H | CH₂COOH |
| 681 | 0 | NCCH₂— | CH₂C₆H₅ | O | H | CH₂COOH |
| 682 | 0 | O₂NCH₂— | CH₂C₆H₅ | O | H | CH₂COOH |
| 683 | 0 | CH₃OC(O)CH₂— | CH₂C₆H₅ | O | H | CH₂COOH |
| 684 | 0 | HOC(O)CH₂— | CH₂C₆H₅ | O | H | CH₂COOH |
| 685 | 0 | CH₃COCH₂— | CH₂C₆H₅ | O | H | CH₂COOH |
| 686 | 0 | H₂NCH₂ | CH₂C₆H₅ | O | H | CH₂COOH |

TABLE 35-continued

| No. | n | R¹—Y— | R² | R³, R⁴ | R⁵ | R⁶ |
|---|---|---|---|---|---|---|
| 687 | 0 | HOCH₂— | CH₂C₆H₅ | O | H | CH₂COOH |
| 688 | 0 | HONH— | CH₂C₆H₅ | O | H | CH₂COOH |
| 689 | 0 | CH₃C(O)NCl— | CH₂C₆H₅ | O | H | CH₂COOH |
| 690 | 0 | O₂NNH— | CH₂C₆H₅ | O | H | CH₂COOH |
| 691 | 0 | CH₃ONH— | CH₂C₆H₅ | O | H | CH₂COOH |
| 692 | 0 | CH₂CHS(O)— | CH₂C₆H₅ | O | H | CH₂COOH |
| 693 | 0 | CH₂CHS(O)₂— | CH₂C₆H₅ | O | H | CH₂COOH |
| 694 | 0 | 2-Thiazolylsulfonyl | CH₂C₆H₅ | O | H | CH₂COOH |
| 695 | 0 | CH₂CHCH(OH)— | CH₂C₆H₅ | O | H | CH₂COOH |

TABLE 36

| No. | n | R¹—Y— | R² | R³, R⁴ | R⁵ | R⁶ |
|---|---|---|---|---|---|---|
| 696 | 0 | C₆H₁₁O— | CH₂C₆H₅ | O | H | CH₂COOH |
| 697 | 0 | C₆H₁₁S— | CH₂C₆H₅ | O | H | CH₂COOH |
| 698 | 0 | C₆H₁₁NH— | CH₂C₆H₅ | O | H | CH₂COOH |
| 699 | 0 | C₆H₁₁CHCH— | CH₂C₆H₅ | O | H | CH₂COOH |
| 700 | 0 | C₆H₁₁S(O)— | CH₂C₆H5 | O | H | CH₂COOH |
| 701 | 0 | NCCO— | CH₂C₆H₅ | O | H | CH₂COOH |
| 702 | 0 | NCCHCH— | CH₂C₆H₅ | O | H | CH₂COOH |
| 703 | 0 | NCS— | CH₂C₆H₅ | O | H | CH₂COOH |
| 704 | 0 | C₆H₁₁S(O)₂— | CH₂C₆H₅ | O | H | CH₂COOH |
| 705 | 0 | HOC(O)C(O)— | CH₂C₆H₅ | O | H | CH₂COOH |
| 706 | 0 | H₃COC(O)NH— | CH₂C₆H₅ | O | H | CH₂COOH |
| 707 | 0 | HOC(O)CHCH— | CH₂C₆H₅ | O | H | CH₂COOH |
| 708 | 0 | HOC(O)CH(OH)— | CH₂C₆H₅ | O | H | CH₂COOH |
| 709 | 0 | HOO— | CH₂C₆H₅ | O | H | CH₂COOH |
| 710 | 0 | HOC(O)— | CH₂C₆H₅ | O | H | CH₂COOH |
| 711 | 0 | CH₃OC(O)CHCH— | CH₂C₆H₅ | O | H | CH₂COOH |
| 712 | 0 | CH₃OC(O)SCHCH— | CH₂C₆H₅ | O | H | CH₂COOH |
| 713 | 0 | (HO)₂CH— | CH₂C₆H₅ | O | H | CH₂COOH |
| 714 | 0 | CH₃O— | CH₂C₆H₅ | O | H | CH₂COOH |
| 715 | 0 | CH₃S— | CH₂C₆H₅ | O | H | CH₂COOH |
| 716 | 0 | CH₃NH— | CH₂C₆H₅ | O | H | CH₂COOH |
| 717 | 0 | CH₃CO— | CH₂C₆H₅ | O | H | CH₂COOH |

TABLE 37

| No. | n | R¹-Y- | R₂ | R³, R⁴ | R⁵ | R⁶ |
|---|---|---|---|---|---|---|
| 718 | 0 | CH₃CHCH— | CH₂C₆H₅ | O | H | CH₂COOH |
| 719 | 0 | C₆H₅C(O)— | CH₂C₆H₅ | O | H | CH₂COOH |
| 720 | 0 | CH₃C(O)— | CH₂C₆H₅ | O | H | CH₂COOH |
| 721 | 0 | CH₃S(O)₂— | CH₂C₆H₅ | O | H | CH₂COOH |
| 722 | 0 | NCCH(OH)— | CH₂C₆H₅ | O | H | CH₂COOH |
| 723 | 0 | CH₃OC(O)CH(OH)— | CH₂C₆H₅ | O | H | CH₂COOH |
| 724 | 0 | CH₃C(O)CH(OH)— | CH₂C₆H₅ | O | H | CH₂COOH |
| 725 | 0 | CH₃CH(OH)— | CH₂C₆H₅ | O | H | CH₂COOH |
| 726 | 0 | CH₂CHO— | CH₂C₆H₅ | O | H | CH₂COOH |
| 727 | 0 | CH₂CHS— | CH₂C₆H₅ | O | H | CH₂COOH |
| 728 | 0 | CH₂CHNH— | CH₂C₆H₅ | O | H | CH₂COOH |
| 729 | 0 | CH₂CHCO— | CH₂C₆H₅ | O | H | CH₂COOH |
| 730 | 0 | CH₂CHCH₂— | CH₂C₆H₅ | O | H | CH₂COOH |
| 731 | 0 | 4-CH₃CH(CH₃)C₆H₄O— | CH₂CH₂CH(C₂H₅)C₂H₅ | O | H | CH₂COOH |
| 732 | 0 | 4-CH₃CH(CH₃)C₆H₄O— | CH₂F | O | H | CH₂COOH |
| 733 | 0 | 4-CH₃CH(CH₃)C₆H₄O— | CH₂OH | O | H | CH₂COOH |
| 734 | 0 | 4-CH₃CH(CH₃)C₆H₄O— | CH₂CH₂OH | O | H | CH₂COOH |
| 735 | 0 | 4-CH₃CH(CH₃)C₆H₄O— | CH₂CH₂CH₂OH | O | H | CH₂COOH |
| 736 | 0 | 4-CH₃CH(CH₃)C₆H₄O— | CH₂CH₂CH₂CH₂OH | O | H | CH₂COOH |
| 737 | 0 | 4-CH₃CH(CH₃)C₆H₄O— | CH₂CH₂CH₂CH₂CH₂OH | O | H | CH₂COOH |
| 738 | 0 | 4-CH₃CH(CH₃)C₆H₄O— | CH(OH)CH₂OH | O | H | CH₂COOH |
| 739 | 0 | 4-CH₃CH(CH₃)C₆H₄O— | CH₂CH(OH)CH₂OH | O | H | CH₂COOH |
| 740 | 0 | 4-CH₃CH(CH₃)C₆H₄O— | CH₂CH(OH)CH₂CH₂OH | O | H | CH₂COOH |

TABLE 38

| No. | n | R¹—Y— | R² | R³, R⁴ | R⁵ | R⁶ |
|---|---|---|---|---|---|---|
| 741 | 0 | C₆H₁₁CH(OH)— | CH₂C₆H₅ | O | H | CH₂COOH |
| 742 | 0 | CH₃C(O)O— | CH₂C₆H₅ | O | H | CH₂COOH |
| 743 | 0 | 4-CH₃CH(CH₃)C₆H₄O— | CH₂CH₂CH(CH₃)C₂H₅ | O | H | CH₂COOH |
| 744 | 0 | CH₃C(O)NH— | CH₂C₆H₅ | O | H | CH₂COOH |
| 745 | 0 | H₂NC(O)— | CH₂C₆H₅ | O | H | CH₂COOH |
| 746 | 0 | C₆H₅CH₂CH₂— | CH₂C₆H₅ | O | H | CH₂COOH |
| 747 | 0 | 2-Pyridylethenyl | CH₂C₆H₅ | O | H | CH₂COOH |
| 748 | 0 | C₆H₅CHCH— | CH₂C₆H₅ | O | H | CH₂COOH |
| 749 | 0 | CH₃C(O)C(O)— | CH₂C₆H₅ | O | H | CH₂COOH |
| 750 | 0 | CH₃C(O)C(O)— | CH₂CH₂C₆H₅ | O | H | CH₂COOH |
| 751 | 0 | Cyclohexanecarbonyl | CH₂C₆H₅ | O | H | CH₂COOH |
| 752 | 0 | 2-Thienylcarbonyl | CH₂C₆H₅ | O | H | CH₂COOH |
| 753 | 0 | CH₃OC(O)— | CH₂C₆H₅ | O | H | CH₂COOH |
| 754 | 0 | CH₃OC(O)CHCH— | CH₂C₆H₅ | O | H | CH₂COOH |
| 755 | 0 | CH₃C(O)NHCHCH— | CH₂C₆H₅ | O | H | CH₂COOH |
| 756 | 0 | CH₃SCHCH— | CH₂C₆H₅ | O | H | CH₂COOH |
| 757 | 0 | CH₃S(O)CHCH— | CH₂C₆H₅ | O | H | CH₂COOH |
| 758 | 0 | CH₃S(O)₂CHCH— | CH₂C₆H₅ | O | H | CH₂COOH |
| 759 | 0 | 4-CH₃CH(CH₃)C₆H₄O— | H | O | H | CH₂COOH |
| 760 | 0 | 4-CH₃CH(CH₃)C₆H₄O— | CH₃ | O | H | CH₂COOH |
| 761 | 0 | 4-CH₃CH(CH₃)C₆H₄O— | CH₂CH₃ | O | H | CH₂COOH |
| 762 | 0 | 4-CH₃CH(CH₃)C₆H₄O— | CH₂CH₂CH₃ | O | H | CH₂COOH |

TABLE 39

| No. | n | R¹—Y— | R² | R³, R⁴ | R⁵ | R⁶ |
|---|---|---|---|---|---|---|
| 763 | 0 | 4-CH₃CH(CH₃)C₆H₄O— | CH₂CH₂CH₂CH₃ | O | H | CH₂COOH |
| 764 | 0 | 4-CH₃CH(CH₃)C₆H₄O— | CH₂CH₂CH₂CH₂CH₃ | O | H | CH₂COOH |
| 765 | 0 | 4-CH₃CH(CH₃)C₆H₄O— | CH(CH₃)CH₃ | O | H | CH₂COOH |
| 766 | 0 | 4-CH₃CH(CH₃)C₆H₄O— | CH₂CH(CH₃)CH₃ | O | H | CH₂COOH |
| 767 | 0 | 4-CH₃CH(CH₃)C₆H₄O— | CH₂CH₂CH(CH₃)CH₃ | O | H | CH₂COOH |
| 768 | 0 | 4-CH₃CH(CH₃)C₆H₄O— | CH₂CH₂CH₂CH(CH₃)CH₃ | O | H | CH₂COOH |
| 769 | 0 | 4-CH₃CH(CH₃)C₆H₄O— | CH₂CH(CH₃)C₂H₅ | O | H | CH₂COOH |
| 770 | 0 | 4-CH₃CH(CH₃)C₆H₄O— | CH(CH₂OH)COOH | O | H | CH₂COOH |
| 771 | 0 | 4-CH₃CH(CH₃)C₆H₄O— | CH(CH₂COOH)COOH | O | H | CH₂COOH |
| 772 | 0 | 4-CH₃CH(CH₃)C₆H₄O— | CH(CH₂CONH₂)COOH | O | H | CH₂COOH |
| 773 | 0 | 4-CH₃CH(CH₃)C₆H₄O— | CH(CH₂CH₂COOH)COOH | O | H | CH₂COOH |

TABLE 39-continued

| No. | n | R¹—Y— | R² | R³, R⁴ | R⁵ | R⁶ |
|---|---|---|---|---|---|---|
| 774 | 0 | 4-CH₃CH(CH₃)C₆H₄O— | CH(CH₂CH₂CONH₂)COOH | O | H | CH₂COOH |
| 775 | 0 | 4-CH₃CH(CH₃)C₆H₄O— | CH(4-Imidazolylmethyl)-COOH | O | H | CH₂COOH |
| 776 | 0 | 4-CH₃CH(CH₃)C₆H₄O— | CH(CH(C₂H₅)CH₃)COOH | O | H | CH₂COOH |
| 777 | 0 | 4-CH₃CH(CH₃)C₆H₄O— | CH(CH₂CH(CH₃)CH₃)COOH | O | H | CH₂COOH |
| 778 | 0 | 4-CH₃CH(CH₃)C₆H₄O— | CH(CH₂CH₂SCH₃)COOH | O | H | CH₂COOH |
| 779 | 0 | 4-CH₃CH(CH₃)C₆H₄O— | CH(CH(OH)CH₃)COOH | O | H | CH₂COOH |
| 780 | 0 | 4-CH₃CH(CH₃)C₆H₄O— | CH(CH₂—(4-HO)C₆H₅)-COOH | O | H | CH₂COOH |
| 781 | 0 | 4-CH₃CH(CH₃)C₆H₄O— | CH₂CH₂CH(OH)CH₂CH₂OH | O | H | CH₂COOH |
| 782 | 0 | 4-CH₃CH(CH₃)C₆H₄O— | CH₂OC(O)NH₂ | O | H | CH₂COOH |
| 783 | 0 | 4-CH₃CH(CH₃)C₆H₄O— | CH₂OC(O)CH₃ | O | H | CH₂COOH |
| 784 | 0 | 4-CH₃CH(CH₃)C₆H₄O— | CH₂COOH | O | H | CH₂COOH |

TABLE 40

| No. | n | R¹—Y— | R² | R³, R⁴ | R⁵ | R⁶ |
|---|---|---|---|---|---|---|
| 785 | 0 | 4-CH₃CH(CH₃)C₆H₄O— | CH₂CH₂COOH | O | H | CH₂COOH |
| 786 | 0 | 4-CH₃CH(CH₃)C₆H₄O— | CH₂CH₂CH₂COOH | O | H | CH₂COOH |
| 787 | 0 | 4-CH₃CH(CH₃)C₆H₄O— | CH₂CH₂CH₂CH₂COOH | O | H | CH₂COOH |
| 788 | 0 | 4-CH₃CH(CH₃)C₆H₄O— | CH₂CH₂CH₂CH₂CH₂COOH | O | H | CH₂COOH |
| 789 | 0 | 4-CH₃CH(CH₃)C₆H₄O— | CH₂COOCH₃ | O | H | CH₂COOH |
| 790 | 0 | 4-CH₃CH(CH₃)C₆H₄O— | CH₂COOC2H₅ | O | H | CH₂COOH |
| 791 | 0 | 4-CH₃CH(CH₃)C₆H₄O— | CH₂COO—n—C₃H₇ | O | H | CH₂COOH |
| 792 | 0 | 4-CH₃CH(CH₃)C₆H₄O— | CH₂COO-i-C₃H₇ | O | H | CH₂COOH |
| 793 | 0 | 4-CH₃CH(CH₃)C₆H₄O— | CH₂COOC₆H₅ | O | H | CH₂COOH |
| 794 | 0 | 4-CH₃CH(CH₃)C₆H₄O— | CH₂COOCH₂C₆H₅ | O | H | CH₂COOH |
| 795 | 0 | 4-CH₃CH(CH₃)C₆H₄O— | CH₂CH₂COOCH₂C₆H₅ | O | H | CH₂COOH |
| 796 | 0 | 4-CH₃CH(CH₃)C₆H₄O— | CH(CH₃)COOH | O | H | CH₂COOH |
| 797 | 0 | 4-CH₃CH(CH₃)C₆H₄O— | CH₂CONH₂ | O | H | CH₂COOH |
| 798 | 0 | 4-CH₃CH(CH₃)C₆H₄O— | CH₂CONHOH | O | H | CH₂COOH |
| 799 | 0 | 4-CH₃CH(CH₃)C₆H₄O— | CH₂CONHCH₃ | O | H | CH₂COOH |
| 800 | 0 | 4-CH₃CH(CH₃)C₆H₄O— | CH₂CONHC₂H₅ | O | H | CH₂COOH |
| 801 | 0 | 4-CH₃CH(CH₃)C₆H₄O— | CH₂CONH-n-C₃H₇ | O | H | CH₂COOH |
| 803 | 0 | 4-CH₃CH(CH₃)C₆H₄O— | CH₂CONH-i-C₃H₇ | O | H | CH₂COOH |
| 803 | 0 | 4-CH₃CH(CH₃)C₆H₄O— | CH₂CON(CH₃)₂ | O | H | CH₂COOH |
| 804 | 0 | 4-CH₃CH(CH₃)C₆H₄O— | CH₂CON(n-C₃H₇)₂ | O | H | CH₂COOH |
| 805 | 0 | 4-CH₃CH(CH₃)C₆H₄O— | CH₂CON(C₂H₅)₂ | O | H | CH₂COOH |
| 806 | 0 | 4-CH₃CH(CH₃)C₆H₄O— | CH₂CONHC₆H₅ | O | H | CH₂COOH |

TABLE 41

| No. | n | R¹—Y— | R² | R³, R⁴ | R⁵ | R⁶ |
|---|---|---|---|---|---|---|
| 807 | 0 | 4-CH₃CR(CH₃)C₆H₄O— | CH₂CH₂COOCH₃ | O | H | CH₂COOH |
| 808 | 0 | 4-CH₃CH(CH₃)C₆H₄O— | Cyclopentyl | O | H | CH₂COOH |
| 809 | 0 | 4-CH₃CH(CH₃)C₆H₄O— | Cyclohexyl | O | H | CH₂COOH |
| 810 | 0 | 4-CH₃CH(CH₃)C₆H₄O— | CH₂C₆H₅ | O | H | CH₂COOH |
| 811 | 0 | 4-CH₃CH(CH₃)C₆H₄O— | CH₂CH₂C₆H₅ | O | H | CH₂COOH |
| 812 | 0 | 4-CH₃CH(CH₃)C₆H₄O— | CH₂C₆H₁₁ | O | H | CH₂COOH |
| 813 | 0 | 4-CH₃CH(CH₃)C₆H₄O— | CH(CH₃)C₆H₅ | O | H | CH₂COOH |
| 814 | 0 | 4-CH₃CH(CH₃)C₆H₄O— | 2-Thienylmethyl | O | H | CH₂COOH |
| 815 | 0 | 4-CH₃CH(CH₃)C₆H₄O— | 2-Furfuryl | O | H | CH₂COOH |
| 816 | 0 | 4-CH₃CH(CH₃)C₆H₄O— | 2-Pyranylmethyl | O | H | CH₂COOH |
| 817 | 0 | 4-CH₃CH(CH₃)C₆H₄O— | 1-Isobenzofurylmethyl | O | H | CH₂COOH |
| 818 | 0 | 4-CH₃CH(CH₃)C₆H₄O— | 2-Pyrrolylmethyl | O | H | CH₂COOH |
| 819 | 0 | 4-CH₃CH(CH₃)C₆H₄O— | 1-Imidazolylmethyl | O | H | CH₂COOH |
| 820 | 0 | 4-CH₃CH(CH₃)C₆H₄O— | 1-Pyrazolylmethyl | O | H | CH₂COOH |
| 821 | 0 | 4-CH₃CH(CH₃)C₆H₄O— | CH(CH₂C₆H₅)COOH | O | H | CH₂COOH |
| 822 | 0 | 4-CH₃CH(CH₃)C₆H₄O— | CH(3-Indolylmethyl)COOH | O | H | CH₂COOH |
| 823 | 0 | 4-CH₃CH(CH₃)C₆H₄O— | CH(1-C₃H₇)COOH | O | H | CH₂COOH |
| 824 | 0 | 4-CH₃CH(CH₃)C₆H₄O— | CH₂CN | O | H | CH₂COOH |
| 825 | 0 | 4-CH₃CH(CH₃)C₆H₄O— | CH₂NO₂ | O | H | CH₂COOH |
| 826 | 0 | 4-CH₃CH(CH₃)C₆H₄O— | CH₂COCH₃ | O | H | CH₂COOH |
| 827 | 0 | 4-CH₃CH(CH₃)C₆H₄O— | CH₂C(OCH₂)₂CH₃ | O | H | CH₂COOH |
| 828 | 0 | 4-CH₃CH(CH₃)C₆H₄O— | CH₂C(SCH₃)₂CH₃ | O | H | CH₂COOH |

TABLE 42

| No. | n | R¹—Y— | R² | R³, R⁴ | R⁵ | R⁶ |
|---|---|---|---|---|---|---|
| 829 | 0 | 4-CH₃CH-(CH₃)C₆H₄O— | C(NH)NH₂ | O | H | CH₂COOH |
| 830 | 0 | 4-CH₃CH-(CH₃)C₆H₄O— | CH₂C(NOH)CH₃ | O | H | CH₂COOH |
| 831 | 0 | 4-CH₃CH-(CH₃)C₆H₄O— | CH₂SH | O | H | CH₂COOH |
| 832 | 0 | 4-CH₃CH-(CH₃)C₆H₄O— | CH₂SO₃H | O | H | CH₂COOH |
| 833 | 0 | 4-CH₃CH-(CH₃)C₆H₄O— | CH₂S(O)₂CH₃ | O | H | CH₂COOH |
| 834 | 0 | 4-CH₃CH-(CH₃)C₆H₄O— | CH₂S(O)CH₃ | O | H | CH₂COOH |
| 835 | 0 | 4-CH₃CH-(CH₃)C₆H₄O— | CH₂S(O)₂NH₃ | O | H | CH₂COOH |
| 836 | 0 | 4-CH₃CH-(CH₃)C₆H₄O— | Cyclobutyl | O | H | CH₂COOH |
| 837 | 0 | 4-CH₃CH-(CH₃)C₆H₄O— | CH₂OCH₃ | O | H | CH₂COOH |
| 838 | 0 | 4-CH₃CH-(CH₃)C₆H₄O— | CH₂CH₂OCH₃ | O | H | CH₂COOH |
| 839 | 0 | 4-CH₃CH-(CH₃)C₆H₄O— | CH₂CH₂CH₂OCH₃ | O | H | CH₂COOH |
| 840 | 0 | 4-CH₃CH-(CH₃)C₆H₄O— | CH₂SCH₃ | O | H | CH₂COOH |
| 841 | 0 | 4-CH₃CH-(CH₃)C₆H₄O— | CH₂CH₂SCH₃ | O | H | CH₂COOH |
| 842 | 0 | 4-CH₃CH-(CH₃)C₆H₄O— | CH₂CH₂CH₂SCH₃ | O | H | CH₂COOH |
| 843 | 0 | 4-CH₃CH-(CH₃)C₆H₄O— | CHCH₂ | O | H | CH₂COOH |
| 844 | 0 | 4-CH₃CH-(CH₃)C₆H₄O— | CH₂CHCH₂ | O | H | CH₂COOH |
| 845 | 0 | 4-CH₃CH-(CH₃)C₆H₄O— | CCH | O | H | CH₂COOH |
| 846 | 0 | 4-CH₃CH-(CH₃)C₆H₄O— | Cyclopropyl | O | H | CH₂COOH |
| 847 | 0 | 4-CH₃CH-(CH₃)C₆H₄O— | 2-Thiazolyl | O | H | CH₂COOH |
| 848 | 0 | 4-CH₃CH-(CH₃)C₆H₄O— | 4-Imidazolyl | O | H | CH₂COOH |
| 849 | 0 | 4-CH₃CH-(CH₃)C₆H₄O— | 3-Pyrazolyl | O | H | CH₂COOH |
| 850 | 0 | 4-CH₃CH-(CH₃)C₆H₄O— | 3-Isoxazolyl | O | H | CH₂COOH |

TABLE 43

| No. | n | R¹—Y— | R² | R³, R⁴ | R⁵ | R⁶ |
|---|---|---|---|---|---|---|
| 851 | 0 | 4-CH₃CH(CH₃)C₆H₄O— | 5-Isothiazolyl | O | H | CH₂COOH |
| 852 | 0 | 4-CH₃CH(CH₃)C₆H₄O— | 2-Pyrimidinyl | O | H | CH₂COOH |
| 853 | 0 | 4-CH₃CH(CH₃)C₆H₄O— | 3-(1,2,4-Triazolyl) | O | H | CH₂COOH |
| 854 | 0 | 4-CH₃CH(CH₃)C₆H₄O— | 2-Pyridyl | O | H | CH₂COOH |
| 855 | 0 | 4-CH₃CH(CH₃)C₆H₄O— | 2-Benzoxazolyl | O | H | CH₂COOH |
| 856 | 0 | 4-CH₃CH(CH₃)C₆H₄O— | 3-Benzothienyl | O | H | CH₂COOH |
| 857 | 0 | 4-CH₃CR(CH₃)C₆H₄O— | 2-Benzofuryl | O | H | CH₂COOH |
| 858 | 0 | 4-CH₃CH(CH₃)C₆H₄O— | 5-Indolyl | O | H | CH₂COOH |
| 859 | 0 | 4-CH₃CH(CH₃)C₆H₄O— | 2-Pyrazinyl | O | H | CH₂COOH |
| 860 | 0 | 4-CH₃CH(CH₃)C₆H₄O— | 3-Quinolyl | O | H | CH₂COOH |
| 861 | 0 | 4-CH₃CH(CH₃)C₆H₄O— | 3-Isothiazolylmethyl | O | H | CH₂COOH |
| 862 | 0 | 4-CH₃CH(CH₃)C₆H₄O— | 3-Jsoxazolylmethyl | O | H | CH₂COOH |
| 863 | 0 | 4-CH₃CH(CH₃)C₆H₄O— | 2-Pyridylmethyl | O | H | CH₂COOH |
| 864 | 0 | 4-CH₃CH(CH₃)C₆H₄O— | 2-Pyrazinylmethyl | O | H | CH₂COOH |
| 865 | 0 | 4-CH₃CH(CH₃)C₆H₄O— | 2-Pyrimidinylmethyl | O | H | CH₂COOH |
| 866 | 0 | 4-CH₃CH(CH₃)C₆H₄O— | 3-Pyridazinylmethyl | O | H | CH₂COOH |
| 867 | 0 | 4-CH₃CH(CH₃)C₆H₄O— | 1-Isoindolylmethyl | O | H | CH₂COOH |
| 868 | 0 | 4-CH₃CH(CH₃)C₆H₄O— | 2-Jndolylmethyl | O | H | CH₂COOH |
| 869 | 0 | 4-CH₃CH(CH₃)C₆H₄O— | 3-(1H-Indazolyl)methyl | O | H | CH₂COOH |
| 870 | 0 | 4-CH₃CH(CH₃)C₆H₄O— | 2-Purinylmethyl | O | H | CH₂COOH |
| 871 | 0 | 4-CH₃CH(CH₃)C₆H₄O— | 1-Isoquinolylmethyl | O | H | CH₂COOH |
| 872 | 0 | 4-CH₃CH(CH₃)C₆H₄O— | 2-Quinolylmethyl | O | H | CH₂COOH |

TABLE 44

| No. | n | R¹—Y— | R² | R³, R⁴ | R⁵ | R⁶ |
|---|---|---|---|---|---|---|
| 873 | 0 | 4-CH$_3$CH(CH$_3$)C$_6$H$_4$O— | 1-Phthalazinylmethyl | O | H | CH$_2$COOH |
| 874 | 0 | 4-CH$_3$CH(CH$_3$)C$_6$H$_4$O— | 2-Naphthylidinylmethyl | O | H | CH$_2$COOH |
| 875 | 0 | 4-CH$_3$CH(CH$_3$)C$_6$H$_4$O— | 2-Quinoxalinylmethyl | O | H | CH$_2$COOH |
| 876 | 0 | 4-CH$_3$CH(CH$_3$)C$_6$H$_4$O— | 2-Quinazolinylmethyl | O | H | CH$_2$COOH |
| 877 | 0 | 4-CH$_3$CH(CH$_3$)C$_6$H$_4$O— | 3-Cinnolinylmethyl | O | H | CH$_2$COOH |
| 878 | 0 | 4-CH$_3$CH(CH$_3$)C$_6$H$_4$O— | 2-Oxazolylmethyl | O | H | CH$_2$COOH |
| 879 | 0 | 4-CH$_3$CH(CH$_3$)C$_6$H$_4$O— | 2-Thiazolylmethyl | O | H | CH$_2$COOH |
| 880 | 0 | 4-CH$_3$CH(CH$_3$)C$_6$H$_4$O— | 2-Benzo[b]furylmethyl | O | H | CH$_2$COOH |
| 881 | 0 | 4-CH$_3$CH(CH$_3$)C$_6$H$_4$O— | 2-Benzo[b]thienylmethyl | O | H | CH$_2$COOH |
| 882 | 0 | 4-CH$_3$CH(CH$_3$)C$_6$H$_4$O— | 3-(1,2,4-Triazinyl)methyl | O | H | CH$_2$COOH |
| 883 | 0 | 4-CH$_3$CH(CH$_3$)C$_6$H$_4$O— | 2-Benz[d]imidazolylmethyl | O | H | CH$_2$COOH |
| 884 | 0 | 4-CH$_3$CH(CH$_3$)C$_6$H$_4$O— | 2-Benz[d]oxazolylmethyl | O | H | CH$_2$COOH |
| 885 | 0 | 4-CH$_3$CH(CH$_3$)C$_6$H$_4$O— | Phenyl | O | H | CH$_2$COOH |
| 886 | 0 | 4-CH$_3$CH(CH$_3$)C$_6$H$_4$O— | 2-Naphthyl | O | H | CH$_2$COOH |
| 887 | 0 | 4-C$_6$H$_5$CH$_2$OC$_6$H$_4$O— | CH$_2$CH$_2$COOCH$_2$C$_6$H$_5$ | O | H | CH$_2$COOH |
| 888 | 0 | 4-HO$_2$CC$_6$H$_4$O— | CH$_2$CH$_2$COOCH$_2$C$_6$H$_5$ | O | H | CH$_2$COOH |
| 889 | 0 | 4-H$_3$COC(O)C$_6$H$_4$O— | CH$_2$CH$_2$COOCH$_2$C$_6$H$_5$ | O | H | CH$_2$COOH |
| 890 | 0 | 4-H$_2$NC(O)C$_6$H$_4$O— | CH$_2$CH$_2$COOCH$_2$C$_6$H$_5$ | O | H | CH$_2$COOH |
| 891 | 0 | 4-HONHC(O)C$_6$H$_4$O— | CH$_2$CH$_2$COOCH$_2$C$_6$H$_5$ | O | H | CH$_2$COOH |
| 892 | 0 | 4-H$_3$CNHC(O)C$_6$H$_4$O— | CH$_2$CH$_2$COOCH$_2$C$_6$H$_5$ | O | H | CH$_2$COOH |
| 893 | 0 | 4-(H$_3$C)$_2$NC(O)C$_6$H$_4$O— | CH$_2$CH$_2$COOCH$_2$C$_6$H$_5$ | O | H | CH$_2$COOH |
| 894 | 0 | 4-O$_2$NC$_6$H$_4$O— | CH$_2$CH$_2$COOCH$_2$C$_6$H$_5$ | O | H | CH$_2$COOH |

TABLE 45

| No. | n | R¹—Y— | R² | R³, R⁴ | R⁵ | R⁶ |
|---|---|---|---|---|---|---|
| 895 | 0 | 4-H$_2$NC$_6$H$_4$O— | CH$_2$CH$_2$COOCH$_2$C$_6$H$_5$ | O | H | CH$_2$COOH |
| 896 | 0 | 4-H$_3$CNHC$_6$H$_4$O— | CH$_2$CH$_2$COOCH$_2$C$_6$H$_5$ | O | H | CH$_2$COOH |
| 897 | 0 | 4-(H$_3$C)$_2$NC$_6$H$_4$O— | CH$_2$CH$_2$COOCH$_2$C$_6$H$_5$ | O | H | CH$_2$COOH |
| 898 | 0 | 4-OHCC$_6$H$_4$O— | CH$_2$CH$_2$COOCH$_2$C$_6$H$_5$ | O | H | CH$_2$COOH |
| 899 | 0 | 4-HONCHC$_6$H$_4$O— | CH$_2$CH$_2$COOCH$_2$C$_6$H$_5$ | O | H | CH$_2$COOH |
| 900 | 0 | 4-OHCNHC$_6$H$_4$O— | CH$_2$CH$_2$COOCH$_2$C$_6$H$_5$ | O | H | CH$_2$COOH |
| 901 | 0 | 4-CH$_3$CH(CH$_3$)C$_6$H$_4$O— | 5-Tetrazolyl | O | H | CH$_2$COOH |
| 902 | 0 | 4-CH$_3$CH(CH$_3$)C$_6$H$_4$O— | Methylsulfonyl | O | H | CH$_2$COOH |
| 903 | 0 | 4-CH$_3$CH(CH$_3$)C$_6$H$_4$O— | Benzenesulfonyl | O | H | CH$_2$COOH |
| 904 | 0 | 4-CH$_3$CH(CH$_3$)C$_6$H$_4$O— | CH$_2$CONHCH$_2$C$_6$H$_5$ | O | H | CH$_2$COOH |
| 905 | 0 | 4-FC$_6$H$_4$O— | CH$_2$CH$_2$COOCH$_2$C$_6$H$_5$ | O | H | CH$_2$COOH |
| 906 | 0 | 2-CH$_3$C$_6$H$_4$O— | CH$_2$CH$_2$COOCH$_2$C$_6$H$_5$ | O | H | CH$_2$COOH |
| 907 | 0 | 3-CH$_3$C$_6$H$_4$O— | CH$_2$CH$_2$COOCH$_2$C$_6$H$_5$ | O | H | CH$_2$COOH |
| 908 | 0 | 4-CH$_3$C$_6$H$_4$O— | CH$_2$CH$_2$COOCH$_2$C$_6$H$_5$ | O | H | CH$_2$COOH |
| 909 | 0 | 2,4-(CH$_3$)$_2$C$_6$H$_3$O— | CH$_2$CH$_2$COOCH$_2$C$_6$H$_5$ | O | H | CH$_2$COOH |
| 910 | 0 | 3,4-(CH$_3$)$_2$C$_6$H$_3$O— | CH$_2$CH$_2$COOCH$_2$C$_6$H$_5$ | O | H | CH$_2$COOH |
| 911 | 0 | 2,3-(CH$_3$)$_2$C$_6$H$_3$O— | CH$_2$CH$_2$COOCH$_2$C$_6$H$_5$ | O | H | CH$_2$COOH |
| 912 | 0 | 3,5-(CH$_3$)$_2$C$_6$H$_3$O— | CH$_2$CH$_2$COOCH$_2$C$_6$H$_5$ | O | H | CH$_2$COOH |
| 913 | 0 | 3,6-(CH$_3$)$_2$C$_6$H$_3$O— | CH$_2$CH$_2$COOCH$_2$C$_6$H$_5$ | O | H | CH$_2$COOH |
| 914 | 0 | 2,6-(CH$_3$)$_2$C$_6$H$_3$O— | CH$_2$CH$_2$COOCH$_2$C$_6$H$_5$ | O | H | CH$_2$COOH |
| 915 | 0 | 2,5-(CH$_3$)$_2$C$_6$H$_3$O— | CH$_2$CH$_2$COOCH$_2$C$_6$H$_5$ | O | H | CH$_2$COOH |
| 916 | 0 | 2,4,6-(CH$_3$)$_3$C$_6$H$_2$O— | CH$_2$CH$_2$COOCH$_2$C$_6$H$_5$ | O | H | CH$_2$COOH |

TABLE 46

| No. | n | R¹—Y— | R² | R³, R⁴ | R⁵ | R⁶ |
|---|---|---|---|---|---|---|
| 917 | 0 | 2,3,5-(CH$_3$)$_3$C$_6$H$_2$O— | CH$_2$CH$_2$COOCH$_2$C$_6$H$_5$ | O | H | CH$_2$COOH |
| 918 | 0 | 4-CH(OCH$_3$)$_2$C$_6$H$_4$O— | CH$_2$CH$_2$COOCH$_2$C$_6$H$_5$ | O | H | CH$_2$COOH |
| 919 | 0 | 4-CH(SCH$_3$)$_2$C$_6$H$_4$O— | CH$_2$CH$_2$COOCH$_2$C$_6$H$_5$ | O | H | CH$_3$CpOH |
| 920 | 0 | 2,4,5-(CH$_3$)$_3$C$_6$H$_2$O— | CH$_2$CH$_2$COOCH$_2$C$_6$H$_5$ | O | H | CH$_2$COOH |
| 921 | 0 | 2,5,6-(CH$_3$)$_3$C$_6$H$_2$O— | CH$_2$CH$_2$COOCH$_2$C$_6$H$_5$ | O | H | CH$_2$COOH |
| 922 | 0 | 4-HOC$_6$H$_4$O— | CH$_2$CH$_2$COOCH$_2$C$_6$H$_5$ | O | H | CH$_2$COOH |
| 923 | 0 | 4-H$_3$COC$_6$H$_4$O— | CH$_2$CH$_2$COOCH$_2$C$_6$H$_5$ | O | H | CH$_2$COOH |
| 924 | 0 | 4-C$_2$H$_5$OC$_6$H$_4$O— | CH$_2$CH$_2$COOCH$_2$C$_6$H$_5$ | O | H | CH$_2$COOH |
| 925 | 0 | 4-CH$_3$CH(CH$_3$)OC$_6$H$_4$O— | CH$_2$CH$_2$CO9CH$_2$C$_6$H$_5$ | O | H | CH$_2$COOH |
| 926 | 0 | 4-C$_6$H$_5$OC$_6$H$_4$O— | CH$_2$CH$_2$COOCH$_2$C$_6$H$_5$ | O | H | CH$_2$COOH |
| 927 | 0 | 2-Benzoxazolylamino | CH$_2$CH$_2$COOCH$_2$C$_6$H$_5$ | O | H | CH$_2$COOH |
| 928 | 0 | 3-Benzothienylamino | CH$_2$CH$_2$COOCH$_2$C$_6$H$_5$ | O | H | CH$_2$COOH |

TABLE 46-continued

| No. | n | R¹—Y— | R² | R³, R⁴ | R⁵ | R⁶ |
|---|---|---|---|---|---|---|
| 929 | 0 | 2-Benzofurylamino | CH₂CH₂COOCH₂C₆H₅ | O | H | CH₂COOH |
| 930 | 0 | 5-Indolylamino | CH₂CH₂COOCH₂C₆H₅ | O | H | CH₂COOH |
| 931 | 0 | 2-Pyrazinylamino | CH₂CH₂COOCH₂C₆H₅ | O | H | CH₂COOH |
| 932 | 0 | 3-Ouinolylamino | CH₂CH₂COOCH₂C₆H₅ | O | H | CH₂COOH |
| 933 | 0 | 5-Tetrazolylamino | CH₂CH₂COOCH₂C₆H₅ | O | H | CH₂COOH |
| 934 | 0 | 2-Iniidazolylthioxy | CH₂CH₂COOCH₂C₆H₅ | O | H | CH₂COOH |
| 935 | 0 | 2-Pyridylthioxy | CH₂CH₂COOCH₂C₆H₅ | O | H | CH₂COOH |
| 936 | 0 | 2-Benzothiazolylthioxy | CH₂CH₂COOCH₂C₆H₅ | O | H | CH₂COOH |
| 937 | 0 | 2-Benzothienylethenyl | CH₂CH₂COOCH₂C₆H₅ | O | H | CH₂COOH |
| 938 | 0 | 2-Benzothienylethynyl | CH₂CH₂COOCH₂C₆H₅ | O | H | CH₂COOH |

TABLE 47

| No. | n | R¹—Y— | R² | R³, R⁴ | R⁵ | R⁶ |
|---|---|---|---|---|---|---|
| 939 | 0 | 2-Benzothienylmethyl | CH₂CH₂COOCH₂C₆H₅ | O | H | CH₂COOH |
| 940 | 0 | 4-CH₃CH(CH₃)C₆H₄S(O)— | CH₂CH₂COOCH₂C₆H₅ | O | H | CH₂COOH |
| 941 | 0 | 4-H₃CC(O)NHC₆H₄O— | CH₂CH₂COOCH₂C₆H₅ | O | H | CH₂COOH |
| 942 | 0 | 4-H₃COC(O)NHC₆H₄O— | CH₂CH₂COOCH₂C₆H₅ | O | H | CH₂COOH |
| 943 | 0 | 4-H₂NC(O)OC₆H₄O— | CH₂CH₂COOCH₂C₆H₅ | O | H | CH₂COOH |
| 944 | 0 | 4-HSC₆H₄O— | CH₂CH₂COOCH₂C₆H₅ | O | H | CH₂COOH |
| 945 | 0 | 4-H₃CSC₆H₄O— | CH₂CH₂COOCH₂C₆H₅ | O | H | CH₂COOH |
| 946 | 0 | 4-H₃CS(O)C₆H₄O— | CH₂CH₂COOCH₂C₆H₅ | O | H | CH₂COOH |
| 947 | 0 | 4-H₃CS(O)₂C₆H₄O— | CH₂CH₂COOCH₂C₆H₅ | O | H | CH₂COOH |
| 948 | 0 | 3,4-(OCH₂O)C₆H₃O— | CH₂CH₂COOCH₂C₆H₅ | O | H | CH₂COOH |
| 949 | 0 | 3,4-(CH₂CH₂CH₂)C₆H₃O— | CH₂CH₂COOCH₂C₆H₅ | O | H | CH₂COOH |
| 950 | 0 | 4-HO₃SC₆H₄O— | CH₂CH₂COOCH₂C₆H₅ | O | H | CH₂COOH |
| 951 | 0 | 4-NCC₆H₄O— | CH₂CH₂COOCH₂C₆H₅ | O | H | CH₂COOH |
| 952 | 0 | 4-H₂NC(NH)C₆H₄O— | CH₂CH₂COOCH₂C₆H₅ | O | H | CH₂COOH |
| 953 | 0 | 2-Pyridylamino | CH₂CH₂COOCH₂C₆H₅ | O | H | CH₂COOH |
| 954 | 0 | 3-Isoxazoloxy | CH₂CH₂COOCH₂C₆H₅ | O | H | CH₂COOH |
| 955 | 0 | 2-Imidazoloxy | CH₂CH₂COOCH₂C₆H₅ | O | H | CH₂COOH |
| 956 | 0 | 2-Benzimidazoloxy | CH₂CH₂COOCH₂C₆H₅ | O | H | CH₂COOH |
| 957 | 0 | 2-Thiazoloxy | CH₂CH₂COOCH₂C₆H₅ | O | H | CH₂COOH |
| 958 | 0 | 5-Benzo[b]thienyloxy | CH₂CH₂COOCH₂C₆H₅ | O | H | CH₂COOH |
| 959 | 0 | 2-Thiazolylamino | CH₂CH₂COOCH₂C₆H₅ | O | H | CH₂COOH |
| 960 | 0 | 4-Imidazolylamino | CH₂CH₂COOCH₂C₆H₅ | O | H | CH₂COOH |

TABLE 48

| No. | n | R¹—Y— | R² | R³, R⁴ | R⁵ | R⁶ |
|---|---|---|---|---|---|---|
| 961 | 0 | 3-Pyrazolylamino | CH₂CH₂COOCH₂C₆H₅ | O | H | CH₂COOH |
| 962 | 0 | 3-Isoxazolylamino | CH₂CH₂COOCH₂C₆H₅ | O | H | CH₂COOH |
| 963 | 0 | 5-Isothiazolylamino | CH₂CH₂COOCH₂C₆H₅ | O | H | CH₂COOH |
| 964 | 0 | 2-Pyrimidinylamino | CH₂CH₂COOCH₂C₆H₅ | O | H | CH₂COOH |
| 965 | 0 | 3-(1,2,4-Triazolyl)amino | CH₂CH₂COOCH₂C₆H₅ | O | H | CH₂COOH |
| 966 | 0 | 4-CH₃CH(CH₃)C₆H₄O— | CH₂CH₂COOCH₂C₆H₅ | O | H | CH(CH₃)-COOH |
| 967 | 0 | 4-CH₃CH(CH₃)C₆H₄O— | CH₂CH₂COOCH₂C₆H₅ | O | H | CH(C₆H₅)-COOH |
| 968 | 0 | 4-CH₃CH(CH₃)C₆H₄O— | CH₂CH₂COOCH₂C₆H₅ | O | H | C(CH₃)₂-COOH |
| 969 | 0 | 4-CH₃CH(CH₃)C₆H₄O— | CH₂CH₂COOCH₂C₆H₅ | O | H | C(C₂H₄)-COOH |
| 970 | 0 | 4-CH₃CH(CH₃)C₆H₄O— | CH₂CH₂COOCH₂C₆H₅ | O | H | C(C₃H₆)-COOH |
| 971 | 0 | 4-CH₃CH(CH₃)C₆H₄O— | CH₂CH₂COOCH₂C₆H₅ | O | H | C(C₄H₈)-COOH |
| 972 | 0 | 4-CH₃CH(CH₃)C₆H₄O— | CH₂CH₂COOCH₂C₆H₅ | O | H | C(C₅H₁₀)-COOH |
| 973 | 0 | 4-CH₃CH(CH₃)C₆H₄O— | CH₂CH₂COOCH₂C₆H₅ | O | H | C(O)COOH |
| 974 | 0 | 4-CH₃CH(CH₃)C₆H₄O— | CH₂CH₂COOCH₂C₆H₅ | O | H | C(NOH)-COOH |
| 975 | 0 | 4-CH₃CH(CH₃)C₆H₄O— | CH₂CH₂COOCH₂C₆H₅ | O | H | C(OCH₃)₂-COOH |

TABLE 48-continued

| No. | n | R¹—Y— | R² | R³, R⁴ | R⁵ | R⁶ |
|---|---|---|---|---|---|---|
| 976 | 0 | 4-CH₃CH(CH₃)C₆H₄O— | CH₂CH₂COOCH₂C₆H₅ | O | H | C(SCH₃)₂-COOH |
| 977 | 0 | 4-CH₃CH(CH₃)C₆H₄O— | CH₂CH₂COOCH₂C₆H₅ | O | H | CH(CH₂-OH)COOH |
| 978 | 0 | 4-CH₃CH(CH₃)C₆H₄O— | CH₂CH₂COOCH₂C₆H₅ | O | H | CH(NH₂)-COOH |
| 979 | 0 | 4-CH₃CH(CH₃)C₆H₄O— | CH₂CH₂COOCH₂C₆H₅ | O | H | CH(NHC-HO)COOH |
| 980 | 0 | 4-CH₃CH(CH₃)C₆H₄O— | CH₂CH₂COOCH₂C₆H₅ | O | H | CH₂CH₂-COOH |
| 981 | 0 | 4-CH₃CH(CH₃)C₆H₄S(O)₂ | CH₂CH₂COOCH₂C₆H₅ | O | H | CH₂COOH |
| 982 | 0 | 4-CH₃CH(CH₃)C₆H₄OS(O)₂ | CH₂CH₂COOCH₂C₆H₅ | O | H | CH₂COOH |

TABLE 49

| No. | n | R¹—Y— | R² | R³, R⁴ | R⁵ | R⁶ |
|---|---|---|---|---|---|---|
| 983 | 0 | 4-CH₃CH(CH₃)C₆H₄S— | CH₂CH₂COOCH₂C₆H₅ | O | H | CH₂COOH |
| 984 | 0 | 4-CH₃CH(CH₃)C₆H₄O— | CH₂CH₂COOCH₂C₆H₅ | O | H | CH(OH)-COOH |
| 985 | 0 | 4-CH₃CH(CH₃)C₆H₄NH— | CH₂CH₂COOCH₂C₆H₅ | O | H | CH₂COOH |
| 986 | 0 | 4-CH₃CH(CH₃)C₆H₄CO— | CH₂CH₂COOCH₂C₆H₅ | O | H | CH₂COOH |
| 987 | 0 | 4-CH₃CH(CH₃)C₆H₄CH-(OH)— | CH₂CH₂COOCH₂C₆H₅ | O | H | CH₂COOH |
| 988 | 0 | 4-CH₃CH(CH₃)C₆H₄OCH₂— | CH₂CH₂COOCH₂C₆H₅ | O | H | CH₂COOH |
| 989 | 0 | 4-CH₃CH(CH₃)C₆H₄OC(O)— | CH₂CH₂COOCH₂C₆H₅ | O | H | CH₂COOH |
| 990 | 0 | 4-CH₃CH(CH₃)C₆H₄CH₂OC-(O)— | CH₂CH₂COOCH₂C₆H₅ | O | H | CH₂COOH |
| 991 | 0 | 4-CH₃CH(CH₃)C₆H₄NHC-(O)— | CH₂CH₂COOCH₂C₆H₅ | O | H | CH₂COOH |
| 992 | 0 | 4-CH₃CH(CH₃)C₆H₄OC-(O)NH— | CH₂CH₂COOCH₂C₆H₅ | O | H | CH₂COOH |
| 993 | 0 | 4-CH₃CH(CH₃)C₆H₄CH₂OC-(O)NH— | CH₂CH₂COOCH₂C₆H₅ | O | H | CH₂COOH |
| 994 | 0 | 4-CH₃CH(CH₃)C₆H₄-CONH— | CH₂CH₂COOCH₂C₆H₅ | O | H | CH₂COOH |
| 995 | 0 | 4-CH₃CH(CH₃)C₆H₄CH₂-CONH— | CH₂CH₂COOCH₂C₆H₅ | O | H | CH₂COOH |
| 996 | 0 | 4-CH₃CH(CH₃)C₆H₄CH₂-CO— | CH₂CH₂COOCH₂C₆H₅ | O | H | CH₂COOH |
| 997 | 0 | 4-CH₃CH(CH₃)C₆H₄CH₂-OCH₂— | CH₂CH₂COOCH₂C₆H₅ | O | H | CH₂COOH |
| 998 | 0 | 4-CH₃CH(CH₃)C₆H₄C-(NOH)— | CH₂CH₂COOCH₂C₆H₅ | O | H | CH₂COOH |
| 999 | 0 | 4-CH₃CH(CH₃)C₆H₄CHCH— | CH₂CH₂COOCH₂C₆H₅ | O | H | CH₂COOH |
| 1000 | 0 | 4-CH₃CH(CH₃)C₆H₄O— | CH₂CH₂COOCH₂C₆H₅ | O | H | CH(OCH₃)-COOH |
| 1001 | 0 | 4-CH₃CH(CH₃)C₆H₄CH₂— | CH₂CH₂COOCH₂C₆H₅ | O | H | CH₂COOH |
| 1002 | 0 | 4-CH₃CH(CH₃)C₆H₄O— | CH₂CH₂COOCH₂C₆H₅ | O | H | CHFCOOH |
| 1003 | 0 | 4-CH₃CH(CH₃)C₆H₄O— | CH₂CH₂COOCH₂C₆H₅ | O | H | CF₂COOH |
| 1004 | 0 | 4-CH₃CH(CH₃)C₆H₄O— | CH₂CH₂COOCH₂C₆H₅ | O | H | CH₂CH₂-NHCH₂C₆H₅ |

TABLE 50

| No. | n | R¹—Y— | R² | R³, R⁴ | R⁵ | R⁶ |
|---|---|---|---|---|---|---|
| 1005 | 0 | 4-CH₃CH(CH₃)C₆H₄O— | CH₂CH₂COOCH₂C₆H₅ | O | H | CH₂CH₂SH |
| 1006 | 0 | 4-CH₃CH(CH₃)C₆H₄O— | CH₂CH₂COOCH₂C₆H₅ | O | H | CH₂CH₂SCH₃ |
| 1007 | 0 | 4-CH₃CH(CH₃)C₆H₄O— | CH₂CH₂COOCH₂C₆H₅ | O | H | CH₂CH₂SO2CH₃ |
| 1008 | 0 | 4-CH₃CH(CH₃)C₆H₄O— | CH₂CH₂COOCH₂C₆H₅ | O | H | CH₂CH₂S(O)CH₃ |
| 1009 | 0 | 4-CH₃CH(CH₃)C₆H₄O— | CH₂CH₂COOCH₂C₆H₅ | O | H | CH₂CONH₂ |
| 1010 | 0 | 4-CH₃CH(CH₃)C₆H₄O— | CH₂CH₂COdCH₂C₆H₅ | O | H | CH₂CONHCH-(CH₃)COOH |
| 1011 | 0 | 4-CH₃CH(CH₃)C₆H₄O— | CH₂CH₂COOCH₂C₆H₅ | O | H | CH₂CONHCH-(CH₂CONH₂)-COOH |
| 1012 | 0 | 4-CH₃CH(CH₃)C₆H₄O— | CH₂CH₂COOCH₂C₆H₅ | O | H | CH₂CONHCH₃ |
| 1013 | 0 | 4-CH₃CH(CH₃)C₆H₄O— | CH₂CH₂COOCH₂C₆H₅ | O | H | CH₂CONHOH |
| 1014 | 0 | 4-CH₃CH(CH₃)C₆H₄O— | CH₂CH₂COOCH₂C₆H₅ | O | H | CH₂CON(CH₃)₂ |
| 1015 | 0 | 4-CH₃CH(CH₃)C₆H₄O— | CH₂CH₂COOCH₂C₆H₅ | O | H | CH₂CONHC₆H₅ |
| 1016 | 0 | 4-CH₃CH(CH₃)C₆H₄O— | CH₂CH₂COOCH₂C₆H₅ | O | H | CH₂COC₆H₅ |

TABLE 50-continued

| No. | n | R¹—Y— | R² | R³, R⁴ | R⁵ | R⁶ |
|---|---|---|---|---|---|---|
| 1017 | 0 | 4-CH₃CH(CH₃)C₆H₄O— | CH₂CH₂COOCH₂C₆H₅ | O | H | CH₂COCH₃ |
| 1018 | 0 | 4-CH₃CH(CH₃)C₆H₄O— | CH₂CH₂COOCH₂C₆H₅ | O | H | CH₂C(OCH₃)₂-CH₃ |
| 1019 | 0 | 4-CH₃CH(CH₃)C₆H₄O— | CH₂CH₂COOCH₂C₆H₅ | O | H | CH₂CH(OCH₃)₂ |
| 1020 | 0 | 4-CH₃CH(CH₃)C₆H₄O— | CH₂CH₂COOCH₂C₆H₅ | O | H | CH₂C(NOR)CH₃ |
| 1021 | 0 | 4-CH₃CH(CH₃)C₆H₄O— | CH₂CH₂COOCH₂C₆H₅ | O | H | CH₂CH(OH)-COOH |
| 1022 | 0 | 4-CH₃CH(CH₃)C₆H₄O— | CH₂CH₂COOCH₂C₆H₅ | O | H | CH(OH)CH₂-COOH |
| 1023 | 0 | 4-CH₃CH(CH₃)C₆H₄O— | CH₂CH₂COOCH₂C₆H₅ | O | H | CH₂CHFCOOH |
| 1024 | 0 | 4-CH₃CH(CH₃)C₆H₄O— | CH₂CH₂COOCH₂C₆H₅ | O | H | CH₂CH₂OH |
| 1025 | 0 | 4-CH₃CH(CH₃)C₆H₄O— | CH₂CH₂COOCH₂C₆H₅ | O | H | CH₂CH₂OCH₃ |
| 1026 | 0 | 4-CH₃CH(CH₃)C₆H₄O— | CH₂CH₂COOCH₂C₆H₅ | O | H | CH₂CH₂OC₆H₅ |

TABLE 51

| No. | n | R¹—Y— | R² | R³, R⁴ | R⁵ | R⁶ |
|---|---|---|---|---|---|---|
| 1027 | 0 | 4-CH₃CH(CH₃)C₆H₄O— | CH₂CH₂COOCH₂C₆H₅ | O | H | CH₂CH₂-OCH₂C₆H₅ |
| 1028 | 0 | 4-CH₃CH(CH₃)C₆H₄O— | CH₂CH₂COOCH₂C₆H₅ | O | H | CH₂CH₂F |
| 1029 | 0 | 4-CH₃CH(CH₃)C₆H₄O— | CH₂CH₂COOCH₂C₆H₅ | O | H | CH₂CH₂NH₂ |
| 1030 | 0 | 4-CH₃CH(CH₃)C₆H₄O— | CH₂CH₂COOCH₂C₆H₅ | O | H | CH₂CH₂-NHCHO |
| 1031 | 0 | 4-CH₃CH(CH₃)C₆H₄O— | CH₂CH₂COOCH₂C₆H₅ | O | H | CH₂CH₂-NHCOOCH₃ |
| 1032 | 0 | 4-CH₃CH(CH₃)C₆H₄O— | CH₂CH₂COOCH₂C₆H₅ | O | H | CH₂CH₂-N(CH₃) |
| 1033 | 0 | 4-CH₃CH(CH₃)C₆H₄O— | CH₂CH₂COOCH₂C₆H₅ | O | H | CH₂CH₂-NH(CH₃) |
| 1034 | 0 | 4-CH₃CH(CH₃)C₆H₄O— | CH₂CH₂COOCH₂C₆H₅ | O | CHCH₂ | H |
| 1035 | 0 | 4-CH₃CH(CH₃)C₆H₄O— | CH₂CH₂COOCH₂C₆H₅ | O | COCH₃ | H |
| 1036 | 0 | 4-CH₃CH(CH₃)C₆H₄O— | CH₂CH₂COOCH₂C₆H₅ | O | COC₆H₅ | H |
| 1037 | 0 | 4-CH₃CH(CH₃)C₆H₄O— | CH₂CH₂COOCH₂C₆H₅ | O | C₆H₅ | H |
| 1038 | 0 | 4-CH₃CH(CH₃)C₆H₄O— | CH₂CH₂COOCH₂C₆H₅ | O | CH₂-C₆H₅ | H |
| 1039 | 0 | 4-CH₃CH(CH₃)C₆H₄O— | CH₂CH₂COOCH₂C₆H₅ | O | Cl | CH₂COOH |
| 1040 | 0 | 4-CH₃CH(CH₃)C₆H₄O— | CH₂CH₂COOCH₂C₆H₅ | O | CN | CH₂COOH |
| 1041 | 0 | 4-CH₃CH(CH₃)C₆H₄O— | CH₂CH₂COOCH₂C₆H₅ | O | COOH | CH₂COOH |
| 1042 | 0 | 4-CH₃CH(CH₃)C₆H₄O— | CH₂CH₂COOCH₂C₆H₅ | O | CH₂-COOH | CH₂COOH |
| 1043 | 0 | 4-CH₃CH(CH₃)C₆H₄O— | CH₂CH₂COOCH₂C₆H₅ | O | CONH₂ | CH₂COOH |
| 1044 | 0 | 4-CH₃CH(CH₃)C₆H₄O— | CH₂CH₂COOCH₂C₆H₅ | O | CONH-CH₃ | CH₂COOH |
| 1045 | 0 | 4-CH₃CH(CH₃)C₆H₄O— | CH₂CH₂COOCH₂C₆H₅ | O | CH₃ | CH₂COOH |
| 1046 | 0 | 4-CH₃CH(CH₃)C₆H₄O— | CH₂CH₂COOCH₂C₆H₅ | O | CHCH₂ | CH₂COOH |
| 1047 | 0 | 4-CH₃CH(CH₃)C₆H₄O— | CH₂CH₂COOCH₂C₆H₅ | O | COCH₃ | CH₂COOH |
| 1048 | 0 | 4-CH₃CH(CH₃)C₆H₄O— | CH₂CH₂COOCH₂C₆H₅ | O | COC₆H₅ | CH₂COOH |

TABLE 52

| No. | n | R¹—Y— | R² | R³, R⁴ | R⁵ | R⁶ |
|---|---|---|---|---|---|---|
| 1049 | 0 | 4-CH₃CH(CH₃)C₆H₄O— | CH₂CH₂COOCH₂C₆H₅ | O | C₆H₅ | CH₂-COOH |
| 1050 | 0 | 4-CH₃CH(CH₃)C₆H₄O— | CH₂CH₂COOCH₂C₆H₅ | O | CH₂C₆H₅ | CH₂-COOH |
| 1051 | 0 | 4-CH₃CH(CH₃)C₆H₄O— | CH₂CH₂COOCH₂C₆H₅ | O | H | CH₂-CHO |
| 1052 | 0 | 4-CH₃CH(CH₃)C₆H₄O— | CH₂CH₂COOCH₂C₆H₅ | O | H | CH₂-CH₂O-CONH₂ |
| 1053 | 0 | 4-CH₃CH(CH₃)C₆H₄O— | CH₂CH₂COOCH₂C₆H₅ | O | H | CH₂-CH₂O-COCH₃ |
| 1054 | 0 | 4-CH₃CH(CH₃)C₆H₄O— | CH₂CH₂COOCH₂C₆H₅ | O | H | CH₂-CH₂O-COC₆H₅ |

TABLE 52-continued

| No. | n | R¹—Y— | R² | R³, R⁴ | R⁵ | R⁶ |
|---|---|---|---|---|---|---|
| 1055 | 1 | 4-CH₃CH(CH₃)C₆H₄O— | CH₂CH₂COOCH₂C₆H₅ | O | H | CH₂-COOH |
| 1056 | 2 | 4-CH₃CH(CH₃)C₆H₄O— | CH₂CH₂COOCH₂C₆H₅ | O | H | CH₂-COOH |
| 1057 | 0 | 4-CH₃CH(CH₃)C₆H₄O— | CH₂CH₂COOCH₂C₆H₅ | O | H | H |
| 1058 | 0 | 4-CH₃CH(CH₃)C₆H₄O— | CH₂CH₂COOCH₂C₆H₅ | O | Cl | H |
| 1059 | 0 | 4-CH₃CH(CH₃)C₆H₄O— | CH₂CH₂COOCH₂C₆H₅ | O | CN | H |
| 1060 | 0 | 4-CH₃CH(CH₃)C₆H₄O— | CH₂CH₂COOCH₂C₆H₅ | O | COOH | H |
| 1061 | 0 | 4-CH₃CH(CH₃)C₆H₄O— | CH₂CH₂COOCH₂C₆H₅ | O | CONH₂ | H |
| 1062 | 0 | 4-CH₃CH(CH₃)C₆H₄O— | CH₂CH₂COOCH₂C₆H₅ | O | CONHCH₃ | H |
| 1063 | 0 | 4-CH₃CH(CH₃)C₆H₄O— | CH₂CH₂COOCH₂C₆H₅ | O | CH₃ | H |

TABLE 53

| No. | n | R¹ᶜ | R¹ᵈ | R² | R³, R⁴ | R⁵ | R⁶ |
|---|---|---|---|---|---|---|---|
| 1064 | 0 | CH₃ | CH₃ | CH₂CONH₂ | O | H | CH₂COOH |
| 1065 | 0 | CH₃ | CH₃ | CH₂CONHOH | O | H | CH₂COOH |
| 1066 | 0 | CH₃ | CH₃ | CH₂CONHCH₃ | O | H | CH₂COOH |
| 1067 | 0 | CH₃ | CH₃ | CH₂CONHC2H₅ | O | H | CH₂COOH |
| 1068 | 0 | CH₃ | CH₃ | CH₂CONH-n-C₃H₇ | O | H | CH₂COOH |
| 1069 | 0 | CH₃ | CH₃ | CH₂CONH-i-C₃H₇ | O | H | CH₂COOH |
| 1070 | 0 | CH₃ | CH₃ | CH₂CON(CH₃)₂ | O | H | CH₂COOH |
| 1071 | 0 | CH₃ | CH₃ | CH₂CON(n-C₃H₇)₂ | O | H | CH₂COOH |
| 1072 | 0 | CH₃ | CH₃ | CH₂CON(C2H₅)₂ | O | H | CH₂COOH |
| 1073 | 0 | CH₃ | CH₃ | CH₂CONHC₆H₅ | O | H | CH₂COOH |
| 1074 | 0 | CH₃ | CH₃ | CH₂CH₂-COOCH₃ | O | H | CH₂COOH |
| 1075 | 0 | CH₃ | CH₃ | CH₂CH₂-COOCH₂C₆H₅ | O | H | CH₂COOH |
| 1076 | 0 | CH₃ | CH₃ | CH(CH₃)COOH | O | H | CH₂CO9H |
| 1077 | 0 | CH₃ | CH₃ | CH(CH₂OH)-COOH | O | H | CH₂COOH |
| 1078 | 0 | CH₃ | CH₃ | CH(CH₂COOH)-COOH | O | H | CH₂COOH |
| 1079 | 0 | CH₃ | CH₃ | CH(CH₂CONH₂)COOH | O | H | CH₂COOH |
| 1080 | 0 | CH₃ | CH₃ | CH(CH₂CH₂-COOH)COOH | O | H | CH₂COOH |
| 1081 | 0 | CH₃ | CH₃ | CH₂COOH | O | H | CH₂COOH |
| 1082 | 0 | CH₃ | CH₃ | CH₂CH₂COOH | O | H | CH₂COOH |
| 1083 | 0 | CH₃ | CH₃ | CH₂CH₂-COOH | O | H | CH₂COOH |
| 1084 | 0 | CH₃ | CH₃ | CH₂CH₂CH₂-CH₂COOH | O | H | CH₂COOH |
| 1085 | 0 | CH₃ | CH₃ | CH₂CH₂CH₂-CH₂CH₂COOH | O | H | CH₂COOH |

TABLE 54

| No. | n | R¹ᶜ | R¹ᵈ | R² | R³, R⁴ | R⁵ | R⁶ |
|---|---|---|---|---|---|---|---|
| 1086 | 0 | CH₃ | CH₃ | CH₂COOCH₃ | O | H | CH₂COOH |
| 1087 | 0 | CH₃ | CH₃ | CH₂COOC₂H₅ | O | H | CH₂COOH |
| 1088 | 0 | CH₃ | CH₃ | CH₂COO-n-C₃H₇ | O | H | CH₂COOH |
| 1089 | 0 | CH₃ | CH₃ | CH₂COO-i-C₃H₇ | O | H | CH₂COOH |
| 1090 | 0 | CH₃ | CH₃ | CH₂COOC₆H₅ | O | H | CH₂COOH |
| 1091 | 0 | CH₃ | CH₃ | CH₂COOCH₂C₆H₅ | O | H | CH₂COOH |
| 1092 | 0 | CH₃ | CH₃ | H | O | H | CH₂COOH |
| 1093 | 0 | CH₃ | CH₃ | CH₂F | O | H | CH₂COOH |
| 1094 | 0 | CH₃ | CH₃ | CH(i-C₃H₇)-COOH | O | H | CH₂COOH |
| 1095 | 0 | CH₃ | CH₃ | CH₂CN | O | H | CH₂COOH |
| 1096 | 0 | CH₃ | CH₃ | CH₂NO₂ | O | H | CH₂COOH |
| 1097 | 0 | CH₃ | CH₃ | CH₂COCH₃ | O | H | CH₂COOH |
| 1098 | 0 | CH₃ | CH₃ | CH₂C(OCH₃)₂CH₃ | O | H | CH₂COOH |
| 1099 | 0 | CH₃ | CH₃ | CH₂C(SCH₃)₂CH₃ | O | H | CH₂COOH |
| 1100 | 0 | CH₃ | CH₃ | C(NH)NH₂ | O | H | CH₂COOH |
| 1101 | 0 | CH₃ | CH₃ | CH₂C(NOH)CH₃ | O | H | CH₂COOH |
| 1102 | 0 | CH₃ | CH₃ | CH₂SH | O | H | CH₂COOH |
| 1103 | 0 | CH₃ | CH₃ | CH₂SO₃H | O | H | CH₂COOH |
| 1104 | 0 | CH₃ | CH₃ | CH₂S(O)₂CH₃ | O | H | CH₂COOH |
| 1105 | 0 | CH₃ | CH₃ | CH₂S(O)CH₃ | O | H | CH₂COOH |
| 1106 | 0 | CH₃ | CH₃ | CH₂S(O)₂NH₂ | O | H | CH₂COOH |
| 1107 | 0 | CH₃ | CH₃ | CH₂SO₃CH₃ | O | H | CH₂COOH |

TABLE 55

| No. | n | R¹ᶜ | R¹ᵈ | R² | R³, R⁴ | R⁵ | R⁶ |
|---|---|---|---|---|---|---|---|
| 1108 | 0 | CH₃ | CH₃ | CH₂OCH₃ | O | H | CH₂CCOH |
| 1109 | 0 | CH₃ | CH₃ | CH₂CH₂OCH₃ | O | H | CH₂COOH |
| 1110 | 0 | CH₃ | CH₃ | CH₂CH₂CH₂-OCH₃ | O | H | CH₂COOH |
| 1111 | 0 | CH₃ | CH₃ | CH₂SCH₃ | O | H | CH₂COOH |
| 1112 | 0 | CH₃ | CH₃ | CH₂CH₂SCH₃ | O | H | CH₂COOH |
| 1113 | 0 | CH₃ | CH₃ | CH₂CH₂CH₂-SCH₃ | O | H | CH₂COOH |
| 1114 | 0 | CH₃ | CH₃ | CHCH₂ | O | H | CH₂COOH |
| 1115 | 0 | CH₃ | CH₃ | CH₂CHCH₂ | O | H | CH₂COCH |
| 1116 | 0 | CH₃ | CH₃ | S(O)₂C₆C₅ | O | H | CH₂COOH |
| 1117 | 0 | CH₃ | CH₃ | Cyclopropyl | O | H | CH₂COOH |
| 1118 | 0 | CH₃ | CH₃ | Cyclobutyl | O | H | CH₂COOH |
| 1119 | 0 | CH₃ | CH₃ | Cyclopentyl | O | H | CH₂COOH |
| 1120 | 0 | CH₃ | CH₃ | Cyclohexyl | O | H | CH₂COOH |
| 1121 | 0 | CH₃ | CH₃ | CH(CH₂CH₂-CONH₂)COOH | O | H | CH₂COOH |
| 1122 | 0 | CH₃ | CH₃ | CH(4-Imidazolyl-methyl)COOH | O | H | CH₂COOH |
| 1123 | 0 | CH₃ | CH₃ | CH(CH(C₂H₅)CH₃)COOH | O | H | CH₂COOH |
| 1124 | 0 | CH₃ | CH₃ | CH(CH₂CH(CH₃)CH₃)COOH | O | H | CH₂COOH |
| 1125 | 0 | CH₃ | CH₃ | CH(CH₂CH₂-SCH₃)COOH | O | H | CH₂COOH |
| 1126 | 0 | CH₃ | CH₃ | CH(CH(OH)CH₃-)COOH | O | H | CH₂COOH |
| 1127 | 0 | CH₃ | CH₃ | CH(CH₂—(4-HO)C₆H₅)COOH | O | H | CH₂COOH |
| 1128 | 0 | CH₃ | CH₃ | CH(CH₂C₆H₅)COOH | O | H | CH₂COOH |
| 1129 | 0 | CH₃ | CH₃ | CH(3-Indolyl-methyl)COOH | O | H | CH₂COOH |
| 1130 | 0 | CH₃ | CH₃ | S(O)₂CH₃ | O | H | CH₂COOH |

TABLE 56

| No. | n | R¹ᶜ | R¹ᵈ | R² | R³, R⁴ | R⁵ | R⁶ |
|---|---|---|---|---|---|---|---|
| 1141 | 0 | $CH_3$ | $CH_3$ | $CH_2C_6H_5$ | O | H | $CH_2COOH$ |
| 1142 | 0 | $CH_3$ | $CH_3$ | $CH_2CH_2C_6H_5$ | O | H | |
| 1143 | 0 | $CH_3$ | $CH_3$ | $CH_2C_6H_{11}$ | O | H | |
| 1144 | 0 | $CH_3$ | $CH_3$ | $CH(CH_3)C_6H_5$ | O | H | $CH_2COOH$ |
| 1145 | 0 | $CH_3$ | $CH_3$ | 2-Thienylmethyl | O | H | $CH_2COOH$ |
| 1146 | 0 | $CH_3$ | $CH_3$ | 2-Furfuryl | O | H | $CH_2COOH$ |
| 1147 | 0 | $CH_3$ | $CH_3$ | 2-Pyranylmethyl | O | H | $CH_2COOH$ |
| 1148 | 0 | $CH_3$ | $CH_3$ | 1-Isobenzo-furanylmethyl | O | H | $CH_2COOH$ |
| 1149 | 0 | $CH_3$ | $CH_3$ | 2-Pyrrolylmethyl | O | H | $CH_2COOH$ |
| 1150 | 0 | $CH_3$ | $CH_3$ | 1-Imidazolyl-methyl | O | H | $CH_2COOH$ |
| 1151 | 0 | $CH_3$ | $CH_3$ | 1-Pyrazolyl-methyl | O | H | $CH_2COOH$ |
| 1152 | 0 | $CH_3$ | $CH_3$ | 3-Isothiazolyl-methyl | O | H | $CH_2COOH$ |
| 1153 | 0 | $CH_3$ | $CH_3$ | 3-Isoxazolyl-methyl | O | H | $CH_2COOH$ |
| 1154 | 0 | $CH_3$ | $CH_3$ | 2-Pyridylmethyl | O | H | $CH_2COOH$ |
| 1155 | 0 | $CH_3$ | $CH_3$ | 2-Pyrazinyl-methyl | O | H | $CH_2COOH$ |
| 1156 | 0 | $CH_3$ | $CH_3$ | 2-Pyrimidinyl-methyl | O | H | $CH_2COOH$ |
| 1157 | O | $CH_3$ | $CH_3$ | 3-Pyridazinyl-methyl | O | H | $CH_2COOH$ |
| 1158 | 0 | $CH_3$ | $CH_3$ | 1-Isoindolyl-methyl | O | H | $CH_2COOH$ |
| 1159 | 0 | $CH_3$ | $CH_3$ | 2-Indolylmethyl | O | H | $CH_2COOH$ |
| 1160 | 0 | $CH_3$ | $CH_3$ | 3-(1H-Indazolyl)-methyl | O | H | $CH_2COOH$ |
| 1161 | 0 | $CH_3$ | $CH_3$ | 2-Purinylmethyl | O | H | $CH_2COOH$ |
| 1162 | 0 | $CH_3$ | $CH_3$ | 1-Isoquinolyl-methyl | O | H | $CH_2COOH$ |

TABLE 57

| No. | n | R¹ᶜ | R¹ᵈ | R² | R³, R⁴ | R⁵ | R⁶ |
|---|---|---|---|---|---|---|---|
| 1163 | 0 | $CH_3$ | $CH_3$ | 2-Quinolylmethyl | O | H | $CH_2COOH$ |
| 1164 | 0 | $CH_3$ | $CH_3$ | 1-Phthalazinyl-methyl | O | H | $CH_2COOH$ |
| 1165 | 0 | $CH_3$ | $CH_3$ | 2-Naphthylidinyl-methyl | O | H | $CH_2COOH$ |
| 1166 | 0 | $CH_3$ | $CH_3$ | 2-Quinoxalinyl-methyl | O | H | $CH_2COOH$ |
| 1167 | 0 | $CH_3$ | $CH_3$ | 2-Quinazolinyl-methyl | O | H | $CH_2COOH$ |
| 1168 | 0 | $CH_3$ | $CH_3$ | 3-Cinnolinyl-methyl | O | H | $CH_2COOH$ |
| 1169 | 0 | $CH_3$ | $CH_3$ | 2-Oxazolylmethyl | O | H | $CH_2COOH$ |
| 1170 | 0 | $CH_3$ | $CH_3$ | 2-Thiazolyl-methyl | O | H | $CH_2COOH$ |
| 1171 | 0 | $CH_3$ | $CH_3$ | 2-Benzo[b]-furylmethyl | O | H | $CH_2COOH$ |
| 1172 | 0 | $CH_3$ | $CH_3$ | 2-Benzo[b]-thienylmethyl | O | H | $CH_2COOH$ |
| 1173 | 0 | $CH_3$ | $CH_3$ | 3-(1,2,4-Tria-zinyl)methyl | O | H | $CH_2COOH$ |
| 1174 | 0 | $CH_3$ | $CH_3$ | 2-Benz[d]-imidazolylmethyl | O | H | $CH_2COOH$ |
| 1175 | 0 | $CH_3$ | $CH_3$ | 2-Benz[d]-oxazolylmethyl | O | H | $CH_2COOH$ |
| 1176 | 0 | $CH_3$ | $CH_3$ | Phenyl | O | H | $CH_2COOH$ |
| 1177 | 0 | $CH_3$ | $CH_3$ | 2-Naphthyl | O | H | $CH_2COOH$ |
| 1178 | 0 | $CH_3$ | $CH_3$ | 2-Thiazolyl | O | H | $CH_2COOH$ |
| 1179 | 0 | $CH_3$ | $CH_3$ | 4-Imidazolyl | O | H | $CH_2COOH$ |
| 1180 | 0 | $CH_3$ | $CH_3$ | 3-Pyrazolyl | O | H | $CH_2COOH$ |
| 1181 | 0 | $CH_3$ | $CH_3$ | 3-Isoxazolyl | O | H | $CH_2COOH$ |
| 1182 | 0 | $CH_3$ | $CH_3$ | 5-Isothiazolyl | O | H | $CH_2COOH$ |
| 1183 | 0 | $CH_3$ | $CH_3$ | 2-Pyrimidinyl | O | H | $CH_2COOH$ |
| 1184 | 0 | $CH_3$ | $CH_3$ | 3-(1,2,4-Triazolyl) | O | H | $CH_2COOH$ |

TABLE 58

| No. | n | R¹ᶜ | R¹ᵈ | R² | R³, R⁴ | R⁵ | R⁶ |
|---|---|---|---|---|---|---|---|
| 1185 | 0 | $CH_3$ | $CH_3$ | 2-Pyridyl | O | H | $CH_2COOH$ |
| 1186 | 0 | $CH_3$ | $CH_3$ | 2-Benzoxa-zolyl | O | H | $CH_2COOH$ |
| 1187 | 0 | $CH_3$ | $CH_3$ | 3-Benzo-thienyl | O | H | $CH_2COOH$ |
| 1188 | 0 | $CH_3$ | $CH_3$ | 2-Benzo-furinyl | O | H | $CH_2COOH$ |
| 1189 | 0 | $CH_3$ | $CH_3$ | 5-Indolyl | O | H | $CH_2COOH$ |
| 1190 | 0 | $CH_3$ | $CH_3$ | 2-Pyrazinyl | O | H | $CH_2COOH$ |
| 1191 | 0 | $CH_3$ | $CH_3$ | 3-Quinolyl | O | H | $CH_2COOH$ |
| 1192 | 0 | $CH_3$ | $CH_3$ | 5-Tetrazolyl | O | H | $CH_2COOH$ |
| 1193 | 0 | $CH_3$ | $CH_3$ | Methyl-sulfonyl | O | H | $CH_2COOH$ |
| 1194 | 0 | $CH_3$ | $CH_3$ | Benzene-sulfonyl | O | H | $CH_2COOH$ |
| 1195 | 0 | $CH_3$ | $CH_3$ | $CH_2CONH$-$CH_2C_6H_5$ | O | H | $CH_2COOH$ |
| 1196 | 0 | $CH_3$ | $CH_3$ | $CH_2CH_2CO$-$OCH_2C_6H_5$ | O | H | $CHFCOOH$ |
| 1197 | 0 | $CH_3$ | $CH_3$ | $CH_2CH_2CO$-$OCH_2C_6H_5$ | O | H | $CF_2COOH$ |
| 1198 | 0 | $CH_3$ | $CH_3$ | $CH_2CH_2O$-$OCH_2C_6H_5$ | O | H | $CH(OH)COOH$ |
| 1199 | 0 | $CH_3$ | $CH_3$ | $CH_2CH_2CO$-$OCH_2C_6H_5$ | O | H | $CH(OCH_3)COOH$ |
| 1200 | 0 | $CH_3$ | $CH_3$ | $CH_2CH_2CO$-$OCH_2C_6H_5$ | O | H | $CH(CH_3)COOH$ |
| 1201 | 0 | $CH_3$ | $CH_3$ | $CH_2CH_2CO$-$OCH_2C_6H_5$ | O | H | $CH(C_6H_5)COOH$ |
| 1202 | 0 | $CH_3$ | $CH_3$ | $CH_2CH_2CO$-$OCH_2C_6H_5$ | O | H | $C(tH3)_2COOH$ |
| 1203 | 0 | $CH_3$ | $CH_3$ | $CH_2CH_2CO$-$OCH_2C_6H_5$ | O | H | $C(C2H_4)COOH$ |
| 1204 | 0 | $CH_3$ | $CH_3$ | $CH_2CH_2CO$-$OCH_2C_6H_5$ | O | H | $C(C_3H_6)COOH$ |
| 1205 | 0 | $CH_3$ | $CH_3$ | $CH_2CH_2CO$-$OCH_2C_6H_5$ | O | H | $C(C_4H_8)COOH$ |
| 1206 | 0 | $CH_3$ | $CH_3$ | $CH_2CH_2CO$-$OCH_2C_6H_5$ | O | H | $C(C_5H_{10})COOH$ |

TABLE 59

| No. | n | R¹ᶜ | R¹ᵈ | R² | R³, R⁴ | R⁵ | R⁶ |
|---|---|---|---|---|---|---|---|
| 1207 | 0 | $CH_3$ | $CH_3$ | $CH_2CH_2$-$COOCH_2C_6H_5$ | O | H | $COCOOH$ |
| 1208 | 0 | $CH_3$ | $CH_3$ | $CH_2CH_2$-$COOCH_2C_6H_5$ | O | H | $C(NOH)COOH$ |
| 1209 | 0 | $CH_3$ | $CH_3$ | $CH_2CH_2$-$COOCH_2C_6H_5$ | O | H | $C(OCH_3)_2$-$COOH$ |
| 1210 | 0 | $CH_3$ | $CH_3$ | $CH_2CH_2$-$COOCH_2C_6H_5$ | O | H | $C(SCH_3)_2$-$COOH$ |
| 1211 | 0 | $CH_3$ | $CH_3$ | $CH_2CH_2$-$COOCH_2C_6H_5$ | O | H | $CH(CH_2OH)$-$COOH$ |
| 1212 | 0 | $CH_3$ | $CH_3$ | $CH_2CH_2$-$COOCH_2C_6H_5$ | O | H | $CH(NH_2)$-$COOH$ |
| 1213 | 0 | $CH_3$ | $CH_3$ | $CH_2CH_2$-$COOCH_2C_6H_5$ | O | H | $CH(NHCHO)$-$COOH$ |
| 1214 | 0 | $CH_3$ | $CH_3$ | $CH_2CH_2$-$COOCH_2C_6H_5$ | O | H | $CH_2CH_2COOH$ |
| 1215 | 0 | $CH_3$ | $CH_3$ | $CH_2CH_2$-$COOCH_2C_6H_5$ | O | H | $CH_2CH(OH)$-$COOH$ |
| 1216 | 0 | $CH_3$ | $CH_3$ | $CH_2CH_2$-$COOCH_2C_6H_5$ | O | H | $CH(OH)CH_2$-$COOH$ |
| 1217 | 0 | $CH_3$ | $CH_3$ | $CH_2CH_2$-$COOCH_2C_6H_5$ | O | H | $CH_2$-$CHFCOOH$ |
| 1218 | 0 | $CH_3$ | $CH_3$ | $CH_2CH_2$-$COOCH_2C_6H_5$ | O | H | $CH_2CH_2OH$ |
| 1219 | 0 | $CH_3$ | $CH_3$ | $CH_2CH_2$-$COOCH_2C_6H_5$ | O | H | $CH_2CH_2OCH_3$ |
| 1220 | 0 | $CH_3$ | $CH_3$ | $CH_2CH_2$-$COOCH_2C_6H_5$ | O | H | $CH_2CH_2$-$OC_6H_5$ |
| 1221 | 0 | $CH_3$ | $CH_3$ | $CH_2CH_2$-$COOCH_2C_6H_5$ | O | H | $CH_2CH_2$-$OCH_2C_6H_5$ |

TABLE 59-continued

| No. | n | $R^{1c}$ | $R^{1d}$ | $R^2$ | $R^3, R^4$ | $R^5$ | $R^6$ |
|---|---|---|---|---|---|---|---|
| 1222 | 0 | $CH_3$ | $CH_3$ | $CH_2CH_2$-$COOCH_2C_6H_5$ | O | H | $CH_2CH_2F$ |
| 1223 | 0 | $CH_3$ | $CH_3$ | $CH_2CH_2$-$COOCH_2C_6H_5$ | O | H | $CH_2CH_2NH_2$ |
| 1224 | 0 | $CH_3$ | $CH_3$ | $CH_2CH_2$-$COOCH_2$-$C_6H_5$ | O | H | $CH_2CH_2$-$NHCHO$ |
| 1225 | 0 | $CH_3$ | $CH_3$ | $CH_2CH_2$-$COOCH_2C_6H_5$ | O | H | $CH_2CH_2$-$NHCOOCH_3$ |
| 1226 | 0 | $CH_3$ | $CH_3$ | $CH_2CH_2$-$COOCH_2C_6H_5$ | O | H | $CH_2CH_2$-$N(CH_3)_2$ |
| 1227 | 0 | $CH_3$ | $CH_3$ | $CH_2CH_2$-$COOCH_2C_6H_5$ | O | H | $CH_2CH_2$-$NH(CH_3)$ |
| 1228 | 0 | $CH_3$ | $CH_3$ | $CH_2CH_2$-$COOCH_2C_6H_5$ | O | H | $CH_2CH_2$-$NHCH_2C_6H_5$ |

TABLE 60

| No. | n | $R^{1c}$ | $R^{1d}$ | $R^2$ | $R^3, R^4$ | $R^5$ | $R^6$ |
|---|---|---|---|---|---|---|---|
| 1229 | 0 | $CH_3$ | $CH_3$ | $CH_2CH_2COOCH_2C_6H_5$ | O | H | $CH_2CH_2SH$ |
| 1230 | 0 | $CH_3$ | $CH_3$ | $CH_2CH_2COOCH_2C_6H_5$ | O | H | $CH_2CH_2SCH_3$ |
| 1231 | 0 | $CH_3$ | $CH_3$ | $CH_2CH_2COOCH_2C_6H_5$ | O | H | $CH_2CH_2S(O)_2CH_3$ |
| 1232 | 0 | $CH_3$ | $CH_3$ | $CH_2CH_2COOCH_2C_6H_5$ | O | H | $CH_2CH_2S(O)CH_3$ |
| 1233 | 0 | $CH_3$ | $CH_3$ | $CH_2CH_2COOCH_2C_6H_5$ | O | H | $CH_2CONH_2$ |
| 1234 | 0 | $CH_3$ | $CH_3$ | $CH_2CH_2COOCH_2C_6H_5$ | O | H | $CH_2CONCH(CH_3)COOH$ |
| 1235 | 0 | $CH_3$ | $CH_3$ | $CH_2CH_2COOCH_2C_6H_5$ | O | H | $CH_2CONHCH_3$ |
| 1236 | 0 | $CH_3$ | $CH_3$ | $CH_2CH_2COOCH_2C_6H_5$ | O | H | $CH_2CONHOH$ |
| 1237 | 0 | $CH_3$ | $CH_3$ | $CH_2CH_2COOCH_2C_6H_5$ | O | H | $CH_2CON(CH_3)_2$ |
| 1238 | 0 | $CH_3$ | $CH_3$ | $CH_2CH_2COOCH_2C_6H_5$ | O | H | $CH_2CONHC_6H_5$ |
| 1239 | 0 | $CH_3$ | $CH_3$ | $CH_2CH_2COOCH_2C_6H_5$ | O | H | $CH_2COC_6H_5$ |
| 1240 | 0 | $CH_3$ | $CH_3$ | $CH_2CH_2COOCH_2C_6H_5$ | O | H | $CH_2COCH_3$ |
| 1241 | 0 | $CH_3$ | $CH_3$ | $CH_2CH_2COOCH_2C_6H_5$ | O | H | $CH4C(OCH_3)_2CH_3$ |
| 1242 | 0 | $CH_3$ | $CH_3$ | $CH_2CH_2COOCH_2C_6H_5$ | O | H | $CH_2CH(OCH_3)_2$ |
| 1243 | 0 | $CH_3$ | $CH_3$ | $CH_2CH_2COOCH_2C_6H_5$ | O | H | $CH_2C(NOH)CH_3$ |
| 1244 | 0 | $CH_3$ | $CH_3$ | $CH_2CH_2COOCH_2C_6H_5$ | O | H | $CH_2CHO$ |
| 1245 | 0 | $CH_3$ | $CH_3$ | $CH_2CH_2COOCH_2C_6H_5$ | O | H | $CH_2CH_2OC(O)NH_2$ |
| 1246 | 0 | $CH_3$ | $CH_3$ | $CH_2CH_2COOCH_2C_6H_5$ | O | H | $CH_2CH_2OC(O)CH_3$ |
| 1247 | 0 | $CH_3$ | $CH_3$ | $CH_2CH_2COOCH_2C_6H_5$ | O | H | $CH_2CH_2OC(O)C_6H_5$ |
| 1248 | 0 | $CH_3$ | $CH_3$ | $CH_2CH_2COOCH_2C_6H_5$ | O | Cl | $CH_2COOH$ |
| 1249 | 0 | $CH_3$ | $CH_3$ | $CH_2CH_2COOCH_2C_6H_5$ | O | CN | $CH_2COOH$ |
| 1250 | 0 | $CH_3$ | $CH_3$ | $CH_2CH_2COOCH_2C_6H_5$ | O | CO-OH | $CH_2COOH$ |

TABLE 61

| No. | n | $R^{1c}$ | $R^{1d}$ | $R^2$ | $R^3, R^4$ | $R^5$ | $R^6$ |
|---|---|---|---|---|---|---|---|
| 1251 | 0 | $CH_3$ | $CH_3$ | $CH_2CH_2COOCH_2C_6H_5$ | O | $CH_2COOH$ | $CH_2COOH$ |
| 1252 | 0 | $CH_3$ | $CH_3$ | $CH_2CH_2COOCH_2C_6H_5$ | O | $CONH_2$ | $CH_2COOH$ |
| 1253 | 0 | $CH_3$ | $CH_3$ | $CH_2CH_2COOCH_2C_6H_5$ | O | $CONHCH_3$ | $CH_2COOH$ |
| 1254 | 0 | $CH_3$ | $CH_3$ | $CH_2CH_2COOCH_2C_6H_5$ | O | $CH_3$ | $CH_2COOH$ |
| 1255 | 0 | $CH_3$ | $CH_3$ | $CH_2CH_2COOCH_2C_6H_5$ | O | $CHCH_2$ | $CH_2COOH$ |
| 1256 | 0 | $CH_3$ | $CH_3$ | $CH_2CH_2COOCH_2C_6H_5$ | O | $COCH_3$ | $CH_2COOH$ |
| 1257 | 0 | $CH_3$ | $CH_3$ | $CH_2CH_2COOCH_2C_6H_5$ | O | $COC_6H_5$ | $CH_2COOH$ |
| 1258 | 0 | $CH_3$ | $CH_3$ | $CH_2CH_2COOCH_2C_6H_5$ | O | $C_6H_5$ | $CH_2COOH$ |
| 1259 | 0 | $CH_3$ | $CH_3$ | $CH_2CH_2COOCH_2C_6H_5$ | O | $CH_2C_6H_5$ | $CH_2COOH$ |
| 1260 | 0 | H | H | $CH_2CH_2COOCH_2C_6H_5$ | O | H | $CH_2COOH$ |
| 1261 | 0 | H | Cl | $CH_2CH_2COOCH_2C_6H_5$ | O | H | $CH_2COOH$ |
| 1262 | 0 | H | NC | $CH_2CH_2COOCH_2C_6H_5$ | O | H | $CH_2COOH$ |
| 1263 | 0 | H | HOC(O) | $CH_2CH_2COOCH_2C_6H_5$ | O | H | $CH_2COOH$ |
| 1264 | 0 | H | $CH_3OC(O)$ | $CH_2CH_2COOCH_2C_6H_5$ | O | H | $CH_2COOH$ |
| 1265 | 0 | H | $H_2NC(O)$ | $CH_2CH_2COOCH_2C_6H_5$ | O | H | $CH_2COOH$ |
| 1266 | 0 | H | $CH_3$ | $CH_2CH_2COOCH_2C_6H_5$ | O | H | $CH_2COOH$ |
| 1267 | 0 | H | $C_6H_5CH_2$ | $CH_2CH_2COOCH_2C_6H_5$ | O | H | $CH_2COOH$ |
| 1268 | 0 | H | $CH_3CONH$ | $CH_2CH_2COOCH_2C_6H_5$ | O | H | $CH_2COOH$ |
| 1269 | 0 | H | $CH_3O$ | $CH_2CH_2COOCH_2C_6H_5$ | O | H | $CH_2COOH$ |
| 1270 | 0 | H | $CH_2CH$ | $CH_2CH_2COOCH_2C_6H_5$ | O | H | $CH_2COOH$ |
| 1271 | 0 | H | $CH_3CHCH$ | $CH_2CH_2COOCH_2C_6H_5$ | O | H | $CH_2COOH$ |
| 1272 | 0 | H | $C_6H_5$ | $CH_2CH_2COOCH_2C_6H_5$ | O | H | $CH_2COOH$ |

TABLE 62

| No. | n | $R^{1c}$ | $R^{1d}$ | $R^2$ | $R^3, R^4$ | $R^5$ | $R^6$ |
|---|---|---|---|---|---|---|---|
| 1273 | 0 | H | 2-Pyridyl | $CH_2CH_2COOCH_2C_6H_5$ | O | H | $CH_2COOH$ |
| 1274 | 0 | Cl | $CH_3$ | $CH_2CH_2COOCH_2C_6H_5$ | O | H | $CH_2COOH$ |
| 1275 | 0 | NC | $CH_3$ | $CH_2CH_2COOCH_2C_6H_5$ | O | H | $CH_2COOH$ |
| 1276 | 0 | HOC(O) | $CH_3$ | $CH_2CH_2COOCH_2C_6H_5$ | O | H | $CH_2COOH$ |
| 1277 | 0 | $CH_3OC(O)$ | $CH_3$ | $CH_2CH_2COOCH_2C_6H_5$ | O | H | $CH_2COOH$ |
| 1278 | 0 | $H_2NC(O)$ | $CH_3$ | $CH_2CH_2COOCH_2C_6H_5$ | O | H | $CH_2COOH$ |
| 1279 | 0 | $CH_3$ | $CH_3$ | $CH_2CH_2COOCH_2C_6H_5$ | O | H | $CH_2COOH$ |
| 1280 | 0 | $C_2H_5$ | $CH_3$ | $CH_2CH_2COOCH_2C_6H_5$ | O | H | $CH_2COOH$ |
| 1281 | 0 | $CH_2CH$ | $CH_3$ | $CH_2CH_2COOCH_2C_6H_5$ | O | H | $CH_2COOH$ |
| 1282 | 0 | $CH_3CHCH$ | $CH_3$ | $CH_2CH_2COOCH_2C_6H_5$ | O | H | $CH_2COOH$ |
| 1283 | 0 | $C_6H_5$ | $CH_3$ | $CH_2CH_2COOCH_2C_6H_5$ | O | H | $CH_2COOH$ |
| 1284 | 0 | 2-Pyridyl | $CH_3$ | $CH_2CH_2COOCH_2C_6H_5$ | O | H | $CH_2COOH$ |
| 1285 | 0 | $C_6H_5$ | $C_6H_5$ | $CH_2CH_2COOCH_2C_6H_5$ | O | H | $CH_2COOH$ |
| 1286 | 0 | $C_6H_5CO$ | H | $CH_2CH_2COOCH_2C_6H_5$ | O | H | $CH_2COOH$ |
| 1287 | 0 | $CH_3CO$ | H | $CH_2CH_2COOCH_2C_6H_5$ | O | H | $CH_2COOH$ |
| 1288 | 0 | $CH_3NHCO$ | H | $CH_2CH_2COOCH_2C_6H_5$ | O | H | $CH_2COOH$ |
| 1289 | 0 | $CH_3S$ | H | $CH_2CH_2COOCH_2C_6H_5$ | O | H | $CH_2COOH$ |
| 1290 | 0 | $CH_3S(O)$ | H | $CH_2CH_2COOCH_2C_6H_5$ | O | H | $CH_2COOH$ |
| 1291 | 0 | $CH_3S(O)_2$ | H | $CH_2CH_2COOCH_2C_6H_5$ | O | H | $CH_2COOH$ |
| 1292 | 0 | $CH_3$ | H | $CH_2CH_2COOCH_2C_6H_5$ | O | H | $CH_2COOH$ |
| 1293 | 0 | $C_2H_5$ | H | $CH_2CH_2COOCH_2C_6H_5$ | O | H | $CH_2COOH$ |
| 1294 | 0 | $CH_2CH$ | H | $CH_2CH_2COOCH_2C_6H_5$ | O | H | $CH_2COOH$ |

Table 63

| No. | n | $R^{1c}$ | $R^{1d}$ | $R^2$ | $R^3, R^4$ | $R^5$ | $R^6$ |
|---|---|---|---|---|---|---|---|
| 1295 | 0 | $CH_3$-CHCH | H | $CH_2CH_2$-$COOCH_2C_6H_5$ | O | H | $CH_2COOH$ |
| 1296 | 0 | $C_6H_5$ | H | $CH_2CH_2$-$COOCH_2C_6H_5$ | O | H | $CH_2COOH$ |
| 1297 | 0 | 2-Pyridyl | H | $CH_2CH_2$-$COOCH_2C_6H_5$ | O | H | $CH_2COOH$ |
| 1298 | 1 | H | H | $CH_2CH_2$-$COOCH_2C_6H_5$ | O | H | $CH_2COOH$ |
| 1299 | 1 | $CH_3$ | $CH_3$ | $CH_2CH_2$-$COOCH_2C_6H_5$ | O | H | $CH_2COOH$ |
| 1300 | 1 | $CH_3$ | H | $CH_2CH_2$-$COOCH_2C_6H_5$ | O | H | $CH_2COOH$ |
| 1301 | 1 | $C_6H_5$ | $C_6H_5$ | $CH_2CH_2$-$COOCH_2C_6H_5$ | O | H | $CH_2COOH$ |
| 1302 | 1 | $C_6H_5$ | H | $CH_2CH_2$-$COOCH_2C_6H_5$ | O | H | $CH_2COOH$ |
| 1303 | 2 | H | H | $CH_2CH_2$-$COOCH_2C_6H_5$ | O | H | $CH_2COOH$ |
| 1304 | 2 | $CH_3$ | $CH_3$ | $CH_2CH_2$-$COOCH_2C_6H_5$ | O | H | $CH_2COOH$ |
| 1305 | 2 | $CH_3$ | H | $CH_2CH_2$-$COOCH_2C_6H_5$ | O | H | $CH_2COOH$ |
| 1306 | 2 | $C_6H_5$ | $C_6H_5$ | $CH_2CH_2$-$COOCH_2C_6H_5$ | O | H | $CH_2COOH$ |
| 1307 | 2 | $C_6H_5$ | H | $CH_2CH_2$-$COOCH_2C_6H_5$ | O | H | $CH_2COOH$ |

TABLE 64

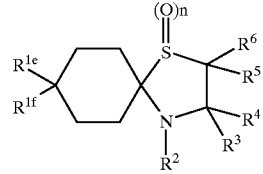

| No. | n | $R^{1e}$ | $R^{1f}$ | $R^2$ | $R^3, R^4$ | $R^5$ | $R^6$ |
|---|---|---|---|---|---|---|---|
| 1308 | 0 | F | $C_6H_5$ | $CH_2C_6H_5$ | O | H | $CH_2COOH$ |
| 1309 | 0 | Cl | $C_6H_5$ | $CH_2C_6H_5$ | O | H | $CH_2COOH$ |
| 1310 | 0 | NC | $C_6H_5$ | $CH_2C_6H_5$ | O | H | $CH_2COOH$ |
| 1311 | 0 | HOC(O) | HOC(O) | $CH_2C_6H_5$ | O | H | $CH_2COOH$ |
| 1312 | 0 | $CH_3OC(O)$ | $CH_3OC(O)$ | $CH_2C_6H_5$ | O | H | $CH_2COOH$ |
| 1313 | 0 | $(CH_3)_2NO$ | $(CH_3)_2NCO$ | $CH_2C_6H_5$ | O | H | $CH_2COOH$ |
| 1314 | 0 | HO | $C_6H_5$ | $CH_2C_6H_5$ | O | H | $CH_2COOH$ |
| 1315 | 0 | $CH_3$ | $C_6H_5$ | $CH_2C_6H_5$ | O | H | $CH_2COOH$ |
| 1316 | 0 | $C_2H_5$ | $C_6H_5$ | $CH_2C_6H_5$ | O | H | $CH_2COOH$ |
| 1317 | 0 | $CH_2CH$ | $C_6H_5$ | $CH_2C_6H_5$ | O | H | $CH_2COOH$ |
| 1318 | 0 | Cyclohexyl | $C_6H_5$ | $CH_2C_6H_5$ | O | H | $CH_2COOH$ |
| 1319 | 0 | Cyclopentyl | $C_6H_5$ | $CH_2C_6H_5$ | O | H | $CH_2COOH$ |
| 1320 | 0 | Cyclobutyl | $C_6H_5$ | $CH_2C_6H_5$ | O | H | $CH_2COOH$ |
| 1321 | 0 | $C_6H_5$ | $C_6H_5$ | $CH_2C_6H_5$ | O | H | $CH_2COOH$ |
| 1322 | 0 | $CH_3OC(O)$ | $C_6H_5$ | $CH_2C_6H_5$ | O | H | $CH_2COOH$ |

TABLE 65

| No. | n | $R^{1e}$ | $R^{1f}$ | $R^2$ | $R^3, R^4$ | $R^5$ | $R^6$ |
|---|---|---|---|---|---|---|---|
| 1323 | 0 | $CH_3S$ | $C_6H_5$ | $CH_2C_6H_5$ | O | H | $CH_2COOH$ |
| 1324 | 0 | $CH_3S(O)$ | $C_6H_5$ | $CH_2C_6H_5$ | O | H | $CH_2COOH$ |
| 1325 | 0 | $CH_3S(O)_2$ | $C_6H_5$ | $CH_2C_6H_5$ | O | H | $CH_2COOH$ |
| 1326 | 0 | $H_2N$ | $C_6H_5$ | $CH_2C_6H_5$ | O | H | $CH_2COOH$ |
| 1327 | 0 | $CH_3CONH$ | $C_6H_5$ | $CH_2C_6H_5$ | O | H | $CH_2COOH$ |
| 1328 | 0 | 2-Thienyl | $C_6H_5$ | $CH_2C_6H_5$ | O | H | $CH_2COOH$ |
| 1329 | 0 | $C_6H_5$ | HO | $CH_2C_6H_5$ | O | H | CHFCOOH |
| 1330 | 0 | $C_6H_5$ | HO | $CH_2C_6H_5$ | O | H | CF2COOH |
| 1331 | 0 | $C_6H_5$ | HO | $CH_2C_6H_5$ | O | H | CH(OH)COOH |
| 1332 | 0 | $C_6H_5$ | HO | $CH_2C_6H_5$ | O | H | $CH(OCH_3)COOH$ |
| 1333 | 0 | $C_6H_5$ | HO | $CH_2C_6H_5$ | O | H | $CH(CH_3)COOH$ |
| 1334 | 0 | $C_6H_5$ | HO | $CH_2C_6H_5$ | O | H | $CH(C_6H_5)COOH$ |
| 1335 | 0 | $C_6H_5$ | HO | $CH_2C_6H_5$ | O | H | $C(CH_3)_2COOH$ |
| 1336 | 0 | $C_6H_5$ | HO | $CH_2C_6H_5$ | O | H | $C(C_2H_4)COOH$ |
| 1337 | 0 | $C_6H_5$ | HO | $CH_2C_6H_5$ | O | H | $C(C_3H_6)COOH$ |
| 1338 | 0 | $C_6H_5$ | HO | $CH_2C_6H_5$ | O | H | $C(C_4H_8)COOH$ |
| 1339 | 0 | $C_6H_5$ | HO | $CH_2C_6H_5$ | O | H | $C(C_5H_{10})COOH$ |
| 1340 | 0 | $C_6H_5$ | HO | $CH_2C_6H_5$ | O | H | COCOOH |
| 1341 | 0 | $C_6H_5$ | HO | $CH_2C_6H_5$ | O | H | C(NOH)COOH |
| 1342 | 0 | $C_6H_5$ | HO | $CH_2C_6H_5$ | O | H | $C(OCH_3)_2COOH$ |
| 1343 | 0 | $C_6H_5$ | HO | $CH_2C_6H_5$ | O | H | $C(SCH_3)_2COOH$ |
| 1344 | 0 | $C_6H_5$ | HO | $CH_2C_6H_5$ | O | H | $CH(CH_2OH)COOH$ |

TABLE 66

| No. | n | $R^{1e}$ | $R^{1f}$ | $R^2$ | $R^3, R^4$ | $R^5$ | $R^6$ |
|---|---|---|---|---|---|---|---|
| 1345 | 0 | $C_6H_5$ | HO | $CH_2C_6H_5$ | O | H | $CH(NH_2)COOH$ |
| 1346 | 0 | $C_6H_5$ | HO | $CH_2C_6H_5$ | O | H | CH(NHCHO)COOH |
| 1347 | 0 | $C_6H_5$ | HO | $CH_2C_6H_5$ | O | H | $CH_2CH_2COOH$ |
| 1348 | 0 | $C_6H_5$ | HO | $CH_2C_6H_5$ | O | H | $CH_2CH(OH)COOH$ |
| 1349 | 0 | $C_6H_5$ | HO | $CH_2C_6H_5$ | O | H | $CH(OH)CH_2COOH$ |
| 1350 | 0 | $C_6H_5$ | HO | $CH_2C_6H_5$ | O | H | $CH_2CHFCOOH$ |
| 1351 | 0 | $C_6H_5$ | HO | $CH_2C_6H_5$ | O | H | $CH_2CH_2OH$ |
| 1352 | 0 | $C_6H_5$ | HO | $CH_2C_6H_5$ | O | H | $CH_2CH_2OCH_3$ |
| 1353 | 0 | $C_6H_5$ | HO | $CH_2C_6H_5$ | O | H | $CH_2CH_2OC_6H_5$ |
| 1354 | 0 | $C_6H_5$ | HO | $CH_2C_6H_5$ | O | H | $CH_2CH_2OCH_2C_6H_5$ |
| 1355 | 0 | $C_6H_5$ | HO | $CH_2C_6H_5$ | O | H | $CH_2CH_2F$ |
| 1356 | 0 | $C_6H_5$ | HO | $CH_2C_6H_5$ | O | H | $CH_2CH_2NH_2$ |
| 1357 | 0 | $C_6H_5$ | HO | $CH_2C_6H_5$ | O | H | $CH_2CH_2NHCHO$ |
| 1358 | 0 | $C_6H_5$ | HO | $CH_2C_6H_5$ | O | H | $CH_2CH_2NHCOOCH_3$ |
| 1359 | 0 | $C_6H_5$ | HO | $CH_2C_6H_5$ | O | H | $CH_2CH_2N(CH_3)_2$ |
| 1360 | 0 | $C_6H_5$ | HO | $CH_2C_6H_5$ | O | H | $CH_2CH_2NH(CH_3)$ |
| 1361 | 0 | $C_6H_5$ | HO | $CH_2C_6H_5$ | O | H | $CH_2CH_2NHCH_2C_6H_5$ |
| 1362 | 0 | $C_6H_5$ | HO | $CH_2C_6H_5$ | O | H | $CH_2CH_2SH$ |
| 1363 | 0 | $C_6H_5$ | HO | $CH_2C_6H_5$ | O | H | $CH_2CH_2SCH_3$ |
| 1364 | 0 | $C_6H_5$ | HO | $CH_2C_6H_5$ | O | H | $CH_2CH_2S(O)_2CH_3$ |
| 1365 | 0 | $C_6H_5$ | HO | $CH_2C_6H_5$ | O | H | $CH_2CH_2S(O)CH_3$ |
| 1366 | 0 | $C_6H_5$ | HO | $CH_2C_6H_5$ | O | H | $CH_2CONH_2$ |

Table 67

| No. | n | $R^{1e}$ | $R^{1f}$ | $R^2$ | $R^3, R^4$ | $R^5$ | $R^6$ |
|---|---|---|---|---|---|---|---|
| 1367 | 0 | $C_6H_5$ | HO | $CH_2C_6H_5$ | O | H | $CH_2CONHCH(CH_3)COOH$ |
| 1368 | 0 | $C_6H_5$ | HO | $CH_2C_6H_5$ | O | H | $CH_2CONHCH_3$ |
| 1369 | 0 | $C_6H_5$ | HO | $CH_2C_6H_5$ | O | H | $CH_2CONHOH$ |
| 1370 | 0 | $C_6H_5$ | HO | $CH_2C_6H_5$ | O | H | $CH_2CON(CH_3)_2$ |
| 1371 | 0 | $C_6H_5$ | HO | $CH_2C_6H_5$ | O | H | $CH_2CONHC_6H_5$ |
| 1372 | 0 | $C_6H_5$ | HO | $CH_2C_6H_5$ | O | H | $CH_2COC_6H_5$ |
| 1373 | 0 | $C_6H_5$ | HO | $CH_2C_6H_5$ | O | H | $CH_2COCH_3$ |
| 1374 | 0 | $C_6H_5$ | HO | $CH_2C_6H_5$ | O | H | $CH_2C(OCH_3)_2CH_3$ |
| 1375 | 0 | $C_6H_5$ | HO | $CH_2C_6H_5$ | O | H | $CH_2CH(OCH_3)_2$ |
| 1376 | 0 | $C_6H_5$ | HO | $CH_2C_6H_5$ | O | H | $CH_2C(NOH)CH_3$ |
| 1377 | 0 | $C_6H_5$ | HO | $CH_2C_6H_5$ | O | H | $CH_2CHO$ |
| 1378 | 0 | $C_6H_5$ | HO | $CH_2C_6H_5$ | O | H | $CH_2CH_2OC(O)NH_2$ |
| 1379 | 0 | $C_6H_5$ | HO | $CH_2C_6H_5$ | O | H | $CH_2CH_2OC(O)CH_3$ |
| 1380 | 0 | $C_6H_5$ | HO | $CH_2C_6H_5$ | O | H | $CH_2CH_2OC(O)C_6H_5$ |
| 1381 | 0 | $C_6H_5$ | HO | $CH_2C_6H_5$ | O | Cl | $CH_2COOH$ |
| 1382 | 0 | $C_6H_5$ | HO | $CH_2C_6H_5$ | O | CN | $CH_2COOH$ |
| 1383 | 0 | $C_6H_5$ | HO | $CH_2C_6H_5$ | O | COOH | $CH_2COOH$ |
| 1384 | 0 | $C_6H_5$ | HO | $CH_2C_6H_5$ | O | $CH_2COOH$ | $CH_2COOH$ |
| 1385 | 0 | $C_6H_5$ | HO | $CH_2C_6H_5$ | O | $CONH_2$ | $CH_2COOH$ |
| 1386 | 0 | $C_6H_5$ | HO | $CH_2C_6H_5$ | O | $CONHCH_3$ | $CH_2COOH$ |
| 1387 | 0 | $C_6H_5$ | HO | $CH_2C_6H_5$ | O | $CH_3$ | $CH_2COOH$ |
| 1388 | 0 | $C_6H_5$ | HO | $CH_2C_6H_5$ | O | $CHCH_2$ | $CH_2COOH$ |

TABLE 68

| No. | n | $R^{1e}$ | $R^{1f}$ | $R^2$ | $R^3, R^4$ | $R^5$ | $R^6$ |
|---|---|---|---|---|---|---|---|
| 1389 | 0 | $C_6H_5$ | HO | $CH_2C_6H_5$ | O | $OCH_3$ | $CH_2COOH$ |
| 1390 | 0 | $C_6H_5$ | HO | $CH_2C_6H_5$ | O | $COC_6H_5$ | $CH_2COOH$ |
| 1391 | 0 | $C_6H_5$ | HO | $CH_2C_6H_5$ | O | $C_6H_5$ | $CH_2COOH$ |
| 1392 | 0 | $C_6H_5$ | HO | $CH_2C_6H_5$ | O | $CH_2C_6H_5$ | $CH_2COOH$ |
| 1393 | 1 | HO | $C_6H_5$ | $CH_2C_6H_5$ | O | H | $CH_2COOH$ |
| 1394 | 2 | HO | $C_6H_5$ | $CH_2C_6H_5$ | O | H | $CH_2COOH$ |
| 1395 | 0 | HO | $C_6H_5$ | H | O | H | $CH_2COOH$ |
| 1396 | 0 | HO | $C_6H_5$ | $CH_3$ | O | H | $CH_2COOH$ |
| 1397 | 0 | HO | $C_6H_5$ | $C_2H_5$ | O | H | $CH_2COOH$ |
| 1398 | 0 | HO | $C_6H_5$ | $CHCH_2$ | O | H | $CH_2COOH$ |
| 1399 | 0 | HO | $C_6H_5$ | Cyclohexyl | O | H | $CH_2COOH$ |
| 1400 | 0 | HO | $C_6H_5$ | Cyclobutyl | O | H | $CH_2COOH$ |
| 1401 | 0 | HO | $C_6H_5$ | $C_6H_5$ | O | H | $CH_2COOH$ |
| 1402 | 0 | HO | $C_6H_5$ | $S(O)_2CH_3$ | O | H | $CH_2COOH$ |
| 1403 | 0 | HO | $C_6H_5$ | $S(O)_2C_6H_5$ | O | H | $CH_2COOH$ |
| 1404 | 0 | HO | $C_6H_5$ | 2-Thienyl | O | H | $CH_2COOH$ |

TABLE 69

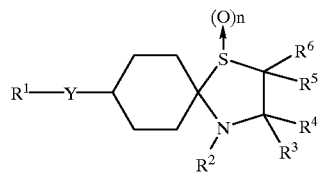

| No. | n | R¹—Y— | R² | R³ | R⁴ | R⁵ | R⁶ |
|---|---|---|---|---|---|---|---|
| 3001 | 0 | 4-CH₃CH(CH₃)C₆H₄O— | COCH₂CH₂CH(CH₃)₂ | COOH | H | H | H |
| 3002 | 0 | 4-CH₃CH(CH₃)C₆H₄O— | COCH₂CH₂CH(CH₃)₂ | COOH | H | CH₃ | CH₃ |
| 3003 | 1 | 4-CH₃CH(CH₃)C₆H₄O— | COCH₂CH₂CH(CH₃)₂ | COOH | H | H | H |
| 3004 | 1 | 4-CH₃CH(CH₃)C₆H₄O— | COCH₂CH₂CH(CH₃)₂ | COOH | H | CH₃ | CH₃ |
| 3005 | 2 | 4-CH₃CH(CH₃)C₆H₄O— | COCH₂CH₂CH(CH₃)₂ | COOH | H | H | H |
| 3006 | 2 | 4-CH₃CH(CH₃)C₆H₄O— | COCH₂CH₂CH(CH₃)₂ | COOH | H | CH₃ | CH₃ |
| 3007 | 0 | 2,3-Dihydro-1H-inden-5-yloxy | COCH₂CH₂CH(CH₃)₂ | COOH | H | H | H |
| 3009 | 0 | 2,3-Dihydro-1H-inden-5-yloxy | COCH₂CH₂CH(CH₃)₂ | COOH | H | CH₃ | CH₃ |
| 3011 | 0 | (CH₃)₂CHOC(O)— | COCH₂CH₂CH(CH₃)₂ | COOH | H | H | H |
| 3012 | 0 | (CH₃)₂CHOC(O)— | COCH₂CH₂CH(CH₃)₂ | COOH | H | CH₃ | CH₃ |
| 3013 | 0 | (CH₃)₂CHC(O)O— | COCH₂CH₂CH(CH₃)₂ | COOH | H | H | H |
| 3014 | 0 | (CH₃)₂CHC(O)O— | COCH₂CH₂CH(CH₃)₂ | COOH | H | CH₃ | CH₃ |
| 3015 | 0 | (CH₃)₂CHNHC(O)— | COCH₂CH₂CH(CH₃)₂ | COOH | H | H | H |
| 3016 | 0 | (CH₃)₂CHNHC(O)— | COCH₂CH₂CH(CH₃)₂ | COOH | H | CH₃ | CH₃ |

TABLE 70

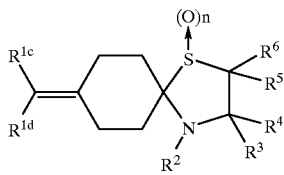

| No. | n | R¹ᶜ | R¹ᵈ | R² | R³ | R⁴ | R⁵ | R⁶ |
|---|---|---|---|---|---|---|---|---|
| 3017 | 0 | (CH₃)₂CH | H | COC₆H₅ | COOH | H | H | H |
| 3018 | 0 | (CH₃)₂CH | H | COC₆H₅ | COOH | H | CH₃ | CH₃ |
| 3019 | 0 | (CH₃)₂CHCH₂ | H | COC₆H₅ | COOH | H | H | H |
| 3020 | 0 | (CH₃)₂CHCH₂ | H | COC₆H₅ | COOH | H | CH₃ | CH₃ |
| 3021 | 0 | (CH₃)₂CHCH₂CH₂ | H | COC₆H₅ | COOH | H | H | H |
| 3022 | 0 | (CH₃)₂CHCH₂CH₂ | H | COC₆H₅ | COOH | H | CH₃ | CH₃ |
| 3023 | 0 | CH₃CH₂CH₂ | H | COC₆H₅ | COOH | H | H | H |
| 3024 | 0 | CH₃CH₂CH₂ | H | COC₆H₅ | COOH | H | CH₃ | CH₃ |
| 3025 | 0 | (CH₃)₂CH | H | COCH₂CH₂CH(CH₃)₂ | COOH | H | H | H |
| 3026 | 0 | (CH₃)₂CH | H | COCH₂CH₂CH(CH₃)₂ | COOH | H | CH₃ | CH₃ |
| 3027 | 0 | (CH₃)₂CHCH₂ | H | COCH₂CH₂CH(CH₃)₂ | COOH | H | H | H |
| 3028 | 0 | (CH₃)₂CHCH₂ | H | COCH₂CH₂CH(CH₃)₂ | COOH | H | CH₃ | CH₃ |
| 3029 | 0 | (CH₃)₂CHCH₂CH₂ | H | COCH₂CH₂CH(CH₃)₂ | COOH | H | H | H |
| 3030 | 0 | (CH₃)₂CHCH₂CH₂ | H | COCH₂CH₂CH(CH₃)₂ | COOH | H | CH₃ | CH₃ |
| 3031 | 0 | CH₃CH₂CH₂ | H | COCH₂CH₂CH(CH₃)₂ | COOH | H | H | H |

TABLE 71

| No. | n | R¹ᶜ | R¹ᵈ | R² | R³ | R⁴ | R⁵ | R⁶ |
|---|---|---|---|---|---|---|---|---|
| 3032 | 0 | CH₃CH₂CH₂ | H | COCH₂CH₂CH(CH₃)₂ | COOH | H | CH₃ | CH₃ |
| 3033 | 0 | (CH₃)₂CHCH₂ | H | COCH₂CH₂CH₂CH₃ | COOH | H | H | H |
| 3034 | 0 | (CH₃)₂CHCH₂ | H | COCH₂CH₂CH₂CH₃ | COOH | H | CH₃ | CH₃ |
| 3035 | 0 | (CH₃)₂CHCH₂ | H | COCH₂CH₂C₅H₉ | COOH | H | H | H |
| 3036 | 0 | (CH₃)₂CHCH₂ | H | COCH₂CH₂C₅H₉ | COOH | H | CH₃ | CH₃ |
| 3037 | 1 | (CH₃)₂CHCH₂ | H | COCH₂CH₂CH(CH₃)₂ | COOH | H | H | H |
| 3038 | 1 | (CH₃)₂CHCH₂ | H | COCH₂CH₂CH(CH₃)₂ | COOH | H | CH₃ | CH₃ |
| 3039 | 2 | (CH₃)₂CHCH₂ | H | COCH₂CH₂CH(CH₃)₂ | COOH | H | H | H |
| 3040 | 2 | (CH₃)₂CHCH₂ | H | COCH₂CH₂CH(CH₃)₂ | COOH | H | CH₃ | CH₃ |

TABLE 72

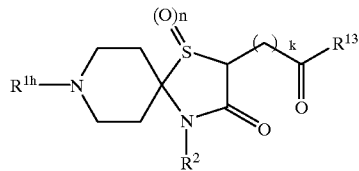

| No. | n | $R^{1h}$ | $R^2$ | $R^{13}$ | k |
|---|---|---|---|---|---|
| 2001 | 0 | 4-CH$_3$CH(CH$_3$)C$_6$H$_4$CO— | H | OH | 1 |
| 2002 | 0 | 4-CH$_3$CH(CH$_3$)C$_6$H$_4$CO— | CH$_3$ | OH | 1 |
| 2003 | 0 | 4-CH$_3$CH(CH$_3$)C$_6$H$_4$CO— | CH$_2$CH$_3$ | OH | 1 |
| 2004 | 0 | 4-CH$_3$CH(CH$_3$)C$_6$H$_4$CO— | CH$_2$CH$_2$CH$_3$ | OH | 1 |
| 2005 | 0 | 4-CH$_3$CH(CH$_3$)C$_6$H$_4$CO— | CH$_2$CH$_2$CH$_2$CH$_3$ | OH | 1 |
| 2006 | 0 | 4-CH$_3$CH(CH$_3$)C$_6$H$_4$CO— | CH$_2$CH$_2$CH$_2$CH$_2$CH$_3$ | OH | 1 |
| 2007 | 0 | 4-CH$_3$CH(CH$_3$)C$_6$H$_4$CO— | CH(CH$_3$)CH$_3$ | OH | 1 |
| 2008 | 0 | 4-CH$_3$CH(CH$_3$)C$_6$H$_4$CO— | CH$_2$CH(CH$_3$)CH$_3$ | OH | 1 |
| 2009 | 0 | 4-CH$_3$CH(CH$_3$)C$_6$H$_4$CO— | CH$_2$CH$_2$CH(CH$_3$)CH$_3$ | OH | 1 |
| 2010 | 0 | 4-CH$_3$CH(CH$_3$)C$_6$H$_4$CO— | CH$_2$CH$_2$CH$_2$CH(CH$_3$)CH$_3$ | OH | 1 |
| 2011 | 0 | 4-CH$_3$CH(CH$_3$)C$_6$H$_4$CO— | CH$_2$CH(CH$_3$)C$_2$H$_5$ | OH | 1 |
| 2012 | 0 | 4-CH$_3$CH(CH$_3$)C$_6$H$_4$CO— | CH$_2$CH$_2$CH(CH$_3$)C$_2$H$_5$ | OH | 1 |
| 2013 | 0 | 4-CH$_3$CH(CH$_3$)C$_6$H$_4$CO— | CH$_2$CH$_2$CH(C$_2$H$_5$)C$_2$H$_5$ | OH | 1 |
| 2014 | 0 | 4-CH$_3$CH(CH$_3$)C$_6$H$_4$CO— | CH$_2$F | OH | 1 |
| 2015 | 0 | 4-CH$_3$CH(CH$_3$)C$_6$H$_4$CO— | CH$_2$OH | OH | 1 |
| 2016 | 0 | 4-CH$_3$CH(CH$_3$)C$_6$H$_4$CO— | CH$_2$CH$_2$OH | OH | 1 |

TABLE 73

| No. | n | $R^{1h}$ | $R^2$ | $R^{13}$ | k |
|---|---|---|---|---|---|
| 2017 | 0 | 4-CH$_3$CH(CH$_3$)C$_6$H$_4$CO— | CH$_2$CH$_2$CH$_2$OH | OH | 1 |
| 2018 | 0 | 4-CH$_3$CH(CH$_3$)C$_6$H$_4$CO— | CH$_2$CH$_2$CH$_2$CH$_2$OH | OH | 1 |
| 2019 | 0 | 4-CH$_3$CH(CH$_3$)C$_6$H$_4$CO— | CH$_2$CH$_2$CH$_2$CH$_2$CH$_2$OH | OH | 1 |
| 2020 | 0 | 4-CH$_3$CH(CH$_3$)C$_6$H$_4$CO— | CH(OH)CH$_2$OH | OH | 1 |
| 2021 | 0 | 4-CH$_3$CH(CH$_3$)C$_6$H$_4$CO— | CH$_2$CH(OH)CH$_2$OH | OH | 1 |
| 2022 | 0 | 4-CH$_3$CH(CH$_3$)C$_6$H$_4$CO— | CH$_2$CH(OH)CH$_2$CH$_2$OH | OH | 1 |
| 2023 | 0 | 4-CH$_3$CH(CH$_3$)C$_6$H$_4$CO— | CH$_2$CH$_2$CH(OH)CH$_2$CH$_2$OH | OH | 1 |
| 2024 | 0 | 4-CH$_3$CH(CH$_3$)C$_6$H$_4$CO— | CH$_2$OC(O)NH$_2$ | OH | 1 |
| 2025 | 0 | 4-CH$_3$CH(CH$_3$)C$_6$H$_4$CO— | CH$_2$OC(O)CH$_3$ | OH | 1 |
| 2026 | 0 | 4-CH$_3$CH(CH$_3$)C$_6$H$_4$CO— | CH$_2$OC(O)CH$_2$C$_6$H$_5$ | OH | 1 |
| 2027 | 0 | 4-CH$_3$CH(CH$_3$)C$_6$H$_4$CO— | CH$_2$COOH | OH | 1 |
| 2028 | 0 | 4-CH$_3$CH(CH$_3$)C$_6$H$_4$CO— | CH$_2$CH$_2$COOH | OH | 1 |
| 2029 | 0 | 4-CH$_3$CH(CH$_3$)C$_6$H$_4$CO— | CH$_2$CH$_2$CH$_2$COOH | OH | 1 |
| 2030 | 0 | 4-CH$_3$CH(CH$_3$)C$_6$H$_4$CO— | CH$_2$CH$_2$CH$_2$CH$_2$COOH | OH | |
| 2031 | 0 | 4-CH$_3$CH(CH$_3$)C$_6$H$_4$CO— | CH$_2$CH$_2$CH$_2$CH$_2$CH$_2$COOH | OH | 1 |
| 2032 | 0 | 4-CH$_3$CH(CH$_3$)C$_6$H$_4$CO— | CH$_2$COOCH$_3$ | OH | |
| 2033 | 0 | 4-CH$_3$CH(CH$_3$)C$_6$H$_4$CO— | CH$_2$COOC$_2$H$_5$ | OH | 1 |
| 2034 | 0 | 4-CH$_3$CH(CH$_3$)C$_6$H$_4$CO— | CH$_2$COO-n-C$_3$H$_7$ | OH | 1 |
| 2035 | 0 | 4-CH$_3$CH(CH$_3$)C$_6$H$_4$CO— | CH$_2$COO-i-C$_3$H$_7$ | OH | 1 |
| 2036 | 0 | 4-CH$_3$CH(CH$_3$)C$_6$H$_4$CO— | CH$_2$COOC$_6$H$_5$ | OH | 1 |
| 2037 | 0 | 4-CH$_3$CH(CH$_3$)C$_6$H$_4$CO— | CH$_2$COOCH$_2$C$_6$H$_5$ | OH | 1 |
| 2038 | 0 | 4-CH$_3$CH(CH$_3$)C$_6$H$_4$CO— | CH$_2$CONH$_2$ | OH | 1 |

TABLE 74

| No. | n | $R^{1h}$ | $R^2$ | $R^{13}$ | k |
|---|---|---|---|---|---|
| 2039 | 0 | 4-CH$_3$CH(CH$_3$)C$_6$H$_4$CO— | CH$_2$CONHOH | OH | 1 |
| 2040 | 0 | 4-CH$_3$CH(CH$_3$)C$_6$H$_4$CO— | CH$_2$CONHCH$_3$ | OH | 1 |
| 2041 | 0 | 4-CH$_3$CH(CH$_3$)C$_6$H$_4$CO— | CH$_2$CONHC$_2$H$_5$ | OH | 1 |
| 2042 | 0 | 4-CH$_3$CH(CH$_3$)C$_6$H$_4$CO— | CH$_2$CONH-n-C$_3$H$_7$ | OH | 1 |
| 2043 | 0 | 4-CH$_3$CH(CH$_3$)C$_6$H$_4$CO— | CH$_2$CONH-i-C$_3$H$_7$ | OH | 1 |
| 2044 | 0 | 4-CH$_3$CH(CH$_3$)C$_6$H$_4$CO— | CH$_2$CON(CH$_3$)$_2$ | OH | 1 |
| 2045 | 0 | 4-CH$_3$CH(CH$_3$)C$_6$H$_4$CO— | CH$_2$CON(n-C$_3$H$_7$)$_2$ | OH | 1 |
| 2046 | 0 | 4-CH$_3$CH(CH$_3$)C$_6$H$_4$CO— | CH$_2$CON(C$_2$H$_5$)$_2$ | OH | 1 |
| 2047 | 0 | 4-CH$_3$CH(CH$_3$)C$_6$H$_4$CO— | CH$_2$CONHC$_6$H$_5$ | OH | 1 |
| 2048 | 0 | 4-CH$_3$CH(CH$_3$)C$_6$H$_4$CO— | CH$_2$CH$_2$COOCH$_3$ | OH | 1 |
| 2049 | 0 | 4-CH$_3$CH(CH$_3$)C$_6$H$_4$CO— | CH$_2$CH$_2$COOCH$_2$C$_6$H$_5$ | OH | 1 |
| 2050 | 0 | 4-CH$_3$CH(CH$_3$)C$_6$H$_4$CO— | CH(CH$_3$)COOH | OH | 1 |
| 2051 | 0 | 4-CH$_3$CH(CH$_3$)C$_6$H$_4$CO— | CH(CH$_2$OH)COOH | OH | 1 |
| 2052 | 0 | 4-CH$_3$CH(CH$_3$)C$_6$H$_4$CO— | CH(CH$_2$COOH)COOH | OH | 1 |
| 2053 | 0 | 4-CH$_3$CH(CH$_3$)C$_6$H$_4$CO— | CH(CH$_2$CONH$_2$)COOH | OH | 1 |

TABLE 74-continued

| No. | n | $R^{1h}$ | $R^2$ | $R^{13}$ | k |
|---|---|---|---|---|---|
| 2054 | 0 | 4-CH$_3$CH(CH$_3$)C$_6$H$_4$CO— | CH(CH$_2$CH$_2$COOH)COOH | OH | 1 |
| 2055 | 0 | 4-CH$_3$CH(CH$_3$)C$_6$H$_4$CO— | CH(CH$_2$CH$_2$CONH$_2$)COOH | OH | 1 |
| 2056 | 0 | 4-CH$_3$CH(CH$_3$)C$_6$H$_4$CO— | CH(4-Imidazolylmethyl)COOH | OH | 1 |
| 2057 | 0 | 4-CH$_3$CH(CH$_3$)C$_6$H$_4$CO— | CH(CH(C$_2$H$_5$)CH$_3$)COOH | OH | 1 |
| 2058 | 0 | 4-CH$_3$CH(CH$_3$)C$_6$H$_4$CO— | CH(CH$_2$CH(CH$_3$)CH$_3$)COOH | OH | 1 |
| 2059 | 0 | 4-CH$_3$CH(CH$_3$)C$_6$H$_4$CO— | CH(CH$_2$CH$_2$SCH$_3$)COOH | OH | 1 |
| 2060 | 0 | 4-CH$_3$CH(CH$_3$)C$_6$H$_4$CO— | CH(CH(OH)CH$_3$)COOH | OH | 1 |

TABLE 75

| No. | n | $R^{1h}$ | $R^2$ | $R^{13}$ | k |
|---|---|---|---|---|---|
| 2061 | 0 | 4-CH$_3$CH(CH$_3$)C$_6$H$_4$CO— | CH(CH$_2$-(4-HO)C$_6$H$_5$)COOH | OH | 1 |
| 2062 | 0 | 4-CH$_3$CH(CH$_3$)C$_6$H$_4$CO— | CH(CH$_2$C$_6$H$_5$)COOH | OH | 1 |
| 2063 | 0 | 4-CH$_3$CH(CH$_3$)C$_6$H$_4$C0— | CH(3-Indolylmethyl)COOH | OH | 1 |
| 2064 | 0 | 4-CH$_3$CH(CH$_3$)C$_6$H$_4$CO— | CH(i-C$_3$H$_7$)COOH | OH | 1 |
| 2065 | 0 | 4-CH$_3$CH(CH$_3$)C$_6$H$_4$C0— | CH$_2$CN | OH | 1 |
| 2066 | 0 | 4-CH$_3$CH(CH$_3$)C$_6$H$_4$CO— | CH$_2$NO$_2$ | OH | 1 |
| 2067 | 0 | 4-CH$_3$CH(CH$_3$)C$_6$H$_4$CO— | CH$_2$COCH$_3$ | OH | 1 |
| 2068 | 0 | 4-CH$_3$CH(CH$_3$)C$_6$H$_4$CO— | CH$_2$C(OCH$_3$)$_2$CH$_3$ | OH | 1 |
| 2069 | 0 | 4-CH$_3$CH(CH$_3$)C$_6$H$_4$CO— | CH$_2$C(SCH$_3$)$_2$CH$_3$ | OH | 1 |
| 2070 | 0 | 4-CH$_3$CH(CH$_3$)C$_6$H$_4$CO— | CH$_2$CH$_2$SH | OH | 1 |
| 2071 | 0 | 4-CH$_3$CH(CH$_3$)C$_6$H$_4$CO— | CH$_2$C(NOH)CH$_3$ | OH | 1 |
| 2072 | 0 | 4-CH$_3$CH(CH$_3$)C$_6$H$_4$CO— | CH$_2$SH | OH | 1 |
| 2073 | 0 | 4-CH$_3$CH(CH$_3$)C$_6$H$_4$CO— | CH$_2$SO$_3$H | OH | 1 |
| 2074 | 0 | 4-CH$_3$CH(CH$_3$)C$_6$H$_4$CO— | CH$_2$S(O)$_2$CH$_3$ | OH | 1 |
| 2075 | 0 | 4-CH$_3$CH(CH$_3$)C$_6$H$_4$CO— | CH$_2$S(O)CH$_3$ | OH | 1 |
| 2076 | 0 | 4-CH$_3$CH(CH$_3$)C$_6$H$_4$CO— | CH$_2$S(O)$_2$NH$_2$ | OH | 1 |
| 2077 | 0 | 4-CH$_3$CH(CH$_3$)C$_6$H$_4$CO— | CH$_2$OCH$_3$ | OH | 1 |
| 2078 | 0 | 4-CH$_3$CH(CH$_3$)C$_6$H$_4$CO— | CH$_2$CH$_2$OCH$_3$ | OH | 1 |
| 2079 | 0 | 4-CH$_3$CH(CH$_3$)C$_6$H$_4$CO— | CH$_2$CH$_2$CH$_2$OCH$_3$ | OH | 1 |
| 2080 | 0 | 4-CH$_3$CH(CH$_3$)C$_6$H$_4$CO— | CH$_2$SCH$_3$ | OH | 1 |
| 2081 | 0 | 4-CH$_3$CH(CH$_3$)C$_6$H$_4$CO— | CH$_2$CH$_2$SCH$_3$ | OH | 1 |
| 2082 | 0 | 4-CH$_3$CH(CH$_3$)C$_6$H$_4$CO— | CH$_2$CH$_2$CH$_2$SCH$_3$ | OH | 1 |

TABLE 76

| No. | n | $R^{1h}$ | $R^2$ | $R^{13}$ | k |
|---|---|---|---|---|---|
| 2083 | 0 | 4-CH$_3$CH(CH$_3$)C$_6$H$_4$CO— | CHCH$_2$ | OH | 1 |
| 2084 | 0 | 4-CH$_3$CH(CH$_3$)C$_6$H$_4$CO— | CH$_2$CHCH$_2$ | OH | 1 |
| 2085 | 0 | 4-CH$_3$CH(CH$_3$)C$_6$H$_4$CO— | Cyclopropyl | OH | 1 |
| 2086 | 0 | 4-CH$_3$CH(CH$_3$)C$_6$H$_4$CO— | Cyclobutyl | OH | 1 |
| 2087 | 0 | 4-CH$_3$CH(CH$_3$)C$_6$H$_4$CO— | Cyclopentyl | OH | 1 |
| 2088 | 0 | 4-CH$_3$CH(CH$_3$)C$_6$H$_4$CO— | Cyclohexyl | OH | 1 |
| 2089 | 0 | 4-CH$_3$CH(CH$_3$)C$_6$H$_4$CO— | CH$_2$C$_6$H$_5$ | OH | 1 |
| 2090 | 0 | 4-CH$_3$CH(CH$_3$)C$_6$H$_4$CO— | CH$_2$CH$_2$C$_6$H$_5$ | OH | 1 |
| 2091 | 0 | 4-CH$_3$CH(CH$_3$)C$_6$H$_4$CO— | CH$_2$C$_6$H$_{11}$ | OH | 1 |
| 2092 | 0 | 4-CH$_3$CH(CH$_3$)C$_6$H$_4$CO— | CH(CH$_3$)C$_6$H$_5$ | OH | 1 |
| 2093 | 0 | 4-CH$_3$CH(CH$_3$)C$_6$H$_4$CO— | 2-Thienylmethyl | OH | 1 |
| 2094 | 0 | 4-CH$_3$CH(CH$_3$)C$_6$H$_4$CO— | 2-Furfuryl | OH | 1 |
| 2095 | 0 | 4-CH$_3$CH(CH$_3$)C$_6$H$_4$Cd— | 2-Pyranylmethyl | OH | 1 |
| 2096 | 0 | 4-CH$_3$CH(CH$_3$)C$_6$H$_4$CO— | 1-Isobenzofurylmethyl | OH | 1 |
| 2097 | 0 | 4-CH$_3$CH(CH$_3$)C$_6$H$_4$CO— | 2-Pyrrolylmethyl | OH | 1 |
| 2098 | 0 | 4-CH$_3$CH(CH$_3$)C$_6$H$_4$CO— | 1-Imidazolylmethyl | OH | 1 |
| 2099 | 0 | 4-CH$_3$CH(CH$_3$)C$_6$H$_4$CO— | 1-Pyrazolylmethyl | OH | 1 |
| 2100 | 0 | 4-CH$_3$CH(CH$_3$)C$_6$H$_4$CO— | 3-Isothiazolylmethyl | OH | 1 |
| 2101 | 0 | 4-CH$_3$CH(CH$_3$)C$_6$H$_4$CO— | 3-Isoxazolylmethyl | OH | 1 |
| 2102 | 0 | 4-CH$_3$CH(CH$_3$)C$_6$H$_4$CO— | 2-Pyridylmethyl | OH | 1 |
| 2103 | 0 | 4-CH$_3$CH(CH$_3$)C$_6$H$_4$CO— | 2-Pyrazinylmethyl | OH | 1 |
| 2104 | 0 | 4-CH$_3$CH(CH$_3$)C$_6$H$_4$CO— | 2-Pyrimidinylmethyl | OH | 1 |

TABLE 77

| No. | n | $R^{1h}$ | $R^2$ | $R^{13}$ | k |
|---|---|---|---|---|---|
| 2105 | 0 | 4-CH$_3$CH(CH$_3$)C$_6$H$_4$CO— | 3-Pyridazinylmethyl | OH | 1 |
| 2106 | 0 | 4-CH$_3$CH(CH$_3$)C$_6$H$_4$CO— | 1-Isoindolylmethyl | OH | 1 |
| 2107 | 0 | 4-CH$_3$CH(CH$_3$)C$_6$H$_4$CO— | 2-Indolylmethyl | OH | 1 |
| 2108 | 0 | 4-CH$_3$CH(CH$_3$)C$_6$H$_4$CO— | 3-(1H-Indazolyl)methyl | OH | 1 |
| 2109 | 0 | 4-CH$_3$CH(CH$_3$)C$_6$H$_4$CO— | 2-Purinylmethyl | OH | 1 |
| 2110 | 0 | 4-CH$_3$CH(CH$_3$)C$_6$H$_4$CO— | 1-Isoquinolylmethyl | OH | 1 |
| 2111 | 0 | 4-CH$_3$CH(CH$_3$)C$_6$H$_4$CO— | 2-Quinolylmethyl | OH | 1 |
| 2112 | 0 | 4-CH$_3$CH(CH$_3$)C$_6$H$_4$CO— | 1-Phthalazinylmethyl | OH | 1 |
| 2113 | 0 | 4-CH$_3$CH(CH$_3$)C$_6$H$_4$CO— | 2-Napthylidinylmethyl | OH | 1 |
| 2114 | 0 | 4-CH$_3$CH(CH$_3$)C$_6$H$_4$CO— | 2-Quinoxalinylmethyl | OH | 1 |
| 2115 | 0 | 4-CH$_3$CH(CH$_3$)C$_6$H$_4$CO— | 2-Quinazolinylmethyl | OH | 1 |
| 2116 | 0 | 4-CH$_3$CH(CH$_3$)C$_6$H$_4$CO— | 3-Cinnolinylmethyl | OH | 1 |
| 2117 | 0 | 4-CH$_3$CH(CH$_3$)C$_6$H$_4$CO— | 2-Oxazolylmethyl | OH | 1 |
| 2118 | 0 | 4-CH$_3$CH(CH$_3$)C$_6$H$_4$CO— | 2-Thiazolylmethyl | OH | 1 |
| 2119 | 0 | 4-CH$_3$CH(CH$_3$)C$_6$H$_4$CO— | 2-Benzo[b]furylmethyl | OH | 1 |
| 2120 | 0 | 4-CH$_3$CH(CH$_3$)C$_6$H$_4$CO— | 2-Benzo[b]thienylmethyl | OH | 1 |
| 2121 | 0 | 4-CH$_3$CH(CH$_3$)C$_6$H$_4$CO— | 3-(1,2,4-Triazinyl)methyl | OH | 1 |
| 2122 | 0 | 4-CH$_3$CH(CH$_3$)C$_6$H$_4$CO— | 2-Benz[d]imidazolylmethyl | OH | 1 |
| 2123 | 0 | 4-CH$_3$CH(CH$_3$)C$_6$H$_4$CO— | 2-Benz[d]oxazolylmethyl | OH | 1 |
| 2124 | 0 | 4-CH$_3$CH(CH$_3$)C$_6$H$_4$CO— | Phenyl | OH | 1 |
| 2125 | 0 | 4-CH$_3$CH(CH$_3$)C$_6$H$_4$CO— | 2-Naphthyl | OH | 1 |
| 2126 | 0 | 4-CH$_3$CH(CH$_3$)C$_6$H$_4$CO— | 2-Thiazolyl | OH | 1 |

TABLE 78

| No. | n | R$^{1h}$ | R$^2$ | R$^{13}$ | k |
|---|---|---|---|---|---|
| 2127 | 0 | 4-CH$_3$CH(CH$_3$)C$_6$H$_4$CO— | 4-Imidazolyl | OH | 1 |
| 2128 | 0 | 4-CH$_3$CH(CH$_3$)C$_6$H$_4$CO— | 3-Pyrazolyl | OH | 1 |
| 2129 | 0 | 4-CH$_3$CH(CH$_3$)C$_6$H$_4$CO— | 3-Isoxazolyl | OH | 1 |
| 2130 | 0 | 4-CH$_3$CH(CH$_3$)C$_6$H$_4$CO— | 5-Isothiazolyl | OH | 1 |
| 2131 | 0 | 4-CH$_3$CH(CH$_3$)C$_6$H$_4$CO— | 2-Pyrimidinyl | OH | 1 |
| 2132 | 0 | 4-CH$_3$CH(CH$_3$)C$_6$H$_4$CO— | 3-(1,2,4-Triazolyl) | OH | 1 |
| 2133 | 0 | 4-CH$_3$CH(CH$_3$)C$_6$H$_4$CO— | 2-Pyridyl | OH | 1 |
| 2134 | 0 | 4-CH$_3$CH(CH$_3$)C$_6$H$_4$CO— | 2-Benzoxazolyl | OH | 1 |
| 2135 | 0 | 4-CH$_3$CH(CH$_3$)C$_6$H$_4$CO— | 3-Benzothienyl | OH | 1 |
| 2136 | 0 | 4-CH$_3$CH(CH$_3$)C$_6$H$_4$CO— | 2-Benzofuryl | OH | 1 |
| 2137 | 0 | 4-CH$_3$CH(CH$_3$)C$_6$H$_4$CO— | 5-Indolyl | OH | 1 |
| 2138 | 0 | 4-CH$_3$CH(CH$_3$)C$_6$H$_4$CO— | 2-Pyrazinyl | OH | 1 |
| 2139 | 0 | 4-CH$_3$CH(CH$_3$)C$_6$H$_4$CO— | 3-Quinolyl | OH | 1 |
| 2140 | 0 | 4-CH$_3$CH(CH$_3$)C$_6$H$_4$CO— | 5-Tetrazolyl | OH | 1 |
| 2141 | 0 | 4-CH$_3$CH(CH$_3$)C$_6$H$_4$CO— | CH$_2$CONHCH$_2$C$_6$H$_5$ | OH | 1 |
| 2142 | 0 | FCH$_2$ | CH$_2$CH$_2$COOCH$_2$C$_6$H$_5$ | OH | 1 |
| 2143 | 0 | HOCH$_2$ | CH$_2$CH$_2$COOCH$_2$C$_6$H$_5$ | OH | 1 |
| 2144 | 0 | HOCH$_2$CH$_2$ | CH$_2$CH$_2$COOCH$_2$C$_6$H$_5$ | OH | 1 |
| 2145 | 0 | HOCH$_2$CH$_2$CH$_2$ | CH$_2$CH$_2$COOCH$_2$C$_6$H$_5$ | OH | 1 |
| 2146 | 0 | HOCH$_2$CH$_2$CH$_2$CH$_2$ | CH$_2$CH$_2$COOCH$_2$C$_6$H$_5$ | OH | 1 |
| 2147 | 0 | HOCH$_2$CH$_2$CH$_2$CH$_2$CH$_2$ | CH$_2$CH$_2$COOCH$_2$C$_6$H$_5$ | OH | 1 |
| 2148 | 0 | HOCH$_2$CH(OH)CH$_2$ | CH$_2$CH$_2$COOCH$_2$C$_6$H$_5$ | OH | 1 |

TABLE 79

| No. | n | R$^{1h}$ | R$^2$ | R$^{13}$ | k |
|---|---|---|---|---|---|
| 2149 | 0 | HOCH$_2$CH$_2$CH(OH)-CH$_2$ | CH$_2$CH$_2$COOCH$_2$C$_6$H$_5$ | OH | 1 |
| 2150 | 0 | HOCH$_2$CH(OH)CH$_2$CH$_2$CH$_2$ | CH$_2$CH$_2$COOCH$_2$C$_6$H$_5$ | OH | 1 |
| 2151 | 0 | H$_2$NC(O)OCH$_2$ | CH$_2$CH$_2$COOCH$_2$C$_6$H$_5$ | OH | 1 |
| 2152 | 0 | CH$_3$C(O)OCH$_2$ | CH$_2$CH$_2$COOCH$_2$C$_6$H$_5$ | OH | 1 |
| 2153 | 0 | HOOCCH$_2$ | CH$_2$CH$_2$COOCH$_2$C$_6$H$_5$ | OH | 1 |
| 2154 | 0 | HOOCCH$_2$CH$_2$ | CH$_2$CH$_2$COOCH$_2$C$_6$H$_5$ | OH | 1 |
| 2155 | 0 | HOOCCH$_2$CH$_2$CH$_2$ | CH$_2$CH$_2$COOCH$_2$C$_6$H$_5$ | OH | 1 |
| 2156 | 0 | HOOCCH$_2$CH$_2$CH$_2$CH$_2$ | CH$_2$CH$_2$COOCH$_2$C$_6$H$_5$ | OH | 1 |
| 2157 | 0 | HOOCCH$_2$CH$_2$CH$_2$CH$_2$CH$_2$ | CH$_2$CH$_2$COOCH$_2$C$_6$H$_5$ | OH | 1 |
| 2158 | 0 | CH$_3$OC(O)CH$_2$ | CH$_2$CH$_2$COOCH$_2$C$_6$H$_5$ | OH | 1 |
| 2159 | 0 | C$_6$H$_5$CH$_2$OC(O)CH$_2$ | CH$_2$CH$_2$COOCH$_2$C$_6$H$_5$ | OH | 1 |
| 2160 | 0 | n-C$_3$H$_7$OC(O)CH$_2$ | CH$_2$CH$_2$COOCH$_2$C$_6$H$_5$ | OH | 1 |
| 2161 | 0 | i-C$_3$H$_7$OC(O)CH$_2$ | CH$_2$CH$_2$COOCH$_2$C$_6$H$_5$ | OH | 1 |
| 2162 | 0 | C$_6$H$_5$OC(O)CH$_2$ | CH$_2$CH$_2$COOCH$_2$C$_6$H$_5$ | OH | 1 |
| 2163 | 0 | H$_2$NC(O)CH$_2$ | CH$_2$CH$_2$COOCH$_2$C$_6$H$_5$ | OH | 1 |
| 2164 | 0 | HONHC(O)CH$_2$ | CH$_2$CH$_2$COOCH$_2$C$_6$H$_5$ | OH | 1 |
| 2165 | 0 | CH$_3$NHC(O)CH$_2$ | CH$_2$CH$_2$COOCH$_2$C$_6$H$_5$ | OH | 1 |
| 2166 | 0 | C$_2$H$_5$NHC(O)CH$_2$ | CH$_2$CH$_2$COOCH$_2$C$_6$H$_5$ | OH | 1 |
| 2167 | 0 | n-C$_3$H$_7$NHC(O)CH$_2$ | CH$_2$CH$_2$COOCH$_2$C$_6$H$_5$ | OH | 1 |
| 2168 | 0 | CH$_3$OC(O)CH$_2$CH$_2$ | CH$_2$CH$_2$COOCH$_2$C$_6$H$_5$ | OH | 1 |
| 2169 | 0 | C$_6$H$_5$OC(O)CH$_2$CH$_2$ | CH$_2$CH$_2$COOCH$_2$C$_6$H$_5$ | OH | 1 |
| 2170 | 0 | H$_2$N | CH$_2$CH$_2$COOCH$_2$C$_6$H$_5$ | OH | 1 |

TABLE 80

| No. | n | R$^{1h}$ | R$^2$ | R$^{13}$ | k |
|---|---|---|---|---|---|
| 2171 | 0 | NCCH$_2$ | CH$_2$CH$_2$COOCH$_2$C$_6$H$_5$ | OH | 1 |
| 2172 | 0 | CH$_3$COCH$_2$ | CH$_2$CH$_2$COOCH$_2$C$_6$H$_5$ | OH | 1 |
| 2173 | 0 | CH$_3$C(OCH$_3$)$_2$CH$_2$ | CH$_2$CH$_2$COOCH$_2$C$_6$H$_5$ | OH | 1 |
| 2174 | 0 | CH$_3$C(SCH$_3$)$_2$CH$_2$ | CH$_2$CH$_2$COOCH$_2$C$_6$H$_5$ | OH | 1 |
| 2175 | 0 | CH$_3$C(NOH)CH$_2$ | CH$_2$CH$_2$COOCH$_2$C$_6$H$_5$ | OH | 1 |
| 2176 | 0 | NSCH$_2$ | CH$_2$CH$_2$COOCH$_2$C$_6$H$_5$ | OH | 1 |
| 2177 | 0 | CH$_3$S(O)$_2$CH$_2$ | CH$_2$CH$_2$COOCH$_2$C$_6$H$_5$ | OH | 1 |
| 2178 | 0 | H$_2$NS(O)$_2$CH$_2$ | CH$_2$CH$_2$COOCH$_2$C$_6$H$_5$ | OH | 1 |
| 2179 | 0 | CH$_3$CH$_2$S(O)$_2$CH$_2$ | CH$_2$CH$_2$COOCH$_2$C$_6$H$_5$ | OH | 1 |
| 2180 | 0 | CH$_3$OCH$_2$ | CH$_2$CH$_2$COOCH$_2$C$_6$H$_5$ | OH | 1 |
| 2181 | 0 | CH$_3$OCH$_2$CH$_2$ | CH$_2$CH$_2$COOCH$_2$C$_6$H$_5$ | OH | 1 |
| 2182 | 0 | CH$_3$OCH$_2$CH$_2$CH$_2$ | CH$_2$CH$_2$COOCH$_2$C$_6$H$_5$ | OH | 1 |
| 2183 | 0 | CH$_3$SCH$_2$ | CH$_2$CH$_2$COOCH$_2$C$_6$H$_5$ | OH | 1 |
| 2184 | 0 | CH$_3$SCH$_2$CH$_2$ | CH$_2$CH$_2$COOCH$_2$C$_6$H$_5$ | OH | 1 |
| 2185 | 0 | CH$_3$SCH$_2$CH$_2$CH$_2$ | CH$_2$CH$_2$COOCH$_2$C$_6$H$_5$ | OH | 1 |
| 2186 | 0 | C$_6$H$_5$CH$_2$ | CH$_2$CH$_2$COOCH$_2$C$_6$H$_5$ | OH | 1 |
| 2187 | 0 | C$_6$H$_5$CH$_2$CH$_2$ | CH$_2$CH$_2$COOCH$_2$C$_6$H$_5$ | OH | 1 |
| 2188 | 0 | C$_6$H$_{11}$CH$_2$ | CH$_2$CH$_2$COOCH$_2$C$_6$H$_5$ | OH | 1 |
| 2189 | 0 | 2-Thienylmethyl | CH$_2$CH$_2$COOCH$_2$C$_6$H$_5$ | OH | 1 |
| 2190 | 0 | 2-Furfuryl | CH$_2$CH$_2$COOCH$_2$C$_6$H$_5$ | OH | 1 |
| 2191 | 0 | 2-Pyranylmethyl | CH$_2$CH$_2$COOCH$_2$C$_6$H$_5$ | OH | 1 |
| 2192 | 0 | 1-Isobenzofurylmethyl | CH$_2$CH$_2$COOCH$_2$C$_6$H$_5$ | OH | 1 |

TABLE 81

| No. | n | R$^{1h}$ | R$^2$ | R$^{13}$ | k |
|---|---|---|---|---|---|
| 2193 | 0 | 2-Pyrrolylmethyl | CH$_2$CH$_2$COOCH$_2$C$_6$H$_5$ | OH | 1 |
| 2194 | 0 | 1-Imidazolylmethyl | CH$_2$CH$_2$COOCH$_2$C$_6$H$_5$ | OH | 1 |
| 2195 | 0 | 1-Pyrazolylmethyl | CH$_2$CH$_2$COOCH$_2$C$_6$H$_5$ | OH | 1 |
| 2196 | 0 | 3-Isothiazolylmethyl | CH$_2$CH$_2$COOCH$_2$C$_6$H$_5$ | OH | 1 |
| 2197 | 0 | 3-Isoxazolylmethyl | CH$_2$CH$_2$COOCH$_2$C$_6$H$_5$ | OH | 1 |
| 2198 | 0 | 2-Pyridylmethyl | CH$_2$CH$_2$COOCH$_2$C$_6$H$_5$ | OH | 1 |
| 2199 | 0 | 2-Pyrazinylmethyl | CH$_2$CH$_2$COOCH$_2$C$_6$H$_5$ | OH | 1 |
| 2200 | 0 | 2-Pyrimidinylmethyl | CH$_2$CH$_2$COOCH$_2$C$_6$H$_5$ | OH | 1 |
| 2201 | 0 | 3-Pyridazinylmethyl | CH$_2$CH$_2$COOCH$_2$C$_6$H$_5$ | OH | 1 |
| 2202 | 0 | 1-Isoindolyl-methyl | CH$_2$CH$_2$COOCH$_2$C$_6$H$_5$ | OH | 1 |
| 2203 | 0 | 2-Indolylmethyl | CH$_2$CH$_2$COOCH$_2$C$_6$H$_5$ | OH | 1 |
| 2204 | 0 | 3-(1H-Indazolyl)-methyl | CH$_2$CH$_2$COOCH$_2$C$_6$H$_5$ | OH | 1 |
| 2205 | 0 | 2-Purinylmethyl | CH$_2$CH$_2$COOCH$_2$C$_6$H$_5$ | OH | 1 |
| 2206 | 0 | 1-Isoquinolylmethyl | CH$_2$CH$_2$COOCH$_2$C$_6$H$_5$ | OH | 1 |
| 2207 | 0 | 2-Quinolylmethyl | CH$_2$CH$_2$COOCH$_2$C$_6$H$_5$ | OH | 1 |
| 2208 | 0 | 1-Phthalazinylmethyl | CH$_2$CH$_2$COOCH$_2$C$_6$H$_5$ | OH | 1 |
| 2209 | 0 | 2-Naphthylidinyl-methyl | CH$_2$CH$_2$COOCH$_2$C$_6$H$_5$ | OH | 1 |
| 2210 | 0 | 2-Quinoxalinylmethyl | CH$_2$CH$_2$COOCH$_2$C$_6$H$_5$ | OH | 1 |
| 2211 | 0 | 2-Quinazolinylmethyl | CH$_2$CH$_2$COOCH$_2$C$_6$H$_5$ | OH | 1 |
| 2212 | 0 | 3-Cinnolinylmethyl | CH$_2$CH$_2$COOCH$_2$C$_6$H$_5$ | OH | 1 |
| 2213 | 0 | 2-Oxazolylmethyl | CH$_2$CH$_2$COOCH$_2$C$_6$H$_5$ | OH | 1 |
| 2214 | 0 | 2-Thiazolylmethyl | CH$_2$CH$_2$COOCH$_2$C$_6$H$_5$ | OH | 1 |

TABLE 82

| No. | n | R$^{1h}$ | R$^2$ | R$^{13}$ | k |
|---|---|---|---|---|---|
| 2215 | 0 | 2-Benzo[b]furylmethyl | CH$_2$CH$_2$COOCH$_2$C$_6$H$_5$ | OH | 1 |
| 2216 | 0 | 2-Benzo[b]thienylmethyl | CH$_2$CH$_2$COOCH$_2$C$_6$H$_5$ | OH | 1 |
| 2217 | 0 | 3-(1,2,4-triazinyl)methyl | CH$_2$CH$_2$COOCH$_2$C$_6$H$_5$ | OH | 1 |
| 2218 | 0 | 2-Benz[d]imidazolylmethyl | CH$_2$CH$_2$COOCH$_2$C$_6$H$_5$ | OH | 1 |
| 2219 | 0 | 2-Benz[d]oxazolylmethyl | CH$_2$CH$_2$COOCH$_2$C$_6$H$_5$ | OH | 1 |
| 2220 | 0 | C$_6$H$_5$CO | CH$_2$CH$_2$COOCH$_2$C$_6$H$_5$ | OH | 1 |
| 2221 | 0 | CH$_3$CO | CH$_2$CH$_2$COOCH$_2$C$_6$H$_5$ | OH | 1 |
| 2222 | 0 | CH$_3$CH$_2$CO | CH$_2$CH$_2$CO9CH$_2$C$_6$H$_5$ | OH | 1 |
| 2223 | 0 | CH$_3$CH$_2$CH$_2$CO | CH$_2$CH$_2$COOCH$_2$C$_6$H$_5$ | OH | 1 |
| 2224 | 0 | CH$_3$CH$_2$CH$_2$CH$_2$CO | CH$_2$CH$_2$COOCH$_2$C$_6$H$_5$ | OH | 1 |
| 2225 | 0 | CH$_3$CH$_2$CH$_2$CH$_2$CH$_2$CO | CH$_2$CH$_2$COOCH$_2$C$_6$H$_5$ | OH | 1 |
| 2226 | 0 | CH$_3$CH(CH$_3$)CO | CH$_2$CH$_2$COOCH$_2$C$_6$H$_5$ | OH | 1 |
| 2227 | 0 | CH$_3$CH$_2$CH(CH$_3$)CO | CH$_2$CH$_2$COOCH$_2$C$_6$H$_5$ | OH | 1 |
| 2228 | 0 | C$_6$H$_5$CH$_2$CO | CH$_2$CH$_2$COOCH$_2$C$_6$H$_5$ | OH | 1 |
| 2229 | 0 | H$_2$NCH(CH$_2$OH)CO | CH$_2$CH$_2$COOCH$_2$C$_6$H$_5$ | OH | 1 |
| 2230 | 0 | H$_2$NCH(CH$_2$COOH)CO | CH$_2$CH$_2$COOCH$_2$C$_6$H$_5$ | OH | 1 |
| 2231 | 0 | H$_2$NCH(CH$_2$CONH$_2$)CO | CH$_2$CH$_2$COOCH$_2$C$_6$H$_5$ | OH | 1 |
| 2232 | 0 | H$_2$NCH(CH$_2$CH$_2$COOH)CO | CH$_2$CH$_2$COOCH$_2$C$_6$H$_5$ | OH | 1 |
| 2233 | 0 | H$_2$NCH(CH$_2$CH$_2$CONH$_2$)CO | CH$_2$CH$_2$COOCH$_2$C$_6$H$_5$ | OH | 1 |
| 2234 | 0 | H$_2$NCH(4-imidazolylmethyl)CO | CH$_2$CH$_2$COOCH$_2$C$_6$H$_5$ | OH | 1 |
| 2235 | 0 | H$_2$NCH(CH(C$_2$H$_5$)CH$_3$)CO | CH$_2$CH$_2$COOCH$_2$C$_6$H$_5$ | OH | 1 |
| 2236 | 0 | H$_2$NCH(CH$_2$CH(CH$_3$)CH$_3$)CO | CH$_2$CH$_2$COOCH$_2$C$_6$H$_5$ | OH | 1 |

TABLE 83

| No. | n | R$^{1n}$ | R$^2$ | R$^{13}$ | k |
|---|---|---|---|---|---|
| 2237 | 0 | H$_2$NCH(CH$_2$CH$_2$SCH$_3$)CO | CH$_2$CH$_2$COOCH$_2$C$_6$H$_5$ | OH | 1 |
| 2238 | 0 | H$_2$NCH(CH(OH)CH$_3$)CO | CH$_2$CH$_2$COOCH$_2$C$_6$H$_5$ | OH | 1 |
| 2239 | 0 | H$_2$NCH(CH$_2$-(4-HO)C$_6$H$_5$)CO | CH$_2$CH$_2$COOCH$_2$C$_6$H$_5$ | OH | 1 |
| 2240 | 0 | H$_2$NCH(CH$_2$C$_6$H$_5$)CO | CH$_2$CH$_2$COOCH$_2$C$_6$H$_5$ | OH | 1 |
| 2241 | 0 | H$_2$NCH(3-indolylmethyl)CO | CH$_2$CH$_2$COOCH$_2$C$_6$H$_5$ | OH | 1 |
| 2242 | 0 | 2-Thienylmethylcarbonyl | CH$_2$CH$_2$COOCH$_2$C$_6$H$_5$ | OH | 1 |
| 2243 | 0 | 2-Furfurylcarbonyl | CH$_2$CH$_2$COOCH$_2$C$_6$H$_5$ | OH | 1 |
| 2244 | 0 | 2-Pyridylmethylcarbonyl | CH$_2$CH$_2$COOCH$_2$C$_6$H$_5$ | OH | 1 |
| 2245 | 0 | 2-Quinolylmethylcarbonyl | CH$_2$CH$_2$COOCH$_2$C$_6$H$_5$ | OH | 1 |
| 2246 | 0 | 2-Benzothienylmethylcarbonyl | CH$_2$CH$_2$COOCH$_2$C$_6$H$_5$ | OH | 1 |
| 2247 | 0 | 2-Naphthylidinylmethylcarbonyl | CH$_2$CH$_2$COOCH$_2$C$_6$H$_5$ | OH | 1 |
| 2248 | 0 | 2-Thiazolylmethylcarbonyl | CH$_2$CH$_2$COOCH$_2$C$_6$H$_5$ | OH | 1 |
| 2249 | 0 | 2-Pyrimidinylmethylcarbonyl | CH$_2$CH$_2$COOCH$_2$C$_6$H$_5$ | OH | 1 |
| 2250 | 0 | 2-Benzoxazolylmethylcarbonyl | CH$_2$CH$_2$COOCH$_2$C$_6$H$_5$ | OH | 1 |
| 2251 | 0 | 2-Indolylmethylcarbonyl | CH$_2$CH$_2$COOCH$_2$C$_6$H$_5$ | OH | 1 |
| 2252 | 0 | 2-Thiazolylcarbonyl | CH$_2$CH$_2$COOCH$_2$C$_6$H$_5$ | OH | 1 |
| 2253 | 0 | 2-Pyrimidinylcarbonyl | CH$_2$CH$_2$COOCH$_2$C$_6$H$_5$ | OH | 1 |
| 2254 | 0 | 2-Indolylcarbonyl | CH$_2$CH$_2$COOCH$_2$C$_6$H$_5$ | OH | 1 |
| 2255 | 0 | 2-Benzothienylcarbonyl | CH$_2$CH$_2$COOCH$_2$C$_6$H$_5$ | OH | 1 |
| 2256 | 0 | 5-Quinolylcarbonyl | CH$_2$CH$_2$COOCH$_2$C$_6$H$_5$ | OH | 1 |

TABLE 83-continued

| No. | n | R$^{1n}$ | R$^2$ | R$^{13}$ | k |
|---|---|---|---|---|---|
| 2257 | 0 | 4-CH$_3$CH(CH$_3$)C$_6$H$_4$CO— | S(O)$_2$CH$_3$ | OH | 1 |
| 2258 | 0 | 4-CH$_3$CH(CH$_3$)C$_6$H$_4$CO— | S(O)$_2$C$_6$H$_5$ | OH | 1 |

TABLE 84

| No. | n | R$^{1h}$ | R$^2$ | R$^{13}$ | k |
|---|---|---|---|---|---|
| 2259 | 0 | 4-CH$_3$CH(CH$_3$)C$_6$H$_4$SO$_2$— | CH$_2$CH$_2$COOCH$_2$C$_6$H$_5$ | OH | 1 |
| 2260 | 0 | 4-CH$_3$CH(CH$_3$)C$_6$H$_4$SO$_2$— | S(O)$_2$CH$_3$ | OH | 1 |
| 2261 | 0 | 4-CH$_3$CH(CH$_3$)C$_6$H$_4$SO$_2$— | S(O)$_2$C$_6$H$_5$ | OH | 1 |
| 2262 | 0 | 4-CH$_3$CH(CH$_3$)C$_6$H$_4$SO$_2$— | H | OH | 2 |
| 2263 | 0 | 4-CH$_3$CH(CH$_3$)C$_6$H$_4$CO— | CH$_2$CH$_2$OH | OH | 2 |
| 2264 | 0 | 4-CH$_3$CH(CH$_3$)C$_6$H$_4$CO— | CH$_2$OCONH$_2$ | OH | 2 |
| 2265 | 0 | 4-CH$_3$CH(CH$_3$)C$_6$H$_4$CO— | CH$_2$OCOCH$_3$ | OH | 2 |
| 2266 | 0 | 4-CH$_3$CH(CH$_3$)C$_6$H$_4$CO— | CH$_2$COOH | OH | 2 |
| 2267 | 0 | 4-CH$_3$CH(CH$_3$)C$_6$H$_4$CO— | CH$_2$CONH$_2$ | OH | 2 |
| 2268 | 0 | 4-CH$_3$CH(CH$_3$)C$_6$H$_4$CO— | CH$_2$CH$_2$C$_6$H$_5$ | OH | 3 |
| 2269 | 1 | 4-CH$_3$CH(CH$_3$)C$_6$H$_4$CO— | H | OH | 1 |
| 2270 | 1 | 4-CH$_3$CH(CH$_3$)C$_6$H$_4$CO— | CH$_2$CH$_2$OH | OH | 1 |
| 2271 | 1 | 4-CH$_3$CH(CH$_3$)C$_6$H$_4$CO— | CH$_2$OCONH$_2$ | OH | 1 |
| 2272 | 1 | 4-CH$_3$CH(CH$_3$)C$_6$H$_4$CO— | CH$_2$OC(O)CH$_3$ | OH | 1 |
| 2273 | 1 | 4-CH$_3$CH(CH$_3$)C$_6$H$_4$CO— | CH$_2$COOH | OH | 1 |
| 2274 | 1 | 4-CH$_3$CH(CH$_3$)C$_6$H$_4$CO— | CH$_2$CONH$_2$ | OH | 1 |
| 2275 | 1 | 4-CH$_3$CH(CH$_3$)C$_6$H$_4$CO— | CH$_2$S(O)$_2$CH$_3$ | OH | 1 |
| 2276 | 2 | 4-CH$_3$CH(CH$_3$)C$_6$H$_4$CO— | H | OH | 1 |
| 2277 | 2 | 4-CH$_3$CH(CH$_3$)C$_6$H$_4$CO— | CH$_2$CH$_2$OH | OH | 1 |
| 2278 | 2 | 4-CH$_3$CH(CH$_3$)C$_6$H$_4$CO— | CH$_2$OCONH$_2$ | OH | 1 |
| 2279 | 2 | 4-CH$_3$CH(CH$_3$)C$_6$H$_4$CO— | CH$_2$OC(O)CH$_3$ | OH | 1 |
| 2280 | 2 | 4-CH$_3$CH(CH$_3$)C$_6$H$_4$CO— | CH$_2$COOH | OH | 1 |

TABLE 85

| No. | n | R$^{1h}$ | R$^2$ | R$^{13}$ | k |
|---|---|---|---|---|---|
| 2281 | 2 | 4-CH$_3$CH(CH$_3$)C$_6$H$_4$CO— | CH$_2$CONH$_2$ | OH | 1 |
| 2282 | 2 | 4-CH$_3$CH(CH$_3$)C$_6$H$_4$CO— | CH$_2$S(O)$_2$CH$_3$ | OH | 1 |
| 2283 | 0 | 4-CH$_3$CH(CH$_3$)C$_6$H$_4$CO— | CH$_2$CH$_2$C$_6$H$_5$ | H | 1 |
| 2284 | 0 | 4-CH$_3$CH(CH$_3$)C$_6$H$_4$CO— | CH$_2$CH$_2$C$_6$H$_5$ | Cl | 1 |
| 2285 | 0 | 4-CH$_3$CH(CH$_3$)C$_6$H$_4$CO— | CH$_2$CH$_2$C$_6$H$_5$ | OCH$_3$ | 1 |
| 2286 | 0 | 4-CH$_3$CH(CH$_3$)C$_6$H$_4$CO— | CH$_2$CH$_2$C$_6$H$_5$ | OC$_2$H$_5$ | 1 |
| 2287 | 0 | 4-CH$_3$CH(CH$_3$)C$_6$H$_4$CO— | CH$_2$CH$_2$C$_6$H$_5$ | OC$_6$H$_5$ | 1 |
| 2288 | 0 | 4-CH$_3$CH(CH$_3$)C$_6$H$_4$CO— | CH$_2$CH$_2$C$_6$H$_5$ | OCH$_2$C$_6$H$_5$ | 1 |
| 2289 | 0 | 4-CH$_3$CH(CH$_3$)C$_6$H$_4$CO— | CH$_2$CH$_2$C$_6$H$_5$ | SCH$_3$ | 1 |
| 2290 | 0 | 4-CH$_3$CH(CH$_3$)C$_6$H$_4$CO— | CH$_2$CH$_2$C$_6$H$_5$ | NH$_2$ | 1 |
| 2291 | 0 | 4-CH$_3$CH(CH$_3$)C$_6$H$_4$CO— | CH$_2$CH$_2$C$_6$H$_5$ | NHOH | 1 |
| 2292 | 0 | 4-CH$_3$CH(CH$_3$)C$_6$H$_4$CO— | CH$_2$CH$_2$C$_6$H$_5$ | NHCH$_3$ | 1 |
| 2293 | 0 | 4-CH$_3$CH(CH$_3$)C$_6$H$_4$CO— | CH$_2$CH$_2$C$_6$H$_5$ | N(CH$_3$)$_2$ | 1 |
| 2294 | 0 | 4-CH$_3$CH(CH$_3$)C$_6$H$_4$CO— | CH$_2$CH$_2$C$_6$H$_5$ | NHCH$_2$C$_6$H$_5$ | 1 |
| 2295 | 0 | 4-CH$_3$CH(CH$_3$)C$_6$H$_4$CO— | CH$_2$CH$_2$C$_6$H$_5$ | NHC$_6$H$_5$ | 1 |
| 2296 | 0 | 4-CH$_3$CH(CH$_3$)C$_6$H$_4$CO— | CH$_2$CH$_2$C$_6$H$_5$ | CH$_3$ | 1 |
| 2297 | 0 | 4-CH$_3$CH(CH$_3$)C$_6$H$_4$CO— | CH$_2$CH$_2$C$_6$H$_5$ | C$_2$H$_5$ | 1 |
| 2298 | 0 | 4-CH$_3$CH(CH$_3$)C$_6$H$_4$CO— | CH$_2$CH$_2$C$_6$H$_5$ | C$_6$H$_5$ | 1 |
| 2299 | 0 | 4-CH$_3$CH(CH$_3$)C$_6$H$_4$CO— | CH$_2$CH$_2$C$_6$H$_5$ | CH$_2$C$_6$H$_5$ | 1 |
| 2300 | 0 | 4-CH$_3$CH(CH$_3$)C$_6$H$_4$CO— | CH$_2$CH$_2$C$_6$H$_5$ | 2-Thienyl | 1 |
| 2301 | 0 | 4-CH$_3$CH(CH$_3$)C$_6$H$_4$CO— | CH$_2$CH$_2$C$_6$H$_5$ | NHCH(CH$_3$)COOH | 1 |
| 2302 | 0 | 4-CH$_3$CH(CH$_3$)C$_6$H$_4$CO— | CH$_2$CH$_2$C$_6$H$_5$ | NHCH(CH$_3$)CONH$_2$ | 1 |
| 2303 | 0 | 4-CH$_3$CH(CH$_3$)C$_6$H$_4$CO— | CH$_2$CH$_2$C$_6$H$_5$ | NHCH(CH$_2$COOH)COOH | 1 |
| 2304 | 0 | 4-CH$_3$CH(CH$_3$)C$_6$H$_4$CO— | CH$_2$CH$_2$C$_6$H$_5$ | NHCH(CH$_2$C$_6$H$_5$)COOH | 1 |

TABLE 86

| No. | n | R$^{1h}$ | R$^2$ | R$^{13}$ | k |
|---|---|---|---|---|---|
| 2305 | 0 | 4-CH$_3$CH(CH$_3$)C$_6$H$_4$CO- | CH$_2$CH$_2$C$_6$H$_5$ | Leu-Leu-OH | 1 |
| 2306 | 0 | 4-CH$_3$CH(CH$_3$)C$_6$H$_4$CO- | CH$_2$CH$_2$C$_6$H$_5$ | Leu-Ala-Leu-OH | 1 |
| 2307 | 0 | OHC- | CH$_2$CH$_2$C$_6$H$_5$ | OH | 1 |
| 2308 | 0 | HOCH$_2$- | CH$_2$CH$_2$C$_6$H$_5$ | OH | 1 |
| 2309 | 0 | H$_2$N- | CH$_2$CH$_2$C$_6$H$_5$ | OH | 1 |
| 2310 | 0 | ClS(O)$_2$- | CH$_2$CH$_2$C$_6$H$_5$ | OH | 1 |
| 2311 | 0 | NCCO- | CH$_2$CH$_2$C$_6$H$_5$ | OH | 1 |
| 2312 | 0 | HOC(O)C(O)- | CH$_2$CH$_2$C$_6$H$_5$ | OH | 1 |
| 2313 | 0 | H$_3$COC(O)NH- | CH$_2$CH$_2$C$_6$H$_5$ | OH | 1 |
| 2314 | 0 | HOC(O)- | CH$_2$CH$_2$C$_6$H$_5$ | OH | 1 |
| 2315 | 0 | CH$_3$NH- | CH$_2$CH$_2$C$_6$H$_5$ | OH | 1 |
| 2316 | 0 | CH$_3$CO- | CH$_2$CH$_2$C$_6$H$_5$ | OH | 1 |
| 2317 | 0 | CH$_2$CHNH- | CH$_2$CH$_2$C$_6$H$_5$ | OH | 1 |
| 2318 | 0 | CH$_2$CHCO- | CH$_2$CH$_2$C$_6$H$_5$ | OH | 1 |
| 2319 | 0 | CH$_2$CHCH$_2$- | CH$_2$CH$_2$C$_6$H$_5$ | OH | 1 |
| 2320 | 0 | CH$_2$CHS(O)$_2$ | CH$_2$CH$_2$C$_6$H$_5$ | OH | 1 |
| 2321 | 0 | C$_6$H$_{11}$NH- | CH$_2$CH$_2$C$_6$H$_5$ | OH | 1 |
| 2322 | 0 | C$_6$H$_{11}$S(O)$_2$ | CH$_2$CH$_2$C$_6$H$_5$ | OH | 1 |
| 2323 | 0 | H$_2$NCO- | CH$_2$CH$_2$C$_6$H$_5$ | OH | 1 |
| 2324 | 0 | CH$_3$OC(O)- | CH$_2$CH$_2$C$_6$H$_5$ | OH | 1 |
| 2325 | 0 | H-Leu-Leu- | CH$_2$CH$_2$COOCH$_2$C$_6$H$_5$ | OH | 1 |
| 2326 | 0 | H-Leu-Ala-Leu- | CH$_2$CH$_2$COOCH$_2$C$_6$H$_5$ | OH | 1 |

Some of the compounds of the present invention represented by general formula [1] or salts thereof have isomers such as optical isomers, geometrical isomers and tautomers. In such cases, the present invention involves such isomers. Further, the present invention involves solvated products, hydrated products and a variety of crystal forms.

Next, the process for producing the compounds of the present invention will be described.

The compounds of the present invention can be synthesized according to, for example, the Production Processes 1 and 2 mentioned below.

[Production Process 1]

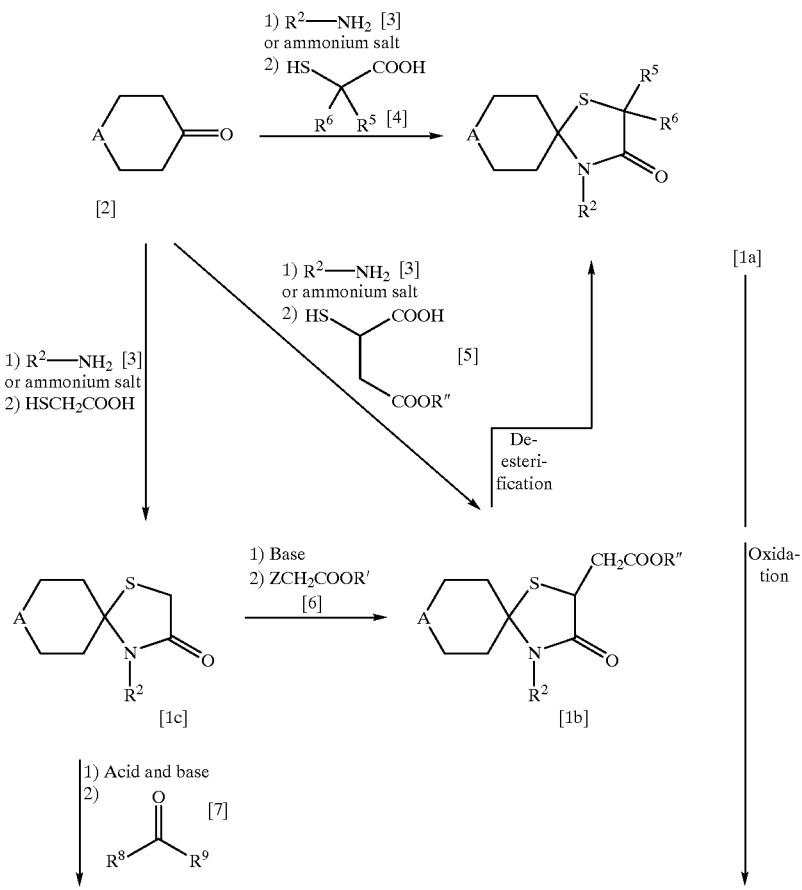

-continued
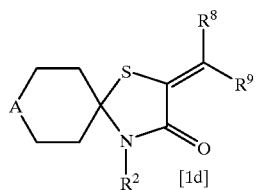 [1d]
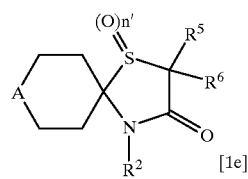 [1e]
[Production Process 2]
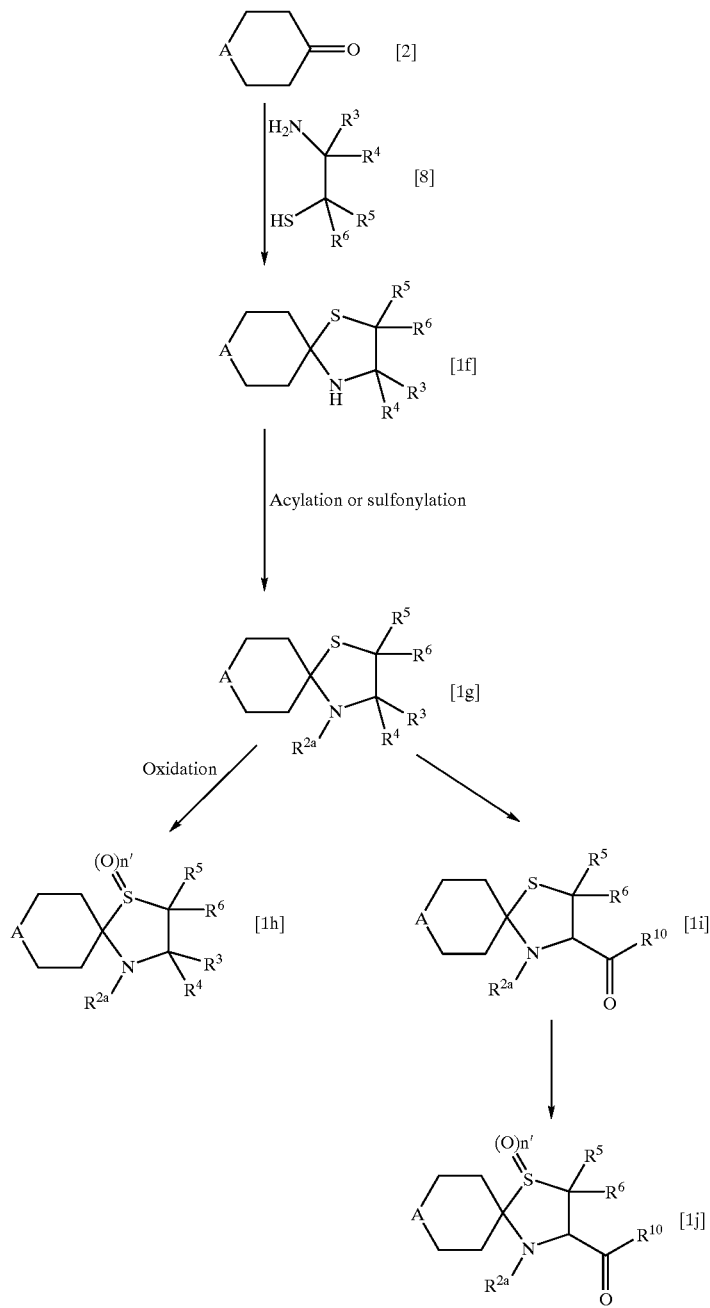
wherein $R^2$, $R^3$, $R^4$, $R^5$, $R^6$ and A are as defined above; $R^{2a}$ represents an unsubstituted or substituted acyl or sulfonyl group; R' represents an unsubstituted or substituted alkyl or aryl group; R" represents tert-butyl group or trichloroethyl group; $R^8$ and $R^9$, same or different, each represents hydrogen atom or an unsubstituted or substituted alkyl, aryl or heterocyclic group; $R^{10}$ represents an unsubstituted or substituted amino group, n' represents 1 or 2; and Z represents halogen atom, alkylsulfonyloxy group or arylsulfonyloxy group.

[Production Process 1]

Next, the process for producing the compounds of the present invention will be described.

The compounds of the present invention can be produced by combining the processes which are known in themselves, namely, according to the production processes mentioned below, for example.

The compound of the general formula [1a] can be produced by, for example, the process mentioned in Yakugaku Zasshi, Vol. 91, No, 3, Pages 363–383 (1971), or the like. More concretely speaking, the compounds of the present invention can be obtained by reacting a compound of general formula [2] with an amine represented by general formula [3] or an ammonium salt and a compound represented by general formula [4] in the presence or absence of a dehydrating agent and/or a catalyst, and subjecting the reaction product to a dehydrating ring closure.

As the amines which can be used in this reaction, primary amines such as methylamine, benzylamine, aniline, phenethylamine or the like and amino acids such as leucine, asparagine, aspartic acid, β-alanine or the like can be referred to. As the ammonium salts, ammonium carbonate, ammonium sulfate and the like can be referred to. The amine of general formula [3] or the ammonium salt is used in an amount of 1–10 mol and preferably 1–2 mol per mol of the compound of general formula [2]. The compound of general formula [4] is used in an amount of 1–10 mol and preferably 1–2 mol per mol of the compound of general formula [2]. As the dehydrating agent which can be used according to the need, zeolam, molecular sieve, calcium chloride, magnesium sulfate, diphosphorus pentoxide and the like can be referred to, and the amount thereof is 1–10 times (w/w) and preferably 1–2 times (w/w) as much as the weight of the compound of general formula [2]. As the catalyst which can be used according to the need, paratoluenesulfonic acid, benzenesulfonic acid, hydrochloric acid, sulfuric acid and the like can be referred to, and the amount thereof is 0.001–3 mol and preferably 0.01–0.1 mol per mol of the compound of general formula [2]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. This reaction is carried out usually at 0–150° C. and preferably at 25–120° C. for a period of 30 minutes to 24 hours.

The compound of general formula [1b] can be obtained, for example, according to the process mentioned in Yakugaku Zasshi, Vol. 91, No. 3, Pages 363–383 (1971), or the like. More concretely speaking, it can be obtained by reacting a compound of general formula [2] with an amine represented by general formula [3] or an ammonium salt and a compound represented by general formula [5] which can be synthesized according to the method described in SYNTHETIC COMMUNICATIONS, Vol. 21, No. 2, Pages 249–263 (1991) or the like in the presence or absence of a dehydrating agent and/or a catalyst, and subjecting the reaction product to a dehydrating ring closure. As the amines which can be used in this reaction, primary amines such as methylamine, benzylamine, aniline, phenethylamine and the like, amino acids such as leucine, asparagine, aspartic acid, β-alanine and the like, etc. can be referred to. As the ammonium salts, ammonium carbonate, ammonium sulfate and the like can be referred to. The amine represented by general formula [3] or the ammonium salt is used in an amount of 1–10 mol and preferably 1–2 mol per mol of the compound of general formula [2]. The compound of general formula [5] is used in an amount of 1–10 mol and preferably 1–2 mol per mol of the compound of general formula [2]. As the dehydrating agent, for example, zeolam, molecular sieve, calcium chloride, magnesium sulfate, diphosphorus pentoxide and the like can be used in an amount of 1–10 times (w/w) and preferably 1–2 times (w/w) as much as the weight of the compound of general formula [2]. As the catalyst which may be used according to the need, paratoluenesulfonic acid, benzenesulfonic acid, hydrochloric acid, sulfuric acid and the like can be referred to, and the amount thereof is 0.001–3 mol and preferably 0.01–0.1 mol per mol of the compound of general formula [2]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. This reaction is carried out usually at 0–150° C. and preferably at 25–120° C. for a period of 30 minutes to 24 hours.

The compound of general formula [1c] can be obtained, for example, according to the process mentioned in Yakugaku Zasshi, Vol. 91, No. 3, Pages 363–383 (1971), or the like. More concretely speaking, it can be obtained by reacting a compound of general formula [2] with an amine represented by general formula [3] or an ammonium salt and mercaptoacetic acid in the presence or absence of a dehydrating agent and/or a catalyst, and subjecting the reaction product to a dehydrating ring closure. As the amines which can be used in this reaction, primary amines such as methylamine, benzylamine, aniline, phenethylamine and the like, amino acids such as leucine, asparagine, aspartic acid, β-alanine and the like, etc. can be referred to. As the ammonium salts, ammonium carbonate, ammonium sulfate and the like can be referred to. The amine represented by general formula [3] or the ammonium salt is used in an amount of 1–10 mol and preferably 1–2 mol per mol of the compound of general formula [2]. The mercaptoacetic acid is used in an amount of 1–10 mol and preferably 1–2 mol per mol of the compound of general formula [2]. As the dehydrating agent which may be used according to the need, for example, zeolam, molecular sieve, calcium chloride, magnesium sulfate, diphosphorus pentoxide and the like can be used in an amount of 1–10 times (w/w) and preferably 1–2 times (w/w) as much as the weight of the compound of general formula [2]. As the catalyst which may be used according to the need, paratoluenesulfonic acid, benzenesulfonic acid, hydrochloric acid, sulfuric acid and the like can be referred to, and the amount thereof is 0.001–3 mol and preferably 0.01–0.1 mol per mol of the compound of general formula [2]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. This reaction is carried out usually at 0–150° C. and preferably at 25–120° C. for a period of 30 minutes to 24 hours. If desired, this reaction may be carried out in an atmosphere of inert gas such as argon or nitrogen.

The compound of general formula [1b] can be obtained by, for example, reacting a compound of general formula [1c] with a compound of general formula [6] in the presence of a base. As the base used in this reaction, for example, there can be referred to organolithium compounds such as n-butyllithium, phenyllithium, lithium diisopropylamide and the like; alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; alkali hydroxides such as sodium hydroxide, potassium hydroxide and the like; etc. The base is used in an amount of 1–5 mol per mol of the compound of general formula [1c]. The compound of general formula [6] is used in an amount of 1–10 mol and preferably 1–2 mol per mol of the compound of general formula [1c]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. This reaction is carried out usually at −78° C. to 150° C. and preferably at −50° C. to 120° C., for a period of 30 minutes to 24 hours. If desired, the reaction may be carried out in an atmosphere of inert gas such as argon or nitrogen.

The compound of general formula [1d] can be obtained by reacting a compound of general formula [1c] with an aldehyde or a ketone represented by general formula [7] in the presence or absence of an acid or a base.

As the acid which may be used in this reaction according to the need, for example, paratoluenesulfonic acid, benzenesulfonic acid, hydrochloric acid, sulfuric acid and the like can be referred to. The amount thereof is 1–10 mol per mol of the compound of general formula [1c]. As the base which may be used according to the need, for example, there can be referred to organolithium compounds such as n-butyllithium, phenyllithium, lithium diisopropylamide and the like; alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; alkali hydroxides such as sodium hydroxide, potassium hydroxide and the like; etc. The base is used in an amount of 1–10 mol per mol of the compound of general formula [1c]. The compound of general formula [7] is used in an amount of 1–10 mol and preferably 1–2 mol per mol of the compound of general formula [1c]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; nitrites such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. This reaction is carried out usually at −78° C. to 150° C. and preferably at −50° C. to 120° C., for a period of 30 minutes to 24 hours.

The compound of general formula [1a] can be obtained by, for example, subjecting a compound of general formula [1b] to a de-esterification reaction in the presence or absence of an acid or a base. As the acid which may be used in this reaction according to the need, for example, hydrochloric acid, sulfuric acid, acetic acid, trifluoro-acetic acid, paratoluenesulfonic acid and the like can be referred to, and the amount thereof is 1–50 mol and preferably 10–30 mol per mol of the compound of general formula [1b]. As the base which may be used according to the need, for example, there can be referred to organolithium compounds such as n-butyllithium, phenyllithium, lithium diisopropylamide and the like; alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; alkali hydroxides such as sodium hydroxide, potassium hydroxide and the like; etc. The base is used in an amount of 1–50 mol and preferably 10–30 mol per mol of the compound of general formula [1b].

The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; nitrites such as acetonitrile and the like; amides such as N,N-dimethylformamide, N,N-dimethylacetamide and the like; halogenated hydrocarbons such as chloroform, methylene chloride and the like; acetic acid; water; and sulfoxides such as dimethyl sulfoxide and the like. These solvents may be used alone or in mixture of two or more. This reaction is carried out usually at 0–150° C. and preferably at 25–120° C., for a period of 30 minutes to 24 hours.

The compound of general formula [1e] can be obtained by, for example, oxidizing a compound of general formula [1a]. As the oxidant which can be used in this reaction, for example, peracids such as peracetic acid, trifluoro-peracetic acid, perbenzoic acid, m-chloroperbenzoic acid and the like; hydrogen peroxide; chromic acid; potassium permanganate and the like can be referred to. The oxidant is used in an amount of 0.5–5 mol and preferably 1–3 mol per mol of the compound of general formula [1a]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; alcohols such as methanol, ethanol and the like; esters such as methyl acetate, ethyl acetate and the like; nitrites such as acetonitrile and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. This reaction is carried out usually at a temperature ranging from 0° C. to reflux temperature of the used solvent and preferably at 0–30° C., for a period of 30 minutes to 24 hours.

[Production Process 2]

The compound of general formula [1f] can be obtained by, for example, the process mentioned in JP-A 53-44574, or the like. More concretely speaking, it can be obtained by reacting a compound of general formula [2] with a compound of general formula [8] in the presence or absence of a base, a dehydrating agent and a catalyst, and subjecting the product to a dehydrating ring closure. Although the compound of general formula [8] used in this reaction is not particularly critical, D-cysteine, L-cysteine, D-penicillamine and L-penicillamine of which C-terminal may optionally be protected and salts thereof can be referred to, for example. The compound of general formula [8] is used in an amount of 0.5–10 mol and preferably 1–2 mol per mol of the compound of general formula [2]. As the base which may be used according to the need, for example, organic amines such as dimethylaminopyridine, triethylamine, pyridine and the like; alkali metal carbonates such as potassium carbonate, sodium carbonate and the like; etc. can be referred to, and the amount thereof is 0.5–10 mol and preferably 1–2 mol per mol of the compound of general formula [2]. As the dehydrating agent which may be used according to the need, zeolam, molecular sieve, calcium chloride, magnesium sulfate, diphosphorus pentoxide and the like can be referred to, and the amount thereof is 1–10 times (w/w) and preferably 1–2 (w/w) times as much as the amount of the compound of general formula [2]. As the catalyst which may be used according to the need, paratoluenesulfonic acid, benzenesulfonic acid, hydrochloric acid, sulfuric acid and the like can be referred to, and the amount thereof is 0.001–1 mol and preferably 0.01–0.1 mol per mol of the compound of general formula [2]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. This reaction is carried out usually at 0–150° C. and preferably at 20–120° C., for a period of 30 minutes to 24 hours.

The compound of general formula [1g] can be obtained by, for example, subjecting a compound of general formula [1] to an acylation reaction or a sulfonylation reaction in the presence or absence of a base. As the acylating agent which can be used in this reaction, for example, acetic anhydride, acetyl chloride, benzoyl chloride, pyrrolecarbonyl chloride, thiazolecarbonyl chloride and the like can be referred to. As the sulfonylating agent, methanesulfonyl chloride, benzenesulfonyl chloride and the like can be referred to. The amounts of said acylating agent and sulfonylating agent are 0.5–10 mol and preferably 1–3 mol per mol of the compound of general formula [1]. As the base which may be used according to the need, organic amines such as dimethylaminopyridine, triethylamine, pyridine and the like and alkali metal carbonates such as potassium carbonate, sodium carbonate and the like can be referred to, and the amount thereof is 0.5–10 mol and preferably 1–3 mol per mol of the compound of general formula [1f].

The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 150° C. and preferably at 0–120° C., for a period of 30 minutes to 24 hours.

The compound of general formula [1h] can be obtained by, for example, oxidizing a compound of general formula [1g]. As the oxidant which can be used in this reaction, for example, peracids such as peracetic acid, trifluoro-peracetic acid, perbenzoic acid, m-chloroperbenzoic acid and the like, hydrogen peroxide, chromic acid, potassium permanganate and the like can be referred to. The oxidant is used in an amount of 0.5–5 mol and preferably 1–3 mol per mol of the compound of general formula [1g]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; alcohols such as methanol, ethanol and the like; esters such as methyl acetate, ethyl acetate and the like; nitrites such as acetonitrile and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. The reaction is carried out usually at a temperature ranging from 0° C. to the reflux temperature of the used solvent and preferably at 0–30° C., for a period of 30 minutes to 24 hours.

The compound of general formula [1i] can be obtained by, for example, subjecting a compound of general formula [1g] to an amidation reaction.

This reaction is a usual amidation reaction, which can be carried out by, for example, a method via an acid chloride, a method via an acid anhydride, a method using a base, a condensing agent and an additive, etc. In a case of using a base, a condensing agent and an additive, the amines which can be used in the reaction include primary amines such as methylamine, benzylamine, aniline, phenethylamine, aminothiazole and the like; secondary amines such as dimethylamine, diethylamine, di-n-propylamine and the like; cyclic amines such as piperidine, morpholine and the like; amino acids such as leucine, asparagine, aspartic acid, β-alanine, methionine and the like; and esters thereof. The amine is used in an amount of 0.5–10 mol and preferably 1–3 mol per mol of the compound of general formula [1g]. As the base which can be use in this reaction, organic amines such as dimethylaminopyridine, triethylamine, pyridine, N-methylmorphline and the like and alkali metal carbonates such as potassium carbonate, sodium carbonate and the like can be referred to, and the amount thereof is 0.5–10 mol and preferably 1–3 mol per mol of the compound of general formula [1g]. As the condensing agent, dicyclohexyl-carbodiimide, diisopropyl-carbodiimide, N-ethyl-N'-3-dimethylaminopropyl carbodiimide, diphenyl phosphoryl azide and the like can be referred to, and as the additive, 1-hydroxybenzotriazole, N-hydroxysuccinimide and the like can be referred to. The amounts of the condensing agent and the additive are both 0.5–10 mol and preferably 1–3 mol per mol of the compound of general formula [1g]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at a temperature of −20° C. to 150° C. and preferably at 0–120° C., for a period of 30 minutes to 24 hours.

The compound of [1j] can be obtained by, for example, oxidizing a compound of general formula [1i].

As the oxidant which can be used in this reaction, peracids such as peracetic acid, trifluoro-peracetic acid, perbenzoic acid, m-chloroperbenzoic acid and the like; hydrogen peroxide; chromic acid and potassium permanganate and the like can be referred to. The oxidant is used in an amount of 0.5–5 mol and preferably 1–3 mol per mol of the compound of general formula [1i]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; alcohols such as methanol, ethanol and the like; esters such as methyl acetate, ethyl acetate and the like; nitrites such as acetonitrile and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. The reaction is carried out usually at a temperature ranging from 0° C. to the reflux temperature of the used solvent and preferably at 0–30° C., for a period of 30 minutes to 24 hours.

Furthermore, it is also possible to synthesize the compounds of the present invention according to the Production Processes 1a and 2a described below.

[Production Process 1a]

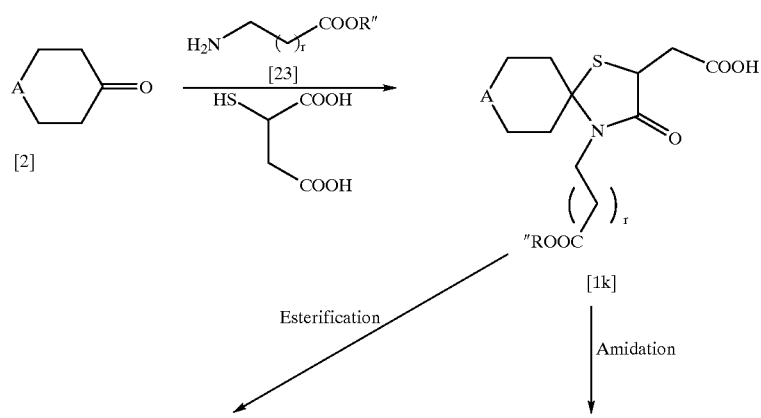

-continued

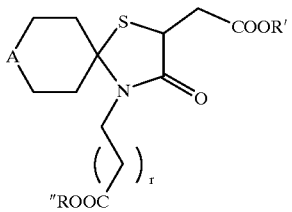

[11]

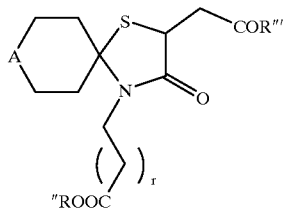

[11a]

↓ De-esterification

↓ De-esterification

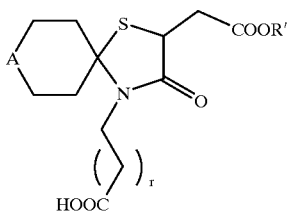

[1m]

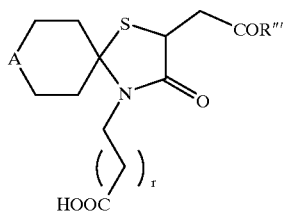

[1ma]

wherein

A is as defined above; R' represents an unsubstituted or substituted alkyl or aryl group; R" represents tert-butyl group; R'" represents an unprotected or protected amino, hydroxyamino, alkylamino, arylamino, acylamino, alkoxycarbonylamino, arylsulfonylamino, alkylsulfonylamino or a group of the following general formula:

$$-(E^2)_{q'}-R^{13'}$$

wherein $E^2$ represents amino acid residue; and $R^{13'}$ represents an unprotected or protected hydroxyl, amino, alkylamino, acylamino, alkoxycarbonylamino, arylsulfonylamino, alkylsulfonylamino, or an unsubstituted or substituted alkyl or alkoxy group; and q' represents 1, 2 or 3; and r represents 0, 1 or 2.

The compound of general formula [1k] can be obtained by, for example, the process mentioned in Yakugaku Zasshi, Vol. 91, No. 3, Pages 363–383 (1971), or the like. More concretely speaking, it can be obtained by reacting a compound of general formula [2] with an amine represented by general formula [23] and mercaptosuccinic acid in the presence or absence of a dehydrating agent and/or a catalyst, and subjecting the product to a dehydrating ring closure.

As the amine which can be used in this reaction, glycine tert-butyl ester, β-alanine tert-butyl ester and the like can be referred to. The amine of general formula [23] is used in an amount of 1–10 mol and preferably 1–2 mol per mol of the compound of general formula [2]. The mercaptosuccinic acid is used in an amount of 1–10 mol and preferably 1–2 mol per mol of the compound of general formula [2]. As the dehydrating agent which may be used according to the need, for example, zeolam, molecular sieve, calcium chloride, magnesium sulfate, diphosphorus pentoxide and the like can be referred to, and the amount thereof is 1–10 times (w/w) and preferably 1–2 times (w/w) as much as the amount of the compound of general formula [2]. As the catalyst which may be used according to the need, paratoluenesulfonic acid, benzenesulfonic acid, hydrochloric acid, sulfuric acid and the like can be referred to, and the amount thereof is 0.001–3 mol and preferably 0.01–0.1 mol per mol of the compound of general formula [2]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methanol, ethanol, isopropyl alcohol and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at 0–150° C. and preferably at 25–120° C., for a period of 30 minutes to 24 hours.

The compound of general formula [11] can be obtained by subjecting a compound of general formula [1k] to an esterification reaction.

This reaction may be practiced according to the usual methods of esterification, such as the method via an acid chloride, the method via an acid anhydride, the method using a base and an alkyl halide, the method of using a condensing agent and an additive, etc. In the case of using a base and an alkyl halide, the base which can be used include organic amines such as dimethylaminopyridine, triethylamine, pyridine, N-methylmorpholine and the like; alkali metal carbonates such as potassium carbonate, sodium carbonate and the like; etc. The amount of the base is 0.5–10 mol and preferably 1–3 mol per mol of the compound of general formula [1k]. As the alkyl halide which can be used in this reaction, methyl iodide, ethyl iodide, benzyl bromide and the like can be referred to, and the amount thereof is 0.5–10 mol and preferably 1–3 mol per mol of the compound of general formula [1k]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide and the like; halogenated hydrocarbons such as chloroform, methylene chloride and the like; and sulfoxides such as dimethyl sulfoxide and the like. The reaction is carried out usually at 0–200° C. and preferably at 25–150° C., for a period of 10 minutes to 24 hours. In the case of using a condensing agent and an additive, the objective compound can be obtained by subjecting an alcohol such as ethanol, benzyl alcohol or the like to a condensation reaction with a condensing agent and an additive. As the condensing agent used in this reaction, for example, dicyclohexyl carbodiimide, diisopropyl carbodiimide, N-ethyl-N'-3-dimethylaminopropyl carbodiimide, diphenyl phosphoryl azide and the like can be referred to. As the additive used in this reaction, for example, 1-hydroxybenzotriazole, N-hydroxysuccinimide and the like can be referred to. The alcohol, condensing agent and additive used in this reaction are used each in an amount of 0.5–10 mol and preferably 1–3 mol per mol of the compound of general formula [1k]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide and the like; halogenated hydrocarbons such as chloroform, methylene chloride and the like; and sulfoxides such as dimethyl sulfoxide and the like. The reaction is carried out usually at 0–200° C. and preferably at 25–150° C., for a period of 10 minutes to 24 hours.

The compound of general formula [1m] can be obtained by, for example, subjecting a compound of general formula [1l] to a de-esterification reaction in the presence of an acid. As the acid which can be used in this reaction according to the need, for example, hydrochloric acid, sulfuric acid, acetic acid, trifluoroacetic acid, paratoluenesulfonic acid and the like can be referred to. The amount thereof is 1–50 mol and preferably 10–30 mol per mol of the compound of general formula [1l]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; halogenated hydrocarbons such as chloroform, methylene chloride and the like; acetic acid; water; and sulfoxides such as dimethyl sulfoxide and the like. These solvents may be used alone or in mixture of two or more. The reaction is carried out usually at 0–150° C. and preferably at 25–120° C., for a period of 30 minutes to 24 hours.

The compound of general formula [1la] can be obtained by, for example, subjecting a compound of general formula [1k] to an amidation reaction.

This reaction is a usual amidation reaction, which can be carried out by, for example, a method via an acid chloride, a method via an acid anhydride, a method using a base, a condensing agent and an additive, etc. In the case of using a base, a condensing agent and an additive, the amines which can be used in the reaction include primary amines such as methylamine, benzylamine, aniline, phenethylamine, aminothiazole and the like; secondary amines such as dimethylamine, diethylamine, di-n-propylamine and the like; cyclic amines such as piperidine, morpholine and the like; amino acids such as leucine, asparagine, aspartic acid, β-alanine, methionine and the like; compounds prepared by substituting the C-terminal carboxyl group may be substituted of the above-mentioned amino acids with an an unsubstituted or substituted alkyloxycarbonyl or carbamoyl group; compounds prepared by condensing 2 or 3 amino acids such as alanylalanine, leucylalanine or the like of which C-terminal carboxyl group may be substituted with an unsubstituted or substituted alkyloxycarbonyl or carbamoyl group; and the like. The amine is used in an amount of 0.5–10 mol and preferably 1–3 mol per mol of the compound of general formula [1k]. As the base which can be use in this reaction, organic amines such as dimethylaminopyridine, triethylamine, pyridine, N-methylmorphline and the like and alkali metal carbonates such as potassium carbonate, sodium carbonate and the like can be referred to, and the amount thereof is 0.5–10 mol and preferably 1–3 mol per mol of the compound of general formula [1k]. As the condensing agent, dicyclohexyl carbodiimide, diisopropyl carbodiimide, N-ethyl-N'-3-dimethylaminopropyl carbodiimide, diphenyl phosphoryl azide and the like can be referred to, and as the additive, 1-hydroxybenzotriazole, N-hydroxysuccinimide and the like can be referred to. The amounts of the condensing agent and the additive are both 0.5–10 mol and preferably 1–3 mol per mol of the compound of general formula [1k]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at a temperature of −20° C. to 150° C. and preferably at 0–120° C., for a period of 30 minutes to 24 hours.

The compound of general formula [1ma] can be obtained by, for example, subjecting a compound of general formula [1la] to a de-esterification reaction in the presence of an acid. As the acid which may be used in this reaction according to the need, for example, hydrochloric acid, sulfuric acid, acetic acid, trifluoroacetic acid, paratoluenesulfonic acid and the like can be referred to, and the amount thereof is 1–50 mol and preferably 10–30 mol per mol of the compound of the general formula [1la]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; halogenated hydrocarbons such as chloroform, methylene chloride and the like; acetic acid; water; and sulfoxides such as dimethyl sulfoxide and the like. These solvents may be used alone or in mixture of two or more. The reaction is carried out usually at 0–150° C. and preferably at 25–120° C., for a period of 30 minutes to 24 hours.

[Production Process 2a]
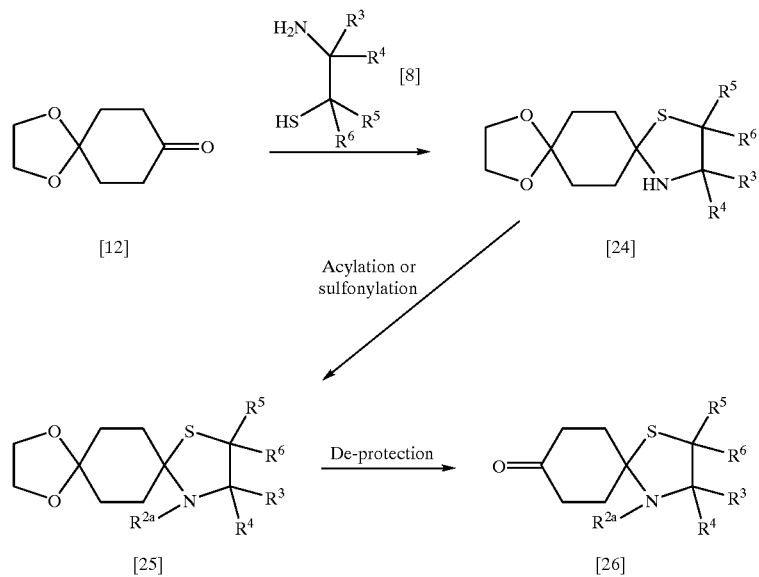
[Production Process 2b]
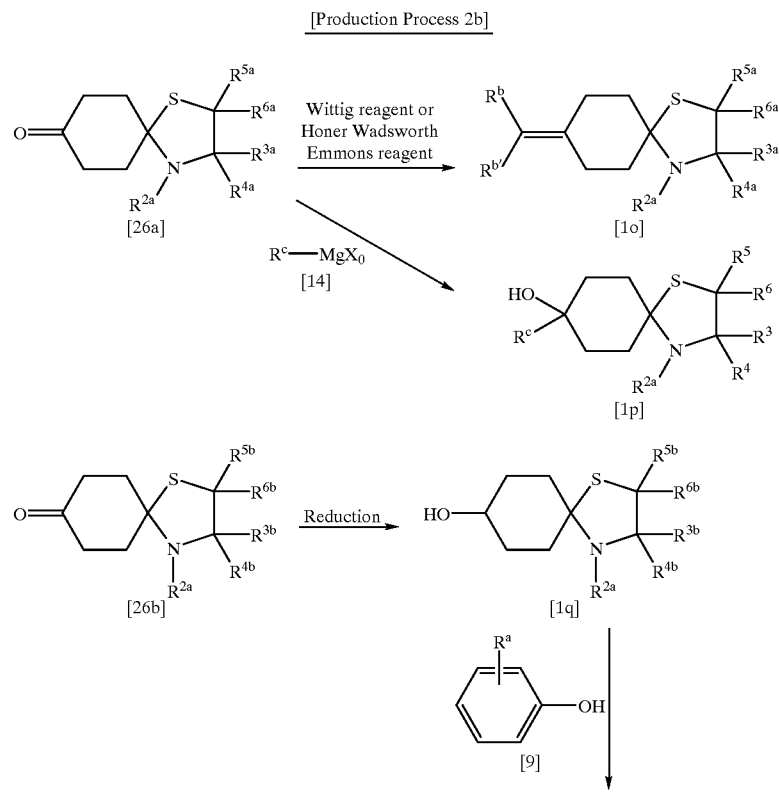

-continued

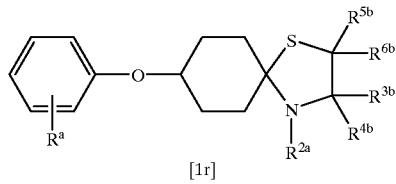

[1r]

wherein $R^3$, $R^4$, $R^5$ and $R^6$ are as defined above; $R^{3a}$ and $R^{4a}$, same or different, each represents hydrogen atom, halogen atom, cyano group, an unprotected or protected carboxyl group, an unprotected or protected hydroxyl group, or an unsubstituted or substituted alkyl, alkenyl, cycloalkyl, alkoxy, alkylthio, alkylsulfinyl, alkylsulfonyl, alkoxycarbonyl, aryl, amino, alkylamino, acylamino, carbamoyl or heterocyclic group or $R^{3a}$ and $R^{4a}$, taken conjointly, represent an oxo group; $R^{5a}$ and $R^{6a}$, same or different, each represents hydrogen atom, halogen atom, cyano group, an unprotected or protected carboxyl group, an unprotected or protected hydroxyl group, an unsubstituted or substituted alkyl, alkenyl, cycloalkyl, alkoxy, alkylthio, alkylsulfinyl, alkylsulfonyl, alkoxycarbonyl, aryl, amino, alkylamino, acylamino, carbamoyl or heterocyclic group or $R^{5a}$ and $R^{6a}$, taken conjointly with the terminal carbon atom to which $R^{5a}$ and $R^{6a}$ are combined, represent an alkenyl group; $R^{3b}$ and $R^{4b}$, same or different, each represents hydrogen atom, halogen atom, cyano group, an unprotected or protected carboxyl group, protected hydroxyl group, or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group or $R^{3b}$ and $R^{4b}$, taken conjointly, represent an oxo group; $R^{5b}$ and $R^{6b}$, same or different, each represents hydrogen atom, halogen atom, cyano group, an unprotected or protected carboxyl group, protected hydroxyl group, or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group or $R^{5b}$ and $R^{6b}$, taken conjointly with the terminal carbon atom to which $R^{5b}$ and $R^{6b}$ are combined, represent an alkenyl group; $R^{2a}$ represents an unsubstituted or substituted acyl or sulfonyl group; $R^a$ represents hydrogen atom, halogen atom, cyano group, nitro group, protected carboxyl group, protected hydroxyl group or an unsubstituted or substituted alkyl, alkenyl, cycloalkyl, aryl, aralkyl, alkoxy, aryloxy, acyl, alkoxycarbonyl, aryloxycarbonyl, carbamoyl, amino or heterocyclic group; $R^b$ and $R^{b'}$, same or different, each represents hydrogen atom, halogen atom, cyano group, nitro group, an unsubstituted or substituted alkyl, alkenyl, cycloalkyl, aryl, aralkyl or alkoxy group, protected amino group, or an unprotected or protected carboxyl group; $X_0$ represents chlorine, bromine or iodine atom; and $R^c$ represents an unsubstituted or substituted alkyl, alkenyl, cycloalkyl or aryl group.

The compound of general formula [24] can be obtained by, for example, according to the method described in JP-A 53-44574, or the like. More concretely speaking, it can be obtained by reacting a compound [12] with a compound of general formula [8] in the presence or absence of a base and a dehydrating agent and subjecting the product to a dehydrating ring closure. Although the compound of general formula [8] which can be used in this reaction is not particularly critical, D-cysteine, L-cycteine, D-penicillamine and L-penicillamine of which C-terminal may optionally be protected and salts thereof can be referred to, for example. The compound of general formula [8] is used in an amount of 0.5–10 mol and preferably 1–2 mol per mol of the compound of general formula [12]. As the base which may be used according to the need, for example, organic amines such as dimethylaminopyridine, triethyamine, pyridine and the like; and alkali metal carbonates such as potassium carbonate, sodium carbonate and the like can be referred to, and the amount thereof is 0.5–10 mol and preferably 1–2 mol per mol of the compound of general formula [12]. As the dehydrating agent which may be used according to the need, zeolam, molecular sieve, calcium chloride, magnesium sulfate, diphosphorus pentoxide and the like can be referred to, and the amount thereof is 1–10 times (w/w) and preferably 1–2 times (w/w) as much as the weight of the compound of general formula [12]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methanol, ethanol, isopropyl alcohol and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. The reaction is carried out usually at 0–150° C. and preferably at 20–120° C., for a period of 30 minutes to 24 hours.

The compound of general formula [25] can be obtained by, for example, subjecting a compound of general formula [24] to an acylation reaction or sulfonylation reaction in the presence or absence of a base. As the acylating agent which can be used in this reaction, for example, acetic anhydride, acetyl chloride, benzoyl chloride, pyrrole carbonyl chloride, thiazole carbonyl chloride and the like can be referred to. As the sulfonylating agent, methanesulfonyl chloride, benzenesulfonyl chloride and the like can be referred to, and the amount thereof is 0.5–10 mol and preferably 1–3 mol per mol of the compound of general formula [24]. As the base which may be used according to the need, organic amines such as dimethylaminopyridine, triethylamine, pyridine and the like; and alkali metal carbonates such as potassium carbonate, sodium carbonate and the like can be referred to, and the amount thereof is 0.5–10 mol and preferably 1–3 mol per mol of the compound of general formula [24].

The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 150° C. and preferably at 0–120° C., for a period of 30 minutes to 24 hours.

The compound of general formula [26] can be obtained by de-protecting a compound of general formula [25] in the presence of an acid. As the acid which can be used in this reaction, mineral acids such as hydrochloric acid, sulfuric acid, hydrobromic acid and the like, and organic acids such as paratoluenesulfonic acid and the like can be referred to, and the amount thereof is 1–50 mol and preferably 5–20 mol per mol of the compound of general formula [25]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methanol, ethanol, isopropyl alcohol and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. The reaction is carried out usually at 0–150° C. and preferably at 25–120° C., for a period of 30 minutes to 24 hours.

The compound of general formula [1o] can be obtained by reacting a compound of general formula [26a] with Wittig reagent or Honer Wadsworth Emmons reagent.

More concretely speaking, the compound of general formula [1o] can be obtained by reacting a compound of general formula [26a] with Wittig reagent which can be synthesized according to the method mentioned in Organic Syntheses Collective Volume, Vol. 5, Pages 751–754 (1973) or Honer Wadsworth Emmons reagent which can be synthesized according to the method mentioned in Organic Syntheses Collective Volume, Vol. 5, Pages 509–513 (1973). The Wittig reagent and the Honer Wadsworth Emmons reagent are used in an amount of 0.5–5 mol and preferably 1–2 mol per mol of the compound of general formula [26a]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −78° C. to 120° C. and preferably at −20° C. to 30° C., for a period of 30 minutes to 24 hours. If desired, this reaction may be carried out in an atmosphere of inert gas such as argon or nitrogen.

The compound of general formula [1p] can be obtained by, for example, subjecting a compound of general formula [26a] and a compound of general formula [14] to Grignard reaction. The Grignard reagent used in this reaction can be synthesized according to the method mentioned in Organic Syntheses Collective Volume, Vol. 5, Page 226 (1955). Examples of the Grignard reagent include alkylmagnesium halides such as methylmagnesium bromide and the like and arylmagnesium halides such as phenylmagnesium bromide and the like.

In this reaction, the compound of general formula [14] is used in an amount of 0.5–5 mol and preferably 0.8–2 mol per mol of the compound of general formula [26a].

The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 120° C. and preferably at 0–70° C. for a period of 30 minutes to 24 hours. If desired, this reaction may be carried out in an atmosphere of inert gas such as argon or nitrogen.

The compound of general formula [1q] can be obtained by reacting a compound of general formula [26b] with a reductant in the presence or absence of a salt. As the salt which may be used according to the need, lithium chloride, magnesium chloride, calcium chloride and the like can be referred to, and the amount thereof is 1–10 mol per mol of the compound of general formula [26b]. As the reductant, sodium boron hydride, lithium boron hydride, aluminum diisobutyl hydride and the like can be referred to, and the amount thereof is 1–10 mol and preferably 1–2 mol per mol of the compound of general formula [26b]. The solvent used in this reaction is not particularly critical so far as the solvent exercises no adverse influence upon the reaction. Examples of the solvent which can be used include halogenated hydrocarbons such as methylene chloride, chloroform, carbon tetrachloride and the like; ethers such as tetrahydrofuran, diethyl ether and the like; alcohols such as methanol, ethanol, isopropyl alcohol and the like; aromatic hydrocarbons such as toluene, benzene, xylene and the like; aliphatic hydrocarbons such as n-hexane, cyclohexane and the like; dimethyl sulfoxide, N,N-dimethylformamide, pyridine, water and the like. These solvents may be used alone or in mixture of two or more. The reaction is carried out usually at a temperature ranging from −78° C. to the reflux temperature of the used solvent and preferably at −78° C. to 30° C., for a period of 30 minutes to 24 hours.

The compound of general formula [1r] can be obtained by subjecting a compound of general formula [9] and a compound of general formula [1q] to a Mitsunobu reaction.

This reaction is carried out by using, for example, an azodicarbonyl compound such as diethylazo dicarboxylate, azodicarbonyl dipiperidine or the like and a triaryl phosphine such as triphenyl phosphine or the like or a trialkylphosphine such as tri-n-butyl phosphine or the like. The compound of general formula [9] is used in an amount of 1–5 mol and preferably 1–3 mol per mol of the compound of general formula [1q].

The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 120° C. and preferably at 0° C. to 30° C., for a period of 30 minutes to 24 hours.

The compounds of general formulas [1a], [1b], [1c], [1d], [1e], [1f], [1g], [1h], [1i], [1j], [1k], [1l], [1la], [1m], [1ma], [1o], [1p], [1q] and [1r] which have been obtained in the above-mentioned manner can be converted to other compounds of general formula [1] by, for example, subjecting them to reactions known in themselves such as oxidation, reduction, rearrangement, substitution, halogenation, dehydration, hydrolysis, etc. or appropriately combining these reactions. The compounds of general formula [1] or salts thereof thus obtained can be isolated and purified by the conventional procedures such as extraction, crystallization and/or column chromatography, etc.

Next, the process for producing the compound of general formula [2] which is a starting material for producing the compound of the present invention will be described. The compound of general formula [2] can be obtained by, for example, the following processes.

[Production Process A]

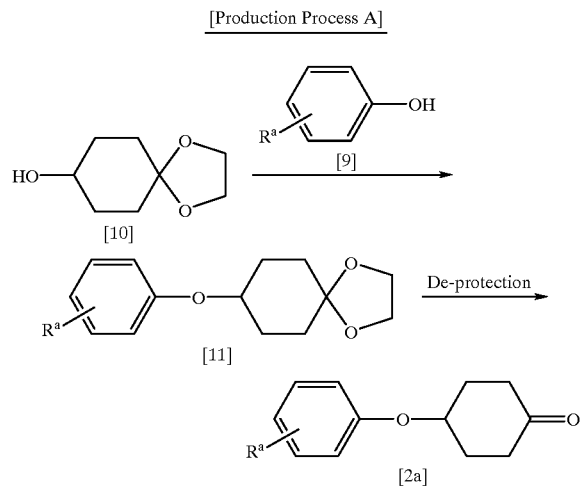

[Production Process B]

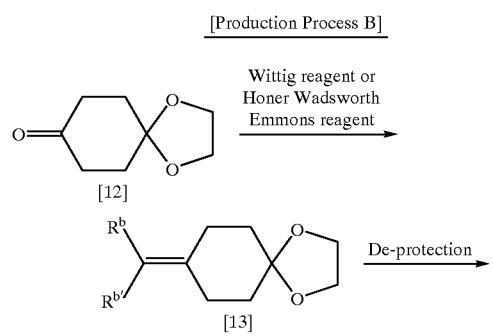

-continued

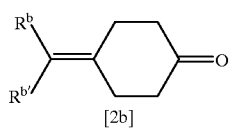

[Production Process C]

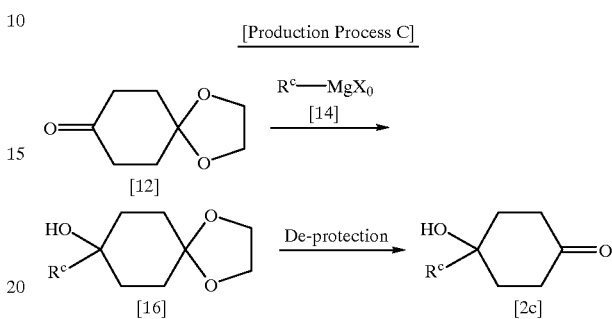

[Production Process D]

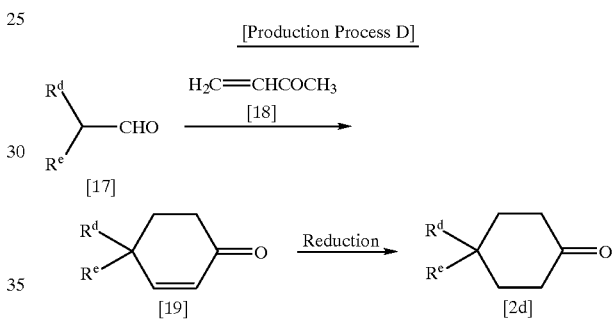

[Production Process E]

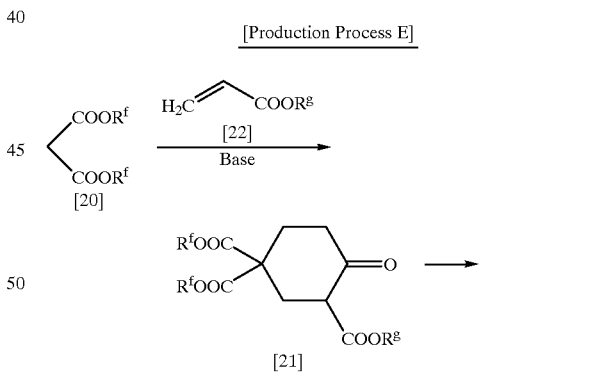

wherein $R^a$ represents hydrogen atom, halogen atom, cyano group, nitro group, protected carboxyl group, protected hydroxyl group or an unsubstituted or substituted alkyl, alkenyl, cycloalkyl, aryl, aralkyl, alkoxy, aryloxy, acyl, alkoxycarbonyl, aryloxycarbonyl, carbamoyl, amino or heterocyclic group; $R^b$ and $R^{b'}$, same or different, each represents hydrogen atom, halogen atom, cyano group, nitro group, an unsubstituted or substituted alkyl, alkenyl, cycloalkyl, aryl, aralkyl or alkoxy group, protected amino group or an unprotected or protected carboxyl group; $R^c$ represents an unsubstituted or substituted alkyl, alkenyl, cycloalkyl or aryl group; $X_0$ represents chlorine, bromine or iodine atom; $R^d$ and $R^e$ represent hydrogen atom, an unsubstituted or substituted alkyl, alkenyl, cycloalkyl, aryl or aralkyl group; and $R^f$ and $R^g$ represent a protecting group for carboxyl group.

[Production Process A]

The compound of general formula [11] can be obtained by subjecting a compound of general formula [9] and a compound of general formula [10] to a Mitsunobu reaction.

This reaction can be carried out by, for example, using an azodicarbonyl compound such as diethylazo dicarboxylate, azodicarbonyl dipiperidine or the like and a triaryl phosphine such as triphenyl phosphine or the like or a trialkyl phosphine such as tri-n-butyl phosphine or the like. The compound of general formula [9] is used in an amount of 1–5 mol and preferably 1–3 mol per mol of the compound of general formula [10].

The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 120° C. and preferably at 0° C. to 30° C., for a period of 30 minutes to 24 hours.

The compound of general formula [2a] can be obtained by, for example, de-protecting a compound of general formula [11] in the presence of an acid. As the acid which can be used in this reaction, mineral acids such as hydrochloric acid, sulfuric acid, hydrobromic acid and the like; and organic acids such as paratoluenesulfonic acid and the like can be referred to, and the amount thereof is 1–50 mol and preferably 5–20 mol per mol of the compound of general formula [11]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. The reaction is carried out usually at 0–150° C. and preferably at 25–120° C., for a period of 30 minutes to 24 hours.

[Production Process B]

The compound of general formula [13] is obtained by reacting a compound of general formula [12] with Wittig reagent or Honer Wadsworth Emmons reagent.

More concretely speaking, the compound of formula [13] can be obtained by reacting a compound of general formula [12] with Wittig reagent which can be synthesized according to the method mentioned in Organic Syntheses Collective Volume, Vol. 5, Pages 751–754 (1973) or Honer Wadsworth Emmons reagent which can be synthesized according to the method mentioned in Organic Syntheses Collective Volume, Vol. 5, Pages 509–513 (1973). The Wittig reagent and the Honer Wadsworth Emmons reagent are used in an amount of 0.5–5 mol and preferably 1–2 mol per mol of the compound of general formula [12]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −78° C. to 120° C. and preferably at −20° C. to 30° C., for a period of 30 minutes to 24 hours. If desired, this reaction may be carried out in an atmosphere of inert gas such as argon or nitrogen.

The compound of general formula [2b] can be obtained by, for example, de-protecting a compound of general formula [13] in the presence of an acid.

As the acid which can be used in this reaction, mineral acids such as hydrochloric acid, sulfuric acid, hydrobromic acid and the like, and organic acids such as paratoluenesulfonic acid, methanesulfonic acid and the like can be referred, and the amount thereof is 1–50 mol and preferably 5–20 mol per mol of the compound of general formula [13]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. The reaction is carried out usually at 0–150° C. and preferably at 25–120° C., for a period of 30 minutes to 24 hours.

[Production Process C]

The compound of general formula [16] can be obtained by, for example, subjecting a compound of general formula [12] and a compound of general formula [14] to Grignard reaction. The Grignard reagent used in this reaction can be synthesized according to the method mentioned in Organic Syntheses Collective Volume, Vol. 5, Page 226 (1955). Examples of the Grignard reagent include alkylmagnesium halides such as methylmagnesium bromide and the like and arylmagnesium halides such as phenylmagnesium bromide and the like.

In this reaction, the compound of general formula [14] is used in an amount of 0.5–5 mol and preferably 0.8–2 mol per mol of the compound of general formula [12].

The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 120° C. and preferably at 0–70° C. for a period of 30 minutes to 24 hours. If desired, this reaction may be carried out in an atmosphere of inert gas such as argon or nitrogen.

The compound of general formula [2c] can be obtained by, for example, de-protecting a compound of general formula [16] in the presence of an acid. As the acid which can be used in this reaction, mineral acids such as hydrochloric acid, sulfuric acid, hydrobromic acid and the like, and organic acids such as paratoluenesulfonic acid, methanesulfonic acid and the like can be referred to, and the amount thereof is 1–50 mol and preferably 5–20 mol per mol of the compound of general formula [16]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. The reaction is carried out usually at 0–150° C. and preferably at 25– 120° C., for a period of 30 minutes to 24 hours.

[Production Process D]

The compound of general formula [19] can be obtained by, for example, the process mentioned in J. Org. Chem., Vol. 45, Pages 5399–5400 (1980), etc. More concretely speaking, it can be obtained by subjecting a compound of general formula [17] and a compound of general formula [18] to Robinson cyclization reaction. The compound of general formula [18] is used in an amount of 1–10 mol and preferably 2–4 mol per mol of the compound of general formula [17].

The reagent used in this reaction is, for example, an aldehyde such as isobutylaldehyde, cyclohexylaldehyde, 2-phenylpropionaldehyde and the like and a ketone such as methyl vinyl ketone, 3-penten-2-one and the like. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 150° C. and preferably at 0–120° C., for a period of 30 minutes to 24 hours.

The compound of general formula [2d] can be obtained by, for example, reducing a compound of general formula [19]. This reaction may be carried out according to the conventional method for reducing carbon-carbon double bonds, for example, by the method of catalytic reduction using palladium-carbon, Raney nickel or platinum catalyst.

In the case of using a palladium-carbon catalyst, the catalyst is used in an amount of 0.01–1 time (w/w) and preferably 0.05–0.2 time (w/w) as much as the amount of the compound of general formula [19]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methyl alcohol, ethyl alcohol, isopropyl alcohol and the like; amides such as N,N-dimethylformamide, N,N-dimethylacetamide and the like; water; acetic acid, etc. These solvents may be used alone or in mixture of two or more. The reaction is carried out usually at −20° C. to 120° C. under normal pressure or elevated pressure, and preferably at 25–50° C., for a period of 30 minutes to 24 hours.

[Production Process E]

It is also possible to obtain the compound of general formula [21] according to the method mentioned in SYNTHETIC COMMUNICATIONS, Vol. 15, Pages 141–149 (1985). More concretely speaking, it can be obtained by subjecting a compound of general formula [20] and twice or more molar quantity, per mol of compound [20], of an acrylic ester represented by general formula [22] to Diekman condensation reaction. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; and amides such as N,N-dimethylformamide, N,N-dimethylacetamide and the like. These solvents may be used alone or in mixture of two or more. This reaction is carried out usually at −20° C. to 150° C. and preferably at 25–100° C., for a period of 30 minutes to 24 hours. If desired, the reaction may be carried out in an atmosphere of an inert gas such as argon or nitrogen.

The compound of general formula [2e] can be obtained by, for example, subjecting a compound of general formula [21] to a de-carboxylation reaction. The reagents used in this reaction are lithium chloride, lithium iodide, sodium chloride, pyridine and the like. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methyl alcohol, ethyl alcohol, isopropyl alcohol and the like; amides such as N,N-dimethylformamide, N,N-dimethylacetamide and the like; water; acetic acid; and the like. These solvents may be used alone or in mixture of two or more. This reaction is carried out usually at 25° C. to 250° C. and preferably at 100–190° C., for a period of 30 minutes to 24 hours.

Next, the processes for producing the compounds of the present invention will be explained.

In the production processes mentioned above, the compounds of general formulas [2], [3], [4], [5], [6], [7], [8], [9], [10], [11], [12], [13], [14], [16], [17], [18], [19], [20], [21], [22], [24], [25], [26], [26a], [26b], [1a], [1b], [1c], [1f], [1g], [1i], [1k], [11], [11a], [1m], [1ma], [1o], [1p], [1q], [1r], [2a], [2b], [2c], [2d] and [2e] can be put to use in the form of salts thereof, too. As salts thereof, the same salts as mentioned in the paragraph of the salts of compound of general formula [1] can be used.

In the production processes mentioned above, the compounds of general formulas [2], [3], [4], [5], [6], [7], [8], [9], [10], [11], [12], [13], [14], [16], [17], [18], [19], [20], [21], [22], [24], [25], [26], [26a], [26b], [1a], [1b], [1c], [1f], [1g], [1i], [1k], [11], [11a], [1m], [1ma], [1o], [1p], [1q], [1r], [2a], [2b], [2c], [2d] and [2e] can have isomers such as optical isomers, geometrical isomers and tautomers. In such cases, these isomers can also be used in the present invention. Further, solvated products, hydrates, and various crystal forms of these compounds can also be used. Further, in the compounds of [2], [3], [4], [5], [6], [7], [8], [9], [10], [11], [12], [13], [14], [16], [17], [18], [19], [20], [21], [22], [24], [25], [26], [26a], [26b], [1a], [1b], [1c], [1f], [1g], [1i], [1k], [11], [11a], [1m], [1ma], [1o], [1p], [1q], [1r], [2a], [2b], [2c], [2d] and [2e], some of the compounds can have an amino group, a hydroxyl group or a carboxyl group. It is also possible to protect these groups previously with conventional protecting groups and, after the reaction, to eliminate these protecting groups according to the methods known in themselves.

In cases where the compound of the present invention is a 1-thia-4,8-diazaspiro[4.5]decane derivative, such a compound can be synthesized according to the Production Processes 3 and 4 mentioned below, for example:

[Production Process 3]

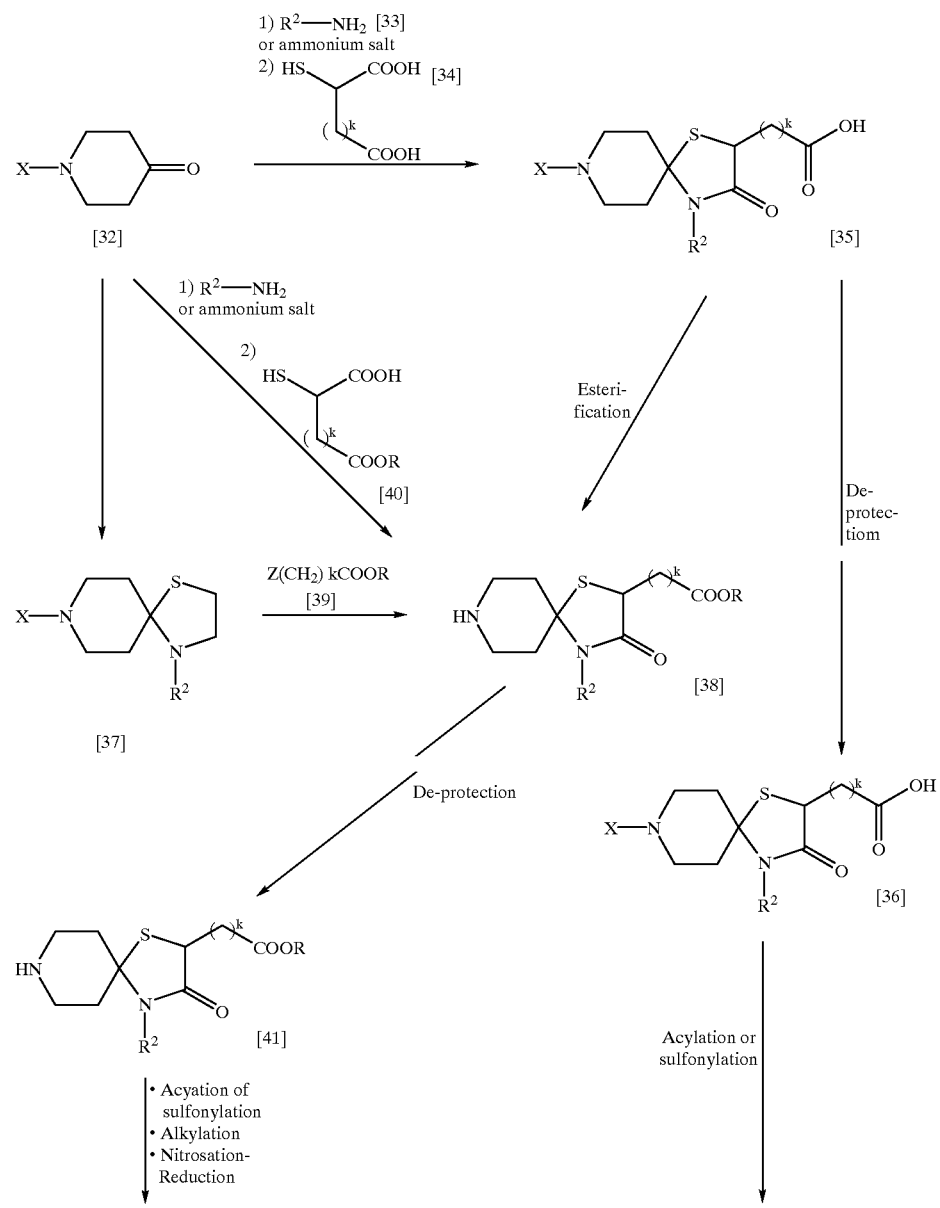

[Production Process 4]

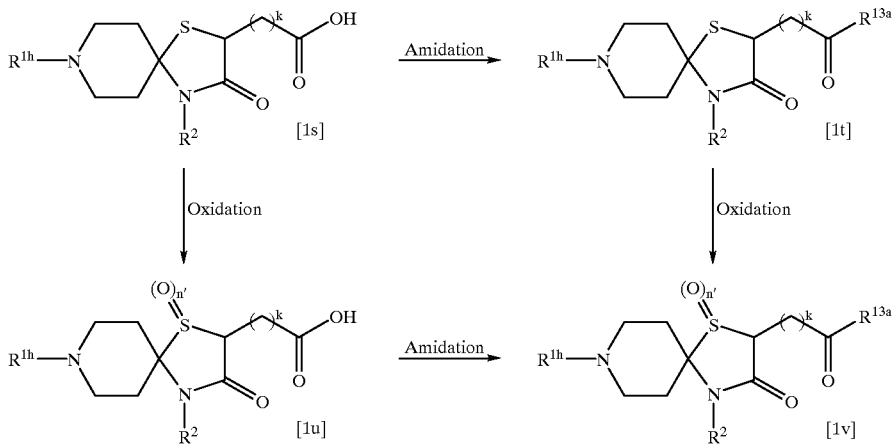

wherein $R^{1h}$, $R^2$, k and n' are as defined above; $R^{13a}$ represents an unprotected or protected amino, alkylamino, arylamino, acylamino, alkoxycarbonylamino, arylsulfonylamino or alkylsulfonylamino group; R represents a protecting group for carboxyl group; X represents a protecting group for amino group; and Z represents halogen atom, alkylsulfonyloxy group or arylsulfonyloxy group.

The compound of general formula [35] can be obtained by, for example, the process mentioned in Yakugaku Zasshi, Vol. 91, No, 3, Pages 363–383 (1971), or the like. More concretely speaking, it can be obtained by reacting a compound of general formula [32] with an amine represented by general formula [33] or an ammonium salt and a compound represented by general formula [34] in the presence or absence of a dehydrating agent and/or a catalyst, and subjecting the reaction product to a dehydrating ring closure.

As the amine represented by general formula [33] or the ammonium salt which can be used in this reaction, for example, primary amines such as methylamine, benzylamine, aniline, phenethylamine or the like, amino acids such as leucine, asparagine, aspartic acid, β-alanine or the like, and ammonium salts such as ammonium carbonate, ammonium sulfate and the like can be referred to. The amine of general formula [33] or the ammonium salt is used in an amount of 1–10 mol and preferably 1–2 mol per mol of the compound of general formula [32]. The compound of general formula [34] is used in an amount of 1–10 mol and preferably 1–2 mol per mol of the compound of general formula [32]. As the dehydrating agent which can be used according to the need, zeolam, molecular sieve, calcium chloride, magnesium sulfate, diphosphorus pentoxide and the like can be referred to, and the amount thereof is 1–10 times (w/w) and preferably 1–2 times (w/w) as much as the-weight of the compound of general formula [32]. As the catalyst which can be used according to the need, paratoluenesulfonic acid, benzenesulfonic acid, hydrochloric acid, sulfuric acid and the like can be referred to, and the amount thereof is 0.001–3 mol and preferably 0.01–0.1 mol per mol of the compound of general formula [32]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. This reaction is carried out usually at 0–150° C. and preferably at 25–120° C. for a period of 30 minutes to 24 hours. If desired, this reaction may be carried out in an atmosphere of inert gas such as argon or nitrogen.

It is also possible to obtain the compound of general formula [36] by de-protecting a compound of general formula [35] in the presence or absence of an acid or a base.

As the acid which may be used in this reaction according to the need, hydrochloric acid, sulfuric acid, acetic acid, trifluoroacetic acid, paratoluenesulfonic acid and the like can be referred to, and the amount thereof is 1–50 mol and preferably 10–30 mol per mol of the compound of general formula [35]. As the base which may be used in this reaction according to the need, organolithium compounds such as n-butyllithium, phenyllithium, lithium diisopropylamine and the like; alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; and alkali hydroxides such as sodium hydroxide, potassium hydroxide and the like can be referred to, and the amount thereof is 1–50 mol and preferably 10–30 mol per mol of the compound of general formula [35]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. This reaction is carried out usually at 0–150° C. and preferably at 25–110° C. for a period of 30 minutes to 24 hours.

The compound of general formula [1s] is obtained by, for example, subjecting a compound of general formula [36] to an acylation reaction or sulfonylation reaction in the presence or absence of a base.

As the acylating agent which can be used in this reaction, for example, acetic anhydride, acetyl chloride, benzoyl chloride, 4-isopropylbenzoyl chloride, ethylsuccinyl chloride and the like can be referred to. As the sulfonylating agent, methanesulfonyl chloride, benzenesulfonyl chloride and the like can be referred to. The amounts of said acylating agent and sulfonylating agent are 1–20 mol and preferably 2–6 mol per mol of the compound of general formula [36]. As the base which may be used according to the need, organic amines such as dimethylaminopyridine, triethylamine, pyridine and the like and alkali metal carbonates such as potassium carbonate, sodium carbonate and the like can be referred to, and the amount thereof is 0.5–10 mol and preferably 2–4 mol per mol of the compound of general formula [36]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 150° C. and preferably at 0–120° C., for a period of 30 minutes to 24 hours.

The compound of general formula [37] can be obtained by, for example, the process mentioned in Yakugaku Zasshi, Vol. 91, No. 3, pages 363–383 (1971). More concretely speaking, it can be obtained by reacting a compound of general formula [32] with an amine represented by general formula [33] or an ammonium salt and mercaptoacetic acid in the presence or absence of a dehydrating agent and/or a catalyst, and subjecting the product to a dehydrating ring closure.

As the amines represented by general formula [33] which can be used in this reaction, primary amines such as methylamine, benzylamine, aniline, phenethylamine or the like and amino acids such as leucine, asparagine, aspartic acid, β-alanine or the like can be referred to. As the ammonium salts, ammonium carbonate, ammonium sulfate and the like can be referred to. The amine of general formula [33] or the ammonium salt is used in an amount of 1–10 mol and preferably 1–2 mol per mol of the compound of general formula [32]. The mercaptoacetic acid is used in amount of 1–10 mol and preferably 1–2 mol per mol of the compound of general formula [32]. As the dehydrating agent which can be used according to the need, zeolam, molecular sieve, calcium chloride, magnesium sulfate, diphosphorus pentoxide and the like can be referred to, and the amount thereof is 1–10 times (w/w) and preferably 1–2 times (w/w) as much as the weight of the compound of general formula [32]. As the catalyst which can be used according to the need, paratoluenesulfonic acid, benzenesulfonic acid, hydrochloric acid, sulfuric acid and the like can be referred to, and the amount thereof is 0.001–3 mol and preferably 0.01–0.1 mol per mol of the compound of general formula [32]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. This reaction is carried out usually at 0–150° C. and preferably at 25–120° C. for a period of 30 minutes to 24 hours. If desired, this reaction may be carried out in an atmosphere of inert gas such as argon or nitrogen.

The compound of general formula [38] can be obtained by, for example, reacting a compound of general formula [37] with a compound of general formula [39] in the presence of a base. As the base used in this reaction, for example, there can be referred to organolithium compounds such as n-butyllithium, phenyllithium, lithium diisopropylamide and the like; alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; alkali hydroxides such as sodium hydroxide, potassium hydroxide and the like; etc. The base is used in an amount of 1–5 mol per mol of the compound of general formula [37]. The compound of general formula [39] is used in an amount of 1–10 mol and preferably 1–2 mol per mol of the compound of general formula [37]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; nitrites such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. This reaction is carried out usually at −78° C. to 150° C. and preferably at −50° C. to 120° C., for a period of 30 minutes to 24 hours. If desired, the reaction may be carried out in an atmosphere of inert gas such as argon or nitrogen.

It is also possible to obtain the compound of general formula [38] by the process mentioned in Yakugaku Zasshi, Vol. 91, No. 3, Pages 363–383 (1971), or the like. More concretely speaking, it can be obtained by reacting a compound of general formula [32] in the presence or absence of a dehydrating agent and/or a catalyst with an amine represented by general formula [33] or an ammonium salt and a compound represented by general formula [40] which can be synthesized according to the method mentioned in SYNTHETIC COMMUNICATIONS, Vol. 21, No. 2, Pages 249–263 (1991) or the like and subjecting the product to a dehydrating ring closure.

As the amine represented by general formula [33] used in this reaction, primary amines such as methylamine, benzylamine, aniline, phenethylamine and the like and amino acids such as leucine, asparagine, aspartic acid, β-alanine and the like can be referred to. As the ammonium salt, ammonium carbonate, ammonium sulfate and the like can be referred to. The amine of general formula [33] or the ammonium salt is used in an amount of 1–10 mol and preferably 1–2 mol per mol of the compound of general formula [32]. The compound of general formula [40] is used in an amount of 1–10 mol and preferably 1–2 mol per mol of the compound of general formula [32]. As the dehydrating agent, for example, zeolam, molecular sieve, calcium chloride, magnesium sulfate, diphosphorus pentoxide and the like can be referred to, and the amount thereof is 1–10 times (w/w) and preferably 1–2 times (w/w) as much as the amount of the compound of general formula [32]. As the catalyst which can be used according to the need, paratoluenesulfonic acid, benzenesulfonic acid, hydrochloric acid, sulfuric acid and the like can be referred to, and the amount thereof is 0.001–3 mol and preferably 0.01–0.1 mol per mol of the compound of general formula [32]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. This reaction is carried out usually at 0–150° C. and preferably at 25–120° C. for a period of 30 minutes to 24 hours. If desired, the reaction may be carried out in an atmosphere of inert gas such as argon or nitrogen.

Further, it is also possible to obtain the compound of general formula [38] by subjecting a compound of general formula [35] to an esterification reaction.

This reaction may be a usual esterification reaction, such as a method via an acid chloride, a method via an acid anhydride, a method using a base and an alkyl halide, a method using a condensing agent and an additive, etc. In a case where a base and an alkyl halide are used, the base which can be used include organic amines such as dimethylaminopyridine, triethylamine, pyridine, N-methylmorpholine and the like; alkali metal carbonates such as potassium carbonate, sodium carbonate and the like; etc. The amount of the base is 0.5–10 mol and preferably 1–3 mol per mol of the compound of general formula [35]. As the alkyl halide which can be used in this reaction, methyl iodide, ethyl iodide, benzyl bromide and the like can be referred to, and the amount thereof is 0.5–10 mol and preferably 1–3 mol per mol of the compound of general formula [35]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; amides such as N,N-dimethylformamide and the like; halogenated hydrocarbons such as chloroform, methylene chloride and the like; and sulfoxides such as dimethyl sulfoxide and the like. These solvents may be used alone or in mixture of two or more. The reaction is carried out usually at 0–200° C. and preferably at 25–150° C., for a period of 10 minutes to 24 hours. In a case where a condensing agent and an additive are used, the objective compound can be obtained by subjecting an alcohol such as ethanol, benzyl alcohol, tert-butanol or the like to a condensation reaction with a condensing agent and an additive. As the condensing agent used in this reaction, for example, dicyclohexyl carbodiimide, diisopropyl carbodiimide, N-ethyl-N'-3-dimethylaminopropyl carbodiimide, diphenyl phosphoryl azide and the like can be referred to. As the additive used in this reaction, for example, 1-hydroxybenzotriazole, N-hydroxysuccinimide and the like can be referred to. The alcohol, condensing agent and additive used in this reaction are used each in an amount of 0.5–10 mol and preferably 1–3 mol per mol of the compound of general formula [35]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide and the like; halogenated hydrocarbons such as chloroform, methylene chloride and the like; and sulfoxides such as dimethyl sulfoxide and the like. These solvents may be used alone or in mixture of two or more. The reaction is carried out usually at 0–200° C. and preferably at 25–150° C., for a period of 10 minutes to 24 hours.

The compound of general formula [41] can be obtained by de-protecting a compound of general formula [38] in the presence or absence of an acid or a base.

As the acid which may be used in this reaction according to the need, hydrochloric acid, sulfuric acid, acetic acid, trifluoroacetic acid, paratoluenesulfonic acid and the like can be referred to, and the amount thereof is 1–50 mol and preferably 10–30 mol per mol of the compound of general formula [38]. As the base which may be used in this reaction according to the need, organolithium compounds such as n-butyllithium, phenyllithium, lithium diisopropylamide and the like; alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; and alkali hydroxides such as sodium hydroxide, potassium hydroxide and the like can be referred to, and the amount thereof is 1–50 mol and preferably 1–30 mol per mol of the compound of general formula [38].

In a case where X is a tert-butyloxycarbonyl group and R is an ethyl group, the acids which can be used are hydrochloric acid, sulfuric acid, trifluoroacetic acid and the like, and the amount thereof is 1–50 mol and preferably 10–30 mol per mol of the compound of general formula [38]. In a case where X is a 9-fluorenylmethoxycarbonyl group and R is a tert-butyl group, the bases which can be used are piperidine, morpholine, dimethylaminopyridine and the like, and the amount thereof is 1–30 mol and preferably 1–5 mol per mol of the compound of general formula [38]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methyl alcohol, ethyl alcohol, isopropyl alcohol and the like; amides such as N,N-dimethylformamide and the like; halogenated hydrocarbons such as chloroform, methylene chloride and the like; water; and sulfoxides such as dimethyl sulfoxide and the like. These solvents may be used alone or in mixture of two or more. This reaction is carried out usually at 0–200° C. and preferably at 20–70° C. for a period of 10 minutes to 5 hours.

The compound of general formula [42] can be obtained by, for example, subjecting a compound of general formula [41] to an acylation reaction or a sulfonylation reaction in the presence or absence of a base.

As the acylating agent which can be used in this reaction, for example, acetic anhydride, acetyl chloride, benzoyl chloride, ethylsuccinyl chloride and the like can be referred to. As the sulfonylating agent, methanesulfonyl chloride, benzenesulfonyl chloride and the like can be referred to. The amount of said acylating agent and sulfonylating agent is each 0.5–10 mol and preferably 1–3 mol per mol of the compound of general formula [41]. As the base used in this reaction, organic amines such as dimethylaminopyridine, triethylamine, pyridine and the like and alkali metal carbonates such as potassium carbonate, sodium carbonate and the like can be referred to, and the amount thereof is 0.5–10 mol and preferably 1–3 mol per mol of the compound of general formula [41]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 150° C. and preferably at 0–120° C., for a period of 30 minutes to 24 hours.

The compound of general formula [42] can be obtained by, for example, subjecting a compound of general formula [41] to an alkylation reaction in the presence of a base. As the alkylating agent which can be used in this reaction, for example, methyl iodide, benzyl bromide and the like can be referred to, and the amount thereof is 1–20 mol and preferably 1–4 mol per mol of the compound of general formula [41]. As the base used in this reaction, organic amines such as dimethylaminopyridine, triethylamine, pyridine and the like and alkali metal carbonates such as potassium carbonate, sodium carbonate and the like can be referred to, and the amount thereof is 2–20 mol and preferably 2–4 mol per mol of the compound of general formula [41]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methyl alcohol, ethyl alcohol, isopropyl alcohol and the like; amides such as N,N-dimethylformamide and the like; halogenated hydrocarbons such as chloroform, methylene chloride and the like; and sulfoxides such as dimethyl sulfoxide and the like. These solvents may be used alone or in mixture of two or more. The reaction is carried out usually at 0–200° C. and preferably at 25–150° C., for a period of 10 minutes to 24 hours.

The compound of general formula [42] can be obtained by, subjecting a compound of general formula [41] to a nitrosation reaction in the presence of a base and then reducing the product. The nitrosation reaction can be carried out according to the procedure mentioned in Organic Syntheses Collective Volume, Vol. 2, Page 211 (1943). As the nitrosating agent, for example, nitrous acid and the like can be used. The nitrosating agent is used in an amount of 1–10 mol and preferably 1–4 mol per mol of the compound of general formula [41]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methyl alcohol, ethyl alcohol, isopropyl alcohol and the like; amides such as N,N-dimethylformamide and the like; halogenated hydrocarbons such as chloroform, methylene chloride and the like; water; and sulfoxides such as dimethyl sulfoxide and the like. These solvents may be used alone or in mixture of two or more. The reaction is carried out usually at 0–200° C. and preferably at 0–100° C., for a period of 10 minutes to 24 hours.

The reduction as a subsequent step can be carried out according to the description of Organic Syntheses Collective Volume, Vol. 2., Page 211 (1943). That is, the objective product can be obtained by reacting the nitroso compound synthesized from the compound of general formula [41] with a reductant such as zinc powder. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methyl alcohol, ethyl alcohol, isopropyl alcohol and the like; amides such as N,N-dimethylformamide and the like; halogenated hydrocarbons such as chloroform, methylene chloride and the like; water; and acetic acid. These solvents may be used alone or in mixture of two or more. The reaction is carried out usually at 0–200° C. and preferably at 0–100° C., for a period of 30 minutes to 24 hours.

The compound of general formula [1s] can be obtained by, for example, subjecting a compound of general formula

[42] to a de-esterification reaction in the presence or absence of an acid or a base.

As the acid which can be used in this reaction according to the need, for example, hydrochloric acid, sulfuric acid, acetic acid, trifluoroacetic acid, paratoluenesulfonic acid and the like can be referred to. The amount thereof is 1–50 mol and preferably 10–30 mol per mol of the compound of general formula [42]. As the base used in this reaction according to the need, for example, there can be referred to organolithium compounds such as n-butyllithium, phenyllithium, lithium diisopropylamide and the like; alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; alkali hydroxides such as sodium hydroxide, potassium hydroxide and the like; etc. The base is used in an amount of 1–50 mol and preferably 10–30 mol per mol of the compound of general formula [42]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; nitrites such as acetonitrile and the like; amides such as N,N-dimethylformamide, N,N-dimethylacetamide and the like; halogenated hydrocarbons such as chloroform, methylene chloride and the like; acetic acid; water; alcohols such as methyl alcohol, ethyl alcohol, isopropyl alcohol and the like; and sulfoxides such as dimethyl sulfoxide and the like. These solvents may be used alone or in mixture of two or more. The reaction is carried out usually at 0–150° C. and preferably at 25–120° C., for a period of 30 minutes to 24 hours.

The compound of general formula [1t] can be obtained by subjecting a compound of general formula [1s] to an amidation reaction.

This reaction may be a usual amidation reaction, such as a method via an acid chloride, a method via an acid anhydride, a method using a base, a condensing agent and an additive, etc. For example, in the case of using a base, a condensing agent and an additive, the amines which can be used in the reaction include primary amines such as methylamine, benzylamine, aniline, phenethylamine, aminothiazole and the like; secondary amines such as dimethylamine, diethylamine, di-n-propylamine and the like; cyclic amines such as piperidine, morpholine and the like; and amino acids such as leucine, asparagine, aspartic acid, β-alanine and the like. The amine is used in an amount of 0.5–10 mol and preferably 1–3 mol per mol of the compound of general formula [1s]. As the base which can be use in this reaction, organic amines such as dimethylaminopyridine, triethylamine, pyridine, N-methylmorpholine and the like and alkali metal carbonates such as potassium carbonate, sodium carbonate and the like can be referred to, and the amount thereof is 0.5–10 mol and preferably 1–3 mol per mol of the compound of general formula [1s]. As the condensing agent, dicyclohexyl carbodiimide, diisopropyl carbodiimide, N-ethyl-N'-3-dimethylaminopropyl carbodiimide, diphenyl phosphoryl azide and the like can be referred to, and as the additive, 1-hydroxybenzotriazole, N-hydroxysuccinimide and the like can be referred to. The amounts of the condensing agent and the additive are both 0.5–10 mol and preferably 1–3 mol per mol of the compound of general formula [1s]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve nd the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at a temperature of –20° C. to 150° C. and preferably at 0–120° C., for a period of 30 minutes to 24 hours.

The compound of general formula [1u] can be obtained by, for example, oxidizing a compound of general formula [1s].

As the oxidant which can be used in this reaction, for example, peracids such as peracetic acid, trifluoro-peracetic acid, perbenzoic acid, m-chloroperbenzoic acid and the like; hydrogen peroxide; chromic acid; potassium permanganate and the like can be referred to. The oxidant is used in an amount of 0.5–5 mol and preferably 1–3 mol per mol of the compound of general formula [1s]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; alcohols such as methanol, ethanol and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. This reaction is carried out usually at a temperature ranging from 0° C. to reflux temperature of the used solvent and preferably at 0–30° C., for a period of 30 minutes to 24 hours.

The compound of general formula [1v] can be obtained by subjecting a compound of general formula [1u] to an amidation reaction. This reaction may be a usual amidation reaction, such as a method via an acid chloride, a method via an acid anhydride, a method using a base, a condensing agent and an additive, etc. For example, in the case of using a base, a condensing agent and an additive, the amines which can be used in the reaction include primary amines such as methylamine, benzylamine, aniline, phenethylamine, aminothiazole and the like; secondary amines such as dimethylamine, diethylamine, di-n-propylamine and the like; cyclic amines such as piperidine, morpholine and the like; and amitno acids such as leucine, asparagine, aspartic acid, β-alanine and the like. The amine is used in an amount of 0.5–10 mol and preferably 1–3 mol per mol of the compound of general formula [1u]. As the base which can be used in this reaction, organic amines such as dimethylaminopyridine, triethylamine, pyridine, N-methylmorpholine and the like and alkali metal carbonates such as potassium carbonate, sodium carbonate and the like can be referred to, and the amount thereof is 0.5–10 mol and preferably 1–3 mol per mol of the compound of general formula [1u]. As the condensing agent, dicyclohexyl carbodiimide, diisopropyl carbodiimide, N-ethyl-N'-3-dimethylaminopropyl carbodiimide, diphenyl phosphoryl azide and the like can be referred to, and as the additive, 1-hydroxybenzotriazole, N-hydroxysuccinimide and the like can be referred to. The amounts of the condensing agent and the additive are both 0.5–10 mol and preferably 1–3 mol per mol of the compound of general formula [1u]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at a temperature of −20° C. to 150° C. and preferably at 0–120° C., for a period of 30 minutes to 24 hours.

The compound of general formula [1v] can be obtained by, for example, oxidizing a compound of general formula [1t].

As the oxidant which can be used in this reaction, for example, peracids such as peracetic acid, trifluoro-peracetic acid, perbenzoic acid, m-chloroperbenzoic acid and the like; hydrogen peroxide; chromic acid; potassium permanganate and the like can be referred to. The oxidant is used in an amount of 0.5–5 mol and preferably 1–3 mol per mol of the compound of general formula [1t]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; alcohols such as methanol, ethanol and the like; esters such as methyl acetate, ethyl acetate and the like; nitrites such as acetonitrile and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. This reaction is carried out usually at a temperature ranging from 0° C. to reflux temperature of the used solvent and preferably at 0–30° C., for a period of 30 minutes to 24 hours.

The compounds of general formulas [1s], [1t], [1u] and [1v] which have been obtained in the above-mentioned manner can be converted to other compounds of general formula [1] by, for example, subjecting them to reactions known in themselves such as oxidation, reduction, rearrangement, substitution, halogenation, dehydration, hydrolysis, etc. or appropriately combining these reactions. The compounds of general formula [1s], [1t], [1u] and [1v] or salts thereof thus obtained can be isolated and purified by the conventional procedures such as extraction, crystallization and/or column chromatography, etc.

By converting the compound of [1s] or [1u], for example, to an acid halide by the conventional method, reacting the acid halide with diethyl malonate and magnesium chloride in the presence of a base such as triethylamine and then subjecting the product to hydrolysis and decarboxylation, there can be obtained a compound in which $R^{13a}$ is an an unsubstituted or substituted alkyl group. By converting the compound of [1s] or [1u] to an acid halide by the conventional method and then reacting the acid halide with alkylmercaptan, there can be obtained a compound in which $R^{13a}$ is an unsubstituted or substituted alkylthio group. Further, by converting the compound of [1s] or [1u] to an acid halide by the conventional method and then subjecting the acid halide to Friedel-Crafts reaction with an aryl or heterocyclic group in the presence of an acid such as aluminum chloride or the like, there can be obtained a compound in which $R^{13a}$ is an unsubstituted or substituted aryl or heterocyclic group.

The compound of general formula [32] which is a starting compound for production of the compound of the present invention can be produced according to the method described in, for example, Synthesis, Page 48 (1986) or the like or a similar method.

In the production processes mentioned above, the compounds of general formulas [32], [33], [34], [35], [36], [37], [38], [39], [40], [41], [42], [1s], [1t] and [1u] can be used in the form of a salt, too. As said salt, the same ones as mentioned in the paragraph of salts of the compound of general formula [1] can be referred to.

The compounds of general formulas [32], [33], [34], [35], [36], [37], [38], [39], [40], [41], [42], [1s], [1t], [1u] and [1v] can be converted to salts thereof. As said salts, the same ones as mentioned in the paragraph of general formula [1] can be referred to.

In the above-mentioned production processes, some of the compounds of general formulas [32], [33], [34], [35], [36], [37], [38], [39], [40], [41], [42], [1s], [1t] and [1u] have isomers such as optical isomer, geometrical isomer, tautomer, etc. In such cases, these isomers are also usable in the present invention. Further, solvated products, hydrates and various crystal forms of these compounds are also usable. In the compounds of general formulas [32], [33], [34], [35], [36], [37], [38], [39], [40], [41], [42], [1s], [1t], [1u] and [1v], some compounds have an amino group, a hydroxyl group, a mercapto group or a carboxyl group. It is possible, if desired, to protect these groups previously with a usual protecting group and, after the reaction, to eliminate the protecting group according to a method known in itself.

It is also possible to obtain the compounds of general formulas [1w], [1x] and [1y] by, for example, the following Production Processes 5–7.

Production Process 5

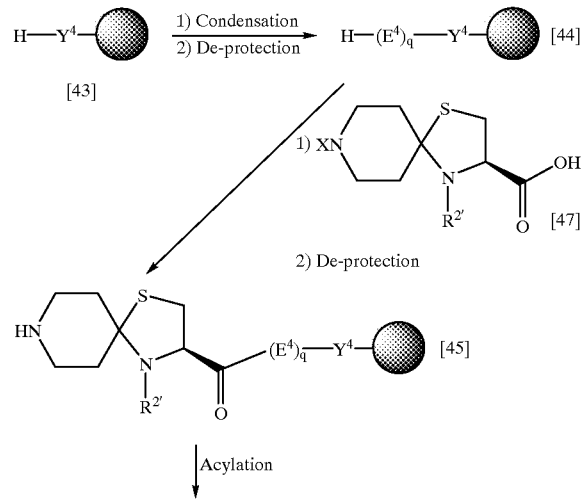

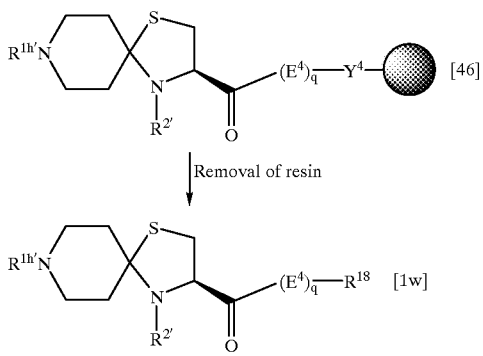

wherein
Y⁴ represents O or NH; q reprsesents 0, 1, 2 or 3, provided that when q is zero, Y⁴ represents NH; E⁴ represents amino acid residue; and R¹ʰ' represents a roup of the following general formula:

R¹⁵'—Y³'— wherein Y³' represents carbonyl group; and R¹⁵' represents hydrogen atom, cyano group, protected carboxyl, hydroxyl or mercapto group or an unsubstituted or substituted alkyl, alkenyl, cycloalkyl, aryl, alkoxy, alkylthio, alkylsulfonyl, arylsulfonyl, sulfamoyl, acyl, acyloxy, alkoxycarbonyl, aryloxycarbonyl, amino, carbamoyl, carbamoyloxy or heterocyclic group; or a group of the following general formula:

R¹⁶—(E³)ₛ— wherein R¹⁶ represents hydrogen atom or a protecting group for amino group; E³ represents amino acid residue; and s represents 2 or 3; and X represents a protecting group for amino group; and R²' represents hydrogen atom or an unsubstituted or substituted acyl group.

The amino acid-bounded resin of general formula [44] can be obtained by reacting a resin of general formula [43] with an amino acid derivative, followed by de-protection. As the resin usable in this reaction, the resins conventionally used in the solid phase method can be referred to, of which examples include benzhydrylamine resin, 4-methylbenzhydrylamine resin, Rink amide resin, oxymethyl resin, oxymethylphenoxymethyl resin and the like. As the amino acid derivatives usable in this reaction, there can be referred to those amino acid derivatives in which t-butyloxycarbonyl (Boc) group or 9-fluorenylmethoxycarbonyl (Fmoc) group is used as protecting group for an α-amino acid, those in which t-butyl ester group, benzyl ester group, cyclohexyl ester group or the like is used as protecting group for the side chain functional group such as the side chain carboxyl group of aspartic acid or glutamic acid; those in which t-butyl group, benzyl group, 2,6-dibromobenzyl group or the like is used as a protecting group for the side chain hydroxyl group of serine, threonine, tyrosine; those in which trityl group, acetamidomethyl group, t-butyl group or the like is used as a protecting group for the side chain thiol group of cycteine; etc. Among these amino acid derivatives, Fmoc-amino acids are preferred.

(1) An amino acid-bounded resin with protected N-terminal can be obtained by condensing a resin with an amino acid derivative. Concretely speaking, it can be obtained by introducing a resin into a reactor, adding a solvent thereto to swell the resin, filtering off the solvent, adding an amino acid derivative and a condensation reagent, again adding a solvent, and then carrying out a reaction. As the condensation reagent used in this reaction, dicyclohexyl carbodiimide, diisopropyl carbodiimide, benzotriazole-1-yl-oxy-tris-pyrrolidino-phosphonium hexafluorophosphate (PyBOP), bromo-tris-pyrrolidino-phosphonium hexafluorophosphate (PyBroP) and the like can be referred to, and the amount thereof is 1–10 equivalents per equivalent of amino group in the resin. In the case of using PyBOP or PyBroP, an amine such as diisopropylethylamine, triethylamine or the like may be added, if desired, in an amount of 1–5 equivalents per equivalent of the condensing agent. It is also allowable to add 0.5–5 equivalents of an ester-activator such as N-hydroxybenzotriazole, N-hydroxy-7-azabenzotriazole or the like per equivalent of the condensation reagent. As the solvents used in this reaction, N,N-dimethylformamide, dichloromethane, chloroform, N-methylpyrrolidone and the like can be referred to. Although the amount of the solvent is not particularly critical, 5–100 ml and preferably 5–20 ml of solvent is used per gram of the resin when used for swelling the resin, and 5–100 ml, preferably 5–50 ml, of solvent is used per gram of the resin when used for reaction. This reaction is carried out usually at 10–40° C. and preferably at 20–30° C. for a period of 5–120 minutes.

(2) An amino acid-bounded resin with de-protected N-terminal can be obtained by reacting an amino acid-bounded resin having a protected N-terminal with a de-protecting agent and thereby eliminating the protecting group for a-amino acid. Concretely speaking, a peptide-bonding resin having a protected N-terminal is reacted in the presence of an acid or a base in the resence or absence of a solvent. The de-protecting group used in this reaction is properly selected in accordance with the kind of protecting group for α-amino acid. For example, in the case where the protecting group for α-amino acid to be eliminated is a Boc group, an acid such as trifluoroacetic acid, methanesulfonic acid and the like is used. In the case where the protecting group for α-amino acid to be eliminated is a Fmoc group, a base such as piperidine, 1,8-diazabicyclo[5.4.0]undec-7-ene or the like is used. The solvent used in this reaction is not critical so far as the solvent exercises no adverse influence on the reaction. When an acid is used for the elimination, dichloromethane, dichloroethane and the like can be used. When a base is used for the elimination, N,N-dimethylformamide, N-methylpyrrolidone and the like can be used. When a solvent is used, the solvent may be used in a proportion of 5–20 ml per one gram of the resin. The reaction is carried out usually at 10–40° C. and preferably at 20–30° C. for a period of 5–120 minutes.

For combining two or more amino acid residues, the procedure mentioned above is repeated.

The resin of general formula [45] can be obtained by reacting an amino acid-bounded resin of general formula [44] with a compound of general formula [47], followed by de-protection. This reaction can be effected in the same manner as above.

The resin of general formula [46] can be btained by acylating a resin of general formula [45]. This reaction can be effected in the same manner as above. In a case where the functional group of the compound bonded to the resin of formula [46] is protected, conversion to other compound can be carried out by de-protection followed by acylation, sulfonylation or the like. These reactions may be effected in the same manner as above.

The compound of general formula [1w] can be obtained by treating a resin of general formula [46] in the presence of an acid to remove the resin therefrom. The acid used in this reaction is properly selected in accordance with the combination of the used resin and the protecting group for amino group. The acids include, for example, trifluoromethanesulfonic acid, anhydrous hydrogen fluoride, trifluoroacetic acid and the like. The solvent used in this reaction is not critical so far as the solvent exercises no adverse influence on the reaction. For example, dichloromethane is used for this purpose. Although the amount of the solvent is not critical, 5–100 ml of the solvent may be used per gram of the resin. The reaction is carried out at −10° C. to 40° C. and preferably at 0–20° C., for a period of 30–300 minutes.

Production Process 6

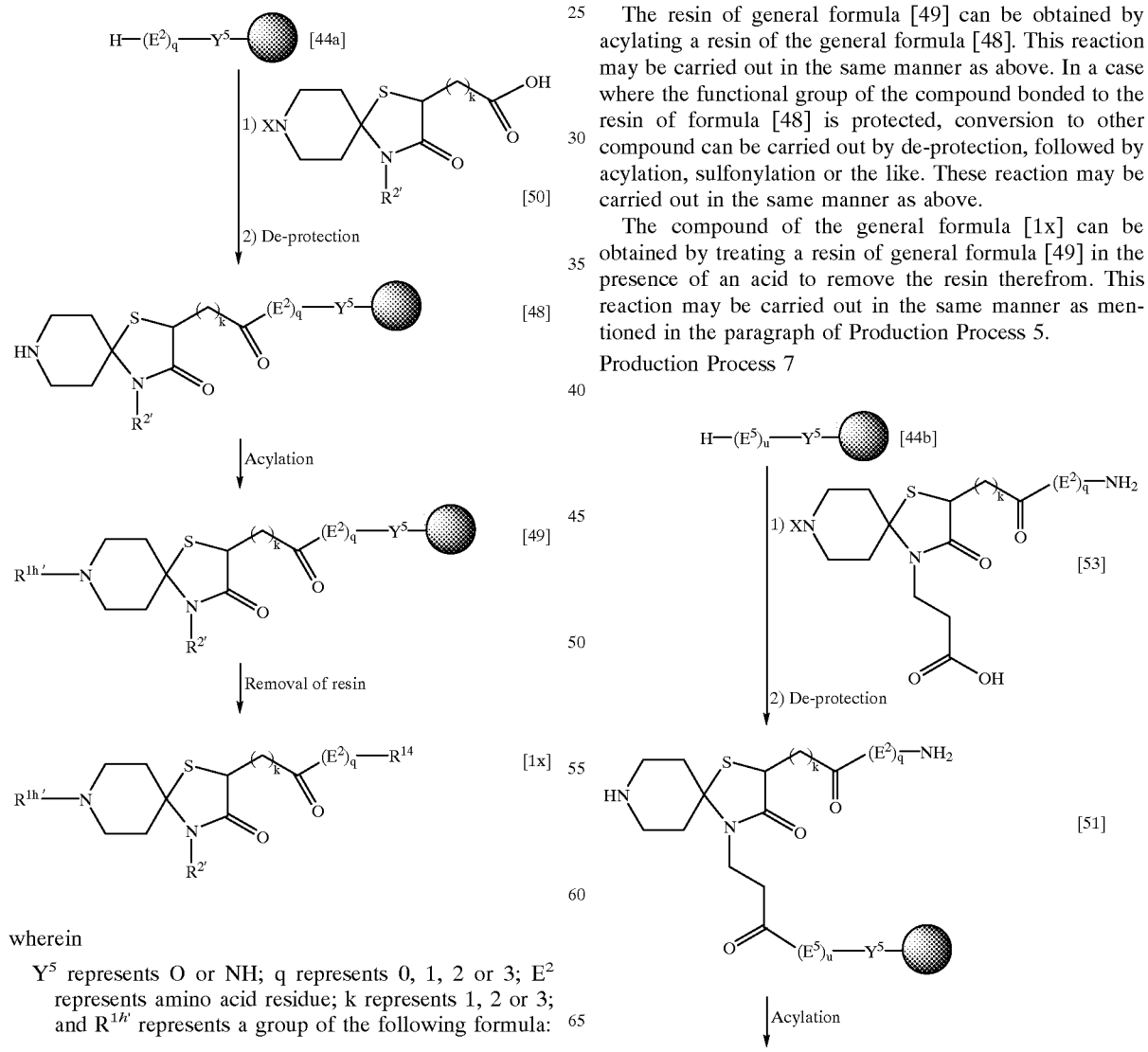

wherein
Y$^5$ represents O or NH; q represents 0, 1, 2 or 3; E$^2$ represents amino acid residue; k represents 1, 2 or 3; and R$^{1h'}$ represents a group of the following formula:

R$^{11'}$—Y$^{2'}$— wherein Y$^{2'}$ represents carbonyl group; and R$^{11'}$ represents hydrogen atom, cyano group, protected carboxyl, hydroxyl or mercapto group, or an unsubstituted or substituted alkyl, alkenyl, cycloalkyl, aryl, alkoxy, alkylthio, alkylsulfonyl, arylsulfonyl, sulfamoyl, acyl, acyloxy, alkoxycarbonyl, aryloxycarbonyl, amino, carbamolyl, carbamoyloxy or heterocyclic group; or a group of the following general formula:

R$^{12}$—(E$^1$)$_j$— wherein R$^{12}$ represents hydrogen atom or a protecting group for amino group; R$^{14}$ represents hydroxyl group or amino group; E$^1$ represents amino acid residue; and j represents 2 or 3; and X represents a protecting group for amino group; and R$^{2'}$ represents hydrogen atom or an unsubstituted or substituted acyl group.

The resin of general formula [48] can be obtained by reacting a resin of general formula [44a] with a compound of general formula [50], followed by de-protection. This reaction may be carried out in the same manner as mentioned in the paragraph of Production Process 5.

The resin of general formula [49] can be obtained by acylating a resin of the general formula [48]. This reaction may be carried out in the same manner as above. In a case where the functional group of the compound bonded to the resin of formula [48] is protected, conversion to other compound can be carried out by de-protection, followed by acylation, sulfonylation or the like. These reaction may be carried out in the same manner as above.

The compound of the general formula [1x] can be obtained by treating a resin of general formula [49] in the presence of an acid to remove the resin therefrom. This reaction may be carried out in the same manner as mentioned in the paragraph of Production Process 5.

Production Process 7

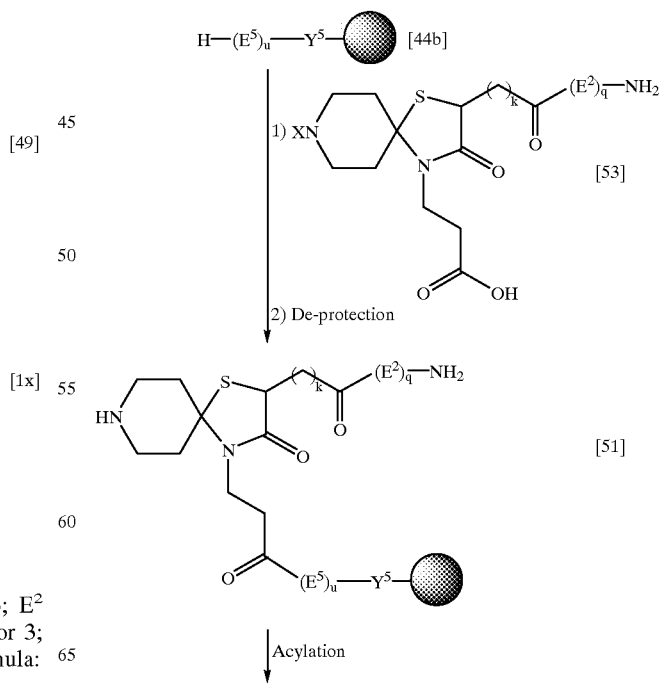

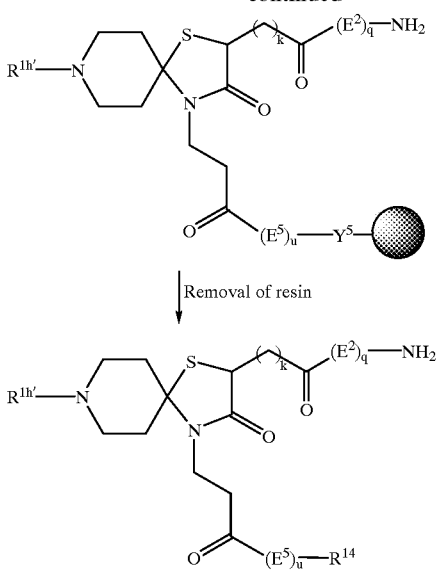

[52]

Removal of resin

[1y]

wherein
Y$^5$ represents O or NH; k represents 1, 2, or 3; q represents 0, 1, 2 or 3; u represents 0, 1, 2 or 3; and R$^{1h'}$ represents a group of the following general formula:

R$^{11'}$—Y$^{2'}$— wherein Y$^{2'}$ represents carbonyl group; and R$^{11'}$ represents hydrogen atom, cyano group, protected carboxyl, hydroxyl or mercapto group, or an unsubstituted or substituted alkyl, alkenyl, cycloalkyl, aryl, alkoxy, alkylthio, alkylsulfonyl, arylsulfonyl, sulfamoyl, acyl, acyloxy, alkoxycarbonyl, aryloxycarbonyl, amino, carbamoyl, carbamoyloxy or heterocyclic group; or a group of the following general formula:

R$^{12}$—(E$^1$)$_j$— wherein R$^{12}$ represents hydrogen atom or a protecting group for amino group; E$^1$ represents amino acid residue; and j represents 2 or 3; and R$^{2'}$ represents hydrogen atom, or an unsubstituted or substituted acyl group; R$^{14}$ represents hydroxyl group or amino group; E$^2$ and E$^5$ each represents amino acid residue; and X represents a protecting group for amino group.

The resin of general formula [51] can be obtained by reacting a resin of general formula [44b] with a compound of general formula [53], followed by de-protection. This reaction may be carried out in the same manner as in the description of Production Process 5.

The resin of general formula [52] can be obtained by acylating a resin of general formula [51]. This reaction may be carried out in the same manner as above. In a case where the functional group of the compound bonded to the resin of formula [52] is protected, conversion to other compounds can be carried out by de-protection, followed by acylation, sulfonylation, etc. These reactions may be carried out in the same manner as above.

The compound of general formula [1y] can be obtained by treating a resin of general formula [52] in the presence of an acid to remove the resin therefrom. This reaction may be carried out in the same manner as mentioned in the paragraph of Production Process 5.

The compound of general formula [55] which is a starting compound for production of the compound of the present invention can be obtained, for example, in the following manner.

[Production Process F]

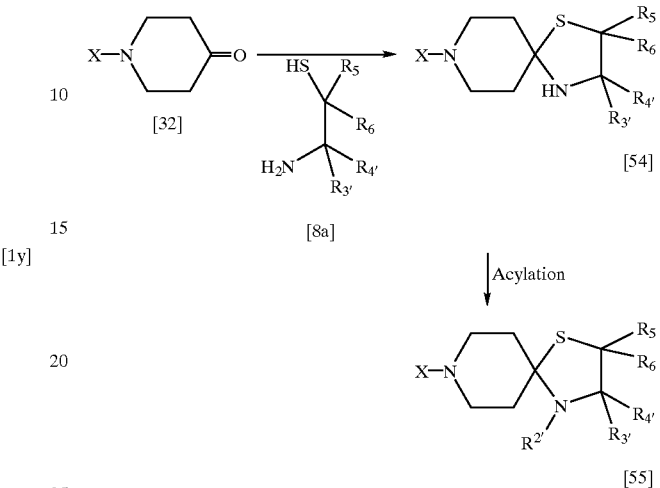

[8a]

Acylation

[55]

wherein X represents a protecting group for amino group; R$^{3'}$, R$^{4'}$, R$^5$ and R$^6$ are as defined above; and R$^{2'}$ represents an unsubstituted or substituted acyl group.

The compound of general formula [54] can be obtained according to, for example, the process mentioned in JP-A 53-44574, or the like. More concretely speaking, it can be obtained by reacting a compound of general formula [32] with a compound of general formula [8a] in the presence or absence of a base, a dehydrating agent and a catalyst, and subjecting the product to a dehydrating ring closure. Although the compound of general formula [8a] used in this reaction is not particularly critical, D-cysteine, L-cysteine, D-penicillamine and L-penicillamine and salts thereof can be referred to, for example. The compound of general formula [8a] is used in an amount of 0.5–10 mol and preferably 1–2 mol per mol of the compound of general formula [32]. As the base which may be used according to the need, for example, organic amines such as dimethylaminopyridine, triethylamine, pyridine and the like, alkali metal carbonates such as potassium carbonate, sodium carbonate and the like; etc. can be referred to, and the amount thereof is 0.5–10 mol and preferably 1–2 mol per mol of the compound of general formula [32]. As the dehydrating agent which may be used according to the need, zeolam, molecular sieve, calcium chloride, magnesium sulfate, diphosphorus pentoxide and the like can be referred to, and the amount thereof is 1–10 times (w/w) and preferably 1–2 times (w/w) as much as the weight of the compound of general formula [32]. As the catalyst which may be used according to the need, paratoluene-sulfonic acid, benzenesulfonic acid, hydrochloric acid, sulfuric acid and the like can be referred to, and the amount thereof is 0.001–1 mol and preferably 0.01–0.1 mol per mol of the compound of general formula [32]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; alcohols such as methyl alcohol, ethyl alcohol, isopropyl alcohol and the like; amides such as N,N-dimethylformamide, N,N-dimethylacetamide and the like; halogenated hydrocarbons such as chloroform, methylene chloride and the like; water; and sulfoxides such as dimethyl sulfoxide and the like. These solvents may be used alone or in mixture of two or more. This reaction is carried out usually at 0–150° C. and preferably at 20–120° C., for a period of 30 minutes to 24 hours.

The compound of general formula [55] can be obtained by, for example, acylating a compound of general formula [54] in the presence or absence of a base. As the acylating agent which can be used in this reaction, for example, acetic anhydride, acetyl chloride, benzoyl chloride, pyrrolecarbonyl chloride, thiazolecarbonyl chloride and the like can be referred to. The amount of said acylating agent is 0.5–10 mol and preferably 1–3 mol per mol of the compound of general formula [54]. As the base which may be used according to the need, organic amines such as dimethylaminopyridine, triethylamine, pyridine and the like and alkali metal carbonates such as potassium carbonate, sodium carbonate and the like can be referred to, and the amount thereof is 0.5–10 mol and preferably 1–3 mol per mol of the compound of general formula [54]. The solvent used in this reaction is not particularly critical so far as the solvent exercises no adverse influence upon the reaction. Examples of the solvent which can be used include aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like. These solvents may be used alone or in mixture of two or more. The reaction is carried out usually at −20° C. to 150° C. and preferably at 0–120° C., for a period of 30 minutes to 24 hours.

It is also possible, if desired, to eliminate the protecting group just after the compound [55] has been obtained and thereafter to convert it to other protecting group.

In the production processes mentioned above, the compounds of general formulas [8a], [32], [43], [44], [44a], [44b], [45], [46], [47], [48], [49], [50], [51], [52], [53], [54], [55], [1w], [1x] and [1y] can be used in the form of a salt, too. As said salt, the same ones as mentioned in the paragraph of salts of the compound of general formula [1] can be referred.

In the above-mentioned Production Processes 5, 6, 7 and F, some of the compounds of general formulas [8a], [32], [43], [44], [44a], [44b], [45], [46], [47], [48], [49], [50], [51], [52], [53], [54], [55], [1w], [1x] and [1y] have isomers such as optical isomer, geometrical isomer, tautomer, etc. In such cases, these isomers are also usable in the present invention. Further, solvated products, hydrates and various crystal forms of these compounds are also usable.

In the compounds of general formulas [8a], [32], [43], [44], [44a], [44b], [45], [46], [47], [48], [49], [50], [51], [52], [53], [54], [55], [1w], [1x] and [1y], some compounds have an amino group, a hydroxyl group, a mercapto group or a carboxyl group. It is possible, if desired, to protect these groups with a usual protecting group previously and, after the reaction, to eliminate the protecting group according to a method known in itself.

When the compound of the present invention is used as a medical drug, conventional adjuvants for preparations such as an excipient, a carrier, a diluent and the like may be appropriately mixed into the composition, and the preparations thus obtained can be orally or non-orally administered in the form of tablet, capsule, powder, syrup, granule, pill, suspension, emulsion, solution, powdery preparation, suppository, ointment, injection and the like according to usual ways. The method, dosage and frequency of administration can properly be selected according to age, body weight and symptom of the patient. Usually, in case of adult patients, the preparation is orally or non-orally (for example, by injection, instillation, rectal application and the like) administered at a dosage of 0.1 to 100 mg/kg per day, at once or in several portions.

Next, pharmacological activities of typical compounds of the present invention will be mentioned below.

[Testing Method]

Test Example 1: Preparation of Transfectant

A reporter plasmid was prepared according to the method of R. I. Scheinman et al. [Mol. Cell. Biol., Vol. 15, Pages 943–953 (1995)]. That is, a plasmid p(TRE)$_5$TK-Luc was constructed by connecting a promoter of thymidine kinase (TK) at an upstream site of luciferase (Luc) gene which is a reporter gene and a 5-times repeated TRE sequence at a further upstream site thereof. The plasmid was co-transfected simultaneously with p3'SS plasmid (prepared by Stratagene Co.) by the electrotranspolation method onto mouse 3T3 fibroblast (ATCC: CCL-163) cultured in a Dulbecco's modified Eagle's medium (DMEM) containing 10% fetal calf serum (FCS). Then the cells were cultured in DMEM containing 10% FCS and 100 μg/ml of Hygromycin B. Using the expression of Hygromycin-resistant gene contained in p3'SS as an indicator, cell strains of the transfectant into which the objective plasmid had been introduced stably were selected. Furthermore in the test mentioned below, cell strains showing expression of Luc gene under stimulation of 12-O-tetradecanoylphorbol 13-acetate (TPA, prepared by Sigma Co.) were used, and DMEM containing 10% FCS and 100 μg/ml of Hygromycin B was used for the culture of cells.

Test Example 2: Luciferase Assay

The cells prepared above were suspended in culture medium, and plated 96 well-plate at 1×10$^4$ cells/0.1 ml. After culturing it overnight, 50 μl of test compounds solution and 40 μl of culture medium were added, and incubated. After one hour 10 μl of 200 ng/ml TPA solution was added and the culture was continued for an additional 16 hours to stimulate the cells. The end of cluture, the cells were recovered, and cell lysis solutions were obtained. The Luc activity of the cell lysates was measured with a chemilluminescent detection kit (Pica Gene; manufactured by Toyo Ink Co.). The suppressive effect of each test compound could be assessed as a decrease of Luc activity, and the inhibition rate (%) was calculated according to the following formula:

Inhibition rate (%)=(1−Luc activity of cells to which the compound is added/Luc activity of cells to which the compound is not added)×100

Test Example 3: XTT Assay (Cytotoxicity Test)

The same culture plate as above was prepared, and test compound and TPA were added under the same conditions as above, after which a culture was carried out for 16 hours. The end of cluture, XTT reagent prepared according to the method of D. A. Scudievo [Cancer Res., Vol. 48, Pages 4827–4833 (1988)] was added and made to react for a prescribed period of time. Then, the amount of formazan formed by alive cells was analyzed by measuring absorbance at 450 nm using a micro plate reader. In this test, a decrease in absorbance is observed when the test compounds show a cytotoxicitic or a growth inhibitory activity. Cell viability (T/C %) was determined according to the following formula:

Cell Viability Rate (T/C %)=(Absorbance of well to which compound is added/Absorbance of well to which the compound was not added)×100

The results are shown in Table 52.

TABLE 52

| Example No. | Concentration μg/ml | Inhibition rate (%) | Cell viability (%) |
|---|---|---|---|
| 1 | 50 | 80 | 80 |
| 2 | 100 | 38 | 81 |
| 6 (3) | 100 | 91 | 83 |
| 6 (5) | 30 | 60 | 106 |
| 12 | 100 | 74 | 84 |
| 13 | 100 | 40 | 80 |
| 14 | 30 | 23 | 100 |
| 15 | 100 | 79 | 87 |
| 16 (11) | 30 | 65 | 94 |
| 17 | 100 | 93 | 79 |
| 18 (1) | 100 | 89 | 97 |
| 18 (4) | 100 | 53 | 83 |
| 18 (8) | 100 | 86 | 86 |
| 18 (17) | 100 | 92 | 83 |
| 18 (18) | 100 | 87 | 78 |
| 18 (19) | 100 | 100 | 98 |
| 20 (1) | 30 | 72 | 98 |
| 20 (2) | 100 | 93 | 92 |
| 21 | 30 | 28 | 74 |
| 29 | 100 | 92 | 110 |
| 40 | 100 | 91 | 108 |
| 41 (2) | 100 | 94 | 71 |
| 41 (3) | 100 | 80 | 97 |
| 41 (4) | 100 | 96 | 82 |
| 41 (5) | 100 | 94 | 90 |
| 41 (6) | 100 | 49 | 97 |
| 41 (7) | 70 | 87 | 71 |
| 41 (8) | 50 | 53 | 78 |
| 41 (9) | 70 | 53 | 95 |
| 41 (10) | 50 | 73 | 75 |
| 41 (11) | 100 | 90 | 85 |
| 41 (12) | 100 | 87 | 79 |
| 41 (13) | 40 | 56 | 77 |
| 41 (14) | 100 | 92 | 73 |
| 41 (15) | 30 | 86 | 100 |
| 44 | 30 | 62 | 75 |
| 47 | 30 | 47 | 83 |
| B-9 | 100 | 46 | 89 |
| B-13 | 10 | 24 | 98 |

The compounds of Example No. 1, 6(3), 6(5), 13, 15, 17, 18(1), 18(8), 20(1) and 20(2) were converted to sodium salts according to the method of Example 42, and then used for the assay.

Test Example 4: Type II Collagen-induced Arthritis in Mice

The compound of Example 20 (1) was tested for the effect on type II collagen-induced arthritis, using 8 weeks old, male DBA/1J mice (Japan Charles River). Emulsion was prepared by mixing an equal volume of bovine type II collagen (prepared by Koken) in 0.1N acetic acid (2 mg/ml) and Freund's complete adjuvant (prepared by Nacalai Tesque). Arthritis was induced by intradermal injection of 0.2 ml (the quantity of antigen: 200 μg/head) of the emulsion into the skin of the tail root twice (day 0 and day 21). The test compound was suspended in 0.5% solution of methyl cellulose, and 100 mg/kg was orally administered once every day from day 21 to day 35. To the control group (negative control group), 0.5% methyl cellulose solution was administered in the same manner as above. Severity of the arthritis was scored 0: no change, 1: only one or two swelling of the joints or slight swelling of the ankle or toes, 2: swelling and/or rubor in further joints, 3: extensive swelling of whole paw, and the maximum possible score for arthritis was 12 points. As to the severity of destruction of joints and bones, X ray photographs of four paws were taken (Softex), and severity of destruction in the second to fifth articulationes interphalangeae, first to fifth articulationes metacarpophalangeae and metatarsophalangeae, and calcaneus was scored by 0 or 1 in accordance with presence or absence of destruction, and the severity of destruction in the carpus and tarsal was scored by 0 to 3. Overall severity of destruction of joints and bones was evaluated by a joint-bone destruction score, taking the total score of the four paws as 50 points [Method in Enzymology, 162, 361–373 (1988)].

The results are shown in Table 53, wherein the scores are mean values.

TABLE 53

| Example No. | Dosage (mg/kg) | Arthritis score | Joint-bone destruction score |
|---|---|---|---|
| Control | — | 10 ± 1 | 20 ± 3 |
| 20 (1) | 100 | 8 ± 1 | 14 ± 3 |

BEST EMBODIMENT FOR CARRYING OUT THE INVENTION

Next, the present invention is explained by referring to referential examples and examples. The present invention is by no means limited by these examples. In the paragraphs of eluents, all the mixing ratios are expressed by volume. The carrier used in the column chromatography is Silica Gel 60, No. 7734 (product of Merck).

Amino acid residues are expressed according to the three-letter system prescribed by IUPAC and IUB. Unless otherwise referred to, meanings of the abbreviations are as follows:

Fmoc: 9-Fluorenylmethoxycarbonyl
PyBOP: Benzotriazol-1-yl-oxy-tris-pyrrolidino-phosphonium hexafluorophosphate
HOBt: N-Hydroxybenzotriazole
DMF: N,N-Dimethylformamide
DIEA: N,N-Diisopropylethylamine
DCM: Dichloromethane
TFA: Trifluoroacetic acid
DIPCDI: Diisopropyl carbodiimide
PMC: 2,2,5,7,8-Pentamethylchroman-6-sulfonyl
DMSO: Dimethyl sulfoxide
Ac: Acetyl
Py: Pyridyl
Cit: Citrolline

EXAMPLE 1

To 20 ml of toluene were added 1.90 g of 4-(3-methylbutylidene)-1-cyclohexanone and 2.05 g of benzyl 3-aminopropionate, and the mixture was stirred at ambient temperature for one hour. Then, 1.72 g of mercaptosuccinic acid was added, and the resulting mixture was heated under reflux for one hour under the condition of azeotropic dehydration by means of Dean Stark. The reaction mixture was added to a mixture of ice water and ethyl acetate, pH was adjusted to 2.0 with 2 mol/L hydrochloric acid, and the organic layer was separated. The organic layer was washed successively with water and saturated aqueous solution of sodium chloride and dried over anhydrous magnesium sulfate, and the solvent was distilled off under reduced pressure. The residue thus obtained was purified by column chromatography [eluent: chloroform:ethanol=50:1] to obtain 3.10 g of 2-[4-[3-(benzyloxy)-3-oxopropyl]-8-(3-methylbutylidene)-3-oxo-1-thia-4-azaspiro[4.5]decan-2-yl]-acetic acid as a light yellow oily product.

NMR (CDCl$_3$+D$_2$O) δ: 0.89(6H,d,J=6.4 Hz), 1.4–2.9 (14H,m), 3.19(1H,dd,J=5.2 Hz,17.0 Hz), 3.4–3.7(2H,m), 4.14(1H,dd,J=5.2 Hz,8.1 Hz), 5.0–5.4(1H,m), 5.12(2H,s), 7.35(5H,s)

EXAMPLE 2

The procedure of Example 1 was repeated to obtain the following compound:

2-[8-(3-methylbutylidene)-3-oxo-4-(5-phenylpentyl)-1-thia-4-azaspiro[4.5]decan-2-yl]-acetic acid NMR (CDCl$_3$) δ: 0.88(6H,d,J=6.1 Hz), 1.1–3.4(23H,m), 4.1–4.3(1H,m), 5.1–5.3(1H,m), 7.21(5H,s), 8.5–9.3(1H,bs)

EXAMPLE 3

To 8 ml of toluene were added 0.75 g of 4-(3-methylbutylidene)-1-cyclohexanone and 0.89 g of benzyl 3-aminopropionate, and the mixture was stirred at ambient temperature for one hour. Then, 1.02 g of β-tert-butyl 2-mercaptosuccinate was added, and the resulting mixture was heated under reflux for 8 hours under the condition of azeotropic dehydration by means of Dean Stark apparatus. The reaction mixture was poured into a mixture of ice water and ethyl acetate, pH was adjusted to 2.0 with 2 mol/L hydrochloric acid, and the organic layer was separated. The organic layer was washed successively with water, saturated aqueous solution of sodium hydrogen carbonate and saturated aqueous solution of sodium chloride and dried over anhydrous magnesium sulfate, and the solvent was distilled off under reduced pressure. The residue thus obtained was purified by column chromatography [eluent: hexane:ethyl acetate=6:1] to obtain 0.75 g of benzyl 3-[2-[2-(tert-butoxy)-2-oxoethyl-8-(3-methylbutylidene)-3-oxo-1-thia-4-azaspiro [4.5]decan-4-yl]-propionate as a light yellow oily product.

NMR (CDCl$_3$) δ: 0.88(6H,d,J=6.4 Hz), 1.4–2.9(14H,m), 1.46(9H,s), 3.15(1H,dd,J=3.8 Hz, 16.7 Hz), 3.4–3.7(2H,m), 4.08(1H,dd,J=3.8 Hz,9.9 Hz), 5.1–5.3(1H,m), 5.11(2H,s), 7.35(5H,s)

EXAMPLE 4

The procedure of Example 3 was repeated to obtain the compounds of Tables 54 and 55.

TABLE 54

| No. | A | R² |
|---|---|---|
| 4 (1) | H₃C-CH(CH₃)-CH₂-CH=C(CH₃)- | —CH₂CH₂—C₆H₅ |
| 4 (2) | H₃C-CH(CH₃)-CH₂-CH=C(CH₃)- | —CH₂-(pyridyl) |
| 4 (3) | H₃C-CH(CH₃)-CH₂-CH=C(CH₃)- | —(thiazolyl) |
| 4 (4) | H₃C-CH(CH₃)-CH₂-CH=C(CH₃)- | —CH(C₆H₅)COOCH₃ |
| 4 (5) | (H₃C)₂CH-C₆H₄-O-C(CH₃)₂- | —CH₂CH₂COOCH₂—C₆H₅ |

TABLE 54-continued
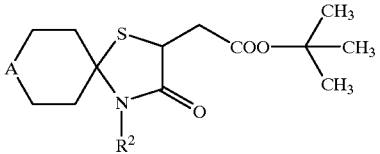
| No. | A | R² |
|---|---|---|
| 4 (6) | 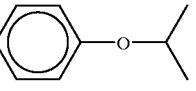 | 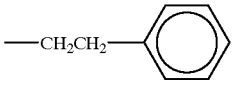 |
| 4 (7) | 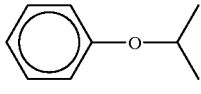 | 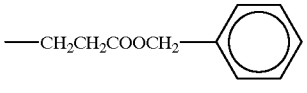 |
TABLE 55
| No. | A | R² |
|---|---|---|
| 4 (8) | 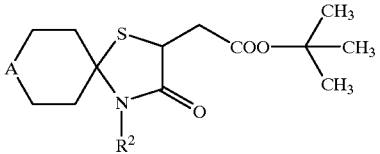 | 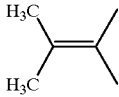 |
| 4 (9) | 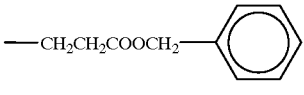 | 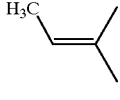 |
| 4 (10) | 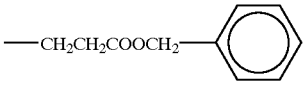 | 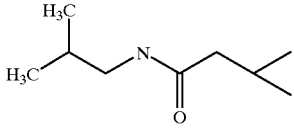 |
| 4 (11) | 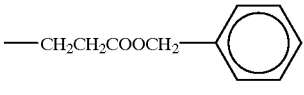 | 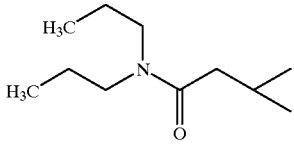 |
| 4 (12) | 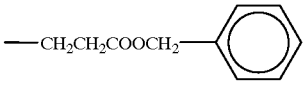 | 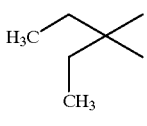 |
| 4 (13) | 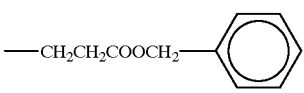 | 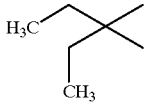 |

TABLE 55-continued

| No. | A | R² |
|-----|---|-----|
| 4 (14) | (CH₃)₂C=CH-CH₂-CH(CH₃)- (H₃C-CH(CH₃)-CH₂-CH=C(CH₃)-) | —CH₂CH₂CH₃ |
| 4 (15) | (CH₃)₂C=CH-CH₂-CH(CH₃)- (H₃C-CH(CH₃)-CH₂-CH=C(CH₃)-) | —CH₂CH₂OCH₃ |

Properties of the compounds of Tables 54 and 55 are shown below.

4(1)
NMR(CDCl₃) δ: 0.89 (6H,d,J=6.3 Hz), 1.3–3.7 (17H,m), 1.48 (9H,s), 4.13 (1H,dd,J=3.7 Hz,10.3 Hz), 5.19 (1H,t,J=7.1 Hz), 7.26 (5H,s)

4(2)
NMR(CDCl₃) δ: 0.87 (6H,d,J=6.1 Hz), 1.2–2.8 (12H,m), 1.48 (9H,s), 3.24 (1H,dd,J=3.8 Hz,16.7 Hz), 4.22 (1H,dd, J=3.8 Hz,9.9 Hz), 4.42 (1H,d,J=15.5 Hz), 4.68 (1H,d,J=15.5 Hz), 5.1–5.3 (1H,m), 7.1–7.4 (1H,m), 7.5–7.8 (1H,m), 8.3–8.7 (2H,m)

4(3)
NMR(CDCl₃) δ: 0.91 (6H,d,J=6.1 Hz), 1.2–3.6 (13H,m), 1.48 (9H,s), 4.33 (1H,dd,J=3.9 Hz,9.3 Hz), 5.1–5.5 (1H,m), 7.06 (1H,d,J=3.5 Hz), 7.50 (1H,d,J=3.5 Hz)

4(4)
NMR(CDCl₃) δ: 0.7–1.0 (6H,m), 1.46 (9H,s), 1.5–3.0 (12H,m), 3.1–3.5 (1H,m), 3.73 (3H,s), 4.0–4.3 (1H,m), 4.84 (1H,bs), 5.0–5.3 (1H,m), 7.34 (5H,s)

4(5)
NMR(CDCl₃) δ: 1.23 (6H,d,J=6.8 Hz), 1.46 (9H,s), 1.4–3.0 (12H,m), 3.16 (1H,dd,J=3.7,16.7 Hz), 3.5–3.8 (2H, m), 4.07 (1H,dd,J=3.7 Hz,10.3 Hz), 4.6–4.8 (1H,m), 5.13 (2H,s), 6.83 (2H,d,J=8.7 Hz), 7.14 (2H,d,J=8.7 Hz), 7.35 (5H,s)

4(6)
NMR(CDCl₃) δ: 1.22 (6H,d,J=6.8 Hz), 1.47 (9H,s), 1.5–2.3 (8H,m), 2.4–3.1 (5H,m), 3.2–3.5 (2H,m), 3.9–4.2 (2H,m), 6.81 (2H,d,J=8.6 Hz), 7.13 (2H,d,J=8.6 Hz), 7.27 (5H,s)

4(7)
NMR(CDCl₃) δ: 1.46 (9H,s), 1.4–2.9 (11H,m), 3.17 (1H, dd,J=3.7 Hz,16.6 Hz), 3.5–3.8 (2H,m), 4.08 (1H,dd,J=3.7 Hz,10.0 Hz), 4.4–4.6 (1H,m), 5.14 (2H,s), 6.8–7.6 (10H,m)

4(8)
NMR(CDCl₃) δ: 1.46 (9H,s), 1.67 (6H,s), 1.6–2.8(11H, m), 3.15 (H,dd,J=3.8 Hz,16.6 Hz), 3.4–3.7 (2H,m), 4.08 (1H,dd,J=3.8 Hz,10.0 Hz), 5.12 (2H,s), 7.34 (5H,s)

4(9)
NMR(CDCl₃) δ: 1.46 (9H,s), 1.58 (3H,d,J=6.8 Hz), 1.7–2.8 (11H,m), 3.15 (1H,dd,J=3.8 Hz,16.7 Hz), 3.4–3.7 (2H,m), 4.08 (1H,dd,J=3.8 Hz,9.9 Hz), 5.11 (2H,s), 5.1–5.3 (1H,m), 7.35 (5H,s)

4(10)
NMR(CDCl₃) δ: 0.91 (6H,d,J=6.4 Hz), 1.2–2.8 (15H,m), 1.46 (9H,s), 3.0–3.3 (3H,m), 3.4–3.7 (2H,m), 4.02 (1H,dd, J=3.7 Hz,10.0 Hz), 5.12 (2H,s), 5.5–5.8 (1H,m), 7.36 (5H,s)

4(11)
NMR(CDCl₃) δ: 0.8–1.0 (6H,m), 1.2–2.8 (18H,m), 1.46 (9H,s), 3.0–3.7 (7H,m), 4.03 (1H,dd,J=3.7 Hz,10.3 Hz), 5.12 (2H,s), 7.36 (5H,s)

4(12)
NMR(CDCl₃) δ: 0.76 (6H,t,J=7.3 Hz), 1.1–2.9 (15H,m), 1.46 (9H,s), 3.13 (1H,dd,J=3.7 Hz,16.6 Hz), 3.5–3.8 (2H,m), 4.03 (1H,dd,J=3.7 Hz,10.0 Hz), 5.13 (2H,s), 7.36 (5H,s)

4(13)
NMR(CDCl₃) δ: 0.76 (6H,t,J=7.3 Hz), 1.1–2.3 (12H,m), 1.47 (9H,s), 2.52 (1H,dd,J=10.3 Hz,16.6 Hz), 2.8–3.7 (5H, m), 4.08 (1H,dd,J=3.7 Hz,10.3 Hz), 7.27 (5H,m)

EXAMPLE 5

In 10 ml of methylene chloride was dissolved 0.50 g of benzyl 3-[2-[2-(tert-butoxy)-2-oxoethyl]-8-(3-methylbutylidene)-3-oxo-1-thia-4-azaspiro[4.5]decan-4-yl]-propionate. After adding 2 ml of trifluoroacetic acid at 0–5° C., the mixture was stirred at ambient temperature of 2 hours. Distillation of the solvent under reduced pressure, followed by an azeotropic distillation with toluene gave 0.37 g of 2-[4-[3-(benzyloxy)-3-oxopropyl]-8-(3-methylbuthylidene)-3-oxo-1-thia-4-azaspiro[4.5]decan-2-yl]-acetic acid as a light yellow oily product.

NMR (CDCl₃+D₂O) δ: 0.89(6H,d,J=6.4 Hz), 1.4–2.9 (14H,m), 3.19 (1H,dd,J=5.2 Hz,17.0 Hz), 3.4–3.7(2H,m), 4.14(1H,dd,J=5.2 Hz, 8.1 Hz), 5.0–5.4(1H,m), 5.12(2H,s), 7.35(5H,s)

EXAMPLE 6

The procedure of Example 5 was repeated to obtain the compounds of Tables 56 and 57.

TABLE 56
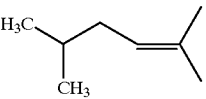
| No. | A | R² |
|---|---|---|
| 6 (1) | 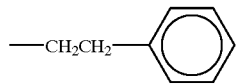 | 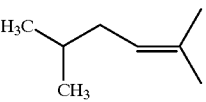 |
| 6 (2) | 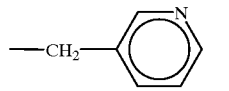 | 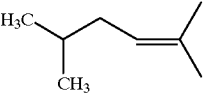 |
| 6 (3) | 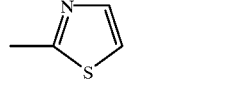 | 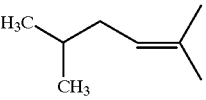 |
| 6 (4) |  | 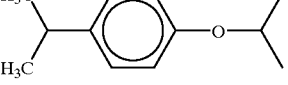 |
| 6 (5) | 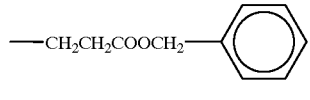 | —CH₂CH₂COOCH₂— |
| 6 (6) | 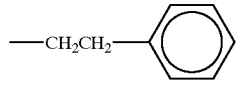 | —CH₂CH₂—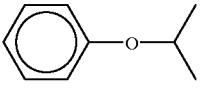 |
| 6 (7) | 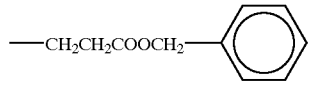 | —CH₂CH₂COOCH₂—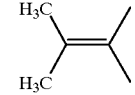 |
TABLE 57
| No. | A | R² |
|---|---|---|
| 6 (8) | 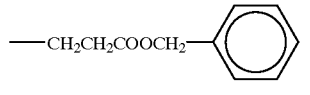 | —CH₂CH₂COOCH₂—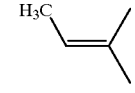 |
| 6 (9) | 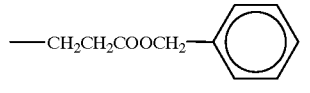 | —CH₂CH₂COOCH₂— |

TABLE 57-continued

| No. | A | R² |
|---|---|---|
| 6 (10) | (H₃C)₂CHCH₂-N(C(=O)C(CH₃)₂-)- | —CH₂CH₂COOCH₂—C₆H₅ |
| 6 (11) | (H₃CCH₂CH₂)₂N-C(=O)C(CH₃)₂- | —CH₂CH₂COOCH₂—C₆H₅ |
| 6 (12) | (H₃C)₃C-CH(CH₃)- | —CH₂CH₂COOCH₂—C₆H₅ |
| 6 (13) | (H₃C)₃C-CH(CH₃)- | —CH₂CH₂—C₆H₅ |
| 6 (14) | H₃C-CH(CH₃)-CH₂-C(CH₃)=C(CH₃)- (prenyl-type) | —CH₂CH₂CH₃ |
| 6 (15) | H₃C-CH(CH₃)-CH₂-C(CH₃)=C(CH₃)- | —CH₂CH₂OCH₃ |

Properties of the compounds of Tables 56 and 57 are shown below.

6(1)
NMR(CDCl₃) δ: 0.89 (6H,d,J=6.1 Hz), 1.3–3.7 (17H,m), 4.20 (1H,dd,J=4.6 Hz,8.5 Hz), 5.20 (1H,t,J=7.2 Hz), 7.26 (5H,s), 8.8–9.2 (1H,bs)

6(2)
NMR(CDCl₃) δ: 0.85 (6H,d,J=6.1 Hz), 1.2–3.4 (13H,m), 4.1–5.6 (4H,m), 7.8–9.2 (4H,m), 11.5–12.4 (1H,bs)

6(3)
NMR(CDCl₃) δ: 0.91 (6H,d,J=5.4 Hz), 1.2–3.6 (13H,m), 4.39 (1H,dd,J=4.4 Hz,8.8 Hz), 5.1–5.4 (1H,m), 7.09 (1H,d, J=3.7 Hz), 7.52 (1H,d,J=3.7 Hz), 6.1–7.0 (1H,bs)

6(4)
NMR(CDCl₃) δ: 0.87 (6H,d,J=6.1 Hz), 1.1–3.0 (12H,m), 3.1–3.5 (1H,m), 3.75 (3H,s), 4.1–4.4 (1H,m), 5.1–5.7 (2H, m), 4.85 (1H,bs), 7.34 (5H,s)

6(5)
NMR(CDCl₃) δ: 1.23 (6H,d,J=6.8 Hz), 1.4–3.0 (12H,m), 3.23 (1H,dd,J=4.6 Hz,17.3 Hz), 3.5–3.8 (2H,m), 4.13 (1H, dd,J=4.6 Hz,8.8 Hz), 4.3–4.6(1H,m), 5.14 (2H,s), 6.83 (2H, d,J=8.7 Hz), 7.14 (2H,d,J=8.7 Hz), 7.35 (5H,s), 8.6–9.4 (1H,bs)

6(6)
NMR(CDCl₃) δ: 1.22 (6H,d,J=6.8 Hz), 1.6–2.3 (8H,m), 2.6–3.7 (7H,m), 3.9–4.3 (2H,m), 6.81 (2H, d,J=8.6 Hz), 7.13 (2H,d,J=8.6 Hz), 7.27 (5H,s), 7.1–7.4 (1H,bs)

6(7)
NMR(CDCl₃+D₂O) δ: 1.4–2.9 (11H,m), 3.21 (1H,dd,J= 4.6 Hz,17.1 Hz), 3.5–3.8 (2H,m), 4.12 (1H,dd,J=4.6 Hz,8.4 Hz), 4.4–4.6 (1H,m), 5.14 (2H,s), 6.8–7.6 (10H,m)

6(8)
NMR(CDCl₃) δ: 1.54 (6H,s), 1.6–2.2 (8H,m), 2.6–2.9 (3H,m), 3.21 (1H,dd,J=4.5 Hz,17.2 Hz), 3.5–3.7 (2H,m), 4.11 (1H,dd,J=4.5 Hz,8.5 Hz), 5.13 (2H,s), 7.36 (5H,s), 8.0–8.6 (1H,bs)

6(9)
NMR(CDCl₃) δ: 1.59 (3H,d,J=6.6 Hz), 1.5–2.9 (11H,m), 3.21 (1H,dd,J=5.0 Hz,17.0 Hz), 3.4–3.7 (2H,m), 4.14 (1H, dd,J=5.0 Hz,8.1 Hz), 5.12 (2H,s), 5.1–5.4 (1H,m), 6.6–7.0 (1H,bs), 7.35 (5H,m)

6(10)
NMR(CDCl₃) δ: 0.91 (6H,d,J=6.6 Hz), 1.2–2.3 (12H,m), 2.5–2.9 (3H,m), 3.0–3.8 (5H,m), 4.09 (1H,dd,J=4.0 Hz,8.9 Hz), 5.13 (2H,s), 5.7–6.0 (1H,m), 6.3–6.7 (1H,bs), 7.35 (5H,s)

6(11)
NMR(CDCl₃) δ: 0.8–1.0 (6H,m), 1.2–2.9 (18H,m), 3.0–3.7 (7H,m), 4.09 (1H,dd,J=4.4 Hz,8.6 Hz), 4.4–4.8 (1H,bs), 5.12 (2H,s), 7.35 (5H,s)

6(12)
NMR(CDCl₃+D₂O) δ: 0.76 (6H,t,J=7.3 Hz), 1.1–2.3 (12H,m), 2.3–2.9 (3H,m), 3.19 (1H,dd,J=5.1 Hz,17.0 Hz), 3.5–3.8 (2H,m), 4.09 (1H,dd,J=5.1 Hz,8.3 Hz), 5.14 (2H,s), 7.36 (5H,s)

6(13)
NMR(CDCl₃+D₂O) δ: 0.76 (6H,t,J=7.4 Hz), 1.1–2.3 (12H,m), 2.5–3.7 (6H,m), 4.16 (1H,dd,J=5.3 Hz,8.4 Hz), 7.26 (5H,s)

6(14)

NMR(CDCl$_3$+D$_2$O) δ: 0.8–1.2 (9H,m), 1.2–3.4 (17H,m), 4.17 (1H,dd,J=4.2 Hz,9.0 Hz), 5.1–5.4 (1H,m)

6(15)

NMR(CDCl$_3$) δ: 0.88 (6H,d,J=6.1 Hz), 1.2–3.7 (17H,m), 3.34 (3H,s), 4.17 (1H,dd,J=5.3 Hz,8.2 Hz), 5.1–5.3 (1H,m), 7.8–8.2 (1H,bs)

EXAMPLE 7

In an atmosphere of nitrogen, 3.32 g of 4-(3-methylbutylidene)-1-cyclohexanone and 5.35 g of benzyl 3-aminopropionate were added to 35 ml of dioxane and stirred at ambient temperature for 30 minutes, after which 2.25 g of mercaptoacetic acid was added and the resulting mixture was stirred under reflux for 3 hours. The reaction mixture was poured into a mixture of ice water and ethyl acetate, pH was adjusted to 2.0 with 2 mol/L hydrochloric acid, and the organic layer was separated. The organic layer was washed successively with water, saturated aqueous solution of sodium hydrogen carbonate and saturated aqueous solution of sodium chloride and then dried over anhydrous magnesium sulfate, and the solvent was distilled off under reduced pressure. Purification of the residue by column chromatography (eluent: hexane:ethyl acetate=6:1) gave 4.36 g of benzyl 3-[8-(3-methylbutylidene)-3-oxo-1-thia-4-azaspiro[4.5]decan-4-yl]-propionate as a light yellow oily product.

NMR (CDCl$_3$) δ: 0.88(6H,d,J=6.1 Hz), 1.4–2.8(13H,m), 3.4–3.7 (2H,m), 3.51 (2H,s), 5.1–5.3(1H,m), 5.12(2H,s), 7.35(5H,s)

EXAMPLE 8

In 40 ml of dioxane was dissolved 4.11 g of benzyl 3-[8-(3-methylbutylidene)-3-oxo-1-thia-4-azaspiro[4.5]decan-4-yl]-propionate. Then, 20.5 ml of 1 mol/L aqueous solution of sodium hydroxide was added at 0–5° C., and the resulting mixture was stirred at ambient temperature for one hour. The reaction mixture was poured into a mixture of chloroform and water, the aqueous layer was separated, ethyl acetate was added to the aqueous layer, pH was adjusted to 2.0 with 2 mol/L hydrochloric acid, and the organic layer was separated. The organic layer was washed successively with water and saturated aqueous solution of sodium chloride and dried over anhydrous magnesium sulfate, and the solvent was distilled off under reduced pressure. Purification of the residue by column chromatography (eluent: chloroform:ethanol=50:1) gave 2.72 g of 3-[8-(3-methylbutylidene)-3-oxo-1-thia-4-azaspiro[4.5]decan-4-yl]-propionic acid as a light yellow oily product.

NMR (CDCl$_3$) δ: 0.88(6H,d,J=6.4 Hz), 1.4–2.8(13H,m), 3.4– 3.7 (2H,m), 3.56(2H,s), 5.1–5.3(1H,m), 7.4–8.1(1H,bs)

EXAMPLE 9

In an atmosphere of nitrogen, 1.97 ml of N,N-diisopropylamine was added to 10 ml of anhydrous tetrahydrofuran, to which was dropwise added 9.50 ml of a solution of n-butyllithium in hexane (1.58 mol/L) at −30° C. The mixture was stirred at the same temperature for 10 minutes and then cooled to −70° C., to which was dropwise added a solution of 1.56 g of 3-[8-(3-methylbutylidene)-3-oxo-1-thia-4-azaspiro[4.5]decan-4-yl]-propionic acid in 20 ml of anhydrous tetrahydrofuran. After stirring the resulting mixture at the same temperature as above for 30 minutes, 0.89 ml of tert-butyl bromoacetate was dropwise added at the same temperature. After elevating the temperature to 0° C., the reaction mixture was poured into a mixture of ice water and ethyl acetate, pH was adjusted to 2.0 with 2 mol/L hydrochloric acid, and the organic layer was separated. The organic layer was washed successively with water and saturated aqueous solution of sodium chloride and dried over anhydrous magnesium sulfate, and the solvent was distilled off under reduced pressure. Thus, 2.23 g of 3-[2-[2-(tert-butoxy)-2-oxoethyl]-8-(3-methylbutylidene)-3-oxo-1-thia-4-azaspiro[4.5]decan-4-yl]-propionic acid was obtained as a yellow oily product.

NMR (CDCl$_3$) δ: 0.87(6H,d,J=6.3 Hz), 1.2–2.8(14H,m), 1.46(9H,s), 3.13(1H,dd,J=3.9 Hz,16.6 Hz), 3.4–3.7(2H,m), 4.11 (1H,dd,J=3.9 Hz,9.6 Hz), 5.1–5.3(1H,m), 6.8–7.6(1H, bs)

EXAMPLE 10

In 10 ml of methylene chloride was dissolved 0.56 g of 3-[2-[2-(tert-butoxy)-2-oxoethyl]-8-(3-methylbutylidene)-3-oxo-1-thia-4-azaspiro[4.5]decan-4-yl]-propionic acid. At ambient temperature, 0.21 g of benzyl alcohol, 0.23 g of 1-hydroxybenzotriazole monohydrate and 0.31 g of dicyclohexyl carbodiimide were successively added. After stirring the resulting mixture for 24 hours at the same temperature as above, the insoluble matter was filtered off. The filtrate was washed successively with 2 mol/L hydrochloric acid, water, saturated aqueous solution of sodium hydrogen carbonate and saturated aqueous solution of sodium chloride, and dried over anhydrous magnesium sulfate, and then the solvent was distilled off under reduced pressure. Purification of the residue by column chromatography [eluent: hexane:ethyl acetate=6:1] gave 0.17 g of benzyl 3-[2-[2-(tert-butoxy)-2-oxoethyl]-8-(3-methylbutylidene)-3-oxo-1-thia-4-azaspiro[4.5]decan-4-yl]-propionate as a light yellow oily product.

NMR (CDCl$_3$) δ: 0.88(6H,d,J=6.4 Hz), 1.4–2.9(14H,m), 1.46(9H,s), 3.15(1H,dd,J=3.8 Hz,16.7 Hz), 3.4–3.7(2H,m), 4.08(1H,dd,J=3.8 Hz,9.9 Hz), 5.1–5.3(1H,m), 5.11(2H,s), 7.35(5H,s)

EXAMPLE 11

In 7 ml of N,N-dimethylformamide was added 0.70 g of 3-[2-[2-(tert-butoxy)-2-oxoethyl]-8-(3-methylbutylidene)-3-oxo-1-thia-4-azaspiro[4.5]decan-4-yl]-propionic acid. After adding 0.14 ml of ethyl iodide and 0.25 g of anhydrous potassium carbonate at 0–5° C., the resulting mixture was stirred at ambient temperature for 3 hours. The resulting mixture was poured into a mixture of ice water and ethyl acetate, pH was adjusted to 2.0 with 2 mol/L hydrochloric acid, and the organic layer was separated. The organic layer was washed successively with water, saturated aqueous solution of sodium hydrogen carbonate and saturated aqueous solution of sodium chloride and dried over anhydrous magnesium sulfate, and the solvent was distilled off under reduced pressure. Thus, 0.70 g of ethyl 3-[2-[2-(tert-butoxy)-2-oxoethyl]-8-(3-methylbutylidene)-3-oxo-1-thia-4-azaspiro[4.5]decan-4-yl]-propionate was obtained as a light yellow oily product.

NMR (CDCl$_3$) δ: 0.88(6H,d,J=6.1 Hz), 1.25(3H,t,J=7.1 Hz), 1.46(9H,s), 1.6–2.8(14H,m), 3.15(1H,dd,J=3.9 Hz,16.6 Hz), 3.4–3.7(2H,m), 3.9–4.2(1H,m), 4.13(2H,q,J=7.1 Hz), 5.1–5.3(1H,m)

EXAMPLE 12

The procedure of Example 11 was repeated to obtain benzyl 3-[2-[2-(methoxy-2-oxoethyl)-8-(3-methylbutylidene)-3-oxo-1-thia-4-azaspiro[4.5]decan-4-yl]-propionate.

NMR (CDCl$_3$) δ: 0.87(6H,d,J=6.1 Hz), 1.4–2.8(14H,m), 3.19 (1H,dd,J=3.9 Hz,16.8 Hz), 3.4–3.8(2H,m), 3.71(3H,s), 4.12 (1H,dd,J=3.9 Hz,9.4 Hz), 5.11(2H,s), 5.1–5.3(1H,m), 7.34(5H,s)

EXAMPLE 13

The procedure of Example 5 was repeated to obtain 2-[4-[3-(ethoxy-3-oxopropyl)-8-(3-methylbutylidene)-3-oxo-1-thia-4-azaspiro[4.5]decan-2-yl]-acetic acid.

NMR (CDCl$_3$) δ: 0.88(6H,d,J=5.4 Hz), 1.26(3H,t,J=7.1 Hz), 1.4–3.8(17H,m), 4.15(2H,q,J=7.1 Hz), 4.0–4.3(1H,m), 5.1–5.3(1H,m), 10.2(1H,bs)

EXAMPLE 14

In 10 ml of methylene chloride was dissolved 0.96 g of 2-[4-[3-(benzyloxy)-3-oxopropyl]-8-(3-methylbutylidene)-3-oxo-1-thia-4-azaspiro[4.5]decan-2-yl]-acetic acid. After adding 0.18 ml of thionyl chloride at ambient temperature, the resulting mixture was stirred for one hour under reflux. The reaction mixture was concentrated under reduced pressure, and the concentrate was dissolved in 10 ml of dioxane. The resulting solution was dropwise added at 0–5° C. to an ethyl ether solution containing diazomethane prepared from 5.00 g of N-methylnitrosourea, 3.00 g of potassium hydroxide, 4.00 ml of water and 15 ml of ethyl ether, and the resulting mixture was stirred at ambient temperature for 30 minutes. The reaction mixture was poured into a mixture of water, acetic acid and ethyl acetate, and the organic layer was separated. The organic layer thus obtained was washed successively with water, saturated aqueous solution of sodium hydrogen carbonate and saturated aqueous solution of sodium chloride and dried over anhydrous magnesium sulfate, and the solvent was distilled off under reduced pressure. The residue was dissolved in a mixture of 10 ml dioxane and 10 ml water, and the resulting solution was added to a mixture of 0.16 g of silver benzoate and 3.00 ml of triethylamine at ambient temperature and stirred for 2 hours. The reaction mixture was poured into a mixture of water and ethyl acetate, pH was adjusted to 2.0 with 2 mol/L hydrochloric acid, and the organic layer was separated. The organic layer thus obtained was washed successively with water and saturated aqueous solution of sodium chloride and dried over anhydrous magnesium sulfate, and the solvent was distilled off under reduced pressure. Purification of the residue by column chromatography [eluent: chloroform:ethanol=80:1] gave 0.36 g of 3-[4-[3-(benzyloxy)-3-oxopropyl]-8-(3-methylbutylidene)-3-oxo-1-thia-4-azaspiro[4.5]decan-2-yl]-propionic acid as a light yellow oily product.

NMR (CDCl$_3$) δ: 0.89(6H,d,J=6.1 Hz), 1.4–2.8(17H,m), 3.4–3.7 (2H,m), 3.8–4.0(1H,m), 5.12(2H,s), 5.1–5.3(1H,m), 7.35(5H,s), 8.1–8.9(1H,bs)

EXAMPLE 15

In a solvent mixture consisting of 21 ml of ethanol and 9 ml of water were dissolved 3.10 g of 4-(4-isopropylphenoxy)-1-cyclohexanone, 2.35 g of L-cysteine hydrochloride monohydrate and 1.10 g of sodium acetate. The mixture was stirred at ambient temperature for 6 hours. The reaction mixture was concentrated under reduced pressure, and water and ethyl ether were added to the concentrate. The deposited crystal was collected by filtration, and there was obtained 2.45 g of (3R)-8-(4-isopropylphenoxy)-1-thia-4-azaspiro[4.5]decan-3-carboxylic acid as a colorless crystalline product.

NMR (d$_6$-DMSO+D$_2$O) δ: 1.17(6H,d,J=6.8 Hz), 1.3–2.3 (8H,m), 2.6–3.4(3H,m), 3.8–4.2(1H,m), 4.2–4.6(1H,m), 6.85(2H,d,J=8.5 Hz), 7.13(2H,d,J=8.5 Hz)

EXAMPLE 16

The procedure of Example 15 was repeated to obtain the compound listed in Tables 58 to 60.

TABLE 58

| No. | A | R$^1$ |
|---|---|---|
| 16(1) | (H$_3$C)$_2$CH—C$_6$H$_4$— | ·····""COOH |
| 16(2) | H$_3$C—O—C(=O)—C$_6$H$_4$—O— | ◂COOH |
| 16(3) | H$_3$C—O—C$_6$H$_4$—O— | ◂COOH |
| 16(4) | H$_3$C—S—C$_6$H$_4$—O— | ◂COOH |
| 16(5) | H$_3$C—S(=O)$_2$—C$_6$H$_4$—O— | ◂COOH |
| 16(6) | CH$_3$—CH$_2$—O—C(=O)—CH(CH$_3$)— | ◂COOH |

TABLE 59

| No. | A | $R^3$ |
|---|---|---|
| 16 (7) | 4-(2-hydroxypropan-2-yl)-substituted cumyl group (CH₃)₂C(OH)-C₆H₄-C(CH₃)₂- | ◂COOH |
| 16 (8) | H₂N-C(O)-CH₂CH₂CH₂-CH=C(CH₃)₂ | ◂COOH |
| 16 (9) | (H₃C-CH₂)₂N-C(O)-CH₂CH₂CH₂-CH=C(CH₃)₂ | ◂COOH |
| 16 (10) | PhCH₂-O-C(O)-CH₂CH₂-NH-C(O)-CH(CH₃)₂ | ◂COOH |
| 16 (11) | (CH₃)₂CH-CH₂-CH=C(CH₃)₂ | ◂COOH |
| 16 (12) | H₃C-CH₂-CH₂-N(CH₃)-C(O)-CH₂-CH(CH₃)₂ | ◂COOH |
| 16 (13) | (CH₃)₂CH-CH₂-CH=C(CH₃)₂ | ⋯COOH |

TABLE 60

| No. | A | $R^{13}$ |
|---|---|---|
| 16 (14) | 5-isopropoxyindanyl | ◂COOH |
| 16 (15) | H₃C-CH₂-CH₂-CH=C(CH₃)₂ | ◂COOH |
| 16 (16) | (CH₃)₂CH-CH=C(CH₃)₂ | ◂COOH |
| 16 (17) | (CH₃)₂CH-CH₂CH₂-CH=C(CH₃)₂ | ◂COOH |

Properties of the compounds shown in Tables 58–60 are as follows.

16(1)
NMR(d₆-DMSO+D₂O) δ: 1.16 (6H,d,J=6.8 Hz), 1.3–2.3 (8H,m), 2.6–3.0 (2H,m), 3.1–3.4 (1H,m), 3.9–4.2 (1H,m), 4.2–4.6 (1H,m), 6.85 (2H,d,J=8.5 Hz), 7.13 (2H,d,J=8.5 Hz)

16(2)
NMR(d₆-DMSO+D₂O) δ: 1.3–2.3 (8H,m), 2.7–3.0 (1H,m), 3.1–3.4 (1H,m), 3.81 (3H,s), 3.9–4.7 (2H,m), 7.06 (2H,d,J=8.7 Hz), 7.89 (2H,d,J=8.7 Hz)

16(3)

NMR(d$_6$-DMSO) δ: 1.3–2.3 (8H,m), 2.7–3.0 (1H,m), 3.1–3.4 (1H,m), 3.69 (3H,s), 3.9–4.1 (1H,m), 4.2–4.5 (1H,m), 4.6–5.6 (2H,bs), 6.8–7.0 (4H,m)

16(4)

NMR(d$_6$-DMSO) δ: 1.3–2.3 (8H,m), 2.42 (3H,s), 2.7–3.0 (1H,m), 3.1–3.4 (1H,m), 3.9–4.1 (1H,m), 4.2–4.6 (1H,m), 4.8–6.2 (2H,bs), 6.92 (2H,d,J=8.7 Hz), 7.23 (2H,d, J=8.7 Hz)

16(5)

NMR(d$_6$-DMSO) δ: 1.4–2.4 (8H,m), 2.7–3.0 (1H,m), 3.1–3.4 (1H,m), 3.15 (3H,s), 3.9–4.1 (1H,m), 4.3–5.2 (3H,m), 7.18 (2H,d,J=8.7 Hz), 7.82 (2H,d,J=8.7 Hz)

16(6)

NMR(d$_6$-DMSO) δ: 1.17 (3H,t,J=7.1 Hz), 1.4–2.5 (9H,m), 2.7–3.0 (1H,m), 3.1–3.4 (1H,m), 3.8–4.3 (1H,m), 5.2–7.2 (2H,bs), 4.05 (2H,q,J=7.1 Hz)

16(7)

NMR(d$_6$-DMSO) δ: 1.27 (9H,s), 1.5–2.4 (8H,m), 2.7–3.0 (1H,m), 3.1–3.4 (1H,m), 3.9–4.2 (1H,m), 4.4–6.4 (3H,bs), 7.35 (4H,s)

16(11)

NMR(CDCl$_3$) δ: 0.87 (6H,d,J=6.4 Hz), 1.2–2.8 (11H,m), 3.1–3.6 (2H,m), 4.35 (1H,t,J=7.6 Hz), 5.19 (1H,t,J=7.3 Hz), 7.7–8.2 (2H,m)

16(13)

NMR(CDCl$_3$) δ: 0.87 (6H,d,J=6.1 Hz), 1.2–2.8 (11H,m), 3.1–3.6 (2H,m), 4.34 (1H,t,J=7.8 Hz), 5.19 (1H,t,J=7.1 Hz), 6.9–7.5 (2H,m)

16(14)

NMR(d$_6$-DMSO) δ: 1.5–2.4 (10H,m), 2.7–3.0 (5H,m), 3.2–3.6 (1H,m), 3.9–4.6 (2H,m), 5.07 (2H,bs), 6.6–6.9 (2H,m), 7.0–7.2 (1H,m)

16(15)

NMR(CDCl$_3$) δ: 0.6–2.8 (15H,m), 3.1–3.6 (2H,m), 4.35 (1H,dd,J=6.8 Hz,7.6 Hz), 5.18 (1H,t,J=7.6 Hz), 7.87 (1H,bs)

16(16)

NMR(d$_6$-DMSO) δ: 0.89 (6H,d,J=5.9 Hz), 1.5–3.5 (11H,m), 3.8–4.2 (1H,m), 4.8–5.2 (1H,m)

16(17)

NMR(CDCl$_3$) δ: 0.89 (6H,d,J=6.3 Hz), 1.0–2.8 (13H,m), 3.1–3.7 (2H,m), 4.2–4.5 (1H,m), 5.12 (1H,t,J=3.5 Hz), 6.36 (2H,bs)

EXAMPLE 17

In 50 ml of methylene chloride were dissolved 2.40 g of (3R)-8-(4-isopropylphenoxy)-1-thia-4-azaspiro[4.5]decan-3-carboxylic acid and 2.23 ml of triethylamine. To the solution thus obtained was dropwise added 1.41 g of benzoyl chloride at 0–5° C., and the resulting mixture was stirred at the same temperature as above for 3 hours. The reaction mixture was poured into ice water, pH was adjusted to 1.0 with 2 mol/L hydrochloric acid, and the organic layer was separated. The organic layer thus obtained was washed successively with water and saturated aqueous solution of sodium chloride and dried over anhydrous magnesium sulfate, and the solvent was distilled off under reduced pressure. Ethyl ether was added to the residue thus obtained, and the deposited crystal was collected by filtration. Thus, 2.10 g of (3R)-4-benzoyl-8-(4-isopropylphenoxy)-1-thia-4-azaspiro[4.5]decan-3-carboxylic acid was obtained as a colorless crystalline product.

NMR (d$_6$-DMSO+D$_2$O) δ: 1.17(6H,d,J=6.8 Hz), 1.3–2.3 (6H,m), 2.6–3.7(5H,m), 4.4–4.6(1H,m), 4.7–4.9(1H,m), 6.87(2H,d,J=8.6 Hz), 7.15(2H,d,J=8.6 Hz), 7.2–7.5(5H,m)

EXAMPLE 18

The procedure of Example 17 was repeated to obtain the compounds listed in Tables 61 to 63.

TABLE 61

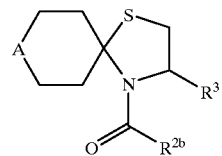

| No. | A | R$^{2b}$ | R$^3$ |
|---|---|---|---|
| 18 (1) | H$_3$C-CH(CH$_3$)-C$_6$H$_4$-O-CH(CH$_3$)$_2$ | phenyl | ···''''COOH |
| 18 (2) | H$_3$C-O-C(=O)-C$_6$H$_4$-O-CH(CH$_3$)$_2$ | phenyl | ◂COOH |
| 18 (3) | H$_3$C-O-C$_6$H$_4$-O-CH(CH$_3$)$_2$ | phenyl | ◂COOH |

TABLE 61-continued

| No. | A | R^{2b} | R^3 |
|---|---|---|---|
| 18 (4) | H3C—S—C6H4—O—CH(CH3)2 | C6H5— | —COOH |
| 18 (5) | H3C—SO2—C6H4—O—CH(CH3)2 | C6H5— | —COOH |
| 18 (6) | PhCH2—O—C(=O)—CH2CH2—NH—C(=O)—CH(CH3)— | C6H5— | —COOH |
| 18 (7) | (H3C)3C—C6H4—C(OH)(CH3)2 | C6H5— | —COOH |

TABLE 62

| No. | A | R^{2b} | R^3 |
|---|---|---|---|
| 18 (8) | (CH3)2CHCH2CH=C(CH3)— | C6H5— | —COOH |
| 18 (9) | (H3C)2CH—C6H4—O—CH(CH3)2 | —CH3 | —COOH |
| 18 (10) | H2C—C(=O)—CH2CH2CH2—CH=C(CH3)2 | C6H5— | —COOH |
| 18 (11) | (H3C-CH2)2N—C(=O)—CH2CH2—CH=C(CH3)CH2— | C6H5— | —COOH |
| 18 (12) | H3C—O—C(=O)—C6H4—O—CH(CH3)2 | —CH2CH2COOEt | —COOH |

TABLE 62-continued

| No. | A | R²ᵇ | R³ |
|---|---|---|---|
| 18 (13) | H₃C-CH(CH₃)-CH₂-CH=C(CH₃)₂ | —CH₂(CH₂)₃—C₆H₄— | ◂COOH |
| 18 (14) | CH₃—CH₂—O—C(=O)—C(CH₃)₂— | —C₆H₄— | ◂COOH |
| 18 (15) | H₃C-CH(CH₃)-CH₂-CH=C(CH₃)₂ | —C₆H₄— | ·······ııııCOOH |
| 18 (16) | (CH₃)₂CHCH₂—NH—C(=O)—CH₂—C(CH₃)₃ | —C₆H₄— | ◂COOH |

TABLE 63

| No. | A | R²ᵇ | R³ |
|---|---|---|---|
| 18 (17) | indanyl-O-CH(CH₃)— | —C₆H₄— | ◂COOH |
| 18 (18) | H₃C-CH(CH₃)-CH₂-CH=C(CH₃)₂ | —CH(CH₃)CH₂CH₃ | ◂COOH |
| 18 (19) | H₃C-CH(CH₃)-CH₂-CH=C(CH₃)₂ | —CH₂CH₂-cyclopentyl | ◂COOH |

Properties of the compounds of Tables 61–63 are as follows.

18(1)

NMR(d₆-DMSO) δ: 1.17 (6H,d,J=6.8 Hz), 1.3–2.3 (6H, m), 2.6–3.7 (5H,m), 4.4–4.6 (1H,m), 4.7–4.9 (1H,m), 6.87 (2H,d,J=8.6 Hz), 7.15 (2H,d,J=8.6 Hz), 7.2–7.6 (6H,m)

18(2)

NMR(d₆-DMSO+D₂O) δ: 1.4–2.4 (6H,m), 3.0–3.7 (4H, m), 3.82 (3H,s), 4.6–4.9 (2H,m), 7.06 (2H,d,J=8.4 Hz), 7.40 (5H,s), 7.93 (2H,d,J=8.4 Hz)

18(3)

NMR(d₆-DMSO+D₂O) δ: 1.3–2.3 (6H,m), 2.9–3.6 (4H, m), 3.69 (3H,s), 4.3–4.6 (1H,m), 4.7–4.9 (1H,m), 6.7–7.0 (4H,m), 7.2–7.6 (5H,m)

18(4)

NMR(d₆-DMSO+D₂O) δ: 1.3–2.3 (6H,m), 2.42 (3H,s), 2.9–3.7 (4H,m), 4.4–4.7 (1H,m), 4.7–4.9 (1H,m), 6.94 (2H, d,J=8.7 Hz), 7.25 (2H,d,J=8.7 Hz), 7.39 (5H,s)

18(5)

NMR(d₆-DMSO+D₂O) δ: 1.3–2.3 (6H,m), 2.8–3.7 (4H, m), 3.16 (3H,s),4.6–4.9 (2H,m), 7.17 (2H,d,J=8.7 Hz), 7.40 (5H,s), 7.86 (2H,d,J=8.7 Hz)

18(6)

NMR(CDCl₃) δ: 1.4–3.8 (15H,m), 4.6–4.9 (1H,m), 5.10 (2H,s), 6.7–7.1 (1H,m), 7.2–7.5 (10H,m), 8.93 (1H,bs)

18(7)

NMR(d₆-DMSO) δ: 1.28 (9H,s), 1.5–2.4 (6H,m), 2.9–3.8 (5H,m), 4.6–5.0 (2H,m), 7.37 (9H,s)

18(8)

NMR(CDCl₃+D₂O) δ: 0.89 (6H,d,J=5.9 Hz), 1.4–3.4 (13H,m), 4.7–4.9 (1H,m), 5.1–5.3 (1H,m), 7.2–7.7 (5H,m)

18(9)

NMR(CDCl₃) δ: 1.21 (6H,d,J=7.1 Hz), 1.4–2.6 (6H,m), 2.11 (3H,s), 2.6–3.6 (5H,m), 4.0–5.2 (3H,m), 6.82 (2H,d,J= 8.7 Hz), 7.12 (2H,d,J=8.7 Hz)

18(10)

NMR(d₆-DMSO) δ: 1.3–3.8 (18H,m), 4.6–4.9 (1H,m), 5.0–5.3 (1H,m), 6.68 (1H,bs), 7.1–7.6 (5H,m)

18(11)

NMR(CDCl$_3$) δ: 1.09 (3H,t,J=7.5 Hz), 1.18 (3H,t,J=7.5 Hz), 1.4–3.6 (20H,m), 4.6–4.9 (1H,m), 5.0–5.3 (1H,m), 7.32 (5H,s), 9.46 (1H,bs)

18(12)

NMR(d$_6$-DMSO+D$_2$O) δ: 1.19 (3H,t,J=7.1 Hz), 1.3–3.7 (14H,m), 3.82 (3H,s), 4.06 (2H,q,J=7.1 Hz), 4.6–4.8 (1H,m), 5.1–5.3 (1H,m), 7.06 (2H,d,J=8.5 Hz), 7.91 (2H,d, J=8.5 Hz)

18(14)

NMR(CDCl$_3$) δ: 1.26 (3H,t,J=7.1 Hz), 1.4–2.6 (7H,m), 2.9–3.4 (4H,m), 4.14 (2H,q,J=7.1 Hz), 4.7–4.9 (1H,m), 7.1–7.5 (5H,m), 8.57 (1H,bs)

18(16)

NMR(d$_6$-DMSO+D$_2$O) δ: 0.84 (6H,d,J=6.6 Hz), 1.3–2.2 (10H,m), 2.6–3.5 (6H,m), 4.6–4.8 (1H,m), 7.1–7.5 (5H,m)

18(17)

NMR(CDCl$_3$) δ: 1.4–2.4 (10H,m), 2.6–3.0 (5H,m), 3.0–3.8 (1H,m), 4.0–4.5 (1H,m), 4.6–4.8 (1H,m), 6.6–6.9 (2H,m), 7.08 (1H,d, J=7.6 Hz), 7.35 (5H,bs), 8.2–8.8 (1H,m)

18(18)

NMR(CDCl$_3$) δ: 0.7–1.1 (12H,m), 1.3–3.4 (16H,m), 4.8–5.3 (2H,m), 8.69 (1H,bs)

18(19)

NMR(CDCl$_3$) δ: 0.88 (6H,d,J=6.1 Hz), 1.0–3.4 (26H,m), 4.9–5.3 (2H,m), 6.8–8.0 (1H,m)

EXAMPLE 19(1)

In a mixture of 0.70 ml of ethanol and 0.30 ml of water were dissolved 0.30 g of 4-(4-isopropylphenoxy)-1-cyclohexanone and 0.21 g of D-penicillamine. The solution thus formed was stirred at ambient temperature for 4 hours. The reaction mixture was poured into a solvent mixture consisting of water and ethyl acetate, and the organic layer was separated. The organic layer was washed successively with water and saturated aqueous solution of sodium chloride and dried over anhydrous magnesium sulfate, and the solvent was distilled off under reduced pressure. Hexane was added to the residue, and the deposited crystal was collected by filtration. Thus, 0.32 g of (3S)-8-(4-isopropylphenoxy)-2,2-dimethyl-1-thia-4-azaspiro[4.5]decane-3-carboxylic acid was obtained as a colorless crystalline product.

NMR (CDCl$_3$) δ: 1.1–2.5 (20H,m), 2.7–3.1(1H,m), 3.9–4.5(2H,m), 4.77(2H,bs), 6.7–7.2(4H,m)

19(2)

Using L-penicillamine, the procedure of 19 (1) was repeated to obtain (3R)-8-(4-isopropylphenoxy)-2,2-dimethyl-1-thia-4-azaspiro[4.5]decane-3-carboxylic acid.

NMR (CDCl$_3$) δ: 1.2–2.5(20H,m), 2.6–3.1(1H,m), 4.0–4.6(2H,m), 5.83(2H,bs), 6.7–7.4(4H,m)

EXAMPLE 20

The procedure of Example 17 was repeated to obtain the following compounds.

20(1)

(3S)-4-Benzoyl-8-(4-isopropylphenoxy)-2,2-dimethyl-1-thia-4-azaspiro[4.5]decane-3-carboxylic acid NMR (CDCl$_3$) δ: 1.22(6H,d,J=6.8 Hz), 1.38(3H,s), 1.69 (3H,s), 1.4–3.7(9H,m), 4.0–4.6(2H,m), 6.1–6.6(1H,bs), 6.84 (2H,d, J=8.6 Hz), 7.14(2H,d,J=8.6 Hz), 7.0–7.5(5H,m)

20(2)

(3R)-4-Benzoyl-8-(4-isopropylphenoxy)-2,2-dimethyl-1-thia-4-azaspiro[4.5]decane-3-carboxylic acid NMR (CDCl$_3$) δ: 1.1–3.8(21H,m), 4.0–4.8(3H,m), 6.8–7.7(9H,m)

EXAMPLE 21

In 56 ml of methylene chloride was dissolved 2.80 g of (3R)-4-benzoyl-8-(4-isopropylphenoxy)-1-thia-4-azaspiro [4.5]decane-3-carboxylic acid, to which were successively added at 0–5° C. 0.56 ml of ethanol, 0.16 g of N,N-dimethylaminopyridine and 1.98 g of dicyclohexyl carbodiimide. After stirring the mixture at ambient temperature for 24 hours, the insoluble matter was filtered off. The filtrate was poured into ice water, pH was adjusted to 2.0 with 2 mol/L hydrochloric acid, and the organic layer was separated. The organic layer thus obtained was washed successively with water, saturated aqueous solution of sodium hydrogen carbonate and saturated aqueous solution of sodium chloride and dried over anhydrous magnesium sulfate, and the solvent was distilled off under reduced pressure. Purification of the residue by column chromatography [eluent: toluene:ethyl acetate=50:1] gave 0.85 g of ethyl (3R)-4-benzoyl-8-(4-isopropylphenoxy)-1-thia-4-azaspiro[4.5]decane-3-carboxylate as a colorless oily product.

NMR (CDCl$_3$) δ: 1.21(6H,d,J=6.8 Hz), 1.21(3H,t,J=7.1 Hz), 1.4–2.4(6H,m), 2.6–3.8(5H,m), 4.13(2H,q,J=7.1 Hz), 4.4–4.6(1H,m), 4.7–5.0(1H,m), 6.88(2H,d,J=8.7 Hz), 7.11 (2H,d,J=8.7 Hz), 7.35(5H,s)

EXAMPLE 22

The procedure of Example 21 was repeated to obtain the following compounds.

22(1)

Ethyl (3S)-4-benzoyl-8-(4-isopropylphenoxy)-1-thia-4-azaspiro[4.5]decane-3-carboxylate NMR (CDCl$_3$) δ:1.21(6H,d,J=6.8 Hz), 1.22(3H,t,J=7.1 Hz), 1.4–2.4(6H,m), 2.6–3.8(5H,m), 4.13(2H,q,J=7.1 Hz), 4.4–4.6(1H,m), 4.8–5.0(1H,m), 6.89(2H,d,J=8.8 Hz), 7.12 (2H,d,J=8.8 Hz), 7.3–7.6(5H,m)

22(2)

Ethyl (3R)-4-benzoyl-3-(tert-butoxycarbonyl)-1-thia-4-azaspiro]4.5]decane-8-carboxylate NMR (CDCl$_3$) δ: 1.25(3H,t,J=7.1 Hz), 1.39(9H,s), 1.4–2.6(7H,m), 2.9–3.5(4H,m), 4.13(2H,q,J=7.1 Hz), 4.67 (1H,dd,J=3.1 Hz,5.0 Hz), 7.34(5H,s)

EXAMPLE 23

In a mixture consisting of 23 ml of ethanol and 23 ml of tetrahydrofuran was dissolved 2.30 g of ethyl (3R)-4-benzoyl-3-(tert-butoxycarbonyl)-1-thia-4-azaspiro[4.5] decane-8-carboxylate. Then, 15.9 ml of 1 mol/L aqueous solution of sodium hydroxide was added at 0–5° C. and the resulting mixture was stirred at ambient temperature for 2 hours. The solvent was distilled off under reduced pressure, the residue thus obtained was added to a mixture of water and ethyl acetate, and the aqueous layer was separated. Ethyl acetate was added to the aqueous layer, pH was adjusted to 2.0 with 2 mol/L hydrochloric acid, and the organic layer was separated. The organic layer was washed successively with water and saturated aqueous solution of sodium chloride and dried over anhydrous magnesium sulfate, and the solvent was distilled off under reduced pressure. Isopropyl ether was added to the residue and the deposited crystal was collected by filtration. Thus, 1.78 g of (3R)-4-benzoyl-3-(tert-butoxycarbonyl)-1-thia-4-azaspiro[4.5]decane-8-carboxylic acid was obtained as a colorless crystalline product.

NMR (CDCl$_3$) δ: 1.39(9H,s), 1.4–2.6(7H,m), 2.9–3.5(4H, m), 4.68(1H,dd,J=3.2 Hz,4.6 Hz), 7.35(5H,s), 9.63(1H,bs)

EXAMPLE 24

In 6 ml of methylene chloride was dissolved 0.40 g of (3R)-4-benzoyl-3-(tert-butoxycarbonyl)-1-thia-4-azaspiro[4.5]decane-8-carboxylic acid. After adding 0.17 ml of oxalyl chloride and 0.06 ml of N,N-dimethylformamide at ambient temperature, the resulting mixture was stirred at the same temperature as above for 2 hours. The solvent was distilled off under reduced pressure, and the residue was subjected to an azeotropic distillation treatment with toluene several times. Thus, 0.40 g of a yellow oily product was obtained.

The 0.40 g of the yellow oily product obtained above dissolved in 4 ml of methylene chloride was dropwise added at 0–5° C. to a solution of 0.28 g of 4-isopropylaniline and 0.15 ml of triethylamine in 4 ml of methylene chloride. The resulting mixture was stirred at the same temperature as above for 30 minutes and then at ambient temperature for one hour. The reaction mixture was poured into ice water, pH was adjusted to 2.0 with 2 mol/L hydrochloric acid, and the organic layer was separated. The organic layer thus obtained was washed successively with water, saturated aqueous solution of sodium hydrogen carbonate and saturated aqueous solution of sodium chloride and dried over anhydrous magnesium sulfate, and the solvent was distilled off under reduced pressure. The residue thus obtained was purified by column chromatography [eluent: hexane:ethyl acetate=3:1] and then treated with a mixture of hexane and isopropyl ether. The deposited crystal was collected by filtration, and there was obtained 0.40 g of tert-butyl (3R)-4-benzoyl-8-[(4-isopropylanilino)carbonyl]-1-thia-4-azaspiro[4.5]-decane-3-carboxylate.

NMR (CDCl$_3$) δ: 1,21(6H,d,J=6.8 Hz), 1.38(9H,s), 1.5–2.5(7H,m), 2.7–3.5(5H,m), 4.66(1H,dd,J=3.1 Hz,4.8 Hz), 7.0–7.7(10H,m)

EXAMPLE 25

The procedure of Example 24 was repeated to obtain tert-butyl (3R)-4-benzoyl-8-{[(4,5-dimethyl-1,3-thiazol-2-yl)amino]carbonyl}-1-thia-4-azaspiro[4.5]-decane-3-carboxylate.

NMR (CDCl$_3$) δ: 1.39(9H,s), 1.5–2.5(7H,m), 2.31(6H,s), 2.9–3.5(4H,m), 4.66(1H,dd,J=3.2 Hz,4.6 Hz), 7.34(5H,s), 7.8–8.5(1H,bs)

EXAMPLE 26

In 7 ml of methylene chloride was dissolved 0.35 g of tert-butyl (3R)-4-benzoyl-8-[(4-isopropylanilino)-carbonyl]-1-thia-4-azaspiro[4.5]-decane-3-carboxylate. After adding 1.8 ml of trifluoroacetic acid at 0–5° C., the resulting mixture was stirred at ambient temperature for 6 hours. After distilling off the solvent under reduced pressure, the residue was several times subjected to an azeotropic distillation treatment together with toluene and then purified by column chromatography [eluent: chloroform:ethanol=20:1]. The residue was treated with ethyl ether, and the deposited crystal was collected by filtration to obtain 0.12 g of (3R)-4-benzoyl-8-[(4-isopropylanilino)carbonyl]-1-thia-4-azaspiro[4.5]decane-3-carboxylic acid as a colorless crystalline product.

NMR (d$_6$-DMSO) δ: 1.17(6H,d,J=6.8 Hz), 1.4–3.7(13H, m), 4.6–4.9(1H,m), 7.0–7.7(9H,m), 9.83(1H,bs)

EXAMPLE 27

The procedure of Example 26 was repeated to obtain (3R)-4-benzoyl-8-{[(4,5-dimethyl-1,3-thiazol-2-yl)amino]-carbonyl}-1-thia-4-azaspiro[4.5]decane-3-carboxylic acid.

NMR (d$_6$-DMSO) δ: 1.6–2.5(7H,m), 2.15(3H,s), 2.22 (3H,s), 2.8–3.8(4H,m), 4.6–4.8(1H,m), 7.38(5H,s), 7.6–8.0 (1H,bs), 11.4–12.4(1H,bs)

EXAMPLE 28

In 10 ml of anhydrous tetrahydrofuran was dissolved 0.50 g of (3R)-4-benzoyl-8-(4-isopropylphenoxy)-1-thia-4-azaspiro[4.5]decane-3-carboxylic acid. Then, at 0–5° C., 0.22 g of benzyl 3-aminopropionate, 0.19 g of 1-hydroxybenzotriazole monohydrate and 0.26 g of dicyclohexyl carbodiimide were added successively. After stirring the resulting mixture at the same temperature as above for 30 minutes and then at ambient temperature for 5 hours, the insoluble matter was filtered off. The filtrate was poured into a mixture of water and ethyl acetate, pH was adjusted to 2.0 with 2 mol/L hydrochloric acid, and the organic layer was separated. The organic layer thus obtained was washed successively with water, saturated aqueous solution of sodium hydrogen carbonate and saturated aqueous solution of sodium chloride and dried over anhydrous magnesium sulfate, and the solvent was distilled off under reduced pressure. Purification of the residue by column chromatography [eluent: hexane:ethyl acetate=2:1] gave 0.55 g of benzyl 3-{[(3R)-4-benzoyl-8-(4-isopropylphenoxy)-1-thia-4-azaspiro[4.5]decan-3-yl]carbonyl}amino-propionate as a colorless oily product.

NMR (CDCl$_3$) δ: 1.21(6H,d,J=6.8 Hz), 1.4–2.3(6H,m), 2.4–3.8(9H,m), 4.4–4.6(1H,m), 4.7–4.9(1H,m), 5.13(2H,s), 6.87(2H,d,J=8.8 Hz), 6.6–7.0(1H,m), 7.12(2H,d,J=8.8 Hz), 7.33(10H,s)

EXAMPLE 29

In 8 ml of ethanol was dissolved 0.38 g of benzyl 3-({[(3R)-4-benzoyl-8-(4-isopropylphenoxy)-1-thia-4-azaspiro[4.5]decan-3-yl]carbonyl}amino)-propionate. Then, 1.90 ml of 1 mol/L aqueous solution of sodium hydroxide was added at 0–5° C., and the resulting mixture was stirred at ambient temperature for 4 hours. The reaction mixture was poured into a mixture of ice water and ethyl acetate, and the aqueous layer was separated. Ethyl acetate was added to the aqueous layer thus obtained, pH was adjusted to 2.0 with 2 mol/L hydrochloric acid, and the organic layer was separated. The organic layer thus obtained was washed successively with water and saturated aqueous solution of sodium chloride and dried over anhydrous magnesium sulfate, and the solvent was distilled off under reduced pressure. Thus, 0.30 g of 3-({[(3R)-4-benzoyl-8-(4-isopropylphenoxy)-1-thia-4-azaspiro[4.5]-decan-3-yl]carbonyl}amino)-propionic acid was obtained as a colorless oily product.

NMR (CDCl$_3$) δ: 1.21 (6H,d,J=6.8 Hz), 1.4–2.3 (6H,m), 2.4–3.8 (9H,m), 4.4–4.6 (1H,m), 4.7–4.9 (1H,m), 6.83 (2H, d,J=8.8 Hz), 7.0–7.5 (6H,m), 7.11 (2H,d,J=8.8 Hz), 8.00 (1H,bs)

EXAMPLE 30

In 4 ml of methanol was suspended 0.40 g of (3R)-4-benzoyl-8-[4-(methoxycarbonyl)phenoxy]-1-thia-4-azaspiro[4.5]decane-3-carboxylic acid. After adding thereto 4.40 ml of 1 mol/L aqueous solution of sodium hydroxide at 0–5° C., the resulting mixture was stirred at ambient temperature for 6 hours. The reaction mixture was poured into ice water, pH was adjusted to 2.0 with 2 mol/L hydrochloric acid, and then the product was extracted with ethyl acetate. The organic layer was washed successively with water and saturated aqueous solution of sodium chloride and dried over anhydrous magnesium sulfate, and the solvent was distilled off under reduced pressure. Ethyl ether and ethyl acetate was added to the residue, and the deposited crystal was collected by filtration to obtain 0.30 g of (3R)-4-benzoyl-8-(4-carboxyphenoxy)-1-thia-4-azaspiro[4.5]-decane-3-carboxylic acid as a colorless crystalline product.

NMR ($d_6$-DMSO+$D_2O$) δ: 1.4–2.4 (6H,m), 3.0–3.7 (4H, m), 4.6–4.9 (2H,m), 7.04 (2H,d,J=8.6 Hz), 7.40 (5H,s),7.92 (2H,d, J=8.6 Hz)

EXAMPLE 31

The procedure of Example 30 was repeated to obtain the following compounds.
31(1)

(3R)-8-(4-Carboxyphenoxy)-4-(3-carboxypropanoyl)-1-thia-4-azaspiro[4.5]decane-3-carboxylic acid NMR ($d_6$-DMSO+$D_2O$) δ: 1.3–3.7 (14H,m) 4.5–4.8 (1H, m), 5.1–5.3 (1H,m), 7.04 (2H,d,J=8.5 Hz), 7.90 (2H,d,J=8.5 Hz)
31(2)

(3R)-4-Benzoyl-8-{[(2-carboxyethyl)amino]-carbonyl}-1-thia-4-azaspiro[4.5]decane-3-carboxylic acid NMR ($d_6$-DMSO+$D_2O$) δ: 1.3–3.6(15H,m), 4.6–4.9(1H, m), 7.1–7.6(5H,bs)

EXAMPLE 32

In 9 ml of anhydrous tetrahydrofuran was dissolved 0.60 g of (3R)-4-benzoyl-8-({[3-(benzoyloxy)-3-oxopropyl]-amino}carbonyl)-1-thia-4-azaspiro[4.5]decane-3-carboxylic acid. At 0–5° C., 0.26 g of L-methionine methyl ester hydrochloride, 0.19 g of 1-hydroxybenzotriazole monohydrate and 0.14 ml of N-methylmorpholine were successively added. After stirring the mixture at the same temperature as above for 30 minutes, 0.27 g of dicyclohexyl carbodiimide was added and the resulting mixture was stirred at the same temperature as above for 30 minutes and then at ambient temperature for 6 hours. The insoluble matter was filtered off, the filtrate was added to a mixture of water and ethyl acetate, pH was adjusted to 2.0 with 2 mol/L hydrochloric acid, and the organic layer was separated. The organic layer was washed successively with water, saturated aqueous solution of sodium hydrogen carbonate and saturated aqueous solution of sodium chloride and dried over anhydrous magnesium sulfate, and the solvent was distilled off under reduced pressure. Purification of the residue by column chromatography [eluent: toluene:ethyl acetate=1:2] gave 0.62 g of methyl (2S)-2-({[(3R)-4-benzoyl-8-({[3-(benzyloxy)-3-oxopropyl]amino}carbonyl)-1-thia-4-azaspiro[4.5]decan-3-yl]carbonyl}amino)-4-(methylthio)butyrate as a colorless oily product.

NMR (CDCl$_3$) δ: 1.5–2.8 (13H,m), 2.06 (3H,s), 2.9–3.7 (6H,m), 3.79 (3H,s), 4.5–4.9 (2H,m), 5.15 (2H,s), 6.0–6.3 (1H,m), 6.6–6.9 (1H,m),7.36 (10H,s)

EXAMPLE 33

The procedure of Example 29 was repeated to obtain (2S)-2-{[((3R)-4-benzoyl-8-{[(2-carboxyethyl)amino]-carbonyl}-1-thia-4-azaspiro[4.5]decan-3-yl)carbonyl] amino}-4-(methylthio)butyric acid.

NMR ($d_6$-DMSO) δ: 1.3–3.8 (19H,m), 2.00 (3H,s), 4.0–4.4 (1H,m), 4.5–4.8 (1H,m), 7.33 (5H,bs), 7.7–8.2 (2H, m), 11.6–13.0 (2H,bs)

EXAMPLE 34

In 5 ml of anhydrous tetrahydrofuran was dissolved 0.50 g of 3-[8-(3-methylbutylidene)-3-oxo-1-thia-4-azaspiro[4.5] decan-4-yl]-propionic acid. After adding 0.25 ml of benzaldehyde and 0.45 g of potassium tert-butoxide at ambient temperature, the resulting mixture was heated under reflux for 6 hours. The reaction mixture was poured into a mixture of water and ethyl acetate, pH was adjusted to 2.0 with 2 mol/L hydrochloric acid, and the organic layer was separated. The organic layer was washed successively with water and saturated aqueous solution of sodium chloride and dried over anhydrous magnesium sulfate, and the solvent was distilled off under reduced pressure. Isopropyl ether was added to the residue and the deposited crystal was collected by filtration. Thus, 0.32 g of 3-[8-(3-methylbutylidene)-3-oxo-2-(1-phenylmethylidene)-1-thia-4-azaspiro[4.5]decan-4-yl]-propionic acid was obtained as a colorless crystalline product.

NMR (CDCl$_3$) δ: 0.91 (6H,d,J=6.4 Hz), 1.4–3.0 (13H,m), 3.5–3.9 (2H,m), 5.1–5.3 (1H,m), 7.0–7.8 (7H,m)

EXAMPLE 35

The procedure of Example 10 was repeated to obtain the following compounds.
35(1)

Benzyl 3-[8-(3-methylbutylidene)-3-oxo-2-(1-phenylmethylidene)-1-thia-4-azaspiro[4.5]decan-4-yl-propionate NMR (CDCl$_3$) δ: 0.91 (6H,d,J=6.1 Hz), 1.4–3.0 (13H,m), 3.6–4.0 (2H,m), 5.1–5.3 (1H,m), 5.14 (2H,s), 7.2–7.7 (11H, m)
35(2)

tert-Butyl 2-[8-(4-isopropylphenoxy)-3-oxo-4-phenethyl-1-thia-4-azaspiro[4.5]decan-2-yl]-acetate NMR (CDCl$_3$) δ: 1.22 (6H,d,J=6.8 Hz), 1.47 (9H,s), 1.5–2.3 (8H,m), 2.4–3.1 (5H,m), 3.2–3.5 (2H,m), 3.9–4.2 (2H,m), 6.81 (2H,d,J=8.6 Hz), 7.13 (2H,d,J=8.6 Hz), 7.27 (5H,s)

EXAMPLE 36

In 7 ml of methylene chloride was dissolved 0.32 g of tert-butyl 2-[8-(4-isopropylphenoxy)-3-oxo-4-phenethyl-1-thia-4-azaspiro[4.5]decan-2-yl]-acetate. After adding 0.33 g of m-chloroperbenzoic acid at 0–5° C., the resulting mixture was stirred at ambient temperature for 24 hours. The reaction mixture was poured into a saturated aqueous solution of sodium hydrogen carbonate, and the organic layer was separated. The organic layer was washed successively with water and saturated aqueous solution of sodium chloride and dried over anhydrous magnesium sulfate, and the solvent was distilled off under reduced pressure. Purification of the residue by column chromatography [eluent: hexane:ethyl acetate=8:1] gave 0.17 g of tert-butyl 2-[8-(4-isopropylphenoxy)-1,1,3-trioxo-4-phenethyl-1-thia-4-azaspiro[4.5]decan-2-yl]-acetate as a colorless oily product.

NMR (CDCl$_3$) δ: 1.24 (6H,d,J=6.8 Hz), 1.50 (9H,s), 1.8–2.5 (8H,m), 2.6–3.9 (7H,m), 4.1–4.3 (1H,m), 4.5–4.7 (1H,m), 6.83 (2H,d,J=8.6 Hz), 7.17 (2H,d,J=8.6 Hz), 7.26 (5H,s)

EXAMPLE 37

The procedure of Example 5 was repeated to obtain 2-[8-(4-isopropylphenoxy)-1,1,3-trioxo-4-phenethyl-1-thia-4-azaspiro[4.5]decan-2-yl]-acetic acid.

NMR (CDCl$_3$) δ: 1.24 (6H,d,J=6.8 Hz), 1.8–2.5 (8H,m), 2.7–4.0 (7H,m), 4.1–4.4 (1H,m), 4.5–4.7 (1H,m), 6.83 (2H, d,J=8.7 Hz), 6.6–6.8 (1H,bs), 7.17 (2H,d,J=8.7 Hz), 7.27 (5H,s)

EXAMPLE 38

In 4 ml of N,N-dimethylformamide was dissolved 0.29 g of 2-[8-(4-isopropylphenoxy)-3-oxo-4-phenethyl-1-thia-4-azaspiro[4.5]decan-2-yl]-acetic acid. After adding 0.10 g of glycine methyl ester hydrochloride and 0.08 g of N-methylmorpholine at ambient temperature, the resulting mixture was stirred at the same temperature as above for 5 minutes. Then, 0.14 g of 1-hydroxybenzotriazole monohydrate and 0.17 g of dicyclohexyl carbodiimide were added at 0–5° C., and the resulting mixture was stirred at ambient temperature for 24 hours. The reaction mixture was poured into a mixture of water and ethyl acetate, pH was adjusted to 2.0 with 2 mol/L hydrochloric acid, and the organic layer was separated. The organic layer thus obtained was washed successively with water, saturated aqueous solution of sodium hydrogen carbonate and saturated aqueous solution of sodium chloride and dried over anhydrous magnesium sulfate, and the solvent was distilled off under reduced pressure. Purification of the residue thus obtained by column chromatography [eluent: toluene:ethyl acetate=2:1] gave 0.35 g of methyl 2-({[2-[8-(4-isopropylphenoxy)-3-oxo-4-phenethyl-1-thia-4-azaspiro[4.5]decan-2-yl]acetyl}amino)-acetate as a colorless oily product.

NMR (CDCl$_3$) δ: 1.23 (6H,d,J=6.8 Hz), 1.4–3.7 (15H,m), 3.77 (3H,s), 4.0–4.3 (3H,m), 4.4–4.6 (1H,m), 6.6–6.9 (1H, bs), 6.82 (2H,d,J=8.9 Hz), 7.16 (2H,d,J=8.9 Hz), 7.29 (5H,s)

EXAMPLE 39

The procedure of Example 8 was repeated to obtain 2-({2-[8-(4-isopropylphenoxy)-3-oxo-4-phenethyl-1-thia-4-azaspiro[4.5]decan-2-yl]acetyl}amino)-acetic acid.

NMR (CDCl$_3$) δ: 1.23 (6H,d,J=6.8 Hz), 1.4–3.1 (11H,m), 3.1–3.9 (4H,m), 4.0–4.3 (3H,m), 4.4–4.6 (1H,m), 6.82 (2H, d,J=8.5 Hz), 7.15 (2H,d,J=8.5 Hz), 7.2–7.5 (7H,m)

EXAMPLE 40

In 15 ml of methylene chloride was suspended 0.30 g of 1H-2-pyrrolecarboxylic acid. To the suspension thus obtained were added at 0–5° C. 0.28 ml of oxalyl chloride and 0.06 ml of N,N-dimethylformamide, and the resulting mixture was stirred at ambient temperature for 24 hours. The solvent was distilled off under reduced pressure from the reaction mixture, and the residue was subjected to an azeotropic distillation treatment with toluene. Thus, 0.36 g of 1H-2-pyrrolecarbonyl chloride was obtained as a brown crystalline product.

In 6 ml of methylene chloride were dissolved 0.30 g of (3R)-8-(4-isopropylphenoxy)-1-thia-4-azaspiro[4.5]decane-3-carboxylic acid and 0.47 ml of triethylamine. After adding 0.18 g of 1H-2-pyrrolecarbonyl chloride at 0–5° C., the resulting mixture was stirred at ambient temperature for 24 hours. The reaction mixture was poured into ice water, pH was adjusted to 2.0 with 2 mol/L hydrochloric acid, and the organic layer was separated. The organic layer thus obtained was washed successively with water and saturated aqueous solution of sodium chloride and dried over anhydrous magnesium sulfate, and the solvent was distilled off under reduced pressure. After purifying the residue by column chromatography [eluent: chloroform:ethanol=200:1], isopropyl ether was added and the deposited crystal was collected by filtration. Thus, 0.14 g of (3R)-8-(4-isopropylphenoxy)-4-(1H-2-pyrrolylcarbonyl)-1-thia-4-azaspiro[4.5]decane-3-carboxylic acid was obtained as a yellow crystalline product.

NMR (d$_6$-DMSO) δ: 1.17 (6H,d,J=6.8 Hz), 1.5–2.4 (6H, m), 2.4–3.8 (6H,m), 4.5–4.7 (1H,m), 5.3–5.6 (1H,m), 6.0–6.4 (2H,m), 6.8–7.4 (6H,m)

EXAMPLE 41

The procedure of Example 40 was repeated to obtain the following compounds.

41(1)

(3R)-8-(4-Isopropylphenoxy)-4-(2-thienylcarbonyl)-1-thia-4-azaspiro[4.5]decane-3-carboxylic acid NMR (CDCl$_3$) δ: 1.21 (6H,d,J=6.8 Hz), 1.4–2.4 (6H,m), 2.6–3.8 (5H,m), 4.4–4.6 (1H,m), 5.1–5.3 (1H,m), 6.8–7.5 (8H,m)

41(2)

(3R)-8-(4-Isopropylphenoxy)-4-(3-quinolylcarbonyl)-1-thia-4-azaspiro[4.5]decane-3-carboxylic acid NMR (CDCl$_3$) δ: 1.22 (6H,d,J=6.8 Hz), 1.4–2.5 (6H,m), 2.7–4.0 (5H,m), 4.5–4.8 (2H,m), 6.8–7.3 (5H,m), 7.5–8.3 (5H,m), 9.2–9.4 (1H,m)

41(3)

(3R)-8-(4-Isopropylphenoxy)-4-[(2-methyl-1,3-thiazol-4-yl)carbonyl]-1-thia-4-azaspiro[4.5]decane-3-carboxylic acid NMR (CDCl$_3$) δ: 1.22 (6H,d,J=6.8 Hz), 1.4–2.3 (6H,m), 2.55 (3H,s), 2.6–3.9 (5H,m), 4.4–4.6 (1H,m), 5.9–6.0 (1H, m), 6.93 (2H,d,J=8.8 Hz), 7.12 (2H,d,J=8.8 Hz), 7.97 (1H,s), 8.9–9.2 (1H,bs)

41(4)

(3R)-8-(4-Isopropylphenoxy)-4-(2-pyrazinylcarbonyl)-1-thia-4-azaspiro[4.5]decane-3-carboxylic acid NMR (d$_6$-DMSO) δ: 1.17 (6H,d,J=6.8 Hz), 1.3–2.3 (6H, m), 2.4–3.8 (5H,m), 4.5–4.7 (1H,m), 5.4–5.6 (1H,m), 6.8–7.3 (5H,m), 8.5–9.0 (3H,m)

41(5)

(3R)-8-(4-Isopropylphenoxy)-4-(4-methoxybenzoyl)-1-thia-4-azaspiro[4.5]decane-3-carboxylic acid NMR (CDCl$_3$) δ: 1.21 (6H,d,J=6.8 Hz), 1.4–2.4 (6H,m), 2.7–3.6 (5H,m), 3.79 (3H,s), 4.4–4.5 (1H,m), 4.8–5.0 (1H, m), 6.7–7.4 (8H,m), 9.4–9.6 (1H,bs)

41(6)

(3R)-4-{4-[(Diethylamino)carbonyl]benzoyl}-8-(4-isopropylphenoxy)-1-thia-4-azaspiro[4.5]decane-3-carboxylic acid NMR (CDCl$_3$) δ: 1.0–1.3 (12H,m), 1.3–2.4 (6H,m) 2.7–3.8 (9H,m), 4.4–4.7 (2H,m), 6.91 (2H,d,J=8.5 Hz), 7.12 (2H,d,J=8.5 Hz), 7.36 (4H,s), 8.4–8.6 (1H,bs)

Further, in the same manner as above, the compounds of Tables 64 and 65 were obtained.

TABLE 64

[Structure: spiro bicyclic system with S, N, substituent A on cyclohexane ring, C(=O)R²ᵇ on nitrogen, and R³ on carbon adjacent to S]

| No. | A | R²ᵇ | R³ |
|---|---|---|---|
| 41 (7) | (CH₃)₂CH-CH₂-CH=C(CH₃)- | (CH₃)₂CH-CH₂-CH₂- | ·······ıCOOH |
| 41 (8) | (CH₃)₂CH-CH₂-CH=C(CH₃)- | (CH₃)₂CH-CH₂-CH₂- | ◂COOH |
| 41 (9) | (CH₃)₂CH-CH₂-CH=C(CH₃)- | CH₃-CH₂-CH₂-CH₂- | ◂COOH |
| 41 (10) | (CH₃)₂CH-CH₂-CH=C(CH₃)- | (CH₃)₂CH-CH₂-CH₂-CH₂- | ◂COOH |
| 41 (11) | CH₃-CH₂-CH₂-CH=C(CH₃)- | (CH₃)₂CH-CH₂-CH₂- | ◂COOH |

TABLE 65

| No. | A | R²ᵇ | R³ |
|---|---|---|---|
| 41 (12) | (CH₃)(CH₃)CH-CH=C(CH₃)- | (CH₃)₂CH-CH₂-CH₂- | ·······ıCOOH |
| 41 (13) | (CH₃)₂CH-CH₂-CH₂-CH=C(CH₃)- | (CH₃)₂CH-CH₂-CH₂- | ◂COOH |
| 41 (14) | 4-iPr-C₆H₄-O-CH(CH₃)- | 4-(CONEt₂)-C₆H₄- | ·······ıCOOH |

TABLE 65-continued

| No. | A | R²ᵇ | R³ |
|---|---|---|---|
| 41 (15) | (structure: H₃C-CH(CH₃)-C₆H₄-O-CH(CH₃)-) | -NH- (pyrrole) | ·······ıııııCOOH |

Properties of the compounds shown in Tables 64 and 65 are as follows.

41(7)
NMR(CDCl₃) δ: 0.7–1.1 (12H,m), 1.2–3.4 (18H,m), 4.8–5.3 (2H,m), 6.9–7.4 (1H,m)

41(8)
NMR(CDCl₃) δ: 0.8–1.1 (12H,m), 1.3–3.5 (18H,m), 4.9–5.3 (2H,m), 8.0–8.2 (1H,m)

41(9)
NMR(CDCl₃) δ: 0.7–1.1 (9H,m), 1.1–3.6 (19H,m), 4.8–5.3 (2H,m), 8.37 (1H,bs)

41(10)
NMR(CDCl₃) δ: 0.87(12H,d,J=6.1 Hz), 0.1–3.4 (20H,m), 4.8–5.3 (2H,m), 6.05 (1H,bs)

41(11)
NMR(CDCl₃) δ: 0.7–1.1 (9H,m), 1.1–3.5 (19H,m), 4.8–5.3 (2H,m), 6.88 (1H,bs)

41(12)
NMR(CDCl₃) δ: 0.6–3.7 (28H,m), 4.8–5.1 (2H,m)

41(13)
NMR(CDCl₃) δ: 0.3–3.6 (32H,m), 4.8–5.5 (2H,m), 8.00 (1H,bs)

41(14)
NMR(CDCl₃) δ: 1.0–2.4 (23H,m), 2.6–3.7 (8H,m), 4.0–4.6 (1H,m), 4.9–5.2 (1H,m), 6.7–7.5 (9H,m)

41(15)
NMR(CDCl₃) δ: 1.1–4.8 (22H,m), 5.0–5.2 (1H,m), 6.0–6.3 (1H,m), 6.4–7.5 (6H,m), 10.0–10.8 (2H,m)

EXAMPLE 42

In 80 ml of acetone was dissolved 8.50 g of 2-[4-[3-(benzyloxy)-3-oxopropyl]-8-(3-methylbutylidene)-3-oxo-1-thia-4-azaspiro[4.5]decan-2-yl]-acetic acid. After adding thereto 40 ml of an aqueous solution containing 1.50 g of sodium hydrogen carbonate, the resulting mixture was stirred at ambient temperature for 30 minutes. The solvent was distilled off under reduced pressure and the residue was subjected to an azeotropic distillation treatment with ethanol to obtain 8.00 g of sodium 2-[4-[3-(benzyloxy)-3-oxopropyl]-8-(3-methylbutylidene)-3-oxo-1-thia-4-azaspiro[4.5]decan-2-yl]-acetate.

NMR(d₆-DMSO) δ: 0.86 (6H,d,J=6.4 Hz), 1.4–2.9 (13H, m), 3.2–3.7 (4H,m), 3.9–4.1 (1H,m), 5.09 (2H,s), 5.0–5.3 (1H,m), 7.37 (5H,s)

EXAMPLE 43

The procedure of 19(2) was repeated to obtain (3R)-2,2-dimethyl-8-(3-methylbutylidene)-1-thia-4-azaspiro[4.5] decane-3-carboxylic acid NMR (CDCl₃) δ: 1.1–2.8(17H,m), 4.03(1H,s), 5.0–5.3 (1H,m)

EXAMPLE 44

The procedure of Example 40 was repeated to obtain (3R)-2,2-dimethyl-8-(3-methylbutylidene)-4-(4-methylpentanoyl)-1-thia-4-azaspiro[4.5]decane-3-carboxylic acid NMR (CDCl₃) δ: 0.5–3.5(34H,m), 4.52(1H,s), 5.0–5.3 (1H,m), 8.96(1H,bs)

EXAMPLE 45

The procedure of Example 1 was repeated to obtain 2-[4-[2-(tert-butoxy)-2-oxoethyl]-8-(3-methylbutylidene)-3-oxo-1-thia-4-azaspiro[4.5]decan-2-yl]-acetic acid.

NMR (CDCl₃) δ: 0.88 (6H,d,J=6.4 Hz), 1.2–2.9 (21H,m), 3.32 (1H,dd,J=17.1,4.9 Hz), 3.89 (2H,d,J=2.2 Hz), 4.24 (1H,dd,J=4.7,5.4 Hz), 5.0–5.4 (1H,m)

EXAMPLE 46

In 10 ml of N,N-dimethylformamide was dissolved 1.0 g of 2-[4-[2-(tert-butoxy)-2-oxoethyl]-8-(3-methylbutylidene)-3-oxo-1-thia-4-azaspiro[4.5]decan-2-yl]-acetic acid. After adding 0.42 ml of 2-iodopropane and 0.67 g of anhydrous potassium carbonate at ambient temperature, the resulting mixture was stirred at ambient temperature for 17 hours. The reaction mixture was poured into a mixture of ice water and ethyl acetate, pH was adjusted to 2.0 with 2 mol/L hydrochloric acid, and the organic layer was separated. The organic layer thus obtained was washed successively with water, saturated aqueous solution of sodium hydrogen carbonate and saturated aqueous solution of sodium chloride and dried over anhydrous magnesium sulfate, and the solvent was distilled off under reduced pressure. Purification of the residue by column chromatography [eluent: hexane:ethyl acetate=17:3] gave 1.0 g of isopropyl 2-[4-[2-(tert-butoxy)-2-oxoethyl]-8-(3-methylbutylidene)-3-oxo-1-thia-4-azaspiro[4.5]decan-2-yl]-acetate as a light yellow oily product.

NMR (CDCl₃) δ: 0.88 (6H,d,J=6.4 Hz), 1.1–2.8 (26H,m), 3.26 (1H,dd,J=16.8,3.7 Hz), 3.8–4.3 (4H,m), 4.8–5.3 (2H, m)

EXAMPLE 47

In 3 ml of diethyl ether was dissolved 0.33 g of isopropyl 2-[4-[2-(tert-butoxy)-2-oxoethyl]-8-(3-methylbutylidene)-3-oxo-1-thia-4-azaspiro[4.5]decan-2-yl]-acetate. Then, 1 ml of a 5.39 mol/L solution of dry hydrogen chloride in dioxane was added and the resulting mixture was stirred at the same temperature as above for 2 hours. Further, 1 ml of 5.39 mol/L solution of dry hydrogen chloride in dioxane was added and the resulting mixture was stirred for one hour, after which 3 ml of 5.39 mol/L solution of dry hydrogen chloride in dioxane was added and the resulting mixture was stirred for one hour. The solvent was distilled off under reduced pressure, and the residue was purified by column chromatography [eluent: chloroform]. Then, hexane was added, and the deposited crystal was collected by filtration. Thus, 0.08 g of 2-[2-(2-isopropoxy-2-oxoethyl)-8-(3- methylbutylidene)-3-oxo-1-thia-4-azaspiro[4.5]decan-4-yl]-acetic acid was obtained as a colorless crystalline product.

NMR (CDCl$_3$) δ: 0.87 (6H,d,J=6.3 Hz), 1.26 (6H,d,J=6.1 Hz), 1.3–2.8 (11H,m), 3.21 (1H,dd,J=16.6,3.8 Hz), 3.9–4.4 (4H,m), 4.9–5.3 (2H,m), 7.10 (1H,bs)

EXAMPLE B-1

In 5 ml of methylene chloride was suspended 0.25 g of 4-isopropylbenzoic acid. Then, at ambient temperature, 0.12 ml of thionyl chloride and 0.03 ml of N,N-dimethylformamide were added. After stirring the mixture at the same temperature as above for one hour, the solvent was distilled off under reduced pressure, and an azeotropic distillation treatment using toluene was carried out to obtain 0.25 g of 4-isopropylbenzoic acid chloride. To a suspension of 0.50 g of trifluoroacetic acid salt of 2-(4-benzyl-3-oxo-1-thia-4,8-diazaspiro[4.5]decan-2-yl]-acetic acid in 5 ml methylene chloride were successively added dropwise at 0–5° C. 0.64 ml of triethylamine and a solution of 0.25 g of 4-isopropylbenzoic acid chloride in 5 ml methylene chloride. The resulting mixture was stirred at ambient temperature for 24 hours. The reaction mixture was poured into ice water, pH was adjusted to 1.0 with 2 mol/L hydrochloric acid, and the organic layer was separated. The organic layer was washed successively with water and saturated aqueous solution of sodium chloride and dried over anhydrous magnesium sulfate, and the solvent was distilled off under reduced pressure. Purification of the residue by column chromatography [eluents: toluene:ethyl acetate=1:1, followed by chloroform] gave 0.30 g of 2-[4-benzyl-8-(4-isopropylbenzoyl)-3-oxo-1-thia-4,8-diazaspiro[4.5]-decan-2-yl]-acetic acid as a light yellow solid product.

NMR (CDCl$_3$) δ: 1.24 (6H,d,J=6.8 Hz), 1.4–2.4 (4H,m), 2.5–3.6 (5H,m), 3.6–4.8 (5H,m), 7.26 (9H,bs), 8.3–8.5 (1H,bs)

EXAMPLE B-2

The procedure of Example B-1 was repeated to obtain the following compounds.

B-2(1)

2-{4-Benzyl-8-[4-(methoxycarbonyl)benzoyl]-3-oxo-1-thia-4,8-diazaspiro[4.5]decan-2-yl]-acetic acid NMR (CDCl$_3$) δ: 1.4–2.3 (4H,m), 2.5–3.8 (5H,m), 3.93 (3H,s), 4.2–4.9 (4H,m), 7.27 (5H,s), 7.40 (2H,d,J=8.1 Hz), 8.07 (2H,d,J=8.1 Hz), 7.8–8.0 (1H,bs)

B-2(2)

2-{4-Benzyl-8-[(4-methylphenyl)sulfonyl]-3-oxo-1-thia-4,8-diazaspiro[4.5]decan-2-yl]-acetic acid NMR (CDCl$_3$) δ: 1.5–1.8 (2H,m), 2.0–2.9 (5H,m), 2.44 (3H,s), 3.1–3.5 (1H,m), 3.7–4.0 (2H,m), 4.1–4.3 (1H,m), 4.46 (1H,d,J=14.0 Hz), 4.68 (1H,d,J=14.0 Hz), 7.1–7.5 (7H,m), 7.61 (2H,d,J=8.1 Hz), 7.9–8.3 (1H,bs)

EXAMPLE B-3

In 2.5 ml of ethanol was dissolved 0.51 g of ethyl 4-[2-(2-ethoxy-2-oxoethyl)-3-oxo-4-phenethyl-1-thia-4,8-diazaspiro[4.5]decan-8-yl]-oxobutanoate. After adding 2.5 ml of 1 mol/L aqueous solution of sodium hydroxide at 0–5° C., the resulting mixture was stirred at ambient temperature for 1.5 hours. The reaction mixture was poured into a mixture of ice water and ethyl acetate, pH was adjusted to 2.0 with 2 mol/L hydrochloric acid, and the organic layer was separated. The organic layer thus obtained was washed successively with water and saturated aqueous solution of sodium chloride and dried over anhydrous magnesium sulfate, and the solvent was distilled off under reduced pressure. Thus, 0.34 g of 4-[2-(carboxymethyl)-3-oxo-4-phenethyl-1-thia-4,8-diazaspiro[4.5]decan-8-yl]-4-oxobutanoic acid was obtained as a yellow oily product.

NMR (d$_6$-DMSO) δ: 1.4–4.7(19H,m), 7.2–7.8(7H,m)

EXAMPLE B-4

The procedure of Example B-3 was repeated to obtain the compounds shown in Table 66.

TABLE 66

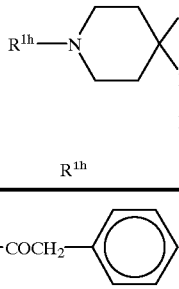

| No. | R$^{1h}$ | R$_2$ |
|---|---|---|
| 4 (1) | 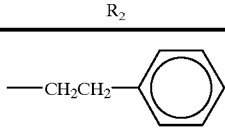 —COCH$_2$— | 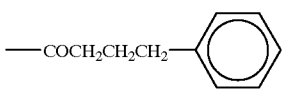 —CH$_2$CH$_2$— |
| 4 (2) | —COCH$_2$CH$_2$CH$_2$— 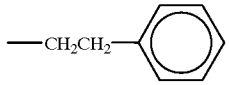 | —CH$_2$CH$_2$— |
| 4(3) | —COCH=CH— 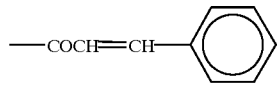 | —CH$_2$CH$_2$— 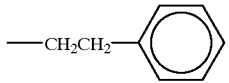 |

TABLE 66-continued

[Structure: spiro compound with piperidine N-R^1h, spiro to thiazolidinone bearing CH2COOH, N-R^2, C=O]

| No. | R^1h | R_2 |
|---|---|---|
| 4 (4) | —COCH(NH₂·HCl)CH₂CH(CH₃)CH₃ | —CH₂CH₂—C₆H₅ |
| 4 (5) | —COCH(NHCOCH₃)CH₂CH₂CONH₂ | —CH₂CH₂CH(CH₃)CH₃ |
| 4 (6) | —COCH₂CH₂COOH | —CH₂CH₂CH(CH₃)CH₃ |
| 4 (7) | —COCH(OH)(C₆H₅) | —CH₂CH₂—C₆H₅ |
| 4 (8) | —CO—C₆H₄—COOH | —CH₂—C₆H₅ |
| 4 (9) | —COO—C(CH₃)₃ | —CH₂CH₂COOH |

Properties of the compounds of Table 66 are as follows.

B-4(1)
NMR (CDCl₃) δ: 1.3–2.2 (4H,m), 2.6–3.6 (6H,m), 3.76 (2H,s), 3.8–4.8 (5H,m), 7.0–7.8 (11H,m)

B-4(2)
NMR (CDCl₃) δ: 1.4–2.2 (6H,m), 2.2–4.0 (13H,m), 4.1–4.3 (1H,m), 4.6–4.9 (1H,m), 7.0–7.7 (11H,m)

B-4(3)
NMR (CDCl₃) δ: 1.6–2.2 (4H,m), 2.4–3.8 (8H,m), 4.0–4.4 (2H,m), 4.6–5.0 (1H,m), 6.3–6.7 (1H,m), 6.85 (1H, d,J=15.4 Hz), 7.1–7.6 (10H,m), 7.70 (1H,d,J=15.4 Hz)

B-4(4)
NMR(d₆-DMSO) δ: 0.8–1.1 (6H,m), 1.4–2.2 (7H,m), 2.3–4.7 (12H,m), 7.28 (5H,s), 8.1–8.6 (3H,bs)

B-4(5) (Measured in the form of sodium salt)
NMR(d₆-DMSO) δ: 0.94 (6H,d,J=5.9 Hz), 1.0–3.6 (17H,m), 1.83 (3H,s), 3.8–4.8 (4H,m), 6.7 (1H,bs), 8.0–8.4 (2H,m)

B-4(6)
NMR(CDCl₃) δ: 0.93 (6H,d,J=5.4 Hz), 1.1–2.5 (7H,m), 2.5–3.6 (10H,m), 3.9–4.9 (3H,m), 8.9 (2H,bs)

B-4(7)
NMR(d₆-DMSO) δ: 1.2–2.0 (4H,m), 2.4–3.8 (8H,m), 3.8–4.2 (2H,m), 4.3–4.7 (1H,m), 5.4–5.8 (2H,m), 7.1–7.5 (11H,m)

B-4(8)
NMR(CDCl₃) δ: 1.1–2.4 (4H,m), 2.4–3.8 (5H,m), 3.9–4.9 (4H,m), 7.28 (5H,s), 7.39 (2H,d,J=8.0 Hz), 8.07 (2H,d,J=8.0 Hz), 8.6–9.0 (2H,bs)

B-4(9)
NMR(d₆-DMSO+D₂O) δ: 1.2–3.7 (12H,m), 1.41 (9H,s), 3.6–4.3 (3H,m), 12.4 (2H,bs)

EXAMPLE B-5

In 1.4 ml of ethanol was dissolved 0.31 g of 4-[2-(carboxymethyl)-3-oxo-4-phenethyl-1-thia-4,8-diazaspiro[4.5]decan-8-yl]-4-oxobutanoic acid. After adding 1.36 ml of 1 mol/L aqueous solution of sodium hydroxide at 0–5° C., the resulting mixture was stirred at ambient temperature for 5 hours. The reaction mixture was poured into a mixture of ice water and ethyl acetate, and the aqueous layer was separated. The aqueous layer thus obtained was concentrated under reduce pressure to obtain 0.32 g of disodium 4-[2-(carboxymethyl)-3-oxo-4-phenethyl-1-thia-4,8-diazaspiro[4.5]decan-8-yl]-4-oxobutanoate as a colorless solid product.

EXAMPLE C-1

DMF was added to 1.875 g (1.200 mmol) of Rink Amide MBHA resin to swell the resin. Then, 2 ml of 20% piperidine/DMF solution was added and shaken for 20 minutes. The resin was six times washed with DMF, 1.28 g of Fmoc-Leu-OH, 552 mg of HOBt.H$_2$O, 0.58 ml of DIPCDI and 18 ml of DMF were added and shaken for 90 minutes. After filtering off the liquid phase, the resin was six times washed with DMF. Then, 24 ml of 20% piperidine/DMF solution was added and shaken for 20 minutes. The resin was six times washed with DMF, and then 1.903 g of (3R)-4-benzoyl-8-[(9H-fluoren-9-ylmethoxy)carbonyl]-1-thia-4,8-diazaspiro[4.5]decan-3-carboxylic acid, 552 mg of HOBt.H$_2$O, 0.58 ml of DIPCDI and 18 ml of DMF were added and shaken for 90 minutes. After filtering off the liquid phase, the resin was six times washed with DMF. The resin was divided into 15 equal portions, and 2 ml of 20% piperidine/DMF solution was added to one of the portions and shaken for 20 minutes. The resin was six times washed with DMF, and 113 mg of Fmoc-Leu-OH, 37 mg of HOBt.H$_2$O, 39 μL of DIPCDI and 1.2 ml of DMF were added and shaken for 2 hours. After filtering off the liquid phase, the resin was washed with DMF six times. Then, 2 ml of 20% piperidine/DMF solution was added and shaken for 20 minutes. After filtering off the liquid phase, the resin was six times washed with DMF. Then, 1.2 ml of DMF-DCM (1:1) mixture, 0.29 ml of acetic anhydride and 0.53 ml of DIEA were added and shaken for one hour. After filtering off the liquid phase, the resin was washed four times with DMF and three times with DCM. The resin thus obtained was shaken for four hours together with 6 ml of TFA-methylene chloride (1:1). The insoluble matter was filtered off, the filtrate was concentrated under reduced pressure, 20 ml of diethyl ether was added to the residue, and the resulting crystal was collected by filtration to obtain 46 mg of (3R)-8-[(2S)-2-(acetylamino)-4-methylpentanoyl]-N -[(1S)-1-(aminocarbonyl)-3-methylbutyl]-4-benzoyl-1-thia-4,8-diazaspiro[4.5]decane-3-carboxamide.

EXAMPLE C-2

The procedure of Example C-1 was repeated to obtain the following compounds.

TABLE 67

| $R^{1h}$ | $R^{18a}$ | $R^2$ | calcd. | found | |
|---|---|---|---|---|---|
| Ac-Leu | NH$_2$ | COC$_6$H$_5$ | 460.6 | 461.4 | M + H |
| Ac-Asp | NH$_2$ | COC$_6$H$_5$ | | | |
| Ac-Asn | NH$_2$ | COC$_6$H$_5$ | | | |
| Ac-Glu | NH$_2$ | COC$_6$H$_5$ | | | |
| Ac-Gln | NH$_2$ | COC$_6$H$_5$ | | | |
| Ac-Phe | NH$_2$ | COC$_6$H$_5$ | | | |
| Ac-Lys | NH$_2$ | COC$_6$H$_5$ | | | |
| Ac-Arg | NH$_2$ | COC$_6$H$_5$ | | | |
| Ac-His | NH$_2$ | COC$_6$H$_5$ | | | |
| Ac-Tyr | NH$_2$ | COC$_6$H$_5$ | | | |
| nC$_3$H$_7$CO | NH$_2$ | COC$_6$H$_5$ | | | |
| 4-ClC$_6$H$_4$CHCHCO | NH$_2$ | COC$_6$H$_5$ | 503.62 | 504.4 | M + H |
| 4-ClC$_6$H$_4$CH$_2$CO | NH$_2$ | COC$_6$H$_5$ | | | |
| 3-PyCO | NH$_2$ | COC$_6$H$_5$ | | | |
| 4-PyCO | NH$_2$ | COC$_6$H$_5$ | | | |
| Ac-Leu | Leu-NH$_2$ | COC$_6$H$_5$ | 573.76 | 574.4 | M + H |
| Ac-Asp | Leu-NH$_2$ | COC$_6$H$_5$ | | | |
| Ac-Asn | Leu-NH$_2$ | COC$_6$H$_5$ | | | |
| Ac-Glu | Leu-NH$_2$ | COC$_6$H$_5$ | | | |
| Ac-Gln | Leu-NH$_2$ | COC$_6$H$_5$ | | | |
| Ac-Phe | Leu-NH$_2$ | COC$_6$H$_5$ | | | |
| Ac-Lys | Leu-NH$_2$ | COC$_6$H$_5$ | | | |
| Ac-Arg | Leu-NH$_2$ | COC$_6$H$_5$ | | | |
| Ac-His | Leu-NH$_2$ | COC$_6$H$_5$ | | | |
| Ac-Tyr | Leu-NH$_2$ | COC$_6$H$_5$ | | | |
| nC$_3$H$_7$CO | Leu-NH$_2$ | COC$_6$H$_5$ | | | |
| 4-ClC$_6$H$_4$CHCHCO | Leu-NH$_2$ | COC$_6$H$_5$ | | | |
| 4-ClC$_6$H$_4$CH$_2$CO | Leu-NH$_2$ | COC$_6$H$_5$ | | | |

EXAMPLE C-3

DMF was added to 173 mg (0.100 mmol) of Wang resin to swell the resin. Then, 90 mg of Fmoc-Gly-OH, 1.22 mg of DMAP, 48 μL of DIPCDI and 1.2 ml of DMF were added to the resin and shaken for 2 hours. After filtering off the liquid phase, the resin was six times washed with DMF. Then, 2 ml of 20% piperidine/DMF solution was added and shaken for 20 minutes. After washing the resin six times with DMF, 160 mg of (3R)-4-benzoyl-8-[(9H-fluoren-9-ylmethoxy)carbonyl]-1-thia-4,8-diazaspiro[4.5]decane-3-carboxylic acid, 46 mg of HOBt.H$_2$O, 48 μL of DIPCDI and 1.2 ml of DMF were added and shaken for 90 minutes. After filtering off the liquid phase, the resin was six times washed with DMF. Then, 2 ml of 20% piperidine/DMF solution was added and shaken for 20 minutes. The resin was six times washed with DMF, and then 266 mg of Fmoc-Arg(Pmc)-OH, 62 mg of HOBt.H$_2$O, 64 μL of DIPCDI and 1.2 ml of DMF were added and shaken for 2 hours. After filtering off the liquid phase, the resin was washed with DMF six times. Then, 2 ml of 20% piperidine/DMF solution was added and shaken for 20 minutes. After filtering off the liquid phase, the resin was washed with DMF six times. Then, 1.2 ml of DMF-DCM (1:1) mixture, 0.29 ml of acetic anhydride and 0.53 ml of DIEA were added and shaken for one hour. The liquid phase was filtered off, and the resin was washed four times with DMF and three times with DCM. Then, 6 ml of TFA-methylene chloride (1:1) was added and shaken for 4 hours. The insoluble matter was filtered off, the filtrate was concentrated under reduced pressure, 20 ml of diethyl ether was added to the residue, and the resulting crystal was collected by filtration to obtain 66 mg of trifluoroacetic acid salt of 2-({[(3R)-8-((2S)-2-(acetylamino)-5-{[amino(imino) methyl]amino}pentanoyl)-4-benzoyl-1-thia-4,8-diazaspiro [4.5]decan-3-yl]-carbonyl}amino)-acetic acid.

EXAMPLE C-4

The procedure of Example C-3 was repeated to obtain the following compounds.

DIPCDI and 2 ml of DMF were added and shaken for 90 minutes. After filtering off the liquid phase, the resin was six times washed with DMF. Then, 2 ml of 20% piperidine/ DMF solution was added and shaken for 20 minutes. After washing the resin with DMF six times, 190 mg of 2-{4-[3- (benzoyloxy)-3-oxopropyl]-8-[(9H-fluoren-9-ylmethoxy) carbonyl]-3-oxo-1-thia-4,8-diazaspiro[4.5]decan-2-yl}- acetic acid, 46 mg of HOBt.H$_2$O, 47 μL of DIPCDI and 2 ml of DMF were added and shaken for 90 minutes. After filtering off the liquid phase, the resin was washed six times with DMF. Then, 2 ml of 20% piperidine/DMF solution was added and shaken for 20 minutes. After washing the resin six times with DMF, 115 mg of Fmoc-Ser(tBu)-OH, 46 mg of HOBt.H$_2$O, 47 μL of DIPCDI and 2 ml of DMF were added and shaken for 90 minutes. After filtering off the liquid phase, the resin was washed six times with DMF. Then, 2 ml of 20% piperidine/DMF solution was added and shaken for

TABLE 68

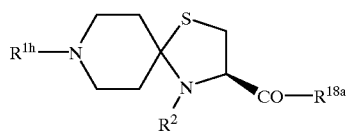

| $R^{1h}$ | $R^{18a}$ | $R^2$ | calcd. | found | |
|---|---|---|---|---|---|
| Ac-Leu | Leu-OH | COC$_6$H$_5$ | 574.75 | 575.4 | M + H |
| Ac-Asp | Leu-OH | COC$_6$H$_5$ | | | |
| Ac-Asn | Leu-OH | COC$_6$H$_5$ | | | |
| Ac-Gln | Leu-OH | COC$_6$H$_5$ | | | |
| Ac-Gln | Leu-OH | COC$_6$H$_5$ | | | |
| Ac-Phe | Leu-OH | COC$_6$H$_5$ | | | |
| Ac-Lys | Leu-OH | COC$_6$H$_5$ | 589.76 | 590.4 | M + H |
| Ac-Arg | Leu-OH | COC$_6$H$_5$ | 617.77 | 618.4 | M + H |
| Ac-His | Leu-OH | COC$_6$H$_5$ | | | |
| Ac-Tyr | Leu-OH | COC$_6$H$_5$ | | | |
| 4-ClC$_6$H$_4$CHCHCO | Leu-OH | COC$_6$H$_5$ | 584.3 | 584.4 | M + H |
| 4-ClC$_6$H$_4$CH$_2$CO | Leu-OH | COC$_6$H$_5$ | | | |
| Ac-Arg | Ala-OH | COC$_6$H$_5$ | | | |
| Ac-Arg | Asp-OH | COC$_6$H$_5$ | | | |
| Ac-Arg | Glu-OH | COC$_6$H$_5$ | | | |
| Ac-Arg | Phe-OH | COC$_6$H$_5$ | | | |
| Ac-Arg | Lys-CH | COC$_6$H$_5$ | | | |
| Ac-Arg | Tyr-OH | COC$_6$H$_5$ | | | |
| Ac-Arg | Pro-OH | COC$_6$H$_5$ | | | |
| Ac-Arg | β-Ala-OH | COC$_6$H$_5$ | | | |
| Ac-Arg | D-ala-OH | COC$_6$H$_5$ | | | |
| Ac-Arg | Leu-OH | COCH$_3$ | | | |
| H-Arg | Leu-OH | COCH$_3$ | | | |
| 4-ClC$_6$H$_4$CHCHCO | Leu-OH | COCH$_3$ | | | |
| 4-ClC$_6$H$_4$CH$_2$CO | Leu-OH | COCH$_3$ | | | |
| 4-H$_2$N(HN)CC$_6$H$_4$CO | Leu-OH | COCH$_3$ | | | |
| 3-(2-Thienyl)-2-propenoyl | Leu-OH | COCH$_3$ | | | |
| 3-(3-Pyridyl)-2-propenoyl | Leu-OH | COCH$_3$ | | | |
| H-Arg | Leu-OH | COC$_6$H$_5$ | | | |
| 4-H$_2$N(HN)CC$_6$H$_4$CO | Leu-OH | COC$_6$H$_5$ | | | |
| 3-(2-Thienyl)-2-propenoyl | Leu-OH | COC$_6$H$_5$ | | | |
| 3-(3-Pyridyl)-2-propenoyl | Leu-OH | COC$_6$H$_5$ | | | |
| 2-Oxo-2H-pyran-5-carbonyl | Leu-OH | COC$_6$H$_5$ | | | |
| 3-Pyridylcarbonyl | Leu-OH | COC$_6$H$_5$ | | | |
| Ac-Arg | Gly-OH | COCH$_3$ | | | |
| Ac-Arg | Gly-Gly-OH | COCH$_3$ | | | |
| Ac-Arg | D-ala-OH | COCH$_3$ | | | |
| Ac-Arg | β-Ala-OH | COCH$_3$ | | | |
| H-Cit | Leu-OH | COCH$_3$ | | | |
| Ac-Cit | Leu-OH | COCH$_3$ | | | |

EXAMPLE C-5

DMF was added to 182 mg (0.100 mmol) of Rink amide MBHA resin to swell the resin. Then, 2 ml of 20% piperidine/DMF solution was added and shaken for 20 minutes. After washing the resin six times with DMF, 106 mg of Fmoc-Leu-OH, 46 mg of HOBt.H$_2$O, 47 μL of 20 minutes. After filtering off the liquid phase, the resin was washed six times with DMF. Then, 2 ml of DMF-DCM (1:1) mixture, 0.29 ml of acetic anhydride and 0.53 ml of DIEA were added, and shaken for 40 minutes. After filtering off the liquid phase, the resin was washed four times with DMF and three times with DCM. Then, 6 ml of TFA-methylene chloride (1:1) was added and shaken for 4 hours. The insoluble matter was filtered off, the filtrate was concentrated under reduced pressure, 20 ml of diethyl ether was added to the residue, and the resulting crystal was collected by filtration to obtain 45 mg of benzyl 3-[8-[(2S)-2-(acetylamino)-3-hydroxypropanoyl]-2-(2-{[(1S)-1-(aminocarbonyl)-3-methylbutyl]amino}-2-oxoethyl)-3-oxo-1-thia-4,8-diazaspiro[4,5]decan-4-yl]-propionate.

EXAMPLE C-6

The procedure of Example C-5 was repeated to obtain the following compounds.

oxo-1-thia-4,8-diazaspiro[4.5]decan-2-yl}-acetic acid, the procedure of Example C-3 was repeated to obtain (2S)-2-({2-[8-((2S)-2-(acetylamino)-5-{[amino(imino)methyl]amino}-pentanoyl)-4-benzyl-3-oxo-1-thia-4,8-diazaspiro[4.5]decan-2-yl]acetyl}amino)-4-methylvaleric acid.

EXAMPLE C-8

The procedure of Example C-7 was repeated to obtain the following compounds.

TABLE 69

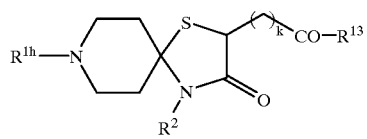

| $R^{1h}$ | $R^{13}$ | $R^2$ | k | calcd. | found | |
|---|---|---|---|---|---|---|
| Ac—Asn | Leu—$NH_2$ | $CH_2CH_2CO_2CH_2C_6H_5$ | 1 | 660.79 | 661.4 | M + H |
| Ac—Ala | Leu—$NH_2$ | $CH_2CH_2CO_2CH_2C_6H_5$ | 1 | 617.77 | 618.3 | M + H |
| Ac—Asp | Leu—$NH_2$ | $CH_2CH_2CO_2CH_2C_6H_5$ | 1 | 661.78 | 662.3 | M + H |
| Ac—Leu | Asp—$NH_2$ | $CH_2CH_2CO_2CH_2C_6H_5$ | 1 | 661.78 | 662.3 | M + H |
| Ac—Asp | Asp—$NH_2$ | $CH_2CH_2CO_2CH_2C_6H_5$ | 1 | 663.72 | 662.4 | M + H |
| Ac—Gln | Asp—$NH_2$ | $CH_2CH_2CO_2CH_2C_6H_5$ | 1 | 676.75 | 677.3 | M + H |
| Ac—Ser | Asp—$NH_2$ | $CH_2CH_2CO_2CH_2C_6H_5$ | 1 | 635.71 | 636.3 | M + H |
| Ac—Asn | Asp—$NH_2$ | $CH_2CH_2CO_2CH_2C_6H_5$ | 1 | 662.72 | 663.3 | M + H |
| Ac—Ala | Asp—$NH_2$ | $CH_2CH_2CO_2CH_2C_6H_5$ | 1 | 619.71 | 620.2 | M + H |
| Ac—Leu | Gln—$NH_2$ | $CH_2CH_2CO_2CH_2C_6H_5$ | 1 | 674.82 | 675.4 | M + H |
| Ac—Gln | Gln—$NH_2$ | $CH_2CH_2CO_2CH_2C_6H_5$ | 1 | 689.79 | 690.3 | M + H |
| Ac—Ser | Gln—$NH_2$ | $CH_2CH_2CO_2CH_2C_6H_5$ | 1 | 648.74 | 649.3 | M + H |
| Ac—Asn | Gln—$NH_2$ | $CH_2CH_2CO_2CH_2C_6H_5$ | 1 | 675.77 | 676.3 | M + H |
| Ac—Ala | Gln—$NH_2$ | $CH_2CH_2CO_2CH_2C_6H_5$ | 1 | 632.74 | 633.3 | M + H |
| Ac—Leu | Leu—$NH_2$ | $CH_2CH_2CO_2CH_2C_6H_5$ | 1 | 659.85 | 660.4 | M + H |
| Ac—Gln | Leu—$NH_2$ | $CH_2CH_2CO_2CH_2C_6H_5$ | 1 | 674.82 | 675.4 | M + H |
| Ac—Glu | Asp—$NH_2$ | $CH_2CH_2CO_2CH_2C_6H_5$ | 1 | 677.74 | 678.4 | M + H |
| Ac—Asp | Asn—$NH_2$ | $CH_2CH_2CO_2CH_2C_6H_5$ | 1 | 662.72 | 661.4 | M − H |
| Ac—Asn | Asn—$NH_2$ | $CH_2CH_2CO_2CH_2C_6H_5$ | 1 | 661.74 | 660.4 | M − H |
| Ac—Asp | Glu—$NH_2$ | $CH_2CH_2CO_2CH_2C_6H_5$ | 1 | 677.74 | 676.4 | M − H |
| Ac—Asn | Glu—$NH_2$ | $CH_2CH_2CO_2CH_2C_6H_5$ | 1 | 676.75 | 675.4 | M − H |
| Ac—Glu | Glu—$NH_2$ | $CH_2CH_2CO_2CH_2C_6H_5$ | 1 | 691.77 | 690.4 | M − H |
| Ac—Gln | Glu—$NH_2$ | $CH_2CH_2CO_2CH_2C_6H_5$ | 1 | 690.78 | 689.4 | M − H |
| Ac—Asp | Gln—$NH_2$ | $CH_2CH_2CO_2CH_2C_6H_5$ | 1 | 676.75 | 675.4 | M − H |
| Ac—Glu | Gln—$NH_2$ | $CH_2CH_2CO_2CH_2C_6H_5$ | 1 | 690.78 | 689.4 | M − H |
| Ac—D-Ala | D-Ala—$NH_2$ | $CH_2CH_2CO_2CH_2C_6H_5$ | 1 | 575.7 | 598.4 | M + Na |
| Ac—Asn | D-Ala—$NH_2$ | $CH_2CH_2CO_2CH_2C_6H_5$ | 1 | 618.71 | 641.4 | M + Na |
| Ac—D-Ala | Asn—$NH_2$ | $CH_2CH_2CO_2CH_2C_6H_5$ | 1 | 618.71 | 641.4 | M + Na |

EXAMPLE C-7

Using Wang resin, Fmoc-Leu-OH, Fmoc-Arg(Pmc)-OH and 2-{4-benzyl-8-[(9H-fluoren-9-ylmethoxy)carbonyl]-3-

TABLE 70

| $R^{1h}$ | $R^{13}$ | $R^2$ | k |
|---|---|---|---|
| Ac-Gln-Leu | Leu-Ala-Leu-OH | $CH_2CH_2CO_2CH_2C_6H_5$ | 1 |
| Ac-Gln | Leu-Ala-Leu-OH | $CH_2CH_2CO_2CH_2C_6H_5$ | 1 |
| Ac-Arg | OH | $CH_2C_6H_5$ | 1 |
| 4-$ClC_6H_4$CHCHCO | OH | $CH_2C_6H_5$ | 1 |

TABLE 70-continued

[Structure: spiro compound with R^1h-N piperidine, S, N-R^2, =O, and (CH)_k-CO-R^13 substituent]

| R^1h | R^13 | R^2 | k |
|---|---|---|---|
| 4-H₂N(HN)CC₆H₄CO | OH | CH₂C₆H₅ | 1 |
| 4-ClC₆H₄CHCHCO | Leu-OH | CH₂C₆H₅ | 1 |
| 4-H₂N(HN)CC₆H₄CO | Leu-OH | CH₂C₆H₅ | 1 |
| 4-H₂N(HN)CC₆H₄CO | Leu-OH | CH₂C₆H₅ | 1 |
| Ac-Arg | OH | H | 1 |
| 4-ClC₆H₄CHCHCO | OH | H | 1 |
| 4-H₂N(HN)CC₆H₄CO | OH | H | 1 |
| Ac-Arg | Leu-OH | H | 1 |
| 4-ClC₆H₄CHCHCO | Leu-OH | H | 1 |
| 4-H₂N(HN)CC₆H₄CO | Leu-OH | H | 1 |
| 4-H₂N(HN)CC₆H₄CO | Leu-OH | H | 1 |
| 4-H₂N(HN)CC₆H₄OCH₂CO | OH | H | 1 |
| 4-H₂N(HN)CC₆H₄OCH₂CO | OH | CH₂C₆H₅ | 1 |

EXAMPLE C-9

DMF was added to 157 mg (0.100 mmol) of Rink amide MBHA resin to swell the resin. Then, 2 ml of 20% piperidine/DMF solution was added and shaken for 20 minutes. After washing the resin six times with DMF, 106 mg of Fmoc-Leu-OH, 46 mg of HOBt.H₂O, 48 μL of DIPCDI and 1.5 ml of DMF were added and shaken for 90 minutes. After filtering off the liquid phase, the resin was six times washed with DMF. Then, 2 ml of 20% piperidine/DMF solution was added and shaken for 20 minutes. After washing the resin six times with DMF, 175 mg of 3-{2-{2-[(2-amino-2-oxoethyl)amino]-2-oxoethyl}-8-[(9H-fluoren-9-ylmethoxy)carbonyl]-3-oxo-1-thia-4,8-diazaspiro[4.5]decan-4-yl}-propionic acid, 46 mg of HOBt.H₂O, 48 μL of DIPCDI and 1.5 ml of DMF were added and shaken for 90 minutes. After filtering off the liquid phase, the resin was six times washed with DMF. Then, 2 ml of 20% piperidine/DMF solution was added and shaken for 20 minutes. After washing the resin six times with DMF, 106 mg of Fmoc-Leu-OH, 46 mg of HOBt.H₂O, 48 μL of DIPCDI and 1.5 ml of DMF were added and shaken for 90 minutes. After filtering off the liquid phase, the resin was washed six times with DMF. Then, 2 ml of 20% piperidine/DMF solution was added and shaken for 20 minutes. After filtering off the liquid phase, the resin was washed six times with DMF. Then, 2 ml of DMF-DCM (1:1) mixture, 0.29 ml of acetic anhydride and 0.53 ml of DIEA were added and shaken for 90 minutes. After filtering off the liquid phase, the resin was washed four times with DMF and three times with DCM. Then, 6 ml of TFA-methylene chloride (1:1) was added and shaken for 2 hours. The insoluble matter was filtered off, the filtrate was concentrated under reduced pressure, 20 ml of diethyl ether was added to the residue, and the resulting crystal was collected by filtration to obtain 55 mg of (2S)-2-{[3-(8-[(2S)-2-(acetylamino)-4-methylpentanoyl]-2-{2-[(2-amino-2-oxoethyl)amino]-2-oxoethyl}-3-oxo-1-thia-4,8-diazaspiro[4.5]decan-4-yl)propanoyl]amino}-4-methylpentanamide.

ESI-MS: m/z 626.4 for (M+H)⁺ (calcd. 625.80 for $C_{28}H_{47}N_7O_7S$)

EXAMPLE C-10

The procedure of Example C-9 was repeated to obtain the following compounds.

TABLE 71

[Structure: spiro compound with R^1h-N piperidine, S, N with R^2b-C(=O)-CH₂- chain, and (CH)_k-CO-R^13 substituent]

| R^1h | R^2b | R^13 | k |
|---|---|---|---|
| Ac-Asp | Gly-NH₂ | Leu-NH₂ | 1 |
| Ac-Asn | Gly-NH₂ | Leu-NH₂ | 1 |
| Ac-Glu | Gly-NH₂ | Leu-NH₂ | 1 |
| Ac-Gln | Gly-NH₂ | Leu-NH₂ | 1 |
| Ac-Ser | Gly-NH₂ | Leu-NH₂ | 1 |
| Ac-Leu | Gly-NH₂ | Asp-NH₂ | 1 |
| Ac-Asp | Gly-NH₂ | Asp-NH₂ | 1 |
| Ac-Asn | Gly-NH₂ | Asp-NH₂ | 1 |
| Ac-Glu | Gly-NH₂ | Asp-NH₂ | 1 |
| Ac-Gln | Gly-NH₂ | Asp-NH₂ | 1 |
| Ac-Ser | Gly-NH₂ | Asp-NH₂ | 1 |
| Ac-Leu | Gly-NH₂ | Glu-NH₂ | 1 |
| Ac-Asp | Gly-NH₂ | Glu-NH₂ | 1 |
| Ac-Asn | Gly-NH₂ | Glu-NH₂ | 1 |
| Ac-Glu | Gly-NH₂ | Glu-NH₂ | 1 |
| Ac-Gln | Gly-NH₂ | Glu-NH₂ | 1 |
| Ac-Ser | Gly-NH₂ | Glu-NH₂ | 1 |
| Ac-Leu | Gly-NH₂ | Gln-NH₂ | 1 |
| Ac-Asp | Gly-NH₂ | Gln-NH₂ | 1 |
| Ac-Asn | Gly-NH₂ | Gln-NH₂ | 1 |
| Ac-Gln | Gly-NH₂ | Gln-NH₂ | 1 |
| Ac-Gln | Gly-NH₂ | Gln-NH₂ | 1 |
| Ac-Ser | Gly-NH₂ | Gln-NH₂ | 1 |

Referential Example 1

In an atmosphere of nitrogen, 139 g of isobutyltriphenylphosphonium iodide was suspended in 350 ml of anhydrous tetrahydrofuran and cooled to −20° C. At the same temperature as above, 176 ml of 1.66 mol/L solution of n-butyllithium in hexane was dropwise added and the resulting mixture was stirred for one hour. After elevating the temperature up to the ambient temperature, 175 ml of a solution of 35.0 g of 1,4-cyclohexandione monoethylene ketal in anhydrous tetrahydrofuran was dropwise added while cooling the mixture with water. After stirring the mixture at the same temperature for one hour, the reaction mixture was poured into a mixture of ice water, aqueous solution of ammonium chloride and ethyl acetate, and the organic layer was separated. The organic layer was washed successively with water and saturated aqueous solution of sodium chloride and dried over anhydrous magnesium sulfate, and the solvent was distilled off under reduced pressure. Ethyl ether was added to the residue, the deposited insoluble matter was filtered off, and the filtrate was concentrated under reduced pressure. To the residue thus obtained were added 150 ml of anhydrous tetrahydrofuran and 150 ml of 6 mol/L hydrochloric acid, and the resulting mixture was stirred at ambient temperature for 24 hours. The reaction mixture was poured into a mixture of water and ethyl acetate, and the organic layer was separated. The organic layer was washed successively with water and saturated aqueous solution of sodium chloride and dried over anhydrous magnesium sulfate, and the solvent was distilled off under reduced pressure. Purification of the residue by column chromatography [eluent: hexane:ethyl acetate=20:1] gave 28.0 go f 4-(3-methylbutylidene)-1-cyclohexanone as a colorless oily product.

NMR (CDCl$_3$) δ: 0.91(6H,d,J=6.4 Hz), 1.4–2.1(3H,m), 2.44(8H,bs), 5.3–5.5(1H,m)

Referential Example 2

In 40 ml of anhydrous tetrahydrofuran were dissolved 4.00 g of 4-isopropylphenol, 5.10 g of 1,4-dioxaspiro[4.5]decan-8-ol and 8.47 g of triphenylphosphine. Then, 14.1 g of 40% solution of diethyl azodicarboxylate in toluene was dropwise added at 0–5° C., and the resulting mixture was stirred at ambient temperature for 24 hours. The reaction mixture was poured into ice water and extracted with ethyl acetate. The organic layer was washed successively with water and saturated aqueous solution of sodium chloride and dried over anhydrous magnesium sulfate, and the solvent was distilled off under reduce pressure. Ethyl ether was added to the residue, the deposited insoluble matter was filtered off, and the filtrate was concentrated under reduced pressure. The residue thus obtained was mixed with 60 ml of anhydrous tetrahydrofuran and 40 ml of 6 mol/L hydrochloric acid and stirred at ambient temperature for 24 hours. The reaction mixture was poured in a mixture of water and ethyl acetate, and the organic layer was separated. The organic layer was washed successively with water and saturated aqueous solution of sodium chloride and dried over anhydrous magnesium sulfate, and the solvent was distilled off under reduced pressure. Purification of the residue by column chromatography [eluents: toluene:ethyl acetate=20:1, followed by hexane:ethyl acetate=20:1] gave 2.40 g of 4-(4-isopropylphenoxy)-1-cyclohexanone as a colorless oily product.

NMR (CDCl$_3$) δ: 1.23 (6H,d,J=6.8 Hz), 1.8–3.1(9H,m), 4.5–4.8(1H,m), 6.88(2H,d,J=8.5 Hz), 7.17(2H,d,J=8.5 Hz)

Referential Example 3

The procedure of Referential Example 1 was repeated to obtain the following compounds.
3(1)

4-(1-Methylethylidene)-1-cyclohexanone

NMR (CDCl$_3$) δ: 1.72(6H,s), 2.2–2.7(8H,m)
3(2)

4-Ethylidene-1-cyclohexanone

NMR (CDCl$_3$) δ: 1.65(3H,d,J=6.8 Hz), 2.2–3.2(8H,m), 5.41(1H,q, J=6.8 Hz)
3(3)

5-(4-Oxocyclohexylidene)-valeric acid

NMR (CDCl$_3$) δ: 1.5–2.8(14H,m), 5.34(1H,t,J=7.1 Hz), 9.6– 10.4(1H,bs)
3(4)

4-Butylidenecyclohexanone

NMR (CDCl$_3$) δ: 0.7–2.7(15H,m), 5.35(1H,t,J=7.2 Hz),
3(5)

4-(2-Methylpropylidene)cyclohexanone

NMR (CDCl$_3$) δ: 0.98(6H,d,J=6.8 Hz), 1.5–2.8(9H,m), 5.18 (1H,d,J=9.3 Hz)
3(6)

4-(4-Methylpentylidene)cyclohexanone

Referential Example 4

The procedure of Referential Example 2 was repeated to obtain the following compounds.
4(1)

4-Phenoxy-1-cyclohexanone

NMR (CDCl$_3$) δ: 1.9–3.0(8H,m), 4.5–4.9(1H,m), 6.8–7.5 (5H,m)
4(2)

Methyl 4-[(4-oxocyclohexyl)oxy]-benzoate

NMR (CDCl$_3$) δ: 1.9–3.0(8H,m), 3.89(3H,s), 4.7–5.0(1H, m), 6.97(2H,d,J=9.0 Hz), 8.00(2H,d,J=9.0 Hz)
4(3)

4-[4-(Methylthio)phenoxy]-1-cyclohexanone

NMR (CDCl$_3$) δ: 1.9–3.0(8H,m), 2.46(3H,s), 4.5–4.8(1H, m), 6.91(2H,d,J=8.9 Hz), 7.28(2H,d,J=8.9 Hz)
4(4)

4-(4-Methoxyphenoxy)-1-cyclohexanone

NMR (CDCl$_3$) δ: 1.8–3.0(8H,m), 3.77(3H,s), 4.4–4.7(1H, m), 6.9–7.0 (4H,m)
4(5)

4-(2,3-Dihydro-1H-inden-5-yloxy)cyclohexanone

NMR (CDCl$_3$) δ: 1.8–3.1(14H,m), 4.5–4.8(1H,m), 6.6–7.0(2H,m), 7.14(1H,d,J=8 Hz)

Referential Example 5

In 50 ml of methylene chloride was dissolved 2.50 g of 4-[4-(methylthio)phenoxy]-1-cyclohexanone. After adding 5.48 g of m-chloroperbenzic acid at 0–5° C., the resulting mixture was stirred at ambient temperature for 4 hours. The reaction mixture was poured into water, pH was adjusted to 8.0 with saturated aqueous solution of sodium hydrogen carbonate, and the organic layer was separated. The organic layer thus obtained was washed successively with aqueous solution of sodium thiosulfate, water and saturated aqueous solution of sodium chloride and dried over anhydrous magnesium sulfate, and the solvent was distilled off under reduced pressure. Recrystallization of the residue from ethanol gave 2.05 g of 4-[4-(methylsulfonyl)phenoxy]-1-cyclohexanone as a colorless crystalline product.

NMR (CDCl$_3$) δ: 2.0–3.0(8H,m), 3.06(3H,s), 4.7–5.0(1H, m), 7.10 (2H,d,J=9.0 Hz), 7.90(2H,d,J=9.0 Hz)

Referential Example 6

In 21 ml of anhydrous tetrahydrofuran were dissolved 1.50 g of 5-(4-oxocyclohexylidene)-valeric acid and 1.17 ml of triethylamine. Then, 4.50 ml of a solution of 0.80 ml of ethyl chloroformate in anhydrous tetrahydrofuran was dropwise added at −20° C., and the resulting mixture was stirred at the same temperature as above for one hour. Then, 4.50 ml of a solution of anhydrous tetrahydrofuran containing 2.00 ml of diethylamine was dropwise added at the same temperature, and the resulting mixture was stirred at ambient temperature for one hour. The reaction mixture was poured into ice water, pH was adjusted to 2.0 with 2 mol/L hydrochloric acid, and the mixture was extracted with ethyl acetate. The organic layer was washed successively with water, saturated aqueous solution of sodium hydrogen carbonate and saturate aqueous solution of sodium chloride and dried over anhydrous magnesium sulfate, and the solvent was distilled off under reduced pressure. Purification of the residue by column chromatography [eluent: toluene:ethyl acetate=1:1] gave 1.30 g of N,N-diethyl-5-(4-oxocyclohexylidene)-valeramide as a colorless oily product.

NMR (CDCl$_3$) δ: 1.11(3H,t,J=7.0 Hz), 1.17(3H,t,J=7.0 Hz), 1.5–2.7(14H,m), 3.31(2H,q,J=7.0 Hz), 3.38(2H,q,J=7.0 Hz), 5.37 (1H,t,J=7.0 Hz)

Referential Example 7

The procedure of Referential Example 6 was repeated to obtain the following compounds.
7(1)

5-(4-Oxocyclohexylidene)-valeramide

NMR (CDCl$_3$) δ: 1.5–2.8(14H,m), 5.34(1H,t,J=7.0 Hz), 5.5–6.4(2H,m)
7(2)

Benzyl 3-{[(4-oxocyclohexyl)carbonyl]amino}-propionate

NMR (CDCl$_3$) δ: 1.6–2.8(11H,m), 3.4–3.7(2H,m), 5.14 (2H,s), 6.1–6.5(1H,m), 7.35(5H,s)
7(3)

N-Isobutyl-2-(4-oxocyclohexyl)acetamide

NMR (CDCl$_3$) δ: 0.92(6H,d,J=6.6 Hz), 1.2–2.6(12H,m), 3.0–3.2(2H,m), 5.6–5.9(1H,bs)
7(4)

N,N-Dipropyl-2-(4-oxocyclohexyl)-acetamide

NMR (CDCl$_3$) δ: 0.7–1.0(6H,m), 1.2–2.5(15H,m), 3.1–3.4(4H,m)

Referential Example 8

In an atmosphere of nitrogen, 0.23 g of magnesium powder was suspended in 2 ml of anhydrous ethyl ether. While refluxing the suspension, a solution of 2.00 g of 4-tert-butyl-1-bromobenzene in 10 ml anhydrous ethyl ether was dropwise added. After stirring the resulting mixture under reflux for one hour, a solution of 1.17 g of 1,4-cyclohexandione monoethylene ketal in 10 ml anhydrous tetrahydrofuran was dropwise added at 0–5° C., and the temperature was elevated to ambient temperature. After stirring the mixture at the same temperature as above, the reaction mixture was poured into a mixture of water and acetic acid, stirred at ambient temperature for 20 minutes, and extracted with ethyl acetate. The organic layer was washed successively with water and saturated aqueous solution of sodium chloride and dried over anhydrous magnesium sulfate, and the solvent was distilled off under reduced pressure. Purification of the residue by column chromatography [eluent: hexane:ethyl acetate=3:1] gave 1.25 of 8-[4-(tert-butyl)phenyl]-1,4-dioxaspiro[4.5]decan-8-ol as a light yellow oily product.

NMR (CDCl$_3$) δ: 1.31(9H,s), 1.5–2.3(9H,m), 3.97(4H,s), 7.3–7.6(4H,m)

Referential Example 9

In 10 ml of tetrahydrofuran was dissolved 1.10 g of 8-[4-(tert-butyl)phenyl]-1,4-dioxaspiro[4.5]decane-8-ol. Then, 5.00 ml of 6 mol/L hydrochloric acid and 5.00 ml of water were added at an ice-cooled temperature and the resulting mixture was stirred at ambient temperature for 2 hours. The reaction mixture was poured into a mixture of water and ethyl acetate, and the organic layer was separated. The organic layer was washed successively with water and saturated aqueous solution of sodium chloride and dried over anhydrous magnesium sulfate, and the solvent was distilled off under reduced pressure. Hexane was added to the residue, and the resulting crystal was collected by filtration to obtain 0.67 g of 4-[4-(tert-butyl)phenyl]-4-hydroxy-1-cyclohexanone as a colorless crystalline product.

NMR (CDCl$_3$) δ: 1.32(9H,s), 2.0–2.5(7H,m), 2.6–3.2(2H, m), 7.43(4H,s)

Referential Example 10

In 75 ml of benzene was dissolved 15.0 g of 2-ethylbutanal, to which were added 10.5 g of 3-buten-2-one and 0.15 ml of concentrated sulfuric acid at ambient temperature. While heating the mixture under reflux, an azeotropic distillation treatment was carried out for 3 hours by means of Dean Stark apparatus. The reaction mixture was poured into a mixture of ice water and ethyl acetate, pH was adjusted to 7.0 with a saturated aqueous solution of sodium hydrogen carbonate, and the organic layer was separated. The organic layer was washed successively with water and saturated aqueous solution of sodium chloride and dried over anhydrous magnesium sulfate, and the solvent was distilled off under reduced pressure. Purification of the residue by distillation under reduced pressure gave 4.90 g of 4,4-diethyl-2-cyclohexen-1-one as a light yellow oily product.

NMR (CDCl$_3$) δ: 0.89(6H,t,J=7.3 Hz), 1.85(2H,t,J=6.8 Hz), 1.4–1.8(4H,m), 2.44(2H,t,J=6.8 Hz), 5.92(1H,d,J=10.3 Hz), 6.72(1H,d,J=10.3 Hz)

Referential Example 11

In 22 ml of acetic acid was dissolved 2.20 g of 4,4-diethyl-2-cyclohexen-1-one, to which was added 0.22 g of 5% palladium-carbon. Under a pressure of 5 atmospheres, the mixture was stirred at ambient temperature for one hour under a stream of hydrogen. The reaction mixture was filtered, and the solvent was distilled off under reduced pressure. Purification of the residue by column chromatography [eluent: hexane:ethyl acetate=10:1] gave 1.90 g of 4,4-diethyl-1-cyclohexanone as a colorless oily product.

NMR (CDCl$_3$) δ: 0.84(6H,t,J=7.3 Hz), 1.2–1.8(8H,m), 2.32(4H,t,J=6.8 Hz)

Referential Example 12

In an atmosphere of nitrogen, 280 ml of anhydrous tetrahydrofuran was added to 23.0 g of sodium hydride, to which was dropwise added a solution of 40.0 g of diethyl malonate in 80 ml of anhydrous tetrahydrofuran furan at 40° C. over a period 30 minutes. After stirring the mixture at the same temperature as above for one hour, the mixture was cooled to 15° C., and a solution of 52.5 g of ethyl acrylate in 80 ml of anhydrous tetrahydrofuran was dropwise added thereto over a period of 30 minutes. After a reaction at 45° C. for 30 minutes followed by cooling, the reaction mixture was poured into a mixture of ice water and ethyl acetate. After adjusting pH value to 2.0 with 6 mol/L hydrochloric acid, the organic layer was separated. The organic layer was washed successively with water, saturated aqueous solution of sodium hydrogen carbonate and saturated aqueous solution of sodium chloride and dried over anhydrous magnesium sulfate, the solvent was distilled off under reduced pressure. Purification of the residue by distillation under reduced pressure gave 61.8 g of 2,4,4-tricarbethoxy-cyclohexanone as a light yellow oily product.

Boiling point: 140–153° C. (2.0–2.5 mmHg)

Referential Example 13

To 540 ml of dimethyl sulfoxide were added 21.9 g of lithium chloride, 13.9 ml of pyridine and 9.3 ml of water, and the resulting mixture was gently heated under reflux. While refluxing the mixture, 100 ml of a solution of 54.0 g of 2,4,4-tricarbethoxy-cyclohexanone in dimethyl sulfoxide was dropwise added thereto over one hour. After a reaction at the same temperature as above for 2 hours, the mixture was cooled and poured into a mixture of ice water and ethyl acetate, and the organic layer was separated. The organic layer was washed with saturated aqueous solution of sodium chloride and dried over anhydrous magnesium sulfate, and the solvent was distilled off under reduced pressure. Purification of the residue by distillation under reduced pressure gave 13.5 g of 4-carbethoxycyclohexanone as a light yellow oily product.

Boiling point: 103–107° C. (2.5–3.5 mmHg)

Referential Example 14

In 120 ml of methylene chloride was suspended 6.0 g of 4-(methoxycarbonyl)-benzoic acid, to which were added 3.5 ml of oxalyl chloride and 0.05 ml of N,N-dimethylformamide at 0–5° C. After a reaction at the same temperature as above for 3 hours, the mixture was stirred at ambient temperature for 24 hours. Then, a 90.7 g portion of the reaction mixture was taken out, and 6.9 ml of diethylamine was added thereto. The mixture was stirred at ambient temperature for 3 hours, and then poured into ice water. pH was adjusted to 1.0 with 6 mol/L hydrochloric acid, and the organic layer was separated. The organic layer was washed successively with water, saturated aqueous solution of sodium hydrogen carbonate and saturated aqueous solution of sodium chloride and dried over anhydrous magnesium sulfate, and the solvent was distilled off under reduced pressure. Thus, 5.89 g of methyl 4-[(diethylamino) carbonyl]-benzoate was obtained as a red oily product.

Referential Example 15

In 25 ml of methanol was dissolved 5.44 g of methyl 4-[(diethylamino)carbonyl]-benzoate. After adding 25 ml of 1 mol/L aqueous solution of sodium hydroxide at 0–5° C., the mixture was stirred at ambient temperature for 2 hours. The reaction mixture was poured into a mixture of water and ethyl acetate, and the aqueous layer was separated. The aqueous layer was mixed with ethyl acetate, pH was adjusted to 1.5 with 6 mol/L hydrochloric acid, and the organic layer was separated. The organic layer was washed successively with water and saturated aqueous solution of sodium chloride and dried over magnesium sulfate, and the solvent was distilled off under reduced pressure. Diisopropyl ether was added to the residue, and the deposited crystal was collected by filtration to obtain 2.94 g of 4-[(diethylamino) carbonyl]-benzoic acid as a colorless crystalline product.

Referential Example 16

In 2.3 ml of methylene chloride was added 0.470 g of 5-phenylvaleric acid, to which were added at ambient temperature 0.287 ml of thionyl chloride and 0.020 ml of N,N-dimethylformamide. After a reaction at the same temperature as above for 4 hours, the reaction mixture was concentrated under reduced pressure, 5.0 ml of toluene was added and the resulting mixture was further concentrated under reduced pressure. Thus, 0.510 g of 5-phenylvaleric acid chloride was obtained as a light yellow oily product.

Referential Example 17

In 20 ml of N,N-dimethylformamide was suspended 1.11 g of 60% sodium hydride, to which was dropwise added 5.0 ml of ethyl diethylphosphonoacetate over 5 minutes at an ice-cooled temperature. The resulting mixture was stirred at ambient temperature for 90 minutes. Then, 2.49 ml of isovalerylaldehyde was dropwise added at an ice-cooled temperature over a period of 5 minutes, and the resulting mixture was stirred at ambient temperature for one hour. The reaction mixture was poured into a mixture of chloroform and water, pH was adjusted to 1.0 with 2 mol/L hydrochloric acid, and the organic layer was separated. The organic layer was washed successively with water and saturated aqueous solution of sodium chloride and dried over anhydrous magnesium sulfate, and the solvent was distilled off under reduced pressure. Purification of the residue by silica gel column chromatography [eluent: n-hexane:ethyl acetate= 10:1] gave 3.27 g of ethyl (E)-5-methyl-2-hexenoate as a colorless oily product.

NMR (CDCl$_3$) δ: 0.93(6H,d,J=6.3 Hz), 1.29(3H,t,J=7.1 Hz), 1.5–1.9((1H,m), 2.0–2.3(2H,m), 4.19(2H,q,J=7.1 Hz), 5.7–5.9(1H,m), 6.9–7.0(1H,m)

Referential Example 18

In 15 ml of ethanol was dissolved ethyl (E)-5-methyl-2-hexenoate, to which was added 0.50 g of 5% palladium-carbon. Under a stream of hydrogen, the mixture was stirred at ambient temperature for 2 hours. The reaction mixture was filtered with Celite, and the solvent was distilled off under reduced pressure. Thus, 2.2 g of ethyl 5-methylhexanoate was obtained as a colorless oily product.

NMR (CDCl$_3$) δ: 0.88(6H,d,J=6.3 Hz), 1.1–2.1(8H,m), 2.28(2H,t,J=7.4 Hz), 4.12(2H,q,J=7.2 Hz)

Referential Example 19

In 20 ml of ethanol was dissolved 2.0 g of ethyl 5-methylhexanoate. After adding 10 ml of 2 mol/L aqueous solution of sodium hydroxide at ambient temperature, the resulting mixture was stirred for 30 minutes. The ethanol was distilled off under reduced pressure, the residue was poured into a mixture of water and chloroform, pH was adjusted to 1.0 with 2 mol/L hydrochloric acid, and the organic layer was separated. The organic layer was washed successively with water and saturated aqueous solution of sodium chloride and dried over anhydrous magnesium sulfate, and the solvent was distilled off under reduced pressure. Diisopropyl ether was added to the residue, and the deposited crystal was collected by filtration. Thus, 1.56 g of 5-methylhexanoic acid was obtained as a colorless oily product.

NMR (CDCl$_3$) δ: 0.89(6H,d,J=6.1 Hz), 1.1–2.1(5H,m), 2.34(2H,t,J=7.3 Hz)

Referential Example B-1

In 200 ml of toluene were dissolved 20.00 g of tert-butyl 4-oxo-1-piperidinecarboxylate and 12.6 ml of β-phenethylamine. After stirring the resulting solution at ambient temperature for 30 minutes, 15.07 g of mercaptosuccinic acid was added, and the resulting mixture was subjected to an azeotropic distillation treatment under reflux for 6 hours. The reaction mixture was poured into a mixture of ice water and ethyl acetate, and the organic layer was separated. The organic layer was washed successively with water and saturated aqueous solution of sodium chloride and dried over anhydrous magnesium sulfate, and the solvent was distilled off under reduced pressure. Purification of the residue by column chromatography [eluent: toluene:ethyl acetate=5:1] gave 22.10 g of 2-[8-(tert-butoxycarbonyl)-3-oxo-4-phenethyl-1-thia-4,8-diazaspiro[4.5]decan-2-yl]-acetic acid as a yellow oily product.

NMR (CDCl$_3$) δ: 1.47(9H,s), 1.4–2.2(4H,m), 2.4–3.8(8H, m), 3.8–4.4(3H,m), 7.1–7.4(6H,m)

Referential Example B-2

The procedure of Referential Example B-1 was repeated to obtain the compounds listed in Table 72.

TABLE 72

| No. | X | R$^2$ |
|---|---|---|
| 2 (1) | —COO—C(CH$_3$)$_3$ | —CH$_2$CH$_2$COOCH$_2$—C$_6$H$_5$ |
| 2 (2) | —COO—C(CH$_3$)$_3$ | —CH$_2$—C$_6$H$_5$ |
| 2 (3) | —COO—C(CH$_3$)$_3$ | -CH$_2$CH$_2$CH$_2$CH$_3$ |
| 2 (4) | —COO—C(CH$_3$)$_3$ | -CH$_2$CH$_2$OCH$_3$ |
| 2 (5) | -COCH$_3$ | —CH$_2$CH$_2$COOCH$_2$—C$_6$H$_5$ |
| 2 (6) | —COOCH$_2$CH(CH$_3$)$_2$ | —CH$_2$CH$_2$COOCH$_2$—C$_6$H$_5$ |
| 2 (7) | —COO—C(CH$_3$)$_3$ | H |

TABLE 72-continued

[Structure: X—N(piperidine spiro)—S—CH—CH2COOH with spiro ring containing N—R², C=O]

| No. | X | R² |
|---|---|---|
| 2 (8) | —COO—C(CH₃)₃ (tert-butyl ester shown as C with three CH₃) | —CH₂CH₂CH(CH₃)₂ |

Properties of the compounds of Table 72 are as mentioned below.

B-2(1)
NMR (CDCl$_3$) δ: 1.1–2.3 (4H,m), 1.46 (9H,s), 2.3–3.8 (8H,m), 3.8–4.4 (3H,m), 5.12 (2H,s), 6.0–6.7 (1H,bs), 7.0–7.2 (5H,m)

B-2(2)
NMR (CDCl$_3$) δ: 1.44 (9H,s), 1.5–2.2 (4H,m), 2.6–3.5 (4H,m), 3.9–4.3 (3H,m), 4.48 (1H,d,J=16.8 Hz), 4.69 (1H, d,J=16.8 Hz), 7.27 (5H,s), 9.13 (1H,bs)

B-2(3)
NMR (CDCl$_3$) δ: 0.92 (3H,t,J=7.2 Hz), 1.1–2.3 (8H,m), 1.47 (9H,s), 2.3–3.6 (6H,m), 3.9–4.4 (3H,m), 6.0–6.4 (1H, bs)

B-2(4)
NMR (CDCl$_3$) δ: 1.2–2.3 (4H,m), 1.46 (9H,s), 2.5–3.7 (8H,m), 3.47 (3H,s), 4.0–4.4 (3H,m), 5.9–6.5 (1H,bs)

B-2(5)
NMR (CDCl$_3$) δ: 2.12 (3H,s), 1.6–2.2 (4H,m), 2.5–4.0 (9H,m), 4.14 (1H,dd,J=3.9 Hz,8.8 Hz), 4.6–4.9 (1H,m), 5.12 (2H,s), 6.4 (1H,bs), 7.3–7.6 (5H,s)

B-2(7)
NMR (d$_6$-DMSO) δ: 1.39 (9H,s), 1.4–2.2 (4H,m), 2.3–3.5 (4H,m), 3.5–4.2 (2H,m), 4.04 (1H,dd,J=3.8 Hz,9.9 Hz), 8.89 (1H,s), 12.48 (1H,bs)

B-2(8)
NMR (CDCl$_3$) δ: 0.93 (6H,d,J=5.9 Hz), 1.0–2.4 (7H,m), 1.47 (9H,s), 2.5–3.5 (6H,m), 4.0–4.4 (3H,m), 6.2–6.8 (1H, bs)

Referential Example B-3

In 200 ml of N,N-dimethylformamide was dissolved 22.0 g of 2-[8-(tert-butoxycarbonyl)-3-oxo-4-phenethyl-1-thia-4,8-diazaspiro[4.5]decan-2-yl]-acetic acid. After adding 8.40 g of anhydrous potassium carbonate at 0–5° C., 4.90 ml of ethyl iodide was dropwise added over a period of 5 minutes. The resulting mixture was stirred at the same temperature as above for 10 minutes and then at ambient temperature for 2 hours, the reaction mixture was poured into a mixture of ice water and ethyl acetate, pH was adjusted to 2.0 with 6 mol/L hydrochloric acid, and the organic layer was separated. The organic layer was washed successively with water and saturated aqueous solution of sodium chloride and dried over anhydrous magnesium sulfate, and the solvent was distilled off under reduced pressure. Purification of the residue by column chromatography [eluent: hexane:ethyl acetate=2:1] gave 19.85 g of tert-butyl 2-(2-ethoxy-2-oxoethyl)-3-oxo-4-phenethyl-1-thia-4,8-diazaspiro]4.5]decane-8-carboxylate as a yellow oily product.

NMR (CDCl$_3$ δ: 1.47(9H,s), 1.28(3H,t,J=7.2 Hz), 1.4–2.2 (4H,m), 2.5–3.6(8H,m), 4.0–4.4(5H,m), 7.27(5H,s)

Referential Example B-4

The procedure of Referential Example B-3 was repeated to obtain the following compound:

tert-Butyl 2-(2-ethoxy-2-oxoethyl)-4-isopentyl-3-oxo-1-thia-4,8-diazaspiro[4.5]decan-8-carboxylate NMR (CDCl$_3$) δ: 0.93(6H,d,J=5.9 Hz), 1.0–3.4(13H,m), 1.27(3H,t,J=7.1 Hz), 1.47(9H,s), 3.9–4.4(5H,m)

Referential Example B-5

In 56 ml of methylene chloride was dissolved 18.50 g of tert-butyl 2-(2-ethoxy-2-oxoethyl)-3-oxo-4-phenethyl-1-thia-4,8-diazaspiro[4.5]decane-8-carboxylate. After adding 56 ml of trifluoroacetic acid at 0–5° C., the resulting mixture was stirred at the same temperature as above for 30 minutes and then at ambient temperature for 5 hours. The solvent was distilled off under reduced pressure, the residue was poured into a mixture of ice water and ethyl acetate, pH was adjusted to 8.0 with saturated aqueous solution of sodium hydrogen carbonate, and the organic layer was separated. The organic layer was washed successively with water and saturated aqueous solution of sodium chloride and dried over anhydrous magnesium sulfate and the solvent was distilled off under reduced pressure. Thus, 7.26 g of ethyl 2-(3-oxo-4-phenethyl-1-thia-4,8-diazaspiro[4.5]decan-2-yl)-acetate was obtained as a yellow oily product.

NMR (CDCl$_3$) δ: 1.29(3H,t,J=7.0 Hz), 1.2–1.8(2H,m), 2.2–3.6(13H,m), 4.0–4.4(3H,m), 7.25(5H,s)

Referential Example B-6

The procedure of Referential Example B-5 was repeated to obtain the following compounds.

B-6(1)

Trifluoroacetic acid salt of 2-(4-benzyl-3-oxo-1-thia-4,8-diazaspiro[4.5]decan-2-yl)-acetic acid NMR (d$_6$-DMSO) δ: 1.6–2.0(2H,m), 2.2–3.6(8H,m), 4.32 (1H,dd,J=3.9 Hz, 9.5 Hz), 4.44(1H,d,J=16.5 Hz), 4.68(1H, d,J=16.5 Hz), 7.29(5H,s), 8.6–9.1(2H,bs)

B-6(2)

Ethyl 2-(4-isopentyl-3-oxo-1-thia-4,8-diazaspiro[4.5]deecan-2-yl)-acetate

NMR (CDCl$_3$) δ: 0.93(6H,d,J=5.6 Hz), 1.27(3H,t,J=7.2 Hz), 1.4–3.4(16H,m), 4.0–4.4(3H,m)

Referential Example B-7

In 5 ml of methylene chloride was dissolved 0.50 g of ethyl 2-(3-oxo-4-phenethyl-1-thia-4,8-diazaspiro[4.5]

decan-2-yl)-acetate. After adding 0.25 ml of triethylamine at 0–5° C., 0.26 ml of ethyl succinyl chloride was dropwise added. After stirring at ambient temperature for 5 hours, the reaction mixture was poured into ice water, pH was adjusted to 2.0 with 2 mol/L hydrochloric acid, and the organic layer was separated. The organic layer was washed successively with water and saturated aqueous solution of sodium chloride and dried over anhydrous magnesium sulfate, and the solvent was distilled off under reduced pressure. Purification of the residue by column chromatography [eluent: hexane-:ethyl acetate=1:1] gave 0.65 g of ethyl 4-[2-(2-ethoxy-2-oxoethyl)-3-oxo-4-phenethyl-1-thia-4,8-diazaspiro[4.5]decan-8-yl]-4-oxobutanoate as a yellow oily product.

NMR (CDCl$_3$) δ: 1.26(3H,t,J=7.1 Hz), 1.29(3H,t,J=7.1 Hz), 1.2–2.5(4H,m), 2.6–5.0(19H,m), 7.26(5H,s)

Referential Example B-8

The procedure of Referential Example B-7 was repeated to obtain the compounds listed in Table 73.

TABLE 73

[Structure: R$^{1h}$–N-piperidine spiro-fused to thiazolidinone with CH$_2$COOEt substituent and N-R$^2$]

| No. | R$^{1h}$ | R$^2$ |
|---|---|---|
| 8 (1) | —COCH$_2$—C$_6$H$_5$ | —CH$_2$CH$_2$—C$_6$H$_5$ |
| 8 (2) | —COCH$_2$CH$_2$CH$_2$—C$_6$H$_5$ | —CH$_2$CH$_2$—C$_6$H$_5$ |
| 8 (3) | —COCH=CH—C$_6$H$_5$ | —CH$_2$CH$_2$—C$_6$H$_5$ |
| 8 (4) | —COCH(NH$_2$·HCl)CH$_2$CH(CH$_3$)$_2$ | —CH$_2$CH$_2$—C$_6$H$_5$ |
| 8 (5) | —COCH(NHCOCH$_3$)CH$_2$CH$_2$CONH$_2$ | —CH$_2$CH$_2$CH(CH$_3$)$_2$ |
| 8 (6) | -COCH$_2$CH$_2$COOEt | —CH$_2$CH$_2$CH(CH$_3$)$_2$ |
| 8 (7) | —COCH(OCOCH$_3$)(C$_6$H$_5$) | —CH$_2$CH$_2$—C$_6$H$_5$ |

Properties of the compounds of Table 73 are as follows.

B-8(1)
NMR (CDCl$_3$) δ: 1.24 (3H,t,J=7.0 Hz), 1.2–2.0 (4H,m), 2.5–4.9 (11H,m), 3.73 (2H,s), 4.14 (2H,q,J=7.0 Hz), 7.0–7.8 (10H,m)

B-8(2)
NMR (CDCl$_3$) δ: 1.28 (3H,t,J=7.1 Hz), 1.5–2.2 (6H,m), 2.2–4.0 (13H,m), 4.0–4.9 (4H,m),7.0–7.4 (10H,m)

B-8(3)
NMR (CDCl$_3$) δ: 1.29 (3H,t,J=7.0 Hz), 1.5–2.3 (4H,m), 2.5–3.8 (8H,m), 4.0–4.9 (5H,m), 6.86 (1H,d,J=15.4 Hz), 7.1–7.7 (10H,m), 7.69 (1H,d,J=15.4 Hz)

B-8(5)

NMR (CDCl₃) δ: 0.93 (6H,d,J=5.6 Hz), 1.28 (3H,t,J=7.2 Hz), 1.2–3.6 (17H,m), 2.10 (3H,s), 4.0–4.4 (4H,m), 4.5–5.2 (2H,m), 5.4–7.0 (3H,m)

B-8(6)

NMR (CDCl₃) δ: 0.93 (6H,d,J=5.8 Hz), 1.27 (6H,t,J=7.1 Hz), 1.1–2.4 (7H,m), 2.5–3.7 (10H,m), 3.8–4.9 (7H,m)

B-8(7)

NMR (CDCl₃) δ: 1.26 (3H,t,J=7.2 Hz), 1.4–2.2 (2H,m), 2.18 (3H,s), 2.4–4.9 (13H,m), 4.17 (2H,q,J=7.2 Hz), 6.21 (1H,s), 7.0–7.6 (10H,m)

Referential Example C-1

Using 9H-fluoren-9-ylmethyl 4-oxo-1-piperidinecarboxylate, the procedure of Referential Example B-1 was repeated to obtain 2-{4-[3-(tert-butoxy)-3-oxopropyl]-8-[(9H-fluoren-9-ylmethoxy)carbonyl]-3-oxo-1-thia-4,8-diazaspiro[4.5]decan-2-yl}-acetic acid.

Referential Example C-2

The procedure of Example 38 was repeated to obtain 9H-fluoren-9-ylmethyl 2-{2-[(2-amino-2-oxoethyl)amino]-2-oxoethyl}-4-[3-(tert-butoxy)-3-oxopropyl]-3-oxo-1-thia-4,8-diazaspiro[4.5]decan-8-carboxylate.

Referential Example C-3

The procedure of Example 5 was repeated to obtain 3-{2-{2-[(2-amino-2-oxoethyl)amino]-2-oxoethyl}-8-[(9H-fluoren-9-ylmethoxy)carbonyl]-3-oxo-1-thia-4,8-diazaspiro[4.5]decan-4-yl}-propionic acid.

Referential Example C-4

The procedure of Example 15 was repeated to obtain (3R)-8-(tert-butoxycarbonyl)-1-thia-4,8-diazaspiro[4.5]decane-3-carboxylic acid.

Referential Example C-5

The procedure of Example 17 was repeated to obtain (3R)-4-benzoyl-8-(tert-butoxycarbonyl)-1-thia-4,8-diazaspiro[4.5]decane-3-carboxylic acid.

Referential Example C-6

The procedure of Referential Example B-5 was repeated to obtain (3R)-4-benzoyl-1-thia-4,8-diazaspiro[4.5]decane-3-carboxylic acid.

Referential Example C-7

Using 9-fluorenylmethyloxycarbonyl-N-hydroxysuccinimide, the procedure of Referential Example B-7 was repeated to obtain (3R)-4-benzoyl-8-[(9H-fluoren-9-ylmethoxy)carbonyl]-1-thia-4,8-diazaspiro[4.5]decane-3-carboxylic acid.

Industrial Utilizability

The compounds of the present invention exhibit an AP-1 activity-inhibitory action and, based on the AP-1 inhibitory action thereof, suppress the expression of a wide variety of genes and are useful as an agent for treating and preventing autoimmune diseases with lessened side reactions.

What is claimed is:

1. A spiro compound represented by the following general formula:

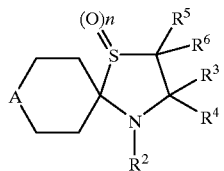

wherein A represents a group of the following general formula:

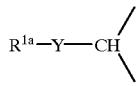

wherein $R^{1a}$ represents a hydrogen atom, a halogen atom, a cyano group, a nitro group, an unprotected or protected carboxyl group, an unprotected or protected hydroxyl group or an unsubstituted or substituted alkyl, alkenyl, cycloalkyl, aryl, aralkyl, alkoxy, aryloxy, acyl, alkoxycarbonyl, aryloxycarbonyl, carbamoyl, amino or heterocyclic group; and Y represents an oxygen atom, a sulfur atom, an unsubstituted or substituted imino group, a carbonyl group, a vinylene group, a sulfinyl group, a sulfonyl group or a group —CH(OH)—;

a group of the following general formula:

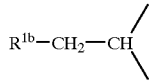

wherein $R^{1b}$ represents a halogen atom, a cyano group, a nitro group, an unprotected or protected carboxyl group, an unprotected or protected hydroxyl group, a substituted alkyl group, or an unsubstituted or substituted alkenyl, cycloalkyl, aryl, aralkyl, alkoxy, aryloxy, acyl, alkoxycarbonyl, aryloxycarbonyl, carbamoyl, amino or heterocyclic group;

a group of the following general formula:

wherein $R^{1c}$ and $R^{1d}$, which may be the same or different, each represent a hydrogen atom, a halogen atom, a cyano group, a nitro group, an unprotected or protected carboxyl group, an unprotected or protected hydroxyl group, a mercapto group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group;

a group of the following general formula:

wherein $R^{1e}$ and $R^{1f}$, which may be the same or different, each represent a halogen atom, a cyano group, a nitro group, an unprotected or protected carboxyl group, an unprotected or protected hydroxyl group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group; or a group of the following general formula:

wherein $R^{1g}$ represents an unsubstituted or substituted heterocyclic group;

$R^2$ represents a hydrogen atom, a formyl group, an alkanoyl group, an aralkylcarbonyl group, or an unsubstituted or substituted alkyl, alkenyl, cycloalkyl, aroyl, heterocyclic carbonyl, aryl, aralkyl, alkylsulfonyl, arylsulfonyl or heterocyclic group;

$R^3$ and $R^4$, which may be the same or different, each represent a hydrogen atom, a halogen atom, a cyano group, an unprotected or protected carboxyl group, an unprotected or protected hydroxyl group or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group, or a group of the following general formula:

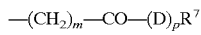

—(CH$_2$)$_m$—CO—(D)$_p$R$^7$ wherein D represents an amino acid residue, $R^7$ represents a hydroxyl group or an amino group, p is 1, 2 or 3, and m is 0, 1, 2, or 3, or alternatively, $R^3$ and $R^4$, taken conjointly, represent an oxo group;

$R^5$ and $R^6$, which may be the same or different, each represent a hydrogen atom, a halogen atom, a cyano group, an unprotected or protected carboxyl group, an unprotected or protected hydroxyl group, an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group, or alternatively, $R^5$ and $R^6$, taken conjointly with the terminal carbon atom to which $R^5$ and $R^6$ are connected, represent an alkenyl group; and n represents 0, 1 or 2;

and salts of these spiro compounds.

2. A spiro compound represented by the following general formula:

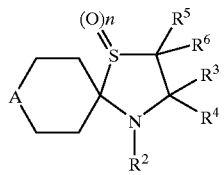

wherein A represents a group of the following general formula:

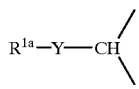

wherein $R^{1a}$ represents a hydrogen atom, a halogen atom, a cyano group, a nitro group, an unprotected or protected carboxyl group, an unprotected or protected hydroxyl group, or an unsubstituted or substituted alkyl, alkenyl, cycloalkyl, aryl, aralkyl, alkoxy, aryloxy, acyl, alkoxycarbonyl, aryloxycarbonyl, carbamoyl, amino or heterocyclic group; and Y represents an oxygen atom, a sulfur atom, an unsubstituted or substituted imino group, carbonyl group, a vinylene group, a sulfinyl group, a sulfonyl group or a group —CH(OH)—;

a group of the following general formula:

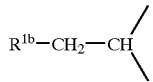

wherein $R^{1b}$ represents a halogen atom, a cyano group, a nitro group, an unprotected or protected carboxyl group, an unprotected or protected hydroxyl group, a substituted alkyl group, or an unsubstituted or substituted alkenyl, cycloalkyl, aryl, aralkyl, alkoxy, aryloxy, acyl, alkoxycarbonyl, aryloxycarbonyl, carbamoyl, amino or heterocyclic group;

a group of the following general formula:

wherein $R^{1c}$ and $R^{1d}$, which may be the same or different, each represent a hydrogen atom, a halogen atom, a cyano group, a nitro group, an unprotected or protected carboxyl group, an unprotected or protected hydroxyl group, a mercapto group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group;

a group of the following formula:

wherein $R^{1e}$ and $R^{1f}$, which may be the same or different, each represent a halogen atom, a cyano group, a nitro group, an unprotected or protected carboxyl group, an unprotected or protected hydroxyl group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group; or a group of the following general formula;

wherein $R^{1g}$ represents an unsubstituted or substituted heterocyclic group;

$R^2$ represents a hydrogen atom, a formyl group, an alkanoyl group, an aralkylcarbonyl group, or an unsubstituted or substituted alkyl, alkenyl, cycloalkyl, aroyl, heterocyclic carbonyl, aryl, aralkyl, alkylsulfonyl, arylsulfonyl or heterocyclic group;

$R^3$ and $R^4$, which may be the same or different, each represent a hydrogen atom, a halogen atom, a cyano group, an unprotected or protected carboxyl group, an unprotected or protected hydroxyl group, or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group, or alternatively, $R^3$ and $R^4$, taken conjointly, represent an oxo group;

$R^5$ and $R^6$, which may be the same or different, each represent a hydrogen atom, a halogen atom, a cyano group, an unprotected or protected carboxyl group, an unprotected or protected hydroxyl group, an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group, or alternatively, $R^5$ and $R^6$, taken conjointly with the terminal carbon atom to which $R^5$ and $R^6$ are combined, represent an alkenyl group; and n represents 0, 1 or 2;

or a salt thereof.

3. A spiro compound or a salt thereof according to claim 2, wherein A represents a group of the following general formula:

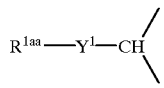

wherein $R^{1aa}$ represents an unsubstituted or substituted alkyl, alkenyl, aryl or heterocyclic group; and $Y^1$ represents an oxygen atom or a vinylene group;

a group of the following general formula:

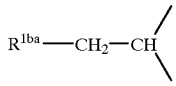

wherein $R^{1ba}$ represents a substituted alkyl group or an unsubstituted or substituted alkenyl, aryl or heterocyclic group;

a group of the following general formula:

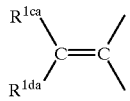

wherein $R^{1ca}$ and $R^{1da}$, which may be the same or different, each represent a hydrogen atom, an unsubstituted or substituted alkyl, alkenyl, aryl or heterocyclic group;

or a group of the following general formula:

wherein $R^{1ea}$ and $R^{1fa}$, which may be the same or different, each represent an unprotected or protected hydroxyl group, or an unsubstituted or substituted aryl group;

$R^2$ represents a hydrogen atom, a formyl group, an alkanoyl group, an aralkylcarbonyl group, or an unsubstituted or substituted alkyl, alkenyl, aroyl, heterocyclic carbonyl, aryl, aralkyl or heterocyclic group;

$R^3$ and $R^4$, which may be the same or different, each represent a hydrogen atom, an unsubstituted or substituted alkoxycarbonyl or carbamoyl group, or a group of the following general formula:

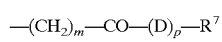

wherein D represents an amino acid residue;

$R^7$ represents a hydroxyl group or an amino group;

p represents 1, 2 or 3; and m represents 0, 1, 2 or 3;

or alternatively, $R^3$ and $R^4$, taken conjointly, represent an oxo group;

$R^5$ and $R^6$, which may be the same or different, each represent a hydrogen atom or an unsubstituted or substituted alkyl group; and n represents 0 or 2.

4. A pharmaceutical composition comprising a spiro compound or a salt thereof according to any one of claim 1 or 2.

5. A pharmaceutical composition comprising a spiro compound or a salt thereof according to any one of claim 1 or 2 wherein said spiro compound or salt thereof is an AP-1 inhibitor.

6. A pharmaceutical composition comprising a spiro compound represented by the following general formula:

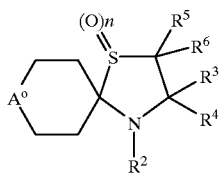

wherein $A^o$ represents a group of the following general formula:

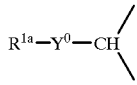

wherein $R^{1a}$ represents a hydrogen atom, a halogen atom, a cyano group, a nitro group, an unprotected or protected carboxyl group, an unprotected or protected hydroxyl group, or an unsubstituted or substituted alkyl, alkenyl, cycloalkyl, aryl, aralkyl, alkoxy, aryloxy, acyl, alkoxycarbonyl, aryloxycarbonyl, carbamoyl, amino or heterocyclic group; and $Y^0$ represents an oxygen atom, sulfur atom, an unsubstituted or substituted imino group, a carbonyl group, a methylene group, a vinylene group, a sulfinyl group, a sulfonyl group or a group —CH(OH)—;

a group of the following general formula:

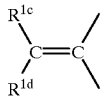

wherein $R^{1c}$ and $R^{1d}$, which may be the same or different, each represent a hydrogen atom, a halogen atom, a cyano group, a nitro group, an unprotected or protected carboxyl group, an unprotected or protected hydroxyl group, a mercapto group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group;

a group of the following general formula:

wherein $R^{1e}$ and $R^{1f}$, which may be the same or different, each represent a halogen atom, a cyano group, a nitro group, an unprotected or protected carboxyl group, an unprotected or protected hydroxyl group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group; or a group of the following general formula:

wherein $R^{1g}$ represents an unsubstituted or substituted heterocyclic group;

$R^{2a}$ represents a hydrogen atom or an unsubstituted or substituted alkyl, alkenyl, cycloalkyl, acyl, aryl, aralkyl, alkylsulfonyl, arylsulfonyl or heterocyclic group;

$R^3$ and $R^4$, which may be the same or different, each represent a hydrogen atom, a halogen atom, a cyano group, an unprotected or protected carboxyl group, an unprotected or protected hydroxyl group, or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group, or alternatively, $R^3$ and $R^4$, taken conjointly, represent an oxo group;

$R^5$ and $R^6$, which may be the same or different, each represent a hydrogen atom, a halogen atom, a cyano group, an unprotected or protected carboxyl group, an unprotected or protected hydroxyl group, an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group, or alternatively, $R^5$ and $R^6$, taken conjointly with the terminal carbon atom to which $R^5$ and $R^6$ are connected, represent an alkenyl group; and n represents 0, 1 or 2;

or a salt thereof.

7. A pharmaceutical composition comprising a spiro compound represented by the following general formula:

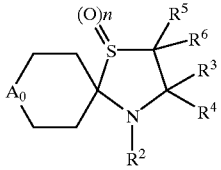

wherein $A^0$ represents a group of the following general formula:

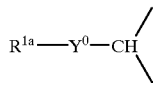

wherein $R^{1a}$ represents a hydrogen atom, a halogen atom, a cyano group, a nitro group, an unprotected or protected carboxyl group, an unprotected or protected hydroxyl group, or an unsubstituted or substituted alkyl, alkenyl, cycloalkyl, aryl, aralkyl, alkoxy, aryloxy, acyl, alkoxycarbonyl, aryloxycarbonyl, carbamoyl, amino or heterocyclic group; and $Y^0$ represents an oxygen atom, a sulfur atom, an unsubstituted or substituted imino group, a carbonyl group, a methylene group, a vinylene group, a sulfinyl group, a sulfonyl group or a group —CH(OH)—;

a group of the following general formula:

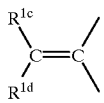

wherein $R^{1c}$ and $R^{1d}$, which may be the same or different, each represent a hydrogen atom, a halogen atom, a cyano group, a nitro group, an unprotected or protected carboxyl group, an unprotected or protected hydroxyl group, a mercapto group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group;

a group of the following general formula:

wherein $R^{1e}$ and $R^{1f}$, which may be the same or different, each represent a halogen atom, a cyano group, a nitro group, an unprotected or protected carboxyl group, an unprotected or protected hydroxyl group, or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, amino or heterocyclic group; or a group of the following general formula:

wherein $R^{1g}$ represents an unsubstituted or substituted heterocyclic group;

$R^{2a}$ represents a hydrogen atom or an unsubstituted or substituted alkyl, alkenyl, cycloalkyl, acyl, aryl, aralkyl, alkylsulfonyl, arylsulfonyl or heterocyclic group;

$R^3$ and $R^4$, which may be the same or different, each represent a hydrogen atom, a halogen atom, a cyano group, an unprotected or protected carboxyl group, an unprotected or protected hydroxyl group, or an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group, or alternatively, $R^3$ and $R^4$, taken conjointly, represent an oxo group;

$R^5$ and $R^6$, which may be the same or different, each represent a hydrogen atom, a halogen atom, a cyano group, an unprotected or protected carboxyl group, an unprotected or protected hydroxyl group, an unsubstituted or substituted alkyl, alkenyl, cycloalkyl, alkoxy, alkylthio, alkylsulfinyl, alkylsulfonyl, acyl, alkoxycarbonyl, aryl, amino, alkylamino, acylamino, carbamoyl or heterocyclic group, or alternatively, $R^5$ and $R^6$, taken conjointly with the terminal carbon atom to which $R^5$ and $R^6$ are connected, represent an alkenyl group; and n represents 0, 1 or 2;

or a salt thereof, wherein said spiro compound or salt thereof is an AP-1 inhibitor.

8. A composition comprising the compound of claim 1 or claim 2, in the form of a tablet, capsule, powder, syrup, granule, pill, suspension, emulsion, solution, powdery preparation, suppository, ointment, or injection.

9. A method for preventing or treating an autoimmune or inflammatory disease comprising administering an effective amount of a compound of claim 1 or 2 to a subject in need thereof.

10. A method for inhibiting AP-1 activity comprising by administering an amount of the compound of claim 1 or 2 effective to inhibit an activity of AP-1.

11. A method for suppressing the expression of a gene through inhibition of AP-1 activity, comprising administering an effective amount of a compound of claim 1 or 2 for a time and under conditions suitable for suppressing the expression of said gene.

* * * * *